(12) United States Patent
Meyers et al.

(10) Patent No.: US 7,781,428 B2
(45) Date of Patent: Aug. 24, 2010

(54) PYRAZOLINE COMPOUNDS

(75) Inventors: Marvin J. Meyers, St. Charles, MO (US); Graciela B. Arhancet, St. Louis, MO (US); Xiangyang Chen, Chesterfield, MO (US); Susan Hockerman, Kirkwood, MO (US); David B. Reitz, Chesterfield, MO (US); Joseph G. Rico, O'Fallon, MO (US)

(73) Assignee: Pfizer Inc., New York, NY (US)

( * ) Notice: Subject to any disclaimer, the term of this patent is extended or adjusted under 35 U.S.C. 154(b) by 276 days.

(21) Appl. No.: 11/923,248

(22) Filed: Oct. 24, 2007

(65) Prior Publication Data

US 2008/0167294 A1  Jul. 10, 2008

Related U.S. Application Data

(60) Provisional application No. 60/863,606, filed on Oct. 31, 2006.

(51) Int. Cl.
*A61K 31/546* (2006.01)
*A61P 9/00* (2006.01)
*A61P 9/12* (2006.01)
*C07D 231/54* (2006.01)

(52) U.S. Cl. .................. 514/222.5; 514/349; 514/403; 548/359.1

(58) Field of Classification Search .................. None
See application file for complete search history.

(56) References Cited

U.S. PATENT DOCUMENTS

| | | | |
|---|---|---|---|
| 3,447,943 A | 6/1969 | Keats et al. | 117/33.5 |
| 3,816,438 A | 6/1974 | Houlihan | 260/294.8 B |
| 3,843,666 A | 10/1974 | Coombs et al. | 260/296 T |
| 3,932,430 A | 1/1976 | Habeck et al. | 260/296 T |
| 4,866,025 A | 9/1989 | Byers et al. | 503/227 |
| 5,550,152 A | 8/1996 | Koch et al. | 514/458 |
| 6,080,781 A | 6/2000 | Yoshihama et al. | 514/456 |
| 6,432,974 B1 | 8/2002 | Kelly et al. | 514/292 |

FOREIGN PATENT DOCUMENTS

| | | |
|---|---|---|
| EP | 1844768 | 10/2007 |
| WO | WO9507262 | 3/1995 |
| WO | WO9734893 | 9/1997 |
| WO | WO9809969 | 3/1998 |
| WO | WO9855118 | 12/1998 |
| WO | WO9955335 | 11/1999 |
| WO | WO03078394 | 9/2003 |
| WO | WO03079973 | 10/2003 |
| WO | WO2004013140 | 2/2004 |
| WO | WO2004026306 | 4/2004 |
| WO | WO2004052847 | 6/2004 |
| WO | WO2004067529 | 8/2004 |
| WO | WO2005066161 | 7/2005 |
| WO | WO2005097118 | 10/2005 |
| WO | WO2006010142 | 1/2006 |
| WO | WO2006012642 | 2/2006 |
| WO | WO2006076202 | 7/2006 |
| WO | WO2006077821 | 7/2006 |
| WO | WO2006086358 | 8/2006 |

OTHER PUBLICATIONS

Jewell, et al., *Cardiovascular & Hematological Agents in Medicinal Chemistry*, vol. 4, pp. 129-153 (2004).
Mauger, et al., *Advanced Synthesis and Catalysis*, vol. 347, pp. 773-782 (2005).
Reiter, et al., *Biorganic & Medicinal Chemistry Letters*, vol. 7, No. 17, pp. 2307-2312 (1997).
Cannon, et al., *Journal of Medicinal Chemistry*, vol. 32, pp. 2210-2214 (1989).
Koch, et al., *Journal of Organic Chemistry*, vol. 59, pp. 1216-1218 (1994).
Beugelmans, et al., *Journal of Organic Chemistry*, vol. 50, pp. 4933-4938 (1985).
Ferraz, et al., *Tetrahedron*, vol. 59, pp. 5817-5821 (2003).
Haddad, et al., *Tetrahedron Letters*, vol. 43, pp. 2171-2173 (2002).
Haddad, et al., *Tetrahedron Letters*, vol. 45, pp. 5935-5937 (2004).
Baxter, et al., *Molecular and Cellular Endocrinology*, vol. 217, pp. 151-165 (2004).

*Primary Examiner*—Kamal A Saeed
(74) *Attorney, Agent, or Firm*—Jennifer Kispert; A. Dean Olson

(57) ABSTRACT

Compounds and pharmaceutically acceptable salts of the compounds are disclosed, wherein the compounds have the structure of Formula I:

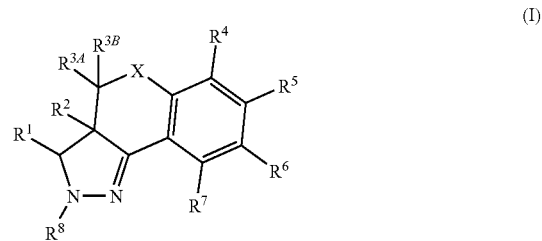

(I)

wherein $R^1$, $R^2$, $R^{3A}$, $R^{3B}$, $R^4$, $R^5$, $R^6$, $R^7$, $R^8$, and X are as defined in the detailed description of the invention. Corresponding pharmaceutical compositions, methods of treatment, and intermediates are also disclosed.

18 Claims, No Drawings

PYRAZOLINE COMPOUNDS

This application claims priority from U.S. Provisional Application No. 60/863,606 filed Oct. 31, 2006.

FIELD OF THE INVENTION

The present invention comprises a class of pyrazoline compounds having the structure of Formula I and pharmaceutical compositions comprising a compound of Formula I. The present invention also comprises methods of treating a subject by administering a therapeutically effective amount of a compound of Formula I to the subject. The present invention further comprises methods for making a compound of Formula I and corresponding intermediates.

BACKGROUND OF THE INVENTION

Hypertension affects about 20% of the adult population in developed countries. In the adult population aged 60 years or older, this percentage increases to about 60% to 70%. Hypertension also is associated with an increased risk of other physiological complications including stroke, myocardial infarction, atrial fibrillation, heart failure, peripheral vascular disease and renal impairment. Although a number of antihypertensive drugs are available in various pharmacological categories, the efficacy and safety of such drugs can vary from patient to patient.

Mineralocorticoid receptor antagonists are one class of drugs that can be used to treat hypertension and/or related physiological complications (Jewell, C. W., et al., Cardiovascular & Hematological Agents in Medicinal Chemistry (2006) Vol. 4, pgs. 129-153). Mineralocorticoids, such as aldosterone, are involved in regulating salt and water balance in mammals. Activation of the mineralocorticoid receptor can induce hypertension and cause other detrimental cardiovascular and physiological effects. Two mineralocorticoid receptor antagonists, spironolactone (ALDACTONE™) and eplerenone (INSPRA™), are presently available and indicated for the treatment of hypertension and heart failure (Baxter, J. D., et al., Molecular and Cellular Endocrinology (2004) Vol. 217, pgs. 151-165).

The identification of additional compounds that are mineralocorticoid receptor antagonists is desirable. Such compounds can be used to treat subjects suffering from or susceptible to hypertension and/or related physiological problems and further expand the range of treatment options available for such subjects. Both spironolactone and eplerenone have a steroidal structure. The present invention is particularly directed to mineralocorticoid receptor antagonists that are non-steroidal compounds. Use of a non-steroidal mineralocorticoid receptor antagonist potentially provides certain advantages over a steroidal mineralocorticoid receptor antagonist including, e.g., further improvement in selectivity with respect to the sex hormone receptors; less complex and costly chemical synthesis; and the like.

Non-steroidal compounds useful as mineralocorticoid receptor antagonists have been reported in the literature. For example:

WO 06/076202 (published Jul. 20, 2006) reports a class of imidazole carboxamides as mineralocorticoid receptor antagonists.

WO 06/012642 (published Feb. 2, 2006) reports a class of pyrrole carboxamides as mineralocorticoid receptor antagonists.

WO 04/052847 (published Jun. 24, 2004) reports a class of dibenzosuberanes as mineralocorticoid receptor antagonists.

WO 05/066161 (published Jul. 21, 2005) reports a class of dibenzosuberanes as mineralocorticoid receptor antagonists.

WO 03/078394 (published Sep. 25, 2003) reports a class of 3,3-bisaryl oxindoles as mineralocorticoid receptor antagonists.

WO 05/097118 (published Oct. 20, 2005) reports a class of 4-aryl-1,4-dihydropyridines as mineralocorticoid receptor antagonists.

WO 04/067529 (published Aug. 12, 2004) reports a class of 3-benzyl indoles as mineralocorticoid receptor antagonists.

WO 06/077821 (published Jul. 27, 2006) reports classes of benzoxazine/thiones and tetrahydroquinolines as mineralocorticoid receptor antagonists.

WO 06/010142 (published Jan. 26, 2006) reports a class of aryl benzoxazinones/thiones as mineralocorticoid receptor antagonists.

SUMMARY OF THE INVENTION

In one embodiment, the invention comprises a class of compounds having the structure of Formula I:

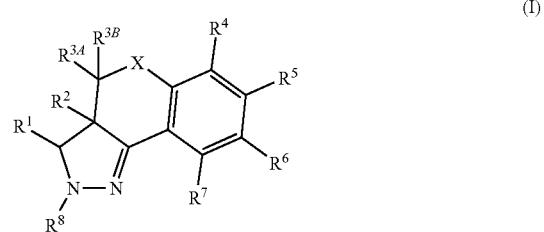

(I)

and the pharmaceutically acceptable salts thereof; wherein $R^1$, $R^2$, $R^{3,4}$, $R^4$, $R^5$, $R^5$, $R^6$, $R^7$, $R^8$, and X are as defined in the Detailed Description of the Invention.

In another embodiment, the invention comprises a pharmaceutical composition comprising a compound having the structure of Formula I, or a pharmaceutically acceptable salt thereof; and a pharmaceutically-acceptable carrier.

In another embodiment, the invention comprises a pharmaceutical composition comprising a compound having the structure of Formula I, or a pharmaceutically acceptable salt thereof; one or more additional pharmaceutically active compounds; and a pharmaceutically-acceptable carrier.

In another embodiment, the invention comprises methods of treating a condition in a subject by administering to a subject a therapeutically effective amount of a compound having the structure of Formula I. The conditions that can be treated in accordance with the present invention include cardiovascular conditions (including hypertension and heart failure), renal conditions, liver conditions, vascular conditions, retinopathy, neuropathy (including peripheral neuropathy), insulinopathy, edema, endothelial dysfunction, baroreceptor dysfunction, and the like.

In another embodiment, the invention comprises methods of treating a condition in a subject by administering a compound having the structure of Formula I in combination with another pharmaceutically active compound. The conditions that can be treated in accordance with the present invention include cardiovascular conditions (including hypertension and heart failure), renal conditions, liver conditions, vascular conditions, retinopathy, neuropathy (including peripheral neuropathy), insulinopathy, edema, endothelial dysfunction, baroreceptor dysfunction, and the like.

In another embodiment, the invention comprises use of a compound having the structure of Formula I, or a pharmaceutically acceptable salt thereof, for the manufacture of a medicament for the treatment of a condition in a subject. The conditions that can be treated in accordance with the present invention include cardiovascular conditions (including hypertension and heart failure), renal conditions, liver conditions, vascular conditions, retinopathy, neuropathy (including peripheral neuropathy), insulinopathy, edema, endothelial dysfunction, baroreceptor dysfunction, and the like.

In another embodiment, the invention comprises methods for making a compound having the structure of Formula I, or a pharmaceutically acceptable salt thereof.

In another embodiment, the invention comprises intermediates useful in making a compound having the structure of Formula I, or a pharmaceutically acceptable salt thereof.

DETAILED DESCRIPTION OF THE INVENTION

This detailed description of embodiments is intended only to acquaint others skilled in the art with Applicants' invention, its principles, and its practical application so that others skilled in the art may adapt and apply the inventions in their numerous forms, as they may be best suited to the requirements of a particular use. These inventions, therefore, are not limited to the embodiments described in this specification, and may be variously modified.

A. Abbreviations and Definitions

As used in reference to $^1$H NMR, the symbol "δ" refers to a $^1$H NMR chemical shift.

As used in reference to $^1$H NMR, the abbreviation "br" refers to a broad $^1$H NMR signal.

As used in reference to $^1$H NMR, the abbreviation "d" refers to a doublet $^1$H NMR peak.

As used in reference to $^1$H NMR, the abbreviation "dd" refers to a doublet of doublets $^1$H NMR peak.

The abbreviation "HRMS" refers to High Resolution Mass Spectroscopy (electrospray ionisation positive scan).

The abbreviation "m/z" refers to a Mass spectrum peak.

As used in reference to $^1$H NMR, the abbreviation "m" refers to a multiplet $^1$H NMR peak.

As used in reference to $^1$H NMR, the abbreviation "q" refers to a quartet $^1$H NMR peak.

As used in reference to $^1$H NMR, the abbreviation "s" refers to a singlet $^1$H NMR peak.

As used in reference to $^1$H NMR, the abbreviation "t" refers to a triplet $^1$H NMR peak.

The term "alkyl" refers to a linear or branched-chain saturated hydrocarbyl substituent (i.e., a substituent containing only carbon and hydrogen) containing in one embodiment, from about one to about twenty carbon atoms; in another embodiment from about one to about twelve carbon atoms; in another embodiment, from about one to about ten carbon atoms; in another embodiment, from about one to about eight carbon atoms; in another embodiment, from about one to about six carbon atoms; in another embodiment, from about three to about six carbons; in another embodiment, from about one to about 4 carbons; in another embodiment, from about one to about three carbons; and in another embodiment, from about one to about two carbon atoms. Examples of such substituents include methyl, ethyl, propyl (including n-propyl and isopropyl), butyl (including n-butyl, isobutyl, sec-butyl and tert-butyl), pentyl, iso-amyl, hexyl and the like.

The term "alkenyl" refers to a linear or branched-chain hydrocarbyl substituent containing one or more double bonds and from about two to about twenty carbon atoms; in another embodiment, from about two to about twelve carbon atoms; in another embodiment, from about two to about six carbon atoms; in another embodiment, from about three to about six carbons; and in another embodiment, from about two to about four carbon atoms. Examples of alkenyl include ethenyl (also known as vinyl), allyl, propenyl (including 1-propenyl and 2-propenyl) and butenyl (including 1-butenyl, 2-butenyl and 3-butenyl). The term "alkenyl" embraces substituents having "cis" and "trans" orientations, or alternatively, "E" and "Z" orientations.

The term "benzyl" refers to methyl radical substituted with phenyl.

The term "cycloalkyl" refers to a saturated carbocyclic substituent having three to about fourteen carbon atoms. In another embodiment, a cycloalkyl substituent has three to about eight carbon atoms. In another embodiment, a cycloalkyl substituent has from three to about six carbons; in another embodiment, from three to about four carbons. Examples of cycloalkyl include cyclopropyl, cyclobutyl, cyclopentyl and cyclohexyl.

The term "aryl" refers to a carbocyclic aromatic system containing one, two or three rings wherein such rings may be attached together in a pendent manner or may be fused. The term "aryl" refers to aromatic substituents such as phenyl, naphthyl and anthracenyl.

The term "arylalkyl" refers to alkyl substituted with aryl.

In some instances, the number of carbon atoms in a hydrocarbyl substituent (e.g., alkyl, alkenyl, alkynyl, cycloalkyl, cycloalkenyl, aryl, etc.) is indicated by the prefix "$C_x$-$C_y$-," wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl refers to saturated carbocyclyl containing from 3 to 6 carbon ring atoms.

The terms "hydroxy" and "hydroxyl" each refer to —OH. Hydroxyl may be used alone to indicate the substituent, as in "a hydroxyl group." When used in combination with another term(s), the prefix "hydroxy" indicates that the substituent to which the prefix is attached is substituted with one or more hydroxyl substituents. Compounds bearing a carbon to which one or more hydroxyl substituents include, for example, alcohols, enols and phenol.

The term "hydroxyalkyl" refers to an alkyl that is substituted with at least one hydroxy substituent. Examples of hydroxyalkyl include hydroxymethyl, hydroxyethyl, hydroxypropyl and hydroxybutyl.

The term "alkylamino" refers to an amino group, wherein at least one alkyl chain is bonded to the amino nitrogen in place of a hydrogen atom. Examples of alkylamino substituents include monoalkylamino such as methylamino (exemplified by the formula —NH(CH$_3$)), and dialkylamino such as dimethylamino, (exemplified by the formula —N((CH$_3$)$_2$).

The term "aminocarbonyl" refers to —C(O)—NH$_2$.

The term "halogen" refers to fluorine, chlorine, bromine, or iodine (which may be depicted as —I).

In one embodiment, the halogen is chlorine. In another embodiment, the halogen is fluorine.

The prefix "halo" indicates that the substituent to which the prefix is attached is substituted with one or more independently selected halogen substituents. For example, haloalkyl refers to an alkyl that is substituted with at least one halogen substituent. Where there is more than one hydrogen replaced with a halogen, the halogen replacements may be the identical or different. Examples of haloalkyls include chloromethyl, dichloromethyl, difluorochloromethyl, dichlorofluoromethyl, trichloromethyl, 1-bromoethyl, fluoromethyl, difluoromethyl, trifluoromethyl, 2,2,2-trifluoroethyl, difluoroethyl, pentafluoroethyl, difluoropropyl, dichloropropyl, and heptafluoropropyl. Illustrating further, "haloalkoxy" refers to an alkoxy that is substituted with at least one halogen substituent. Examples of haloalkoxy substituents include chloromethoxy, 1-bromoethoxy, fluoromethoxy, difluoromethoxy, trifluoromethoxy (also known as "perfluoromethyloxy"), and 2,2,2-trifluoroethoxy. It should be recognized that if a substituent is substituted by more than one halogen substituent, those halogen substituents may be identical or different (unless otherwise stated).

The term "oxo" refers to =O.

The term "oxy" refers to an ether substituent, and may be depicted as —O—.

The term "alkoxy" refers to an alkyl linked to an oxygen atom, which may also be represented as —O—R, wherein the R represents the alkyl group. Examples of alkoxy include methoxy, ethoxy, propoxy and butoxy.

The term "alkylcarbonyl" refers to —C(O)-alkyl. For example, "ethylcarbonyl". Examples of other alkylcarbonyl include methylcarbonyl, propylcarbonyl, butylcarbonyl, pentylcarbonyl, and hexylcarbonyl.

The term "aminoalkylcarbonyl" refers to —C(O)-alkyl-$NH_2$. For example, "aminomethylcarbonyl".

The term "alkoxycarbonyl" refers to —C(O)—O-alkyl. For example, "ethoxycarbonyl". Examples of other alkoxycarbonyl include methoxycarbonyl, ethoxycarbonyl, propoxycarbonyl, butoxycarbonyl, pentoxycarbonyl, and hexyloxycarbonyl. In another embodiment, where the carbon atom of the carbonyl is attached to a carbon atom of a second alkyl, the resulting functional group is an ester.

The terms "thio" and "thia" refer to a divalent sulfur atom and such a substituent may be depicted as —S—. For example, a thioether is represented as "alkyl-thio-alkyl" or, alternatively, alkyl-5-alkyl.

The term "thiol" refers to a sulfhydryl substituent, and may be depicted as —SH.

The term "sulfonyl" refers to —$S(O)_2$—. Thus, for example, "alkyl-sulfonyl-alkyl" refers to alkyl-$S(O)_2$-alkyl. Examples of alkylsulfonyl include methylsulfonyl, ethylsulfonyl, and propylsulfonyl.

The term "aminosulfonyl" refers to —$S(O)_2$—$NH_2$

The term "sulfinyl" refers to —S(O)—. Thus, for example, "alkylsulfinylalkyl" or "alkylsulfoxidoalkyl" refers to alkyl-S(O)-alkyl. Exemplary alkylsulfinyl groups include methylsulfinyl, ethylsulfinyl, butylsulfinyl, and hexylsulfinyl.

The term "spiro compound" refers to two or three rings which have only one atom in common and the two or three rings are not linked by a bridge. The common ring atom is designated as the spiro atom. A spiro compound may comprise one or more heteroatoms; such a compound falls within the definition of heterocyclyl, infra.

The term "heterocyclyl" refers to a saturated, partially saturated, or completely unsaturated ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include, without limitation, azetidinyl, furanyl, dihydrofuranyl, tetrahydrofuranyl, thiofuranyl, dihydrothiofuranyl, tetrahydrothiofuranyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, isoxazolyl, thiazolyl, isothiazolyl, thiazolinyl, isothiazolinyl, thiazolidinyl, oxathiazolyl, oxadiazolyl, furazanyl, oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiolanyl, pyranyl (including 1,2-pyranyl or 1,4-pyranyl), dihydropyranyl, pyridinyl (also known as "pyridyl"), piperidinyl, pyridazinyl, pyrimidinyl (also known as "pyrimidyl"), pyrazinyl, piperazinyl, triazinyl, oxazinyl, oxazolidinyl, isoxazolidinyl, oxathiazinyl, oxadiazinyl, morpholinyl, azepinyl, oxepinyl, thiepinyl, and diazepinyl.

A heterocyclyl may also comprise 2 or 3 rings fused together, wherein at least one such ring contains at least one heteroatom as a ring atom (e.g., nitrogen, oxygen, or sulfur). Examples of 2-fused-ring heterocyclyls include, without limitation, indolizinyl, 4H-quinolizinyl, purinyl, naphthyridinyl, pteridinyl, indolyl, isoindolyl, indoleninyl, phthalazinyl, quinoxalinyl, quinazolinyl, benzodiazinyl, benzopyranyl, benzothiopyranyl, benzoxazolyl, benzodioxolyl, benzodioxanyl, benzoxadiazolyl, benzofuranyl, isobenzofuranyl, benzothienyl, benzothiazolyl, benzothiadiazolyl, benzimidazolyl, benzotriazolyl, benzoxazinyl, tetrahydroisoquinolinyl, carbazolyl, xanthenyl, and acridinyl. Additional examples of fused ring heterocyclyls include tetrahydrodioxolopyrrolyl and tetrahydrotriazolopyrazinyl.

The term "heteroaryl" refers to an aromatic heterocyclyl containing from 5 to 14 ring atoms. A heteroaryl may be a single ring or 2 or 3 fused rings. Examples of heteroaryl substituents include 6-membered ring substituents such as pyridinyl (also known as "pyridyl"), pyrazyl, pyrimidinyl (also know as "pyrimidyl"), and pyridazinyl; 5-membered ring substituents such as triazolyl, imidazoyl, furanyl, thiofuranyl, pyrazolyl, oxazolyl, isoxazolyl, thiazolyl, oxadiazolyl and isothiazolyl; 6/5-membered fused ring substituents such as benzothiofuranyl, benzisoxazolyl, benzoxazolyl, and purinyl; and 6/6-membered fused rings such as quinolinyl, isoquinolinyl, cinnolinyl, and quinazolinyl.

The term "heterocyclylalkyl" refers to alkyl substituted with a heterocyclyl.

The term "heterocycloalkyl" refers to a fully saturated heterocyclyl.

A substituent is "substitutable" if it comprises at least one carbon, sulfur, oxygen or nitrogen atom that is bonded to one or more hydrogen atoms. Thus, for example, hydrogen, halogen, and cyano do not fall within this definition.

If a substituent is described as being "substituted," a non-hydrogen substituent is in the place of a hydrogen substituent on a carbon or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

A prefix attached to a multi-moiety substituent only applies to the first moiety. To illustrate, the term "alkylcycloalkyl" contains two moieties: alkyl and cycloalkyl. Thus, the $C_1$-$C_6$- prefix on $C_1$-$C_6$-alkylcycloalkyl means that the alkyl moiety of the alkylcycloalkyl contains from 1 to 6 carbon atoms; the $C_1$-$C_6$- prefix does not describe the cycloalkyl moiety. To illustrate further, the prefix "halo" on haloalkoxyalkyl indicates that only the alkoxy moiety of the alkoxyalkyl substituent is substituted with one or more halogen substituents. If halogen substitution may alternatively or additionally occur on the alkyl moiety, the substituent would instead be described as "halogen-substituted alkoxyalkyl" rather than "haloalkoxyalkyl." And finally, if the halogen substitution may only occur on the alkyl moiety, the substituent would instead be described as "alkoxyhaloalkyl."

When a substituent is comprised of multiple moieties, unless otherwise indicated, it is the intention for the final moiety to serve as the point of attachment to the remainder of the molecule.

For example, in a substituent A-B-C, moiety C is attached to the remainder of the molecule. In a substituent A-B-C-D, moiety D is attached to the remainder of the molecule. Similarly, in a substituent aminocarbonylmethyl, the methyl moiety is attached to the remainder of the molecule. In a substituent trifluoromethylaminocarbonyl, the carbonyl moiety is attached to the remainder of the molecule.

Parentheses may be used to describe a substituent when multiple first moieties are intended to substitute a single second moiety. In a substituent (hydroxymethyl)(ethyl)piperidinyl, both the hydroxymethyl moiety and ethyl moiety are directly attached to the piperidinyl moiety. Alternatively, if a substituent is not substitutable, no parentheses are necessary. For example, a "fluorochloromethane" describes a carbon atom bonded directly to a chlorine, a fluorine, and two hydrogen atoms.

If substituents are described as being "independently selected" from a group, each substituent is selected independent of the other. Each substituent therefore may be identical to or different from the other substituent(s).

The term "pharmaceutically acceptable carrier" refers to a carrier that is compatible with the other ingredients of the composition and is not deleterious to the subject. Such carriers may be pharmaceutically acceptable material, composition or vehicle, such as a liquid or solid filler, diluent, excipient, solvent or encapsulating material, involved in carrying or transporting a chemical agent. The preferred composition depends on the method of administration.

The terms "prevent," "prevention" or "preventing" refer to either preventing the onset of a preclinically evident condition altogether or preventing the onset of a preclinical evident stage of a condition in a subject. Prevention includes, but is not limited to, prophylactic treatment of a subject at risk of developing a condition.

The term "therapeutically effective amount" refers to that amount of drug or pharmaceutical agent that will elicit the biological or medical response of a tissue, system or animal that is being sought by a researcher or clinician.

The term "treatment" (and corresponding terms "treat" and "treating") includes palliative, restorative, and preventative treatment of a subject. The term "palliative treatment" refers to treatment that eases or reduces the effect or intensity of a condition in a subject without curing the condition. The term "preventative treatment" (and the corresponding term "prophylactic treatment") refers to treatment that prevents the occurrence of a condition in a subject. The term "restorative treatment" refers to treatment that halts the progression of, reduces the pathologic manifestations of, or entirely eliminates a condition in a subject.

B. Compounds

The present invention is directed to a class of compounds (including pharmaceutically acceptable salts and tautomers of the compounds), wherein the compounds have the structure of Formula I:

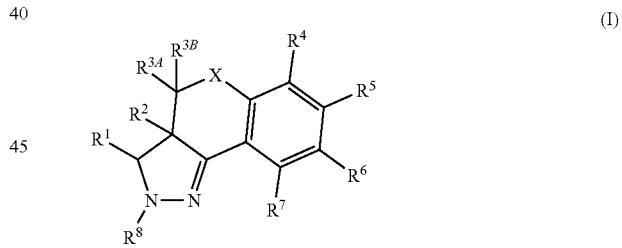

wherein:

X is selected from the group consisting of —$CH_2$— and —O—;

$R^1$ is selected from the group consisting of alkyl, cycloalkyl, cycloalkenyl, phenyl, and heterocyclyl; wherein the heterocyclyl substituent is a five- or six-membered ring heterocyclyl comprising at least one ring heteroatom selected from oxygen, sulfur and nitrogen; and wherein the alkyl, cycloalkyl, cycloalkenyl, phenyl, and heterocyclyl substituents may be optionally substituted with one or more substituents independently selected from the group consisting of hydroxy, halogen, alkyl, and haloalkyl;

$R^2$ is selected from the group consisting of hydrogen and alkyl;

$R^{3A}$ and $R^{3B}$ are independently selected from the group consisting of hydrogen and alkyl $R^4$, $R^6$, and $R^7$ are independently selected from the group consisting of hydrogen, halogen, hydroxy, alkyl, haloalkyl, hydroxyalkyl, and alkoxy;

$R^5$ is selected from the group consisting of hydrogen, —$(CH_2)_mOR^{50}$, $(CH_2)_mC(O)R^{50}$, $(CH_2)_mC(O)OR^5$, $(CH_2)_mC(O)NR^{51}R^{52}$, —$(CH_2)_mNR^{51}R^{52}$, —$(CH_2)_mN(R^{51})C(O)R^{52}$, and —$(CH_2)_mS(O)_nR^{50}$;

m is 0, 1, 2, 3, 4, 5, or 6;

n is 0, 1, or 2;

$R^{50}$ is selected from the group consisting of hydrogen and alkyl;

$R^{51}$ and $R^{52}$ are independently selected from the group consisting of hydrogen and alkyl; or $R^{51}$ and $R^{52}$ together with the nitrogen to which they are attached form a five- or six-membered ring heterocyclyl; wherein the $R^{50}$, $R^{51}$ and $R^{52}$ alkyl substituents and the $R^{51}/R^{52}$ heterocyclyl substituent may be independently and optionally substituted with one or more substituents selected from the group consisting of halogen, pyrrolidinyl, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_pR^{53}$, and —$S(O)_pNR^{54}R^{55}$ p is 0, 1, or 2;

$R^{53}$ is selected from the group consisting of hydrogen, alkyl, haloalkyl, hydroxyalkyl, and carboxyalkyl;

$R^{54}$ and $R^{55}$ are independently selected from the group consisting of hydrogen, alkyl, haloalkyl, hydroxyalkyl, and carboxyalkyl; or $R^{54}$ and $R^{55}$ together with the nitrogen to which they are attached form a five- or six-membered ring heterocyclyl;

$R^{56}$ is selected from the group consisting of hydrogen and alkyl; and $R^8$ is selected from the group consisting of phenyl, pyridinyl and pyrimidinyl; wherein the phenyl, pyridinyl and pyrimidinyl substituents may be optionally substituted with one or more substituents independently selected from the group consisting of halogen, cyano, hydroxy, carboxy, alkyl, haloalkyl, cyanoalkyl, hydroxyalkyl, carboxyalkyl, alkoxy, haloalkoxy, cyanoalkoxy, amino, alkylamino, dialkylamino, and alkoxycarbonyl.

In one embodiment of the compounds of Formula I, $R^{3A}$, $R^{3B}$, $R^4$, $R^6$ and $R^7$ are each hydrogen. In another embodiment, $R^2$, $R^{3A}$, $R^{3B}$, $R^4$, $R^6$ and $R^7$ are each hydrogen. In still another embodiment, X is —$CH_2$—; and $R^2$, $R^{3A}$, $R^3$, $R^4$, $R^6$ and $R^7$ are each hydrogen. In still another embodiment, X is —O—; and $R^2$, $R^{3A}$, $R^{3B}$, $R^4$, $R^6$ and $R^7$ are each hydrogen.

In another embodiment of the compounds of Formula I, $R^2$, $R^{3A}$, $R^{3B}$, $R^4$, $R^6$ and $R^7$ are each hydrogen; and $R^1$ is selected from the group consisting of cycloalkyl and phenyl; wherein the $R^1$ cycloalkyl and phenyl substituents may be optionally substituted with one or more substituents independently selected from the group consisting of halogen, alkyl, and haloalkyl.

In another embodiment of the compounds of Formula I, $R^2$, $R^{3A}$, $R^{3B}$, $R^4$, $R^6$ and $R^7$ are each hydrogen; and $R^8$ is phenyl; wherein the $R^8$ phenyl substituent may be optionally substituted with one or more substituents independently selected from the group consisting of halogen, cyano, hydroxy, carboxy, alkyl, haloalkyl, cyanoalkyl, hydroxyalkyl, carboxyalkyl, alkoxy, haloalkoxy, cyanoalkoxy, amino, alkylamino, dialkylamino, and alkoxycarbonyl. In still another embodiment, the $R^8$ phenyl substituent may be optionally substituted with one or more substituents independently selected from the group consisting of halogen, cyano, and alkyl.

In another embodiment of the compounds of Formula I, $R^2$, $R^{3A}$, $R^{3B}$, $R^4$, $R^6$ and $R^7$ are each hydrogen; and $R^8$ is pyridinyl; wherein the $R^8$ pyridinyl substituent may be optionally substituted with one or more substituents independently selected from the group consisting of halogen, cyano, hydroxy, carboxy, alkyl, haloalkyl, cyanoalkyl, hydroxyalkyl, carboxyalkyl, alkoxy, haloalkoxy, cyanoalkoxy, amino, alkylamino, dialkylamino, and alkoxycarbonyl. In still another embodiment, the $R^8$ pyridinyl substituent may be optionally substituted with one or more substituents independently selected from the group consisting of halogen, cyano, and alkyl.

In another embodiment of the compounds of Formula I, $R^2$, $R^{3A}$, $R^{3B}$, $R^4$, $R^6$ and $R^7$ are each hydrogen; and $R^5$ is selected from the group consisting of —$(CH_2)_mOR^{50}$, $(CH_2)_mC(O)OR^{50}$, and, $(CH_2)_mC(O)NR^{51}R^{52}$; wherein m is 0, 1, 2, 3, 4, 5, or 6; $R^{50}$ is selected from the group consisting of hydrogen and alkyl; $R^{51}$ and $R^{52}$ are independently selected from the group consisting of hydrogen and alkyl; or $R^{51}$ and $R^{52}$ together with the nitrogen to which they are attached form a five- or six-membered ring heterocyclyl; wherein the $R^{50}$, $R^{51}$ and $R^{52}$ alkyl substituents and the $R^{51}/R^{52}$ heterocyclyl substituent may be independently and optionally substituted with one or more substituents selected from the group consisting of halogen, pyrrolidinyl, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_pR^{53}$, and —$S(O)_pNR^{54}R^{55}$; p is 0, 1 or 2; $R^{53}$ is selected from the group consisting of hydrogen, alkyl, haloalkyl, hydroxyalkyl, and carboxyalkyl; $R^{54}$ and $R^{55}$ are independently selected from the group consisting of hydrogen, alkyl, haloalkyl, hydroxyalkyl, and carboxyalkyl; or $R^{54}$ and $R^{55}$ together with the nitrogen to which they are attached form a five- or six-membered ring heterocyclyl; and $R^{56}$ is selected from the group consisting of hydrogen and alkyl. In still another embodiment, $R^5$ is —$(CH_2)_mC(O)OR^{50}$; m is 0; and $R^{50}$ is selected from the group consisting of hydrogen and alkyl. In still another embodiment, $R^5$ is —$(CH_2)_mC(O)OR^{50}$; m is 0; and $R^{50}$ is hydrogen.

In another embodiment of the compounds of Formula I, $R^2$, $R^{3A}$, $R^{3B}$, $R^4$, $R^6$ and $R^7$ are each hydrogen; $R^1$ is selected from the group consisting of $(C_3-C_7)$-cycloalkyl and phenyl; wherein the $R^1$ $(C_3-C_7)$-cycloalkyl and phenyl substituents may be optionally substituted with one or more substituents independently selected from the group consisting of halogen, $(C_1-C_6)$-alkyl, and halo-$(C_1-C_6)$-alkyl; $R^5$ is selected from the group consisting of —$(CH_2)_mOR^{50}$, —$(CH_2)_mC(O)OR^{50}$, and —$(CH_2)_mC(O)NR^{51}R^{52}$; wherein m is 0, 1, 2, 3, 4, 5, or 6; $R^{50}$ is selected from the group consisting of hydrogen and $(C_1-C_6)$-alkyl; $R^{51}$ and $R^{52}$ are independently selected from the group consisting of hydrogen and $(C_1-C_6)$-alkyl; or $R^{51}$ and $R^{52}$ together with the nitrogen to which they are attached form a five- or six-membered ring heterocyclyl; wherein the $R^{50}$, $R^{51}$ and $R^{52}$ $(C_1-C_6)$-alkyl substituents and the $R^{51}/R^{52}$ heterocyclyl substituent may be independently and optionally substituted with one or more substituents selected from the group consisting of halogen, pyrrolidinyl, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_pR^{53}$, and —$S(O)_pNR^{54}R^{55}$; p is 0, 1 or 2; $R^{53}$ is selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; $R^{54}$ and $R^{55}$ are independently selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; or $R^{54}$ and $R^{55}$ together with the nitrogen to which they are attached form a five- or six-membered ring heterocyclyl; and $R^{56}$ is selected from the group consisting of hydrogen and $(C_1-C_6)$-alkyl; and $R^8$ is selected from the group consisting of phenyl and pyridinyl; wherein the $R^8$ phenyl and pyridinyl substituents may be optionally substituted with one or more substituents independently selected from the group consisting of halogen, cyano, hydroxy, carboxy, $(C_1-C_6)$-alkyl, halo-$(C_1-C_6)$-alkyl, cyano-$(C_1-C_6)$-alkyl, hydroxy-$(C_1-C_6)$-alkyl, carboxy-$(C_1-C_6)$-alkyl, $(C_1-C_6)$-alkoxy, halo-$(C_1-C_6)$-alkoxy, cyano-$(C_1-C_6)$-alkoxy, amino, $(C_1-C_6)$-alkylamino, di-$(C_1-C_6)$-alkylamino, and —$(C_1-C_6)$-alkoxycarbonyl. In still another embodiment, X is —$CH_2$—. In still another embodiment, X is —O—.

In another embodiment of the compounds of Formula I, $R^2$, $R^{3A}$, $R^{3B}$, $R^4$, $R^6$ and $R^7$ are each hydrogen; $R^1$ is $(C_3-C_7)$-cycloalkyl; wherein the $R^1$ $(C_3-C_7)$-cycloalkyl substituent may be optionally substituted with one or more substituents independently selected from the group consisting of halogen, $(C_1-C_6)$-alkyl, and halo-$(C_1-C_6)$-alkyl; $R^5$ is selected from the group consisting of —$(CH_2)_m OR^{50}$, —$(CH_2)_m C(O)OR^{50}$, and —$(CH_2)_m C(O)NR^{51}R^{52}$; wherein m is 0, 1, 2, 3, 4, 5, or 6; $R^{50}$ is selected from the group consisting of hydrogen and $(C_1-C_6)$-alkyl; $R^{51}$ and $R^{52}$ are independently selected from the group consisting of hydrogen and $(C_1-C_6)$-alkyl; or $R^{51}$ and $R^{52}$ together with the nitrogen to which they are attached form a five- or six-membered ring heterocyclyl; wherein the $R^{50}$, $R^{51}$ and $R^{52}$ $(C_1-C_6)$-alkyl substituents and the $R^{51}/R^{52}$ heterocyclyl substituent may be independently and optionally substituted with one or more substituents selected from the group consisting of halogen, pyrrolidinyl, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_p R^{53}$, and —$S(O)_p NR^{54}R^{55}$; p is 0, 1 or 2; $R^{53}$ is selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; $R^{54}$ and $R^{55}$ are independently selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; or $R^{54}$ and $R^{55}$ together with the nitrogen to which they are attached form a five- or six-membered ring heterocyclyl; and $R^{56}$ is selected from the group consisting of hydrogen and $(C_1-C_6)$-alkyl; and $R^8$ is selected from the group consisting of phenyl and pyridinyl; wherein the $R^8$ phenyl and pyridinyl substituents may be optionally substituted with one or more substituents independently selected from the group consisting of halogen, cyano, hydroxy, carboxy, $(C_1-C_6)$-alkyl, halo-$(C_1-C_6)$-alkyl, cyano-$(C_1-C_6)$-alkyl, hydroxy-$(C_1-C_6)$-alkyl, carboxy-$(C_1-C_6)$-alkyl, $(C_1-C_6)$-alkoxy, halo-$(C_1-C_6)$-alkoxy, cyano-$(C_1-C_6)$-alkoxy, amino, $(C_1-C_6)$-alkylamino, di-$(C_1-C_6)$-alkylamino, and —$(C_1-C_6)$-alkoxycarbonyl. In still another embodiment, X is —$CH_2$—. In still another embodiment, X is —O—. In still another embodiment, $R^1$ is selected from the group consisting of cyclohexyl, cyclopentyl, cyclobutyl and cyclopropyl. In still another embodiment, $R^1$ is cyclopentyl.

In another embodiment of the compounds of Formula I, $R^2 R^{3A}$, $R^{3B}$, $R^4$, $R^6$ and $R^7$ are each hydrogen; $R^1$ is phenyl; wherein the $R^1$ phenyl substituent may be optionally substituted with one or more substituents independently selected from the group consisting of halogen, $(C_1-C_6)$-alkyl, and halo-$(C_1-C_6)$-alkyl; $R^5$ is selected from the group consisting of —$(CH_2)_m OR^{50}$, $(CH_2)_m C(O)OR^{50}$, and —$(CH_2)_m C(O)NR^{51}R^{52}$; wherein m is 0, 1, 2, 3, 4, 5, or 6; $R^{50}$ is selected from the group consisting of hydrogen and $(C_1-C_6)$-alkyl; $R^{51}$ and $R^{52}$ are independently selected from the group consisting of hydrogen and $(C_1-C_6)$-alkyl; or $R^{51}$ and $R^{52}$ together with the nitrogen to which they are attached form a five- or six-membered ring heterocyclyl; wherein the $R^{50}$, $R^{51}$ and $R^{52}$ $(C_1-C_6)$-alkyl substituents and the $R^{51}/R^{52}$ heterocyclyl substituent may be independently and optionally substituted with one or more substituents selected from the group consisting of halogen, pyrrolidinyl, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_p R^{53}$, and —$S(O)_p NR^{54}R^{55}$; p is 0, 1 or 2; $R^{53}$ is selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; $R^{54}$ and $R^{55}$ are independently selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; or $R^{54}$ and $R^{55}$ together with the nitrogen to which they are attached form a five- or six-membered ring heterocyclyl; and $R^{56}$ is selected from the group consisting of hydrogen and $(C_1-C_6)$-alkyl; and $R^8$ is selected from the group consisting of phenyl and pyridinyl; wherein the $R^8$ phenyl and pyridinyl substituents may be optionally substituted with one or more substituents independently selected from the group consisting of halogen, cyano, hydroxy, carboxy, $(C_1-C_6)$-alkyl, halo-$(C_1-C_6)$-alkyl, cyano-$(C_1-C_6)$-alkyl, hydroxy-$(C_1-C_6)$-alkyl, carboxy-$(C_1-C_6)$-alkyl, $(C_1-C_6)$-alkoxy, halo-$(C_1-C_6)$-alkoxy, cyano-$(C_1-C_6)$-alkoxy, amino, $(C_1-C_6)$-alkylamino, di-$(C_1-C_6)$-alkylamino, and —$(C_1-C_6)$-alkoxycarbonyl. In still another embodiment, the $R^1$ phenyl substituent may be optionally substituted with one or more substituents independently selected from the group consisting of halogen, $(C_1-C_6)$-alkyl and halo-$(C_1-C_6)$-alkyl. In still another embodiment, the $R^1$ phenyl substituent is substituted with one or more halogen substituents. In still another embodiment, the $R^1$ phenyl substituent may be optionally substituted with one or more substituents independently selected from the group consisting of chloro and fluoro. In still another embodiment, the $R^1$ phenyl substituent is substituted with one or more fluoro.

In another embodiment of the compounds of Formula I, $R^2$, $R^{3A}$, $R^{3B}$, $R^4$, $R^6$ and $R^7$ are each hydrogen; $R^1$ is selected from the group consisting of $(C_3-C_7)$-cycloalkyl and phenyl; wherein the $R^1$ $(C_3-C_7)$-cycloalkyl and phenyl substituents may be optionally substituted with one or more substituents independently selected from the group consisting of halogen, $(C_1-C_6)$-alkyl, and halo-$(C_1-C_6)$-alkyl; $R^5$ is selected from the group consisting of —$(CH_2)_m OR^{50}$, —$(CH_2)_m C(O)OR^{50}$, and —$(CH_2)_m C(O)NR^{51}R^{52}$; wherein m is 0, 1, 2, 3, 4, 5, or 6; $R^{50}$ is selected from the group consisting of hydrogen and $(C_1-C_6)$-alkyl; $R^{51}$ and $R^{52}$ are independently selected from the group consisting of hydrogen and $(C_1-C_6)$-alkyl; or $R^{51}$ and $R^{52}$ together with the nitrogen to which they are attached form a five- or six-membered ring heterocyclyl; wherein the $R^{50}$, $R^{51}$ and $R^{52}$ $(C_1-C_6)$-alkyl substituents and the $R^{51}/R^{52}$ heterocyclyl substituent may be independently and optionally substituted with one or more substituents selected from the group consisting of halogen, pyrrolidinyl, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_p R^{53}$, and —$S(O)_p NR^{54}R^{55}$; p is 0, 1 or 2; $R^{53}$ is selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; $R^{54}$ and $R^{55}$ are independently selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; or $R^{54}$ and $R^{55}$ together with the nitrogen to which they are attached form a five- or six-membered ring heterocyclyl; and $R^{56}$ is selected from the group consisting of hydrogen and $(C_1-C_6)$-alkyl; and $R^8$ is phenyl; wherein the $R^8$ phenyl substituent is substituted with one or more cyano substituents and, optionally, may be further substituted with one or more substituents independently selected from the group consisting of halogen, hydroxy, carboxy, $(C_1-C_6)$-alkyl, halo-$(C_1-C_6)$-alkyl, cyano-$(C_1-C_6)$-alkyl, hydroxy-$(C_1-C_6)$-alkyl, carboxy-$(C_1-C_6)$-alkyl, $(C_1-C_6)$-alkoxy, halo-$(C_1-C_6)$-alkoxy, cyano-$(C_1-C_6)$-alkoxy, amino, $(C_1-C_6)$-alkylamino, di-$(C_1-C_6)$-alkylamino, and $(C_1-C_6)$-alkoxycarbonyl. In still another embodiment, the $R^8$ phenyl substituent is substituted with one or more cyano substituents and, optionally, may be further substituted with one or more substituents independently selected from the group consisting of halogen, $(C_1-C_6)$-alkyl and $(C_1-C_6)$-alkoxy. In still another embodiment, the $R^8$ phenyl substituent is substituted with one or more cyano substituents and, optionally, may be further substituted with one or more halogen substituents. In still another embodiment, the $R^8$ phenyl substituent is substituted with one or more cyano substituents and, optionally, may be further substituted with one or more substituents independently selected from the group consisting of chloro and fluoro. In still another embodiment, the $R^8$ phenyl substituent is substituted with one or more cyano substituents and, optionally, may be further substituted with one or more chloro. In still another embodiment, the $R^8$ phenyl substituent is substituted with one or more cyano substituents and, optionally, may be further substituted with one or more $(C_1-C_6)$-alkyl substituents. In still another embodiment, the $R^8$ phenyl substituent is substituted with one or more cyano substituents and, optionally, may be further substituted with one or more $(C_1-C_4)$-alkyl substituents. In still another embodiment, $R^8$ phenyl substituent is substituted with one or more cyano substituents and, optionally, may be further substituted with one or more methyl substituents.

In another embodiment of the compounds of Formula I, $R^2$, $R^{3A}$, $R^{3B}$, $R^4$, $R^6$ and $R^7$ are each hydrogen; $R^1$ is selected from the group consisting of $(C_3-C_7)$-cycloalkyl and phenyl; wherein the $R^1$ $(C_3-C_7)$-cycloalkyl and phenyl substituents may be optionally substituted with one or more substituents independently selected from the group consisting of halogen, $(C_1-C_6)$-alkyl, and halo-$(C_1-C_6)$-alkyl; $R^5$ is —$(CH_2)_mC(O)OR^{50}$; wherein m is 0, 1, 2, 3, 4, 5, or 6; $R^{50}$ is selected from the group consisting of hydrogen and $(C_1-C_6)$-alkyl; wherein the $R^{50}$ $(C_1-C_6)$-alkyl substituent may be independently and optionally substituted with one or more substituents selected from the group consisting of —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_pR^{53}$, and —$S(O)_pNR^{54}R^{55}$; p is 0, 1 or 2; $R^{53}$ is selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; $R^{54}$ and $R^{55}$ are independently selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; or $R^{54}$ and $R^{55}$ together with the nitrogen to which they are attached form a five- or six-membered ring heterocyclyl; and $R^{56}$ is selected from the group consisting of hydrogen and $(C_1-C_6)$-alkyl; and $R^8$ is selected from the group consisting of phenyl and pyridinyl; wherein the $R^8$ phenyl and pyridinyl substituents may be optionally substituted with one or more substituents independently selected from the group consisting of halogen, cyano, hydroxy, carboxy, $(C_1-C_6)$-alkyl, halo-$(C_1-C_6)$-alkyl, cyano-$(C_1-C_6)$-alkyl, hydroxy-$(C_1-C_6)$-alkyl, carboxy-$(C_1-C_6)$-alkyl, $(C_1-C_6)$-alkoxy, halo-$(C_1-C_6)$-alkoxy, cyano-$(C_1-C_6)$-alkoxy, amino, $(C_1-C_6)$-alkylamino, di-$(C_1-C_6)$-alkylamino, and —$(C_1-C_6)$-alkoxycarbonyl. In still another embodiment, m is 0. In still another embodiment, $R^{50}$ is hydrogen. In still another embodiment, m is 0, and $R^{50}$ is hydrogen.

In another embodiment of the compounds of Formula I, $R^2$, $R^{3A}$, $R^{3B}$, $R^4$, $R^6$ and $R^7$ are each hydrogen; $R^1$ is selected from the group consisting of $(C_3-C_7)$-cycloalkyl and phenyl; wherein the $R^1$ $(C_3-C_7)$-cycloalkyl and phenyl substituents may be optionally substituted with one or more substituents independently selected from the group consisting of halogen, $(C_1-C_6)$-alkyl, and halo-$(C_1-C_6)$-alkyl; $R^5$ is —$(CH_2)_mC(O)NR^{51}R^{52}$; wherein m is 0, 1, 2, 3, 4, 5, or 6; $R^{51}$ and $R^{52}$ are independently selected from the group consisting of hydrogen and $(C_1-C_6)$-alkyl; or $R^{51}$ and $R^{52}$ together with the nitrogen to which they are attached form a five- or six-membered ring heterocyclyl; wherein the $R^{51}$ and $R^{52}$ $(C_1-C_6)$-alkyl substituents and the $R^{51}/R^{52}$ heterocyclyl substituent may be independently and optionally substituted with one or more substituents selected from the group consisting of halogen, pyrrolidinyl, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_pR^{53}$, and —$S(O)_pNR^{54}R^{55}$; p is 0, 1 or 2; $R^{53}$ is selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; $R^{54}$ and $R^{55}$ are independently selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; or $R^{54}$ and $R^{55}$ together with the nitrogen to which they are attached form a five- or six-membered ring heterocyclyl; and $R^{56}$ is selected from the group consisting of hydrogen and $(C_1-C_6)$-alkyl; and $R^8$ is selected from the group consisting of phenyl and pyridinyl; wherein the $R^8$ phenyl and pyridinyl substituents may be optionally substituted with one or more substituents independently selected from the group consisting of halogen, cyano, hydroxy, carboxy, $(C_1-C_6)$-alkyl, halo-$(C_1-C_6)$-alkyl, cyano-$(C_1-C_6)$-alkyl, hydroxy-$(C_1-C_6)$-alkyl, carboxy-$(C_1-C_6)$-alkyl, $(C_1-C_6)$-alkoxy, halo-$(C_1-C_6)$-alkoxy, cyano-$(C_1-C_6)$-alkoxy, amino, $(C_1-C_6)$-alkylamino, di-$(C_1-C_6)$-alkylamino, and —$(C_1-C_6)$-alkoxycarbonyl. In still another embodiment, m is 0. In still another embodiment, $R^{50}$ is hydrogen. In still another embodiment, m is 0; and $R^{51}$ and $R^{52}$ are independently selected from the group consisting of hydrogen and $(C_1-C_6)$-alkyl. In still another embodiment, m is 0; and $R^{51}$ and $R^{52}$ are independently selected from the group consisting of hydrogen and $(C_1-C_6)$-alkyl; wherein the $R^{51}$ and $R^{52}$ $(C_1-C_6)$-alkyl substituents may be independently and optionally substituted with one or more substituents selected from the group consisting of —$OR^{53}$ and —$S(O)_pR^{53}$; p is 0, 1 or 2; and $R^{53}$ is selected from the group consisting of hydrogen and $(C_1-C_6)$-alkyl.

In another embodiment of the compounds of Formula I, $R^2$, $R^{3A}$, $R^{3B}$, $R^4$, $R^6$ and $R^7$ are each hydrogen; $R^1$ is selected from the group consisting of cyclopentyl and phenyl; wherein the $R^1$ cyclopentyl and phenyl substituents may be optionally substituted with one or more substituents independently selected from the group consisting of halogen, $(C_1-C_6)$-alkyl, and halo-$(C_1-C_6)$-alkyl; $R^5$ is selected from the group consisting of —$(CH_2)_mOR^{50}$, —$(CH_2)_mC(O)OR^{50}$, and —$(CH_2)_mC(O)NR^{51}R^{52}$; wherein m is 0, 1, 2, or 3; $R^{50}$ is selected from the group consisting of hydrogen and $(C_1-C_6)$-alkyl; $R^{51}$ and $R^{52}$ are independently selected from the group consisting of hydrogen and $(C_1-C_6)$-alkyl; wherein the $R^{50}$, $R^{51}$ and $R^{52}$ $(C_1-C_6)$-alkyl substituents may be independently and optionally substituted with one or more substituents selected from the group consisting of halogen, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_pR^{53}$, and —$S(O)_pNR^{54}R^{55}$; p is 0, 1 or 2; $R^{53}$ is selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; $R^{54}$ and $R^{55}$ are independently selected from the group consisting of hydrogen, $(C_1-C_6)$-alkyl, halo-$(C_1-C_6)$-alkyl, hydroxy-$(C_1-C_6)$-alkyl, and carboxy-$(C_1-C_6)$-alkyl; and $R^{56}$ is selected from the group consisting of hydrogen and $(C_1-C_6)$-alkyl; and $R^8$ is selected from the group consisting of phenyl and pyridinyl; wherein the $R^8$ phenyl and pyridinyl substituents may be optionally substituted with one or more substituents independently selected from the group consisting of halogen, cyano, hydroxy, carboxy, $(C_1-C_6)$-alkyl, halo-$(C_1-C_6)$-alkyl, cyano-$(C_1-C_6)$-alkyl, hydroxy-$(C_1-C_6)$-alkyl, carboxy-$(C_1-C_6)$-alkyl, $(C_1-C_6)$-alkoxy, halo-$(C_1-C_6)$-alkoxy, cyano-$(C_1-C_6)$-alkoxy, amino, $(C_1-C_6)$-alkylamino, di-$(C_1-C_6)$-alkylamino, and —($C_1$-$C_6$)-alkoxycarbonyl. In still another embodiment, X is —$CH_2$—. In still another embodiment, X is —O—.

In another embodiment of the compounds of Formula I, $R^2$, $R^{3A}$, $R^{3B}$, $R^4$, $R^6$ and $R^7$ are each hydrogen; $R^1$ is selected from the group consisting of cyclopentyl and phenyl; wherein the $R^1$ cyclopentyl and phenyl substituents may be optionally substituted with one or more substituents independently selected from the group consisting of halogen, ($C_1$-$C_6$)-alkyl, and halo-($C_1$-$C_6$)-alkyl; $R^5$ is selected from the group consisting of —$(CH_2)_m OR^{50}$, —$(CH_2)_m C(O)OR^{50}$, and —$(CH_2)_m C(O)NR^{51}R^{52}$; wherein m is 0, 1, 2, or 3; $R^{50}$ is selected from the group consisting of hydrogen and ($C_1$-$C_6$)-alkyl; $R^{51}$ and $R^{52}$ are independently selected from the group consisting of hydrogen and ($C_1$-$C_6$)-alkyl; wherein the $R^{50}$, $R^{51}$ and $R^{52}$ ($C_1$-$C_6$)-alkyl substituents may be independently and optionally substituted with one or more substituents selected from the group consisting of halogen, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_p R^{53}$, and —$S(O)_p NR^{54}R^{55}$; p is 0, 1 or 2; $R^{53}$ is selected from the group consisting of hydrogen, ($C_1$-$C_6$)-alkyl, halo-($C_1$-$C_6$)-alkyl, hydroxy-($C_1$-$C_6$)-alkyl, and carboxy-($C_1$-$C_6$)-alkyl; $R^{54}$ and $R^{55}$ are independently selected from the group consisting of hydrogen, ($C_1$-$C_6$)-alkyl, halo-($C_1$-$C_6$)-alkyl, hydroxy-($C_1$-$C_6$)-alkyl, and carboxy-($C_1$-$C_6$)-alkyl; and $R^{56}$ is selected from the group consisting of hydrogen and ($C_1$-$C_6$)-alkyl; and $R^8$ is selected from the group consisting of phenyl and pyridinyl; wherein the $R^8$ phenyl and pyridinyl substituents may be optionally substituted with one or more substituents independently selected from the group consisting of halogen, cyano, hydroxy, carboxy, ($C_1$-$C_6$)-alkyl, halo-($C_1$-$C_6$)-alkyl, cyano-($C_1$-$C_6$)-alkyl, hydroxy-($C_1$-$C_6$)-alkyl, carboxy-($C_1$-$C_6$)-alkyl, ($C_1$-$C_6$)-alkoxy, halo-($C_1$-$C_6$)-alkoxy, cyano-($C_1$-$C_6$)-alkoxy, amino, ($C_1$-$C_6$)-alkylamino, di-($C_1$-$C_6$)-alkylamino, and —($C_1$-$C_6$)-alkoxycarbonyl. In still another embodiment, X is —$CH_2$—. In still another embodiment, X is —. In still another embodiment, $R^1$ is cyclopentyl; wherein the $R^1$ cyclopentyl substituent may be optionally substituted with one or more substituents independently selected from the group consisting of halogen, ($C_1$-$C_4$)-alkyl, and halo-($C_1$-$C_4$)-alkyl. In still another embodiment, $R^1$ is phenyl; wherein the $R^1$ phenyl substituent may be optionally substituted with one or more substituents independently selected from the group consisting of halogen, ($C_1$-$C_4$)-alkyl, and halo-($C_1$-$C_4$)-alkyl. In still another embodiment, $R^5$ is —$(CH_2)_m C(O)OR^{50}$; m is 0; and $R^{50}$ is selected from the group consisting of hydrogen and alkyl. In still another embodiment, $R^5$ is —$(CH_2)_m C(O)OR^{50}$; m is 0; and $R^{50}$ is hydrogen. In still another embodiment, $R^8$ is phenyl; wherein the $R^8$ phenyl substituent may be optionally substituted with one or more substituents independently selected from the group consisting of halogen, cyano, hydroxy, carboxy, ($C_1$-$C_6$)-alkyl, halo-($C_1$-$C_6$)-alkyl, cyano-($C_1$-$C_6$)-alkyl, hydroxy-($C_1$-$C_6$)-alkyl, carboxy-($C_1$-$C_6$)-alkyl, ($C_1$-$C_6$)-alkoxy, halo-($C_1$-$C_6$)-alkoxy, cyano-($C_1$-$C_6$)-alkoxy, amino, ($C_1$-$C_6$)-alkylamino, di-($C_1$-$C_6$)-alkylamino, and —($C_1$-$C_6$)-alkoxycarbonyl. In still another embodiment, $R^8$ is pyridinyl; wherein the $R^8$ pyridinyl substituent may be optionally substituted with one or more substituents independently selected from the group consisting of halogen, cyano, hydroxy, carboxy, ($C_1$-$C_6$)-alkyl, halo-($C_1$-$C_6$)-alkyl, cyano-($C_1$-$C_6$)-alkyl, hydroxy-($C_1$-$C_6$)-alkyl, carboxy-($C_1$-$C_6$)-alkyl, ($C_1$-$C_6$)-alkoxy, halo-($C_1$-$C_6$)-alkoxy, cyano-($C_1$-$C_6$)-alkoxy, amino, ($C_1$-$C_6$)-alkylamino, di-($C_1$-$C_6$)-alkylamino, and —($C_1$-$C_6$)-alkoxycarbonyl.

In another embodiment of the compounds of Formula I, $R^2$, $R^{3A}$, $R^{3B}$, $R^4$, $R^6$ and $R^7$ are each hydrogen; $R^1$ is selected from the group consisting of cyclopentyl and phenyl; wherein the $R^1$ cyclopentyl and phenyl substituents may be optionally substituted with one or more substituents independently selected from the group consisting of halogen, ($C_1$-$C_6$)-alkyl, and halo-($C_1$-$C_6$)-alkyl; $R^5$ is —$(CH_2)_m C(O)OR^{50}$; wherein m is 0, 1, 2, or 3; $R^{50}$ is selected from the group consisting of hydrogen and ($C_1$-$C_6$)-alkyl; wherein the $R^{50}$ ($C_1$-$C_6$)-alkyl substituent may be independently and optionally substituted with one or more substituents selected from the group consisting of halogen, —$OR^{53}$, —$C(O)R^{53}$, —$C(O)OR^{53}$, —$C(O)NR^{54}R^{55}$, —$NR^{54}R^{55}$, —$N(R^{56})C(O)R^{53}$; —$S(O)_p R^{53}$, and —$S(O)_p NR^{54}R^{55}$; p is 0, 1 or 2; $R^{53}$ is selected from the group consisting of hydrogen, ($C_1$-$C_6$)-alkyl, halo-($C_1$-$C_6$)-alkyl, hydroxy-($C_1$-$C_6$)-alkyl, and carboxy-($C_1$-$C_6$)-alkyl; $R^{54}$ and $R^{55}$ are independently selected from the group consisting of hydrogen, ($C_1$-$C_6$)-alkyl, halo-($C_1$-$C_6$)-alkyl, hydroxy-($C_1$-$C_6$)-alkyl, and carboxy-($C_1$-$C_6$)-alkyl; and $R^{56}$ is selected from the group consisting of hydrogen and ($C_1$-$C_6$)-alkyl; and $R^8$ is selected from the group consisting of phenyl and pyridinyl; wherein the $R^5$ phenyl and pyridinyl substituents may be optionally substituted with one or more substituents independently selected from the group consisting of halogen, cyano, hydroxy, carboxy, ($C_1$-$C_6$)-alkyl, halo-($C_1$-$C_6$)-alkyl, cyano-($C_1$-$C_6$)-alkyl, hydroxy-($C_1$-$C_6$)-alkyl, carboxy-($C_1$-$C_6$)-alkyl, ($C_1$-$C_6$)-alkoxy, halo-($C_1$-$C_6$)-alkoxy, cyano-($C_1$-$C_6$)-alkoxy, amino, ($C_1$-$C_6$)-alkylamino, and di-($C_1$-$C_6$)-alkylamino. In still another embodiment, X is —$CH_2$—. In still another embodiment, X is —O—. In still another embodiment, $R^1$ is cyclopentyl; wherein the $R^1$ cyclopentyl substituent may be optionally substituted with one or more substituents independently selected from the group consisting of halogen, ($C_1$-$C_4$)-alkyl, and halo-($C_1$-$C_4$)-alkyl. In still another embodiment, $R^1$ is phenyl; wherein the $R^1$ phenyl substituent may be optionally substituted with one or more substituents independently selected from the group consisting of halogen, ($C_1$-$C_4$)-alkyl, and halo-($C_1$-$C_4$)-alkyl. In still another embodiment, $R^5$ is —$(CH_2)_m C(O)OR^{50}$; m is 0; and $R^{50}$ is selected from the group consisting of hydrogen and ($C_1$-$C_6$)-alkyl. In still another embodiment, $R^5$ is —$(CH_2)_m C(O)OR^{50}$; m is 0; and $R^{50}$ is hydrogen. In still another embodiment, $R^8$ is phenyl; wherein the $R^8$ phenyl substituent may be optionally substituted with one or more substituents independently selected from the group consisting of halogen, cyano, hydroxy, carboxy, ($C_1$-$C_6$)-alkyl, halo-($C_1$-$C_6$)-alkyl, cyano-($C_1$-$C_6$)-alkyl, hydroxy-($C_1$-$C_6$)-alkyl, carboxy-($C_1$-$C_6$)-alkyl, ($C_1$-$C_6$)-alkoxy, halo-($C_1$-$C_6$)-alkoxy, cyano-($C_1$-$C_6$)-alkoxy, amino, ($C_1$-$C_6$)-alkylamino and di-($C_1$-$C_6$)-alkylamino. In still another embodiment, $R^8$ is pyridinyl; wherein the $R^8$ pyridinyl substituent may be optionally substituted with one or more substituents independently selected from the group consisting of halogen, cyano, hydroxy, carboxy, ($C_1$-$C_6$)-alkyl, halo-($C_1$-$C_6$)-alkyl, cyano-($C_1$-$C_6$)-alkyl, hydroxy-($C_1$-$C_6$)-alkyl, carboxy-($C_1$-$C_6$)-alkyl, ($C_1$-$C_6$)-alkoxy, halo-($C_1$-$C_6$)-alkoxy, cyano-($C_1$-$C_6$)-alkoxy, amino, ($C_1$-$C_6$)-alkylamino and di-($C_1$-$C_6$)-alkylamino.

In another embodiment of the compounds of Formula I, $R^2$, $R^{3A}$, $R^{3B}$, $R^4$, $R^6$ and $R^7$ are each hydrogen; $R^1$ is selected from the group consisting of cyclopentyl and phenyl; wherein the $R^1$ cyclopentyl and phenyl substituents may be optionally substituted with one or more substituents independently selected from the group consisting of halogen, ($C_1$-$C_4$)-alkyl, and halo-($C_1$-$C_4$)-alkyl; $R^5$ is —$(CH_2)_m C(O)OR^{50}$; wherein m is 0, 1, or 2; $R^{50}$ is selected from the group consisting of hydrogen and ($C_1$-$C_4$)-alkyl; wherein the $R^{50}$ ($C_1$-$C_4$)-alkyl substituent may be independently and optionally substituted with one or more substituents selected from the group consisting of halogen, —OR$^{53}$, —C(O)R$^{53}$, and —C(O)OR$^{53}$; R$^{53}$ is selected from the group consisting of hydrogen and (C$_1$-C$_4$)-alkyl; and R$^8$ is selected from the group consisting of phenyl and pyridinyl; wherein the R$^8$ phenyl and pyridinyl substituents may be optionally substituted with one or more substituents independently selected from the group consisting of halogen, cyano, hydroxy, carboxy, (C$_1$-C$_4$)-alkyl, halo-(C$_1$-C$_4$)-alkyl, cyano-(C$_1$-C$_4$)-alkyl, hydroxy-(C$_1$-C$_4$)-alkyl, and carboxy-(C$_1$-C$_4$)-alkyl. In still another embodiment, X is —CH$_2$—. In still another embodiment, X is —O—. In still another embodiment, R$^1$ is cyclopentyl; wherein the R$^1$ cyclopentyl substituent may be optionally substituted with one or more substituents independently selected from the group consisting of halogen, (C$_1$-C$_4$)-alkyl, and halo-(C$_1$-C$_4$)-alkyl. In still another embodiment, R$^1$ is phenyl; wherein the R$^1$ phenyl substituent may be optionally substituted with one or more substituents independently selected from the group consisting of halogen, (C$_1$-C$_4$)-alkyl, and halo-(C$_1$-C$_4$)-alkyl. In still another embodiment, R$^5$ is —(CH$_2$)$_m$C(O)OR$^{50}$; m is 0; and R$^{50}$ is selected from the group consisting of hydrogen and (C$_1$-C$_4$)-alkyl. In still another embodiment, R$^5$ is —(CH$_2$)$_m$C(O)OR$^{50}$; m is 0; and R$^{50}$ is hydrogen. In still another embodiment, R$^8$ is phenyl; wherein the R$^8$ phenyl substituent may be optionally substituted with one or more substituents independently selected from the group consisting of halogen, cyano, hydroxy, carboxy, (C$_1$-C$_4$)-alkyl, halo-(C$_1$-C$_4$)-alkyl, cyano-(C$_1$-C$_4$)-alkyl, hydroxy-(C$_1$-C$_4$)-alkyl and carboxy-(C$_1$-C$_4$)-alkyl. In still another embodiment, R$^8$ is pyridinyl; wherein the R$^8$ pyridinyl substituent may be optionally substituted with one or more substituents independently selected from the group consisting of halogen, cyano, hydroxy, carboxy, (C$_1$-C$_4$)-alkyl, halo-(C$_1$-C$_4$)-alkyl, cyano-(C$_1$-C$_4$)-alkyl, hydroxy-(C$_1$-C$_4$)-alkyl and carboxy-(C$_1$-C$_4$)-alkyl.

The present invention is also directed to a subclass of compounds (including pharmaceutically acceptable salts and tautomers of the compounds), wherein the compounds have the structure of Formula II:

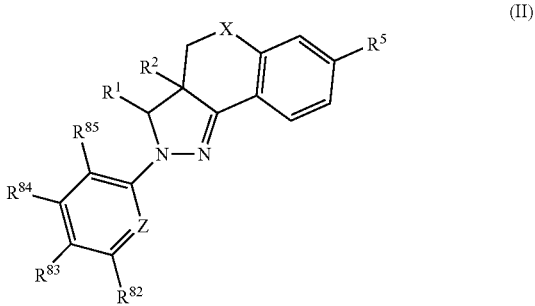

(II)

wherein:

X is selected from the group consisting of —CH$_2$— and —O—;

Z is selected from the group consisting of —C(R$^{81}$)— and —N—;

R$^1$ is selected from the group consisting of cyclopentyl and phenyl; wherein the R$^1$ cyclopentyl and phenyl substituents may be optionally substituted with one or more substituents independently selected from the group consisting of chloro, fluoro, methyl, ethyl, propyl, chloromethyl, dichloromethyl, trichloromethyl, fluoromethyl, difluoromethyl and trifluoromethyl;

R$^2$ is selected from the group consisting of hydrogen or (C$_1$-C$_4$)-alkyl;

R$^5$ is selected from the group consisting of —(CH$_2$)$_m$OR$^{50}$, —(CH$_2$)$_m$C(O)OR$^{50}$, and —(CH$_2$)$_m$C(O)NR$^{51}$R$^{52}$; wherein:

m is 0, 1, 2, or 3;

R$^{50}$ is selected from the group consisting of hydrogen and (C$_1$-C$_6$)-alkyl;

R$^{51}$ and R$^{52}$ are independently selected from the group consisting of hydrogen and (C$_1$-C$_6$)-alkyl; wherein the R$^{50}$, R$^{51}$ and R$^{52}$ (C$_1$-C$_6$)-alkyl substituents may be independently and optionally substituted with one or more substituents selected from the group consisting of halogen, —OR$^{53}$, —C(O)R$^{53}$, —C(O)OR$^{53}$, —C(O)NR$^{54}$R$^{55}$, —NR$^{54}$R$^{55}$, —N(R$^{56}$)C(O)R$^{53}$; —S(O)$_p$R$^{53}$, and —S(O)$_p$NR$^{54}$R$^{55}$;

p is 0, 1 or 2;

R$^{53}$ is selected from the group consisting of hydrogen, (C$_1$-C$_6$)-alkyl, halo-(C$_1$-C$_6$)-alkyl, hydroxy-(C$_1$-C$_6$)-alkyl, and carboxy-(C$_1$-C$_6$)-alkyl;

R$^{54}$ and R$^{55}$ are independently selected from the group consisting of hydrogen, (C$_1$-C$_6$)-alkyl, halo-(C$_1$-C$_6$)-alkyl, hydroxy-(C$_1$-C$_6$)-alkyl, and carboxy-(C$_1$-C$_6$)-alkyl; and R$^{81}$, R$^{82}$, R$^{83}$, R$^{84}$, and R$^{85}$ are independently selected from the group consisting of hydrogen, chloro, fluoro, cyano, hydroxy, carboxy, methyl, ethyl, trichloromethyl, trifluoromethyl, cyanomethyl, hydroxymethyl, carboxymethyl, methoxy, amino, methylamino, and dimethylamino.

In one embodiment of the compounds of Formula II, R$^2$ is methyl.

In another embodiment of the compounds of Formula II, R$^2$ is hydrogen.

In another embodiment of the compounds of Formula II, R$^2$ is hydrogen; R$^5$ is —(CH$_2$)$_m$C(O)OR$^{50}$; wherein m is 0, 1, 2, or 3; R$^{50}$ is selected from the group consisting of hydrogen and (C$_1$-C$_6$)-alkyl; wherein the R$^{50}$ (C$_1$-C$_6$)-alkyl substituent may be independently and optionally substituted with one or more substituents selected from the group consisting of halogen, —OR$^{53}$, —C(O)R$^{53}$, —C(O)OR$^{53}$, —C(O)NR$^{54}$R$^{55}$, —NR$^{54}$R$^{55}$, —N(R$^{56}$)C(O)R$^{53}$; —S(O)$_p$R$^{53}$, and —S(O)$_p$NR$^{54}$R$^{55}$; p is 0, 1 or 2; R$^{53}$ is selected from the group consisting of hydrogen, (C$_1$-C$_6$)-alkyl, halo-(C$_1$-C$_6$)-alkyl, hydroxy-(C$_1$-C$_6$)-alkyl, and carboxy-(C$_1$-C$_6$)-alkyl; and R$^{54}$ and R$^{55}$ are independently selected from the group consisting of hydrogen, (C$_1$-C$_6$)-alkyl, halo-(C$_1$-C$_6$)-alkyl, hydroxy-(C$_1$-C$_6$)-alkyl, and carboxy-(C$_1$-C$_6$)-alkyl.

In another embodiment of the compounds of Formula II, R$^2$ is hydrogen; R$^5$ is —(CH$_2$)$_m$C(O)OR$^{50}$; wherein m is 0, 1, or 2; R$^{50}$ is selected from the group consisting of hydrogen and (C$_1$-C$_4$)-alkyl; wherein the R$^{50}$ (C$_1$-C$_4$)-alkyl substituent may be independently and optionally substituted with one or more substituents selected from the group consisting of halogen, —OR$^{53}$, —C(O)R$^{53}$, and —C(O)OR$^{53}$; and R$^{53}$ is selected from the group consisting of hydrogen and (C$_1$-C$_4$)-alkyl.

In another embodiment of the compounds of Formula II, R$^2$ is hydrogen; Z is selected from the group consisting of —C(R$^{81}$)— and —N—; R$^1$ is selected from the group consisting of cyclopentyl and phenyl; wherein the R$^1$ cyclopentyl and phenyl substituents may be optionally substituted with one or more substituents independently selected from the group consisting of chloro, fluoro, methyl, and trifluoromethyl; R$^5$ is —(CH$_2$)$_m$C(O)OR$^{50}$; wherein m is 0, 1, or 2; R$^{50}$ is selected from the group consisting of hydrogen and (C$_1$-C$_4$)-alkyl; wherein the R$^{50}$ (C$_1$-C$_4$)-alkyl substituent may be independently and optionally substituted with one or more substituents selected from the group consisting of halogen, —OR$^{53}$, —C(O)R$^{53}$, and —C(O)OR$^{53}$; and R$^{53}$ is selected from the group consisting of hydrogen and (C$_1$-C$_4$)-alkyl; and $R^{81}$, $R^{82}$, $R^{83}$, $R^{84}$, and $R^{85}$ are independently selected from the group consisting of hydrogen, chloro, fluoro, cyano, hydroxy, carboxy, methyl, ethyl, cyanomethyl, hydroxymethyl, carboxymethyl, methoxy, amino, methylamino, and dimethylamino.

In another embodiment of the compounds of Formula II, $R^2$ is hydrogen; Z is selected from the group consisting of —C($R^{81}$)— and —N—; $R^1$ is selected from the group consisting of cyclopentyl and phenyl; wherein the $R^1$ cyclopentyl and phenyl substituents may be optionally substituted with fluoro; $R^1$ is —(CH$_2$)$_m$C(O)OR$^{50}$; wherein m is 0; $R^{50}$ is selected from the group consisting of hydrogen and (C$_1$-C$_4$)-alkyl; and $R^{81}$ and $R^{85}$ are each hydrogen; and $R^{82}$, $R^{83}$, and $R^{84}$ are independently selected from the group consisting of chloro, cyano, and methyl.

In another embodiment of the compounds of Formula II, $R^2$ is hydrogen; X is —CH$_2$—; Z is —C($R^{81}$)—; $R^1$ is selected from the group consisting of cyclopentyl and phenyl; wherein the $R^1$ phenyl substituent may be optionally substituted with fluoro; $R^5$ is —(CH$_2$)$_m$C(O)OR$^{50}$; wherein m is 0; $R^{50}$ is hydrogen; $R^{81}$, $R^{84}$ and $R^{85}$ are each hydrogen; and $R^{82}$ and $R^{83}$ are independently selected from the group consisting of chloro, cyano, and methyl. In still another embodiment, $R^{82}$ is selected from the group consisting of chloro and methyl; and $R^{83}$ is cyano. In still another embodiment, $R^{82}$ is chloro and $R^{83}$ is cyano. In still another embodiment, $R^1$ is cyclopentyl. In still another embodiment, $R^1$ is phenyl; wherein the $R^1$ phenyl substituent may be optionally substituted with fluoro. In still another embodiment, $R^1$ is phenyl; wherein the $R^1$ phenyl substituent may be optionally substituted with fluoro at the para position.

In another embodiment of the compounds of Formula II, $R^2$ is hydrogen; X is —O—; Z is —C($R^{81}$)—; $R^1$ is selected from the group consisting of cyclopentyl and phenyl; wherein the $R^1$ phenyl substituent may be optionally substituted with fluoro; $R^5$ is —(CH$_2$)$_m$C(O)OR$^{50}$; wherein m is 0; $R^{50}$ is hydrogen; $R^{81}$, $R^{84}$ and $R^{85}$ are each hydrogen; and $R^{82}$ and $R^{83}$ are independently selected from the group consisting of chloro, cyano, and methyl. In still another embodiment, $R^{82}$ is selected from the group consisting of chloro and methyl; and $R^{83}$ is cyano. In still another embodiment, $R^{82}$ is chloro and $R^{83}$ is cyano. In still another embodiment, $R^1$ is cyclopentyl. In still another embodiment, $R^1$ is phenyl; wherein the $R^1$ phenyl substituent may be optionally substituted with fluoro. In still another embodiment, $R^1$ is phenyl; wherein the $R^1$ phenyl substituent may be optionally substituted with fluoro at the para position.

In another embodiment of the compounds of Formula II, $R^2$ is hydrogen; X is —CH$_2$—; Z is —N—; $R^1$ is selected from the group consisting of cyclopentyl and phenyl; wherein the $R^1$ phenyl substituent may be optionally substituted with fluoro; $R^5$ is —(CH$_2$)$_m$C(O)OR$^{50}$; wherein m is 0; $R^{50}$ is hydrogen; $R^{81}$, $R^{84}$ and $R^{85}$ are each hydrogen; and $R^{82}$ and $R^{83}$ are independently selected from the group consisting of chloro, cyano, and methyl. In still another embodiment, $R^{82}$ is selected from the group consisting of chloro and methyl; and $R^{83}$ is cyano. In still another embodiment, $R^{82}$ is chloro and $R^{83}$ is cyano. In still another embodiment, $R^1$ is cyclopentyl. In still another embodiment, $R^1$ is phenyl; wherein the $R^1$ phenyl substituent may be optionally substituted with fluoro. In still another embodiment, $R^1$ is phenyl; wherein the $R^1$ phenyl substituent may be optionally substituted with fluoro at the para position.

In another embodiment of the compounds of Formula II, $R^2$ is hydrogen; X is —O—; Z is —N—; $R^1$ is selected from the group consisting of cyclopentyl and phenyl; wherein the $R^1$ phenyl substituent may be optionally substituted with fluoro; $R^5$ is —(CH$_2$)$_m$C(O)OR$^{50}$; wherein m is 0; $R^{50}$ is hydrogen; $R^{81}$, $R^{84}$ and $R^{85}$ are each hydrogen; and $R^{82}$ and $R^{83}$ are independently selected from the group consisting of chloro, cyano, and methyl. In still another embodiment, $R^{82}$ is selected from the group consisting of chloro and methyl; and $R^{83}$ is cyano. In still another embodiment, $R^{82}$ is chloro and $R^{83}$ is cyano. In still another embodiment, $R^1$ is cyclopentyl. In still another embodiment, $R^1$ is phenyl; wherein the $R^1$ phenyl substituent may be optionally substituted with fluoro. In still another embodiment, $R^1$ is phenyl; wherein the $R^1$ phenyl substituent may be optionally substituted with fluoro at the para position.

In another embodiment, the compounds of Formula I are selected from the group consisting of:
2-(3-chloro-4-cyanophenyl)-3-(4-fluorophenyl)-3,3a,4,5-tetrahydro-2H-benzo[g]indazole-7-carboxylic acid;
3-(4-fluorophenyl)-7-hydroxy-3,3a,4,5-tetrahydrobenzo[g]indazol-2-yl)-2-methylbenzonitrile;
3-(4-fluorophenyl)-7-hydroxy-3,3a,4,5-tetrahydrobenzo[g]indazol-2-yl)-2-(trifluoromethyl)benzonitrile;
2-chloro-4-(3-(4-fluorophenyl)-7-hydroxy-3,3a,4,5-tetrahydrobenzo[g]indazol-2-yl)benzonitrile;
2-(3-chloro-4-cyanophenyl)-3-(4-fluorophenyl)-N-(2-(methylsulfonyl)ethyl)-3,3a,4,5-tetrahydro-2H-benzo[g]indazole-7-carboxamide; and
2-(3-chloro-4-cyanophenyl)-3-(4-fluorophenyl)-N-(2-(methylsulfonyl)ethyl)-3,3a,4,5-tetrahydro-2H-benzo[g]indazole-7-carboxamide.

In another embodiment, the compounds of Formula I are selected from the group consisting of:
2-(3-chloro-4-cyanophenyl)-3-cyclopentyl-3,3a,4,5-tetrahydro-2H-benzo[g]indazole-7-carboxylic acid;
2-(4-cyanophenyl)-3-cyclopentyl-3,3a,4,5-tetrahydro-2H-benzo[g]indazole-7-carboxylic acid;
2-(4-cyano-3-methylphenyl)-3-cyclopentyl-3,3a,4,5-tetrahydro-2H-benzo[g]indazole-7-carboxylic acid;
2-(5-cyano-6-methylpyridin-2-yl)-3-cyclopentyl-3,3a,4,5-tetrahydro-2H-benzo[g]indazole-7-carboxylic acid;
2-(4-cyano-3-methoxyphenyl)-3-cyclopentyl-3,3a,4,5-tetrahydro-2H-benzo[g]indazole-7-carboxylic acid;
N-(-2-(3-chloro-4-cyanophenyl)-3-cyclopentyl-3,3a,4,5-tetrahydro-2H-benzo[g]indazol-7-yl)acetamide;

In another embodiment, the compounds of Formula I are selected from the group consisting of:
methyl 2-(3-chloro-4-cyanophenyl)-3-cyclopentyl-3,3a,4,5-tetrahydro-2H-benzo[g]indazole-7-carboxylate;
2-(3-chloro-4-cyanophenyl)-3-cyclopentyl-3a-methyl-3,3a,4,5-tetrahydro-2H-benzo[g]indazole-7-carboxylic acid;
2-(3-chloro-4-cyanophenyl)-3-cyclopentyl-N-(2-(methylsulfonyl)ethyl)-3,3a,4,5-tetrahydro-2H-benzo[g]indazole-7-carboxamide;
2-(3-chloro-4-cyanophenyl)-3-cyclopentyl-N-(2-hydroxyethyl)-3,3a,4,5-tetrahydro-2H-benzo[g]indazole-7-carboxamide; and
2-(4-cyano-3-methylphenyl)-3-cyclopentyl-2,3,3a,4-tetrahydrochromeno[4,3-c]pyrazole-7-carboxylic acid.

In another embodiment, the compounds of Formula I are selected from the group consisting of:
2-(3-chloro-4-cyanophenyl)-3-cyclobutyl-3,3a,4,5-tetrahydro-2H-benzo[g]indazole-7-carboxylic acid;
2-(3-chloro-4-cyanophenyl)-3-cyclopentenyl-3,3a,4,5-tetrahydro-2H-benzo[g]indazole-7-carboxylic acid; and
2-(4-cyano-3-methylphenyl)-3-cyclopentenyl-3,3a,4,5-tetrahydro-2H-benzo[g]indazole-7-carboxylic acid.

In another embodiment, the compounds of Formula I are selected from the group consisting of:

2-(3-chloro-4-cyanophenyl)-3-(5-methyl-2-furyl)-3,3a,4,5-tetrahydro-2H-benzo[g]indazole-7-carboxylic acid;

2-(3-chloro-4-cyanophenyl)-3-(3-furyl)-3,3a,4,5-tetrahydro-2H-benzo[g]indazole-7-carboxylic acid;

2-(3-chloro-4-cyanophenyl)-3-(5-methyl-2-furyl)-N-[2-(methylsulfonyl)ethyl]-3,3a,4,5-tetrahydro-2H-benzo[g]indazole-7-carboxamide; and 2-(3-chloro-4-cyanophenyl)-N-[2-(methylsulfonyl)ethyl]-3-(2-methyl-1,3-thiazol-5-yl)-3,3a,4,5-tetrahydro-2H-benzo[g]indazole-7-carboxamide.

In another embodiment, the compounds of Formula I are selected from the group consisting of:

2-(3-chloro-4-cyanophenyl)-3-cyclopentyl-2,3,3a,4-tetrahydrochromeno[4,3-c]pyrazole-7-carboxylic acid;

2-[4-cyano-3-(trifluoromethyl)phenyl]-3-cyclopentyl-2,3,3a,4-tetrahydrochromeno[4,3-c]pyrazole-7-carboxylic acid;

2-(4-cyano-3-methylphenyl)-3-cyclopentenyl-2,3,3a,4-tetrahydrochromeno[4,3-c]pyrazole-7-carboxylic acid; and 2-(3-chloro-4-cyanophenyl)-3-cyclopentenyl-2,3,3a,4-tetrahydrochromeno[4,3-c]pyrazole-7-carboxylic acid.

C. Isomers

The compounds of the present invention can be present as stereoisomers, such as enantiomers and diastereomers. For example, the compounds (including the compounds of Formulae I and II) generally comprise two or more asymmetric carbon atoms and can be present in the form of one or more stereoisomers (e.g., individual enantiomers, diastereomers, and mixtures thereof). More specifically, the compounds of the present invention can be present as the 3R,3aR stereoisomer, the 3S,3aS stereoisomer, the 3S,3aR stereoisomer, the 3R,3aS stereoisomer, or a mixture of two or more of these stereoisomers.

In one embodiment, the compound of Formulae I or II has the 3R,3aR configuration.

In another embodiment, the compound of Formulae I or II has the 3S,3aS configuration.

In another embodiment, the compound of Formulae I or II has the 3S,3aR configuration.

In another embodiment, the compound of Formulae I or II has the 3R,3aS configuration.

In another embodiment, the compound of Formulae I or II is present as a mixture of two or more stereoisomers selected from the group consisting of the 3R,3aR stereoisomer, the 3S,3aS stereoisomer, the 3S,3aR stereoisomer, and the 3R,3aS stereoisomer.

In addition, when a compound of the present invention contains an alkenyl group or moiety, geometric isomers may arise D. Tautomeric Forms The present invention comprises the tautomeric forms of compounds of Formulae I and II. Where structural isomers are interconvertible via a low energy barrier, tautomeric isomerism ('tautomerism') can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

E. Salts

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), an exemplary salt is pharmaceutically acceptable. The term "pharmaceutically acceptable salt" refers to a salt prepared by combining a compound of Formulae I or II with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, e.g. hydrochloric, hydrobromic, hydrofluoric, boric, fluoroboric, phosphoric, metaphosphoric, nitric, carbonic, sulfonic, and sulfuric acids, and organic acids, e.g. acetic, benzenesulfonic, benzoic, citric, malic, ethanesulfonic, fumaric, gluconic, glycolic, isothionic, lactic, lactobionic, maleic, methanesulfonic, trifluoromethanesulfonic, succinic, toluenesulfonic, tartaric, and trifluoroacetic acids.

Suitable organic acids generally include, for example, aliphatic, cycloaliphatic, aromatic, araliphatic, heterocyclylic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In another embodiment, examples of suitable addition salts formed include the acetate, aspartate, benzoate, besylate, bicarbonate/carbonate, bisulphate/sulphate, borate, camsyate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, nitrate, orotate, oxalate, palmitate, pamoate, phosphate/hydrogen phosphate/dihydrogen phosphate, saccharate, stearate, succinate, tartrate, tosylate and trifluoroacetate salts. In another embodiment, representative salts include benzenesulfonate, hydrobromide and hydrochloride.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others. In one embodiment, hemisalts of acids and bases may also be formed, for example, hemisulphate and hemicalcium salts.

F. Prodrugs

Also within the scope of the present invention are so-called "prodrugs" of the compounds of Formulae I and II. Thus, certain derivatives of compounds of any of Formulae I or II which may have little or no pharmacological activity themselves can, when administered into or onto the body, be converted into compounds of any of Formulae I or II having the desired activity, for example, by hydrolytic cleavage. Such derivatives are referred to as "prodrugs."

Further information on the use of prodrugs may be found in "Pro-drugs as Novel Delivery Systems, Vol. 14, ACS Symposium Series (T Higuchi and W Stella) and "Bioreversible Carriers in Drug Design," Pergamon Press, 1987 (ed. E B Roche, American Pharmaceutical Association). Prodrugs in accordance with the invention can, for example, be produced by replacing appropriate functionalities present in the compounds of any of Formulae I or II with certain moieties known to those skilled in the art as "pro-moieties" as described, for example, in "Design of Prodrugs" by hours Bundgaard (Elseview, 1985).

G. Methods of Treatment

The present invention further comprises methods for treating a condition in a subject having or susceptible to having such a condition, by administering to the subject a therapeutically-effective amount of one or more compounds of Formulae I and II as described above. In one embodiment, the treatment is preventative treatment. In another embodiment, the treatment is palliative treatment. In another embodiment, the treatment is restorative treatment.

1. Conditions

The conditions that can be treated in accordance with the present invention include, but are not limited to, cardiovascular conditions, renal conditions, liver conditions, vascular conditions, inflammatory conditions, pain, retinopathy, neuropathy (such as peripheral neuropathy), insulinopathy, edema, endothelial dysfunction, baroreceptor dysfunction and the like.

Cardiovascular conditions include, but are not limited to, hypertension, heart failure (such as congestive heart failure), diastolic dysfunction (such as left ventricular diastolic dysfunction, diastolic heart failure, and impaired diastolic filling), systolic dysfunction (such as systolic heart failure), arrhythmia, ischemia, hypertrophic cardiomyopathy, sudden cardiac death, myocardial and vascular fibrosis, impaired arterial compliance, myocardial necrotic lesions, vascular damage, myocardial infarction, left ventricular hypertrophy, decreased ejection fraction, cardiac lesions, vascular wall hypertrophy, endothelial thickening, fibrinoid necrosis of coronary arteries, stroke, and the like.

Renal conditions include, but are not limited to, glomerulosclerosis, end-stage renal disease, diabetic nephropathy, reduced renal blood flow, increased glomerular filtration fraction, proteinuria, decreased glomerular filtration rate, decreased creatinine clearance, microalbuminuria, renal arteriopathy, ischemic lesions, thrombotic lesions, global fibrinoid necrosis, focal thrombosis of glomerular capillaries, swelling and proliferation of intracapillary (endothelial and mesangial) and/or extracapillary cells (crescents), expansion of reticulated mesangial matrix with or without significant hypercellularity, malignant nephrosclerosis (such as ischemic retraction, thrombonecrosis of capillary tufts, arteriolar fibrinoid necrosis, and thrombotic microangiopathic lesions affecting glomeruli and microvessels), and the like.

Liver conditions include, but are not limited to, liver cirrhosis, liver ascites, hepatic congestion, and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD), and the like.

Pain includes, but is not limited to, acute pain, chronic pain (for example, arthralgia), and the like.

Edema includes, but is not limited to, peripheral tissue edema, hepatic congestion, splenic congestion, liver ascites, respiratory or lung congestion, and the like.

Insulinopathies include, but are not limited to, insulin resistance, Type I diabetes mellitus, Type II diabetes mellitus, glucose sensitivity, pre-diabetic state, syndrome X, and the like.

In one embodiment, the condition is selected from the group consisting of cardiovascular conditions, renal conditions, and liver conditions.

In another embodiment, the condition is a cardiovascular condition.

In another embodiment, the condition is a cardiovascular condition selected from the group consisting of hypertension, heart failure (particularly heart failure post myocardial infarction), left ventricular hypertrophy, and stroke.

In another embodiment, the condition is hypertension.

In another embodiment, the condition is heart failure.

In another embodiment, the condition is left ventricular hypertrophy.

In another embodiment, the condition is stroke.

In another embodiment, the condition is a renal condition.

In another embodiment, the condition is nephropathy.

In another embodiment, the condition is Type II diabetes mellitus.

2. Subjects

Suitable subjects to be treated according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

3. Administration and Dosing

The compounds of the present invention are generally administered in a therapeutically effective amount. In one embodiment, the compounds of the present invention are administered in a mineralocorticoid receptor antagonizing amount.

The compounds of the present invention can be administered by any suitable route in the form of a pharmaceutical composition adapted to such a route, and in a dose effective for the treatment intended. Therapeutically effective doses of the compounds of the present invention required to prevent or arrest the progress of, or to treat the medical condition, are readily ascertained by one of ordinary skill in the art using preclinical and clinical approaches familiar to the medicinal arts.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary based on the specific situation. Dosage levels from about 0.001 mg to about 100 mg of the compound of the present invention per kilogram of body weight per day are useful in the treatment of the above-indicated conditions. In one embodiment, the total daily dose of the compound of the present invention (administered in single or divided doses) is typically from about 0.001 mg/kg to about 20 mg/kg (i.e., mg compound/kg body weight). In another embodiment, the total daily dose of the compound of the present invention is from about 0.005 mg/kg to about 10 mg/kg. In another embodiment, the total daily dose is from about 0.005 mg/kg to about 5 mg/kg. In another embodiment, the total daily dose is from about 0.01 mg/kg to about 1 mg/kg. In another embodiment, the total daily dose is from about 0.8 mg/kg to about 15 mg/kg. In another embodiment, the total daily dose is from about 0.2 mg/kg to about 4 mg/kg. These dosages are based on an average human subject having a weight of about 65 kg to about 75 kg. A physician will readily be able to determine doses for subjects whose weight falls outside of this range, such as infants. The administration of the compound of the present invention can be repeated a plurality of times in a day (typically no greater than 4 times) to achieve the desired daily dose.

For convenience the compounds of the present invention can be administered in a unit dosage form. If desired, multiple doses per day of the unit dosage form can be used to increase the total daily dose. The unit dosage form, for example, may be a tablet or capsule containing about 0.01, 0.05, 0.1, 0.5, 1, 5, 10, 15, 20, 25, 30, 35, 40, 45, 50, 55, 60, 65, 70, 75, 80, 85, 90, 95, 100, 125, 150, 175, 200, 250 or 500 mg of the compound of the present invention. In one embodiment, the unit dosage form contains from about 0.01 mg to about 500 mg of the compound of the present invention. In another embodiment, the unit dosage form contains from about 0.05 mg to about 250 mg of the compound of the present invention. In another embodiment, the unit dosage form contains from about 0.1 mg to about 200 mg of the compound of the present invention. In another embodiment, the unit dosage form contains from about 0.5 mg to about 150 mg of the compound of the present invention.

H. Use in the Preparation of a Medicament

The present invention further comprises use of a compound of Formulae I or II for use as a medicament (such as a unit dosage tablet or unit dosage capsule).

In another embodiment, the present invention comprises the use of a compound of Formulae I or II for the manufacture of a medicament (such as a unit dosage tablet or unit dosage capsule) to treat one or more of the conditions previously identified in the above sections discussing methods of treatment. In one embodiment, the condition is hypertension. In another embodiment the condition is heart failure.

I. Pharmaceutical Compositions

For the treatment of the conditions referred to above, the compounds of Formulae I or II can be administered as the compound per se. Alternatively, pharmaceutically acceptable salts are suitable for medical applications because of their greater aqueous solubility relative to the parent compound. In addition, the compounds of the present invention can be administered in the form of a pharmaceutical composition comprising a compound of Formula I or II, or a pharmaceutically acceptable salt thereof, and a pharmaceutically-acceptable carrier. The carrier can be a solid, a liquid, or both, and may be formulated with the compound as a unit-dose composition, for example, a tablet, which can contain from 0.05% to 95% by weight of the active compounds. Other pharmacologically active substances can also be present.

The active compounds of the present invention may be administered by any suitable route, wherein one exemplary form of a pharmaceutical composition is adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formulae I or II are ordinarily combined with one or more adjuvants. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. In still another embodiment, the present invention comprises a dose form for intranasal administration or administration by inhalation. In still another embodiment, the present invention comprises a rectal dose form.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

J. Combinations and Combination Therapy

The compounds of the present invention can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of Formulae I or II and one or more additional pharmaceutically active compounds. In another embodiment, the present invention comprises a pharmaceutical composition comprising one or more compounds of Formulae I or II, one or more additional pharmaceutically active compounds, and a pharmaceutically acceptable carrier.

In one embodiment, one or more compounds of Formulae I or II may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, one or more compounds of Formulae I or II may be co-administered with a loop diuretic. In still another embodiment, the loop diuretic is selected from furosemide and torsemide. In still another embodiment, one or more compounds of Formulae I or II may be co-administered with furosemide. In still another embodiment, one or more compounds of Formulae I or II may be co-administered with torsemide.

In another embodiment, one or more compounds of Formulae I or II may be co-administered with a thiazide-type diuretic. In still another embodiment, the thiazide-type diuretic is selected from the group consisting of chlorothiazide and hydrochlorothiazide. In still another embodiment, one or more compounds of Formulae I or II may be co-administered with chlorothiazide. In still another embodiment, one or more compounds of Formulae I or II may be co-administered with hydrochlorothiazide.

In another embodiment, one or more compounds of Formulae I or II may be co-administered with a phthalimidine-type diuretic. In still another embodiment, the phthalimidine-type diuretic is chlorthalidone.

In another embodiment, one or more compounds of Formulae I or II may be co-administered with one or more angiotensin converting enzyme inhibitors. Examples of suitable angiotensin converting enzyme inhibitors include quinapril (such as ACCUPRIL™), perindopril (such as ACEON™), captopril (such as CAPOTEN™), enalapril (such as VASOTEC™), ENALAPRILAT™, ramipril (such as ALTACE™), cilazapril, delapril, fosenopril (such as MONOPRIL™), zofenopril, indolapril, benazepril (such as LOTENSIN™), lisinopril (such as PRINIVIL™ and ZESTRIL™), spirapril, trandolapril (such as MAVIK™), perindep, pentopril, moexipril (such as UNIVASC™) fasidotril, S-allymercaptocaptopril, and pivopril.

In another embodiment, one or more compounds of Formulae I or II may be co-administered with one or more angiotensin II receptor blockers. Examples of suitable angiotensin II receptor blockers include candesartan (such as ATACAND™), eprosartan (such as TEVETEN™), irbesartan (such as AVEPRO™), losartan (such as COZAAR™), olmesartan, olmesartan medoxomil (such as BENICAR™), tasosartan, telmisartan (such as MICARDIS™), valsartan (such as DIOVAN™), zolasartan, FI-6828K, RNH-6270, UR-7198, Way-126227, KRH-594, TAK-536, BRA-657, and TA-606.

In another embodiment, one or more compounds of Formulae I or II may be co-administered with one or more calcium channel blockers. Examples of suitable calcium channel blockers include nifedipine (such as ADALAT™, ADALAT CC™ and PROCARDIA™), verapamil (such as CALAN™, COVERA-HS™, ISOPTIN SR™ and VERELAN™), diltiazem (such as CARDIZEM™ CARDIZEM CD™, CARDIZEM LA™, CARDIZEM SR™, DILACOR™, TIAMATE™ and TIAZAC™), isradipine (such as DYNACIRC™ and DYNACIRC CR™), amlodipine (such as NORVASC™), felodipine (such as PLENDIL™), nisoldipine (such as SULAR™), bepridil (such as VASCOR™), nicardipine, vatanidipine, clevidipine, lercanidipine, and NNC-55-0396.

In another embodiment, one or more compounds of Formulae I or II may be co-administered with one or more beta blockers. Examples of suitable beta blockers include timolol (such as BLOCARDEN™), carteolol (such as CARTROL™), carvedilol (such as COREG™), nadolol (such as CORGARD™), propranolol (such as INNOPRAN XL™), betaxolol (such as KERLONE™), penbutolol (such as LEVATOLT4), metoprolol (such as LOPRESSOR™ and TOPROL-XL™), atenolol (such as TENORMIN™), pindolol (such as VISKEN™), acebutolol, and bisoprolol.

In another embodiment, one or more compounds of Formulae I or II may be co-administered with one or more alpha blockers. Examples of suitable alpha blockers include prazosin, doxazosin (such as CARDURA™), phenoxybenzamine (such as DIBENZYLINE™), terazosin (such as HYTRIN™), CDRI-93/478 and CR-2991.

In another embodiment, one or more compounds of Formulae I or II may be co-administered with one or more alpha-beta blockers. An example of a suitable alpha-beta blocker is labetalol (such as NORMODYNE™ or TRANDATE™).

In another embodiment, one or more compounds of Formulae I or II may be co-administered with one or more aldosterone receptor antagonists. Examples of suitable aldosterone receptor antagonists include eplerenone (such as INSPRA™) or spironolactone (such as ALDACTONE™).

In another embodiment, one or more compounds of Formulae I or II may be co-administered with one or more renin inhibitors. Examples of suitable renin inhibitors include aliskiren (SPP 100), SPP-500/600 and YS-004-39.

K. Kits

The present invention further comprises kits that are suitable for use in performing the methods of treatment or prevention described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of Formulae I or II and a diuretic.

In another embodiment, the kit of the present invention comprises one or more compounds of Formulae I or II and an angiotensin converting enzyme inhibitor.

In another embodiment, the kit of the present invention comprises one or more compounds of Formulae I or II and an angiotensin II receptor antagonist.

In another embodiment, the kit of the present invention comprises one or more compounds of Formulae I or II and an aldosterone receptor antagonist.

L. Intermediates

In another embodiment, the invention relates to the novel intermediates useful for preparing the compounds of Formulae I or II.

M. General Synthetic Schemes

The compounds of the present invention can be prepared using the methods illustrated in the general synthetic schemes and experimental procedures detailed below. These general synthetic schemes and experimental procedures are presented for purposes of illustration and are not intended to be limiting. The starting materials used to prepare the compounds of the present invention are commercially available or can be prepared using routine methods known in the art (such as those methods disclosed in COMPENDIUM OF ORGANIC SYNTHETIC METHODS, Vol. I-VI (published by Wiley-Interscience) or other standard reference books).

Scheme 1 below illustrates the general preparation of the pyrazoline compounds of the present invention. Unless otherwise stated, the $R^1$, $R^5$, $R^6$, $R^8$, and X substituents shown in Scheme 1 are defined as in the various embodiments of the invention previously disclosed above.

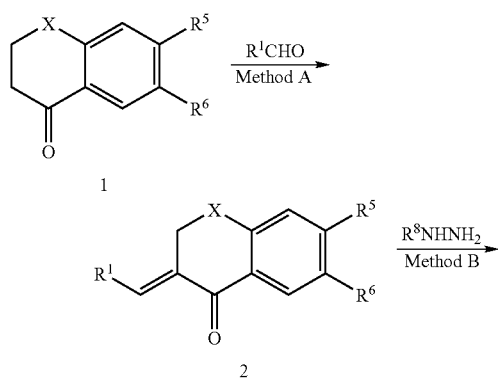

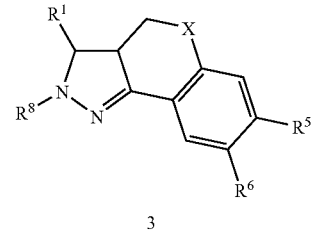

Method A: Preparation of α,β-unsaturated Ketone 2

Method A1

Pyrrolidine (1.2 equivalents), or another cyclic secondary amine base such as piperidine, is added to a mixture of ketone 1 (1 equivalent) and aldehyde $R^1$CHO (2 equivalents) in an alcohol such as methanol (2 mmol ketone 1) at room temperature. About one to six hours later the mixture is cooled to about 0° C. The resulting precipitate is filtered and washed, for example with a cold alcohol such as methanol, to give α,β-unsaturated ketone 2.

Method A2

A mixture of ketone 1 (1.0 equivalent) and aldehyde $R^1$CHO (1.2 equivalents) in concentrated hydrochloric acid and ethanol is refluxed overnight. Alternatively, 4 N hydrogen chloride in dioxane can be used instead of concentrated hydrochloric acid. The refluxed mixture is then diluted with water, filtered, and dried to give α,β-unsaturated ketone 2.

Method A3

A solution of ketone 1 (1 equivalent) in tetrahydrofuran (approximately 2.5 mL/mmol ketone 1) is added dropwise under nitrogen to a 1 M solution of lithium hexamethyldisilazide in tetrahydrofuran (1.05 equivalents) cooled with an ice bath. Once the addition is complete, the resulting mixture is stirred for about 30 minutes. A solution of aldehyde $R^1$CHO (1.05 equivalents) in tetrahydrofuran (approximately 2.5 mmol ketone 1) is added to the mixture which is then allowed to warm to room temperature under stirring. After about two hours, the mixture is quenched with saturated ammonium chloride and extracted with ethyl acetate. The organic layers are dried over sodium sulfate and concentrated. The crude product is purified by silica gel flash chromatography (ethyl acetate/heptanes) or reverse-phase HPLC (acetonitrile/water/0.1% trifluoroacetic acid) to give α,β-unsaturated ketone 2.

Method B: Pyrazoline Condensation

A mixture of α,β-unsaturated ketone 2 (1 mmol), hydrazine ($R^8$NHNH$_2$) hydrochloride (1.2-1.5 mmol), and absolute ethanol (approximately 8 mL/mmol α,β-unsaturated ketone 2) is sparged with argon and stirred at about 80° C. for about 4 to 24 hours. The mixture is cooled to room temperature and filtered. The resulting solids are washed with ethanol to give pyrazoline 3.

Scheme 2 below illustrates the further derivatization of the pyrazoline compounds prepared in accordance with Scheme 1. Unless otherwise stated, the $R^1$, $R^2$, $R^8$, $R^{50}$, $R^{51}$, $R^{52}$ and X substituents shown in Scheme 2 are defined as in the various embodiments of the invention previously disclosed above. Alternatively, pyrazolines 5, 6, 7, and 8 can be obtained using a ketone 1 starting material having the desired $R^5$ and $R^6$ substituents (and protecting and then deprotecting those substituents as needed using conventional protecting chemistry).

SCHEME 2

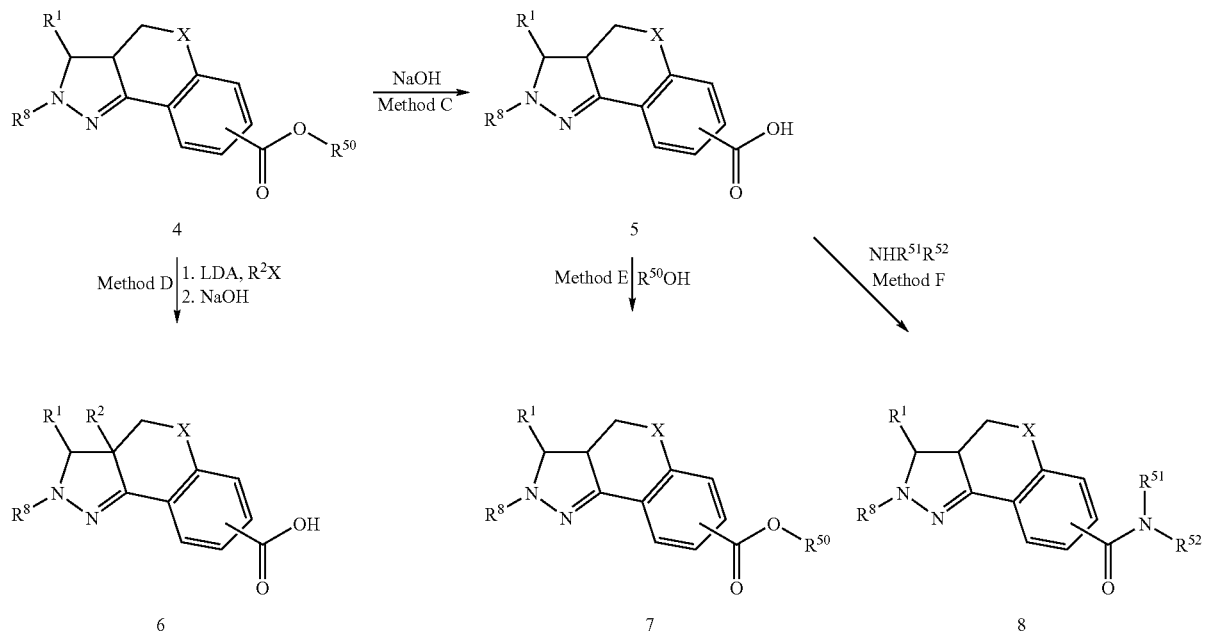

Method C: Pyrazoline Acid Derivatives 2.5 N sodium hydroxide (2 mmol pyrazoline ester 4) is added to a solution of pyrazoline ester 4 (1 equivalent) in tetrahydrofuran (6 mL/mmol pyrazoline ester 4) and methanol (2 mL/mmol pyrazoline ester 4). The resulting mixture is stirred at room temperature until the reaction is complete as determined by HPLC (1 to 24 hours). The mixture is concentrated under a stream of nitrogen to approximately half of its original volume and acidified with aqueous hydrochloric acid to reduce the pH to less than about 4. The mixture is diluted with water and filtered to give the pyrazoline acid 5.

Method D: $R^2$-Substituted Pyrazolines

An $R^2$ substituent can be introduced by treatment of pyrazoline ester 4 with a strong base, such as lithium diisopropylamide (LDA) or lithium hexamethyldisilazide (LHMDS), and an alkylating agent, such as alkyl halide $R^2X$. The alkylated pyrazoline ester can then be hydrolyzed as described in Method C to furnish the alkylated pyrazoline acid 6.

Method E: Pyrazoline Ester Derivatives

N-(3-dimethylaminopropyl)-N'-ethylcarbodiimide hydrochloride (1.2 equivalents) is added under nitrogen to a mixture of pyrazoline acid 5 (1 equivalent), alcohol $R^{50}OH$ (1.2 equiv), and 4-(dimethylamino)-pyridine (1.2 equivalents) in anhydrous tetrahydrofuran (5 mL/200 mg pyrazoline acid 5). The mixture is stirred overnight, treated with excess 1N hydrochloric acid and extracted with ethyl acetate. The organic layer is evaporated. The residue is dissolved in dichloromethane and purified by silica gel chromatography with ethyl acetate/heptanes. The desired fractions are combined and evaporated to give pyrazoline ester 7. If substitution at the $R^2$ position is desired, pyrazoline acid 6 can be used in place of pyrazoline acid 5.

Method F: Pyrazoline Amide Derivatives 2-(1H-benzotriazole-1-yl)-1,1,3,3-tetramethyluronium hexafluorophosphate (1.1 mmol), followed by N,N-diisopropylethylamine (1.5 mmol), are added under nitrogen at room temperature to a solution of pyrazoline acid 5 (1 mmol) in 5 mL of anhydrous dimethylformamide. The mixture is stirred for about five minutes and amine $NHR^{51}R^{52}$ (1.5 mmol) is added. The mixture is stirred for another hour. The mixture is then filtered and purified by reverse-phase HPLC (acetonitrile/water/0.1% trifluoroacetic acid). The fractions containing pure product are combined and lyophilized to give pyrazoline amide 8. If substitution at the $R^2$ position is desired, pyrazoline acid 6 can be used in place of pyrazoline acid 5.

Method G: Chiral Resolution

The pyrazoline compounds of the present invention (including the precursor intermediates) can have two or more chiral centers. Where the synthesis yields a compound as a mixture of enantiomers or diastereomers, the desired enantiomer or diastereomer (or the desired enantiomerically-enriched mixture or diastereomerically-enriched mixture) can be obtained using conventional chiral resolution methods. Conventional methods that can be employed include chromatography (such as HPLC) or supercritical fluid chromatography on an asymmetric resin. Concentration of the luate affords the enriched mixture. The stereoismomerically-enriched pyrazoline can be further derivatized as depicted in Scheme 2 in a manner analogous to that for pyrazolines 5 and 6.

Schemes 3a, 3b, and 3c below illustrate several alternative synthetic schemes that can be used to prepare the $R^8NHNH_2$ hydrazine reagent employed in Scheme 1. Unless otherwise stated, the $R^{81}$, $R^{82}$, $R^{84}$, and $R^{85}$ substituents shown in Scheme 1 are defined as in the various embodiments of the invention previously disclosed above, and Ar represents aryl or heteroaryl.

SCHEME 3a

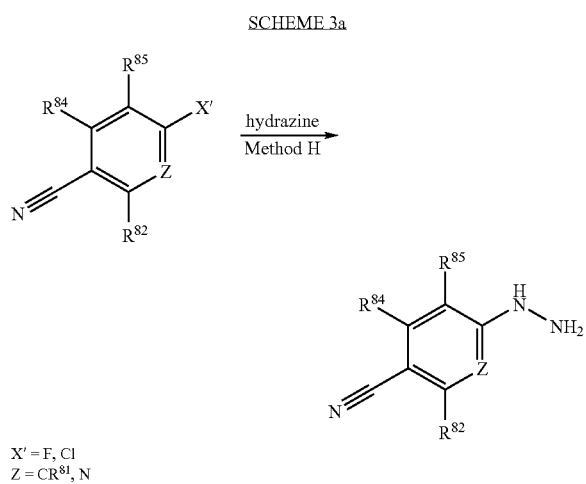

X' = F, Cl
Z = CR$^{81}$, N

SCHEME 3b

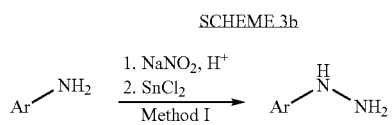

SCHEME 3c

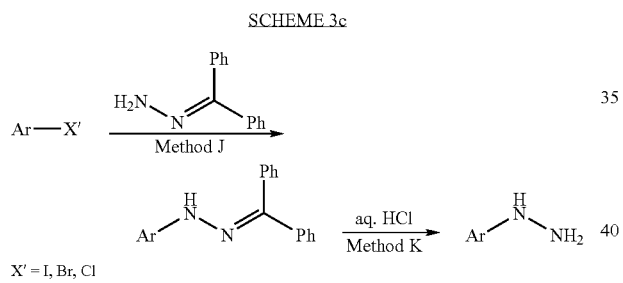

X' = I, Br, Cl

Method H: Preparation from a Halogenated Aryl Nitrile

A solution of a para-halogen, substituted aryl/heteroaryl nitrile is refluxed with an excess of hydrazine monohydrate in an alcohol, such as ethanol. Upon completion of the reaction, the mixture is diluted with water and filtered. The aryl/heteroaryl hydrazine can then be converted to the hydrochloride salt by treatment with an equivalent anhydrous hydrogen chloride in diethyl ether. The resultant hydrazine hydrochloride salt is isolated by filtration.

Method I: Preparation from an Aniline

Aryl or heteroaryl anilines can be converted to the corresponding aryl or heteroaryl hydrazine by diazotization and subsequent reduction. Accordingly, an ice-cold mixture of the aniline in a strong aqueous acid, such as concentrated hydrochloric acid or aqueous sulfuric acid, is treated with sodium nitrite (usually 1 to 1.1 equivalents). After a short period of time, usually 15 to 60 minutes, the resultant mixture is added to an ice-cold suspension of excess stannous chloride in a strong aqueous acid, such as concentrated hydrochloric acid or aqueous sulfuric acid. The mixture is then allowed to warm to room temperature for a few hours. The mixture is then neutralized with aqueous base and extracted with a suitable organic solvent such as ethyl acetate to isolate the aryl/heteroaryl hydrazine. The aryl/heteroaryl hydrazine can then be converted to the hydrochloride salt by treatment with an equivalent anhydrous hydrogen chloride in diethyl ether. The resultant hydrazine hydrochloride salt is isolated by filtration.

Methods J and K: Preparation from Arylhalides

Aryl or heteroaryl hydrazines can be obtained by coupling an aryl/heteroaryl halide with benzophenone hydrazone in the presence of a palladium catalyst, a phosphine ligand, and a base (Mauger and Mignani (2005) Advanced Synthesis and Catalysis 347 (6), 773-782; Haddad, et al. (2004) Tetrahedron Lett. 45, 5935-7; Haddad and Baron (2002) 43(12), 2171-2173; Wagaw et al. (1999) 121(44) 10251-10263 (Method J). The coupled product is subsequently hydrolyzed by refluxing in aqueous acid and an organic co-solvent, such as tetrahydrofuran, to yield the aryl/heteroaryl hydrazine (Method K).

Scheme 4 below illustrates a synthetic scheme that can be used to prepare ketone 11 (i.e., ketone 1 wherein R$^5$ is methoxycarbonyl and R$^6$ is hydrogen) for use as a reagent in Scheme 1.

SCHEME 4

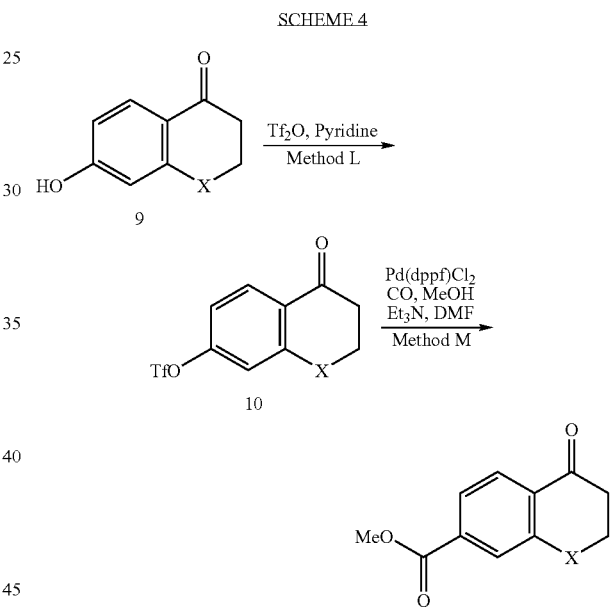

Methods L and M: Preparation of Tetralone 11

In a manner similar to that described by Gerlach and Wollmann in Tetrahedron Letters (1992), 33(38), 5499-5502, ketone 11 can be prepared from phenolic ketone 9 by triflation with triflic anhydride and pyridine in a suitable organic solvent, such as methylene chloride and heptane, followed by subsequent palladium-catalyzed carbonylation with carbon monoxide in dimethylformamide and methanol.

The synthesis of other ketones useful in the preparation of pyrazolines described in Scheme 1 are described in the literature (for example, see Reiter et al., Bioorganic and Medicinal Chemistry Letters, 7, 2307-2312; Koch et al., U.S. Pat. No. 5,550,152 (1996); Ferraz et al. Tetrahedron (2003) 59(31) 5817-5821); Cannon et al., Journal of Medicinal Chemistry (1989) 32(9), 2210-2214; and Beugelmans, et al. Journal of Organic Chemistry (1985), 50(24), 4933-4938). Such ketones may be further derivatized by using routine methods known in the art (such as those methods disclosed in COM- PENDIUM OF ORGANIC SYNTHETIC METHODS, Vol. 1-VI (published by Wiley-Interscience) or other standard reference books).

Scheme 5 below illustrates a synthetic scheme that can be used to prepare pyrazoline acid 14 (i.e., pyrazoline acid 5a wherein X is carbon and the position of the $R^5$ carboxy substituent is as shown) which can be further derivatized as shown in Scheme 2.

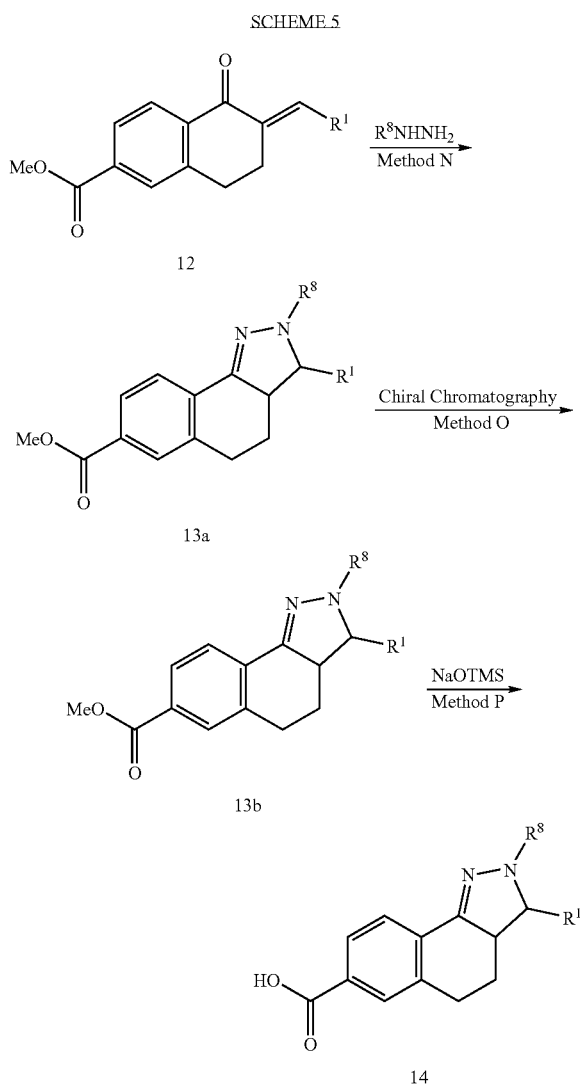

Method N: Pyrazoline Condensation

Pyrazoline 13a can be obtained by condensation of $R^8NHNH_2$ with α,β-unsaturated ketone 12 (prepared as described in Scheme 1, Method A1) in a refluxing alcohol, such as methanol or ethanol, and one to two equivalents of 4 N hydrogen chloride in dioxane or other suitable source hydrogen chloride. After 4 to 24 hours, the reaction mixture is cooled, and pyrazoline ester 13a is isolated by filtration.

Method O: Chiral Resolution

Stereoisomerically-enriched pyrazoline esters 13b generally can be obtained using chromatography such as HPLC on an asymmetric resin with a mobile phase comprising a hydrocarbon or halogenated hydrocarbon, such as heptane, hexane, or dichloromethane, and further containing isopropanol (from about 0% to about 50% by volume, typically from about 2% to about 20% by volume) and alkylamine (e.g., from 0 to 5% by volume, typically about 0.1% diethylamine by volume). Stereoisomerically-enriched compounds generally can also be obtained using supercritical fluid chromatography (SFC) on an asymmetric resin with a mobile phase comprising an alcohol (about 30% to about 60% by volume, typically about 50% by volume) and carbon dioxide. Concentration of the eluate affords the enriched mixture 13b.

Method P: Hydrolysis

A mixture of pyrazoline ester 13b in a suitable organic solvent such as tetrahydrofuran is treated with sodium trimethylsilanoate, usually one to three equivalents, under an inert atmosphere. The reaction is conducted between room temperature and 50° C.

N. Compound Examples

Preparation 1

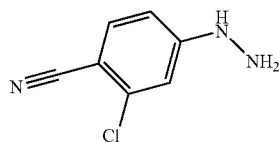

2-chloro-4-hydrazinylbenzonitrile hydrochloride

A mixture of 2-chloro-4-fluorobenzonitrile (20.0 g, 129 mmol), hydrazine monohydrate (9.4 mL, 193 mmol), and ethanol (80 mL) was refluxed for 4 hours. The mixture was diluted with water (200 mL). The precipitate was filtered, washed with water, and dried to give an off-white solid (16.8 g). The solid was suspended in diethyl ether (400 mL) and treated with 2N Hydrogen chloride/ether (50 mL, 100 mmol). The precipitate was filtered, washed with diethyl ether, and dried to give 2-chloro-4-hydrazinylbenzonitrile hydrochloride as a white solid (16.3 g, 79.9 mmol, 62% yield). $^1$H NMR (400 MHz, DMSO-$d_6$) δ ppm 9.63 (br. s., 3H), 9.17 (br. s., 1H), 7.74 (d, J=8.9 Hz, 1H), 7.13 (d, J=2.1 Hz, 1H), 6.92 (dd, J=8.6, 2.1 Hz, 1H). ES-MS m/z 168 (M+H).

Preparation 2

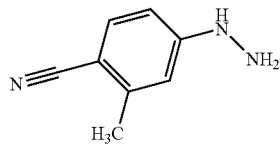

4-hydrazinyl-2-methylbenzonitrile hydrochloride

A mixture of 4-fluoro-2-methylbenzonitrile (20.4 g, 151 mmol), hydrazine monohydrate (14.6 mL, 302 mmol), and ethanol (80 mL) was refluxed for 48 hours. The mixture was diluted with water (200 mL). The precipitate was filtered, washed with water, and dried to give an off-white solid (16.1 g). The solid was suspended in diethyl ether (400 mL) and treated with 2N Hydrogen chloride/ether (55 mL, 110 mmol).

The precipitate was filtered, washed with diethyl ether, and dried to give 4-hydrazinyl-2-methylbenzonitrile hydrochloride as a white solid (15.6 g, 85.0 mmol, 56% yield). $^1$H NMR (400 MHz, DMSO-d$_6$) δ ppm 8.42 (br. s., 1H), 8.33 (br. s., 3H), 7.51 (d, J=8.6 Hz, 1H), 6.81 (d, J=1.9 Hz, 1H), 6.74 (dd, J=8.6, 2.4 Hz, 1H), 2.35 (s, 3H). ES-MS m/z 148 (M+H).

Preparation 3

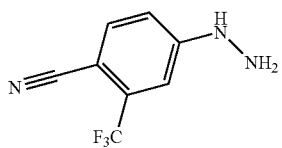

4-hydrazinyl-2-(trifluoromethyl)benzonitrile hydrochloride

The title compound was prepared according to the procedure in Preparation 1 from 4-fluoro-2-(trifluoromethyl)benzonitrile (1.89 g, 10 mmol), instead of 2-chloro-4-fluorobenzonitrile, at 80° C. to give an off-white solid (1.89 g, 8.0 mmol, 80% yield). ES-MS m/z 202 (M+H).

Preparation 4

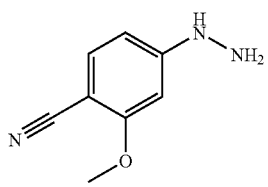

4-hydrazinyl-2-methoxybenzonitrile hydrochloride

The title compound was prepared according to the procedure in Preparation 1 from 4-fluoro-2-methoxybenzonitrile (4.97 g, 32.9 mmol), instead of 2-chloro-4-fluorobenzonitrile, refluxing overnight to give 4-hydrazinyl-2-methoxybenzonitrile hydrochloride (3.54 g, 17.8 mmol. 54% yield) $^1$H NMR (400 MHz, DMSO-d$_6$) δ ppm 3.82 (s, 3H) 6.44 (dd, J=8.46, 2.01 Hz, 1H) 6.64 (d, J=2.15 Hz, 1H) 7.41 (d, J=8.32 Hz, 1H) 7.99 (s, 2H) 8.40 (s, 1H). ES-MS m/z 164 (M+H).

Preparation 5

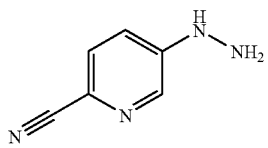

5-hydrazinylpicolinonitrile dihydrochloride

To a solution of 5-aminopicolinonitrile (1.0 g, 8.4 mmol) in 20% sulfuric acid aq. (20 mL) at 0° C., sodium nitrite (590 mg, 9.2 mmol) in water (3 mL) was slowly added, keeping the temperature below 10° C. This solution was stirred on an ice bath for 30 minutes and then treated slowly with an ice cold solution of tin(II) chloride dihydrate (5.7 g, 25.2 mmol) in 20% sulfuric acid (20 mL) keeping the temperature below 10° C. The solution was stirred at 0° C. for 15 minutes and warmed to room temperature over 30 minutes. The reaction was neutralized with ammonium hydroxide, and the resulting tin salts were filtered off. The filtrate was extracted three times with ethyl acetate, dried over magnesium sulfate, filtered and evaporated. The resulting solid residue was dissolved in ethyl acetate and tetrahydrofuran and treated with 4 N Hydrogen chloride in dioxane (approximately 3 mL). The mixture was evaporated and the resulting solid was triturated with diethyl ether and dried on the high vacuum overnight to give a 2:1 mixture of 5-hydrazinylpicolinonitrile dihydrochloride to starting material (875 mg). ES-MS m/z 135 (M+H).

Preparation 6

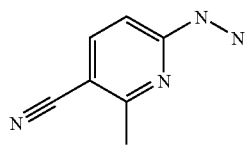

6-hydrazinyl-2-methylnicotinonitrile

To a suspension of 6-chloro-2-methylnicotinonitrile (6.2 mmol) in 6.2 mL of ethanol, hydrazine monohydrate (9.3 mmol) was added. The resulting mixture was then heated to 80° C. overnight. The mixture was cooled to room temperature and 2 mL of water was added. It was heated to 80° C. again to a clear solution and then allowed to cool down to room temperature and finally in an ice-bath. The solid was collected by filtration, washed with cold 50% ethanol, and dried under vacuum to give 550 mg of the desired solid product. $^1$H NMR (400 MHz, DMSO-d$_6$) δ ppm 2.41 (s, 3H), 4.41 (s, 2H), 6.60 (br. s., 1H), 7.66 (d, J=8.59 Hz, 1H), 8.47 (s, 1H); ES-MS m/z 149 (M+H).

Preparation 7

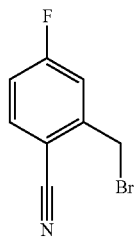

2-(bromomethyl)-4-fluorobenzonitrile

A solution of 2-methyl-4-fluoro-benzonitrile (3.5 g, 25.9 mmol) in 40 mL of carbon tetrachloride was treated with N-Bromosuccinimide (4.6 g, 25.9 mmol) and benzoylperoxide (157 mg, 0.65 mmol). The mixture was heated to reflux for 3 hours, cooled to room temperature and allowed to stir overnight. The solids were filtered off and washed with carbon tetrachloride. The filtrate was condensed and purified by normal phase flash column chromatography on a 50 g silica gel column (5-50% ethyl acetate/hexanes gradient). Two peaks separated. It was determined that the second eluting peak is the desired product. Pure fractions of this peak were pooled and concentrated in vacuo to yield 2-(bromomethyl)-4-fluorobenzonitrile (1.35 g, 0.63 mmol, 25% yield) as a white solid. $^1$H NMR (400 MHz, DMSO-d$_6$) δ ppm 4.79 (s, 2H), 7.44 (dt, J=8.59, 2.69 Hz, 1H), 7.68 (dd, J=9.53, 2.55 Hz, 1H), 8.01 (dd, J=8.59, 5.64 Hz, 1H).

Preparation 8

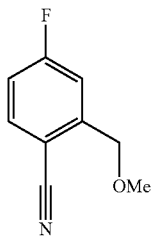

4-fluoro-2-(methoxymethyl)benzonitrile

A solution of 2-(bromomethyl)-4-fluorobenzonitrile (501 mg, 2.3 mmol) in methanol (5 mL) was treated with sodium methoxide (5.6 mL of 0.5 M solution in methanol, 2.81 mmol) and stirred for 1 hour at room temperature then heated to 55° C. for 2 hours. The mixture was cooled to room temperature, condensed to dryness and directly purified by normal phase flash column chromatography on a 20 g silica gel column (5-60% ethyl acetate/hexanes gradient). Pure fractions were pooled and concentrated in vacuo to yield 4-fluoro-2-(methoxymethyl)benzonitrile (110 mg, 0.66 mmol, 28% yield) as an oil. $^1$H NMR (400 MHz, DMSO-d$_6$) δ ppm 7.97 (dd, J=8.46, 5.50 Hz, 1H), 7.46 (dd, J=9.53, 2.55 Hz, 1H), 7.39 (td, J=8.59, 2.69 Hz, 1H), 4.58 (s, 2H), 3.37 (s, 3H).

Preparation 9

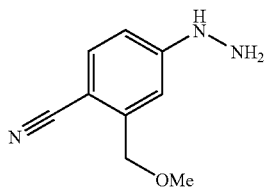

4-hydrazinyl-2-(methoxymethyl)benzonitrile hydrochloride

A mixture of 4-fluoro-2-(methoxymethyl)benzonitrile (110 mg, 0.67 mmol), hydrazine monohydrate (133 mg, 0.13 mL, 2.6 mmol) and ethanol (5 mL) was heated to reflux overnight. The mixture was cooled to room temp and condensed. The residue was dissolved in methanol and treated with 2.0 N Hydrogen chloride in diethyl ether. The solvent was removed and the solid was dried to give 4-hydrazinyl-2-(methoxymethyl)benzonitrile hydrochloride as an off-white solid.

Preparation 10

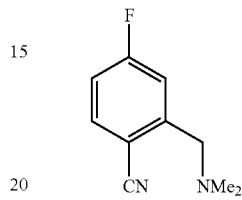

2-((dimethylamino)methyl)-4-fluorobenzonitrile

A mixture of 2-(bromomethyl)-4-fluorobenzonitrile (423 mg, 1.9 mmol) and 2.0 M dimethylamine (4 mL) was stirred at room temperature for thirty minutes. The mixture was then concentrated, purified by normal phase flash column chromatography, on a 20 g silica gel column (5-45% ethyl acetate/hexanes gradient), and concentrated in vacuo to yield 2-((dimethylamino)methyl)-4-fluorobenzonitrile (241 mg, 1.35 mmol, 68%). $^1$H NMR (400 MHz, DMSO-d$_6$) δ ppm 7.92 (dd, J=8.59, 5.37 Hz, 1H), 7.42 (dd, J=9.94, 2.69 Hz, 1H), 7.35 (td, J=8.46, 2.69 Hz, 1H), 3.56 (s, 2H), 2.19 (s, 6H).

Preparation 11

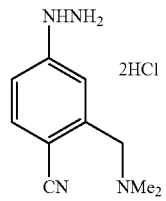

2-((dimethylamino)methyl)-4-hydrazinylbenzonitrile dihydrochloride

A mixture of 2-((dimethylamino)methyl)-4-fluorobenzonitrile (241 mg, 1.35 mmol), hydrazine monohydrate (101 mg, 0.10 mL, 2.0 mmol) and ethanol (5 mL) was heated overnight at 90° C. The mixture was cooled to room temperature and concentrated to dryness. The residue was dissolved in diethyl ether and treated with 2.0 M Hydrogen chloride in diethyl ether. The resulting solid was filtered and dried to give 2-((dimethylamino)methyl)-4-hydrazinylbenzonitrile dihydrochloride (430 mg, 1.63 mmol, >100% yield). $^1$H NMR (400 MHz, DMSO-d$_6$) δ ppm 9.26 (s, 1H), 7.80 (d, J=8.59 Hz, 1H), 7.36 (d, J=2.15 Hz, 1H), 7.08 (dd, J=8.59, 2.15 Hz, 1H), 4.35 (s, 2H), 2.78 (s, 6H). ES-MS m/z 191 (M+H).

Preparation 12

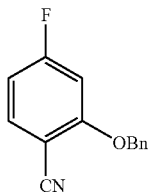

2-(benzyloxy)-4-fluorobenzonitrile

Benzyl alcohol (3.25 g, 30 mmol) was slowly added to a stirred suspension of sodium hydride (1.15 g, 28.7 mmol) in toluene (50 mL) at room temperature. The mixture was stirred for 30 minutes and then 2,4-difluorobenzonitrile was added all at once and stirring continued overnight. The mixture was quenched with water, extracted three times with ethyl acetate, washed with brine, dried over magnesium sulfate, filtered and condensed. The crude product was dissolved in hot ethyl acetate and triturated with hexanes to give 2-(benzyloxy)-4-fluorobenzonitrile (5.4 g, 23.8 mmol, 88% yield) as a white solid. $^1$H NMR (400 MHz, DMSO-$d_6$) δ ppm 5.30 (s, 2H), 6.99 (td, J=8.46, 2.42 Hz, 1H), 7.29-7.51 (m, 6H), 7.86 (dd, J=8.59, 6.44 Hz, 1H).

Preparation 13

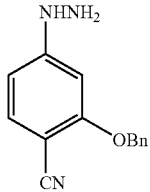

2-(benzyloxy)-4-hydrazinylbenzonitrile

A solution of 2-(benzyloxy)-4-fluorobenzonitrile (4.8 g, 21 mmol), in ethanol (80 mL) was treated with hydrazine monohydrate (2.6 g, 2.5 mL, 53 mmol) and heated to reflux for 3 days. The mixture was cooled to room temperature and concentrated. Water was added and the residue was extracted three times with ethyl acetate, dried over magnesium sulfate, filtered and condensed to give 2-(benzyloxy)-4-hydrazinylbenzonitrile (3.8 g, 15.8 mmol, 75% yield) as an off-white solid. $^1$H NMR (400 MHz, DMSO-$d_6$) δ ppm 4.27 (s, 2H), 5.16 (s, 2H), 6.36 (dd, J=8.73, 1.75 Hz, 1H), 6.61 (d, J=1.61 Hz, 1H), 7.30 (d, J=8.59 Hz, 1H), 7.32-7.51 (m, 5H), 7.78 (s, 1H). ES-MS m/z 240 (M+H)

Preparation 14

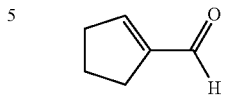

cyclopent-1-enecarbaldehyde

To a solution of sodium periodate (28.3 g, 0.13 mol) in water (250 mL) was added an ethyl ether solution (150 mL) of 1,2-cyclohexanediol (12.0 g, 0.10 mol). The solution was stirred for thirty minutes at ambient temperature. To this solution was added 20% aqueous potassium hydroxide (40 mL) and the solution stirred for one hour. The layers were separated and the organic layer was washed with water and brine and dried over magnesium sulfate. Concentration in vacuo provided cyclopent-1-enecarbaldehyde as a yellow oil (6.0 g, 62% yield). Reversed-phase HPLC on 4.6×50 mm C-18 column, $t_R$=0.825 minutes (10 to 90% acetonitrile/water over 4 minutes at 4 mL/minute with detection 254 nm, at 20° C.); $^1$H NMR (400 MHz, DMSO-$d_6$) δ ppm 1.83-1.93 (m, 2H), 2.36 (td, J=7.65, 2.15 Hz, 2H), 2.50-2.59 (m, 2H), 7.01-7.08 (m, 1H), 9.73 (s, 1H).

Preparation 15

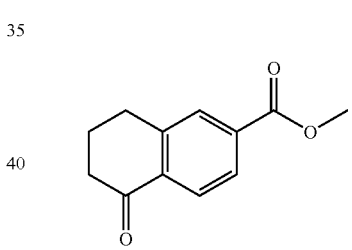

methyl 5-oxo-5,6,7,8-tetrahydronaphthalene-2-carboxylate

A solution of 5-oxo-5,6,7,8-tetrahydronaphthalene-2-carboxylic acid (5.14 g, 27.0 mmol) (Peakdale Molecular) in 4N hydrochloric acid in methanol was heated to reflux for eighteen hours. The solution was returned to ambient temperature and concentrated in vacuo. The residue was diluted with ethyl acetate and washed with saturated sodium bicarbonate solution and saturated sodium chloride and dried over magnesium sulfate. Filtration followed by concentration in vacuo provided methyl 5-oxo-5,6,7,8-tetrahydronaphthalene-2-carboxylate as a brown solid (4.76 g, 86% yield). Reversed-phase HPLC on 4.6×50 mm C-18 column, $t_R$=1.90 minutes (10 to 90% acetonitrile/water over 4 minutes at 4 mL/minute with detection 254 nm, at 20° C.); $^1$H NMR (400 MHz, DMSO-$d_6$) δ ppm 1.99-2.08 (m, 2H), 2.58-2.66 (m, 2H), 2.99 (t, J=6.04 Hz, 2H), 3.85 (s, 3H), 7.83-7.87 (m, 1H), 7.91 (d, J=0.81 Hz, 1H), 7.92-7.97 (m, 1H).

Preparation 16

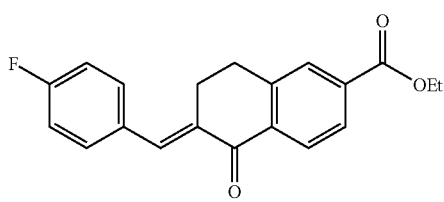

ethyl 6-(4-fluorobenzylidene)-5-oxo-5,6,7,8-tetrahydronaphthalene-2-carboxylate

The title compound was prepared according to Method A2. The crude precipitate was a mixture of ethyl 5-oxo-5,6,7,8-tetrahydronaphthalene-2-carboxylate, ethyl 6-(4-fluorobenzylidene)-5-oxo-5,6,7,8-tetrahydronaphthalene-2-carboxylate and 6-(4-fluorobenzylidene)-5-oxo-5,6,7,8-tetrahydronaphthalene-2-carboxylic acid. The mixture was combined with 4-fluorobenzaldehyde (0.5 mL), ethanol (40 mL) and 4N Hydrogen chloride/dioxane (10 mL) and was refluxed for 20 hours. The solution was poured into 200 mL water, filtered, and dried to give ethyl 6-(4-fluorobenzylidene)-5-oxo-5,6,7,8-tetrahydronaphthalene-2-carboxylate as an off-white solid (826 mg, 2.55 mmol, 49% yield). $^1$H NMR (400 MHz, DMSO-$d_6$) δ ppm 1.33 (t, J=7.12 Hz, 3H), 3.06 (m, 4H), 4.34 (q, J=6.98 Hz, 2H), 7.31 (t, J=8.86 Hz, 2H), 7.62 (dd, J=8.59, 5.64 Hz, 2H), 7.74 (s, 1H), 7.94 (m, 2H), 8.06 (d, J=8.59 Hz, 1H). ES-MS m/z 325 (M+H).

Preparation 17

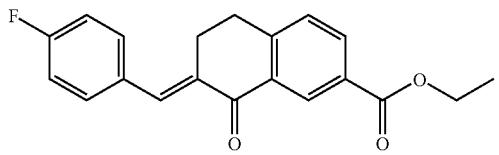

ethyl 7-(4-fluorobenzylidene)-8-oxo-5,6,7,8-tetrahydronaphthalene-2-carboxylate

The title compound was prepared according to Method A2 from 8-oxo-5,6,7,8-tetrahydronaphthalene-2-carboxylic acid and 4-fluorobenzaldehyde as an off-white solid (64% yield). $^1$H NMR (400 MHz, DMSO-$d_6$) δ ppm 1.34 (t, J=7.12 Hz, 3H), 3.05 (m, 4H), 4.34 (q, J=7.25 Hz, 2H), 7.30 (m, 2H), 7.54 (d, J=7.79 Hz, 1H), 7.61 (m, 2H), 7.74 (s, 1H), 8.10 (dd, J=7.92, 2.01 Hz, 1H), 8.49 (d, J=1.88 Hz, 1H). ES-MS m/z 325 (M+H).

Preparation 18

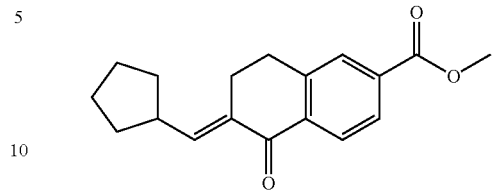

methyl 6-(cyclopentylmethylene)-5-oxo-5,6,7,8-tetrahydronaphthalene-2-carboxylate To a solution of methyl 5-oxo-5,6,7,8-tetrahydronaphthalene-2-carboxylate (3.4 g, 16.7 mmol) in methanol (30 mL) was added cyclopentanecarboxaldehyde (3.3 g, 33.3 mmol) and pyrrolidine (2.78 mL, 33.3 mmol). The solution was stirred for twenty hours at ambient temperature. The reaction was recharged with 0.5 mL of cyclopentanecarboxaldehyde. The resulting precipitate was collected by vacuum filtration to provide methyl 6-(cyclopentylmethylene)-5-oxo-5,6,7,8-tetrahydronaphthalene-2-carboxylate as a solid (2.8 g, 60% yield). LC/MS on 4.6×50 mm C-18 column, $t_R$=6.71 minutes (10 to 90% acetonitrile/water over 8 minutes at 2 mL/minute with detection 254 nm, at 50° C.); ES-MS m/z 285 (M+H); $^1$H NMR (400 MHz, DMSO-$d_6$) δ ppm 1.24-1.39 (m, 2H), 1.52-1.74 (m, 4H), 1.76-1.89 (m, 2H), 2.77 (t, J=5.77 Hz, 2H), 2.79-2.90 (m, 1H), 2.97 (t, J=6.44 Hz, 2H), 3.85 (s, 3H), 6.71 (d, J=9.94 Hz, 1H), 7.88 (d, J=6.44 Hz, 1H), 7.91 (s, 1H), 7.98 (d, J=8.06 Hz, 1H).

Preparation 19

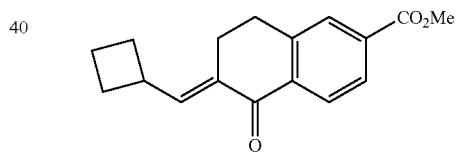

methyl 6-(cyclobutylmethylene)-5-oxo-5,6,7,8-tetrahydronaphthalene-2-carboxylate A solution of methyl 5-oxo-5,6,7,8-tetrahydronaphthalene-2-carboxylate (600 mg, 2.9 mmol) in tetrahydrofuran (10 mL) was cooled to ice bath temperature and treated with 1.0 M lithium hexamethyldisilazide in tetrahydrofuran (5 mL). After stirring for twenty minutes, cyclobutanecarboxaldehyde (J. Med. Chem. 1989, 32, 1001-6) (24 mL of 0.5 M solution in tetrahydrofuran) was slowly added and the mixture allowed to warm to room temperature and stir for 3 days. The mixture was poured into water, extracted three times with ethyl acetate, washed with brine, dried over magnesium sulfate, filtered and concentrated. The crude product was purified by normal phase flash column chromatography on a 50 g silica gel column (5-50% ethyl acetate/hexanes gradient). Pure fractions were pooled and concentrated in vacuo to yield methyl 6-(cyclobutylmethylene)-5-oxo-5,6,7,8-tetrahydronaphthalene-2-carboxylate (300 mg, 1.1 mmol, 38% yield). $^1$H NMR (400 MHz, DMSO-$d_6$) δ ppm 1.81-2.03 (m, 4H), 2.14-2.27 (m, 2H), 2.71 (t, J=6.58 Hz, 2H), 2.93-3.00 (m, 2H), 3.34-3.44 (m, 1H), 3.88 (s, 3H), 6.91 (d, J=9.13 Hz, 1H), 7.84-7.95 (m, 2H), 8.01 (d, J=8.06 Hz, 1H). ES-MS m/z 271 (M+H).

Preparation 20

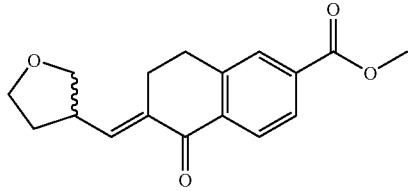

(±)-methyl 5-oxo-6-((tetrahydrofuran-3-yl)methylene)-5,6,7,8-tetrahydronaphthalene-2-carboxylate To a solution of methyl 5-oxo-5,6,7,8-tetrahydronaphthalene-2-carboxylate (240 mg, 1.2 mmol) in methanol (3 mL) was added (±)-tetrahydrofuran-3-carboxaldehyde (240 mg, 2.4 mmol) and pyrrolidine (0.20 mL, 2.4 mmol). The solution was stirred for twenty hours at ambient temperature and for four hours at 45° C. The reaction was concentrated in vacuo. Chromatography (on silica, ethyl acetate/hexane) provided (±)-methyl 5-oxo-6-((tetrahydrofuran-3-yl)methylene)-5,6,7,8-tetrahydronaphthalene-2-carboxylate as an orange oil (200 mg, 58% yield). LC/MS on 4.6×50 mm C-18 column, $t_R$=2.52 minutes (10 to 90% acetonitrile/water over 4 minutes at 4 mL/minute with detection 254 nm, at 50° C.); ES-MS m/z 287 (M+H).

Preparation 21

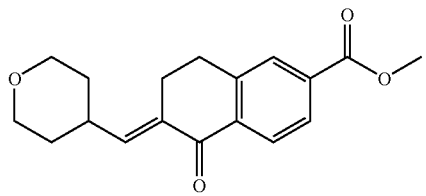

methyl 5-oxo-6-((tetrahydro-2H-pyran-4-yl)methylene)-5,6,7,8-tetrahydronaphthalene-2-carboxylate A solution of methyl 5-oxo-5,6,7,8-tetrahydronaphthalene-2-carboxylate (2.9 mmol), tetrahydro-pyran-4-carbaldehyde (3.2 mmol), and piperidine (3.2 mmol) in 6 mL of methanol was heated to 65° C. overnight. The cooled mixture was diluted with ethyl acetate, washed with water and brine, dried over sodium sulfate, and concentrated. The residue was purified by silica gel, eluting with ethyl acetate in hexane from 10% to 40%, to give 430 mg of the desired product. ES-MS m/z 301 (M+H).

Preparation 22

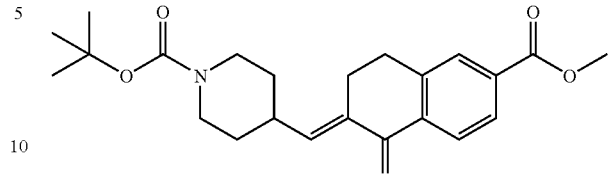

tert-butyl 4-((6-(methoxycarbonyl)-1-oxo-3,4-dihydronaphthalen-2(1H)-ylidene)methyl)piperidine-1-carboxylate Prepared according to the procedure of Preparation 21 except using tert-butyl 4-formylpiperidine-1-carboxylate, instead of methyl 5-oxo-5,6,7,8-tetrahydronaphthalene-2-carboxylate, to give the title compound in 71% yield. ES-MS m/z 422 (M+Na).

Preparation 23

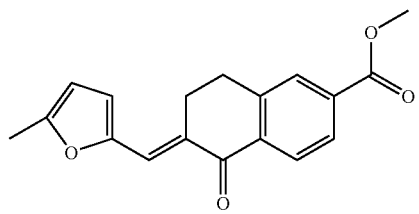

methyl 6-(5-methyl-2-furylmethylene)-5-oxo-5,6,7,8-tetrahydronaphthalene-2-carboxylate The title compound was prepared according to Method A3 from 5-oxo-5,6,7,8-tetrahydronaphtalene-2-carboxylic acid methyl ester (396 mg, 1.9 mmol) and 5-methyl-2-furaldehyde (192 mg, 2.0 mmol). ES-MS m/z 297 (M+H).

Preparation 24

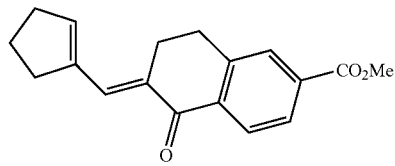

methyl 6-(cyclopent-1-en-1-ylmethylene)-5-oxo-5,6,7,8-tetrahydronaphthalene-2-carboxylate The title compound was prepared from 5-oxo-5,6,7,8-tetrahydronaphtalene-2-carboxylic acid methyl ester (396 mg, 1.9 mmol) and 1-cyclopentene carbaldehyde (220 mg, 2.0 mmol) according to Method A3 in 70% yield. ES-MS m/z 283 (M+H)

Preparation 25

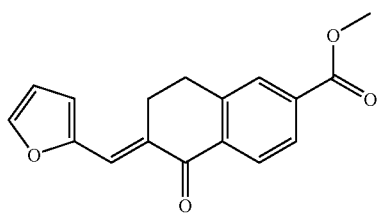

methyl 6-(2-furylmethylene)-5-oxo-5,6,7,8-tetrahydronaphthalene-2-carboxylate

The title compound was prepared from 5-oxo-5,6,7,8-tetrahydronaphtalene-2-carboxylic acid methyl ester (396 mg, 1.9 mmol) and 2-furaldehyde (192 mg, 2.0 mmol) according to Method A3 in 80% yield. ES-MS m/z 283 (M+H).

Preparation 26

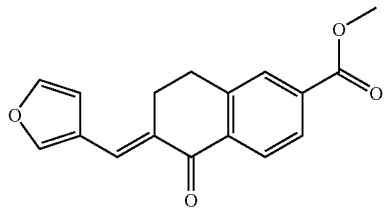

methyl 6-(3-furylmethylene)-5-oxo-5,6,7,8-tetrahydronaphthalene-2-carboxylate

The title compound was prepared from 5-oxo-5,6,7,8-tetrahydronaphtalene-2-carboxylic acid methyl ester (396 mg, 1.9 mmol) and 3-furaldehyde (192 mg, 2.0 mmol) according to Method A3 in 80% yield. ES-MS m/z 283 (M+H)

Preparation 27

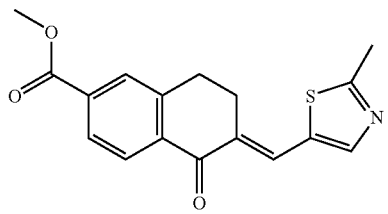

methyl 6-[(2-methyl-1,3-thiazol-5-yl)methylene]-5-oxo-5,6,7,8-tetrahydronaphthalene-2-carboxylate The title compound was prepared from 5-oxo-5,6,7,8-tetrahydronaphtalene-2-carboxylic acid methyl ester (396 mg, 1.9 mmol) and 2-methyl-1,3-thiazole-5-carbaldehyde (220 mg, 2.0 mmol) according to Method A3 in 60% yield. ES-MS m/z 314 (M+H)

Preparation 28

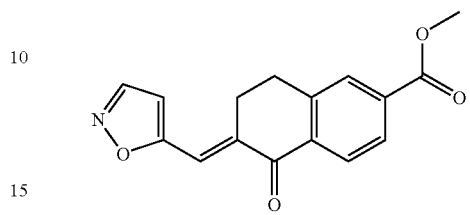

methyl 6-(isoxazol-5-ylmethylene)-5-oxo-5,6,7,8-tetrahydronaphthalene-2-carboxylate The title compound was prepared from 5-oxo-5,6,7,8-tetrahydronaphtalene-2-carboxylic acid methyl ester (396 mg, 1.9 mmol) and isoxazole-5-carbaldehyde (200 mg, 2.0 mmol) according to Method A3 in 55% yield. ES-MS m/z 284 (M+H)

Preparation 29

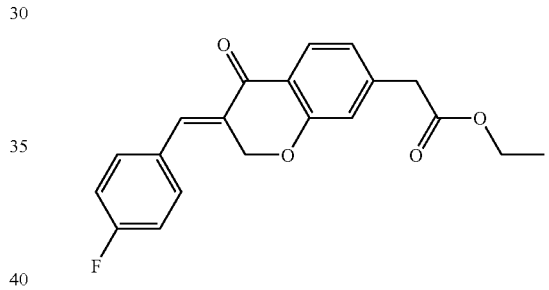

ethyl [3-(4-fluorobenzylidene)-4-oxo-3,4-dihydro-2H-chromen-7-yl]acetate

The title compound was prepared from methyl [4-oxo-3,4-dihydro-2H-chromen-7-yl]acetate (L. A. Reiter et al. Biorganic and Medicinal Chemistry Letters, 1997, 7 2307-2312) and 4-fluorobenzaldehyde according to Method A2 in 45% yield. ES-MS m/z 341 (M+H).

Preparation 30

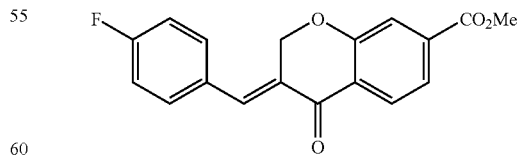

methyl 3-(4-fluorobenzylidene)-4-oxochroman-7-carboxylate

The title compound was prepared from methyl 4-oxochroman-7-carboxylate (Koch, K., and Biggers, M. S. J. Org.

Chem. 1994, 59, 1216-1218) and 4-fluorobenzaldehyde according to Method A2 using methanol and 4 N Hydrogen chloride/dioxane. Off-white solid (76% yield). $^1$H NMR (400 MHz, DMSO-d$_6$) δ ppm 3.88 (s, 3H), 5.48 (s, 1H), 7.35 (t, J=8.59 Hz, 2H), 7.50-7.61 (m, 3H), 7.66 (d, J=7.25 Hz, 1H), 7.80 (s, 1H), 8.01 (d, J=8.06 Hz, 1H).

Preparation 31

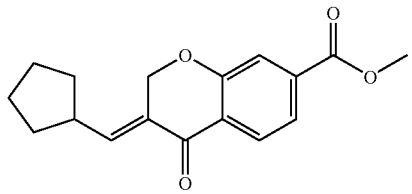

methyl 3-(cyclopentylmethylene)-4-oxochroman-7-carboxylate

The title compound was prepared according to General Method A1 from methyl 4-oxochroman-7-carboxylate (Koch, K., and Biggers, M. S. J. Org. Chem. 1994, 59, 1216-1218) and cyclopentanecarboxaldehyde as an off-white solid (2.12 g, 7.42 mmol, 76% yield). ES-MS m/z 287 (M+H).

Preparation 32

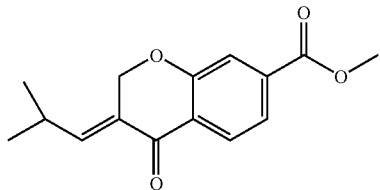

methyl 3-(2-methylpropylidene)-4-oxochroman-7-carboxylate

The title compound was prepared according to General Method A1 from methyl 4-oxochroman-7-carboxylate (Koch, K., and Biggers, M. S. J. Org. Chem. 1994, 59, 1216-1218) and isobutylaldehyde. After stirring overnight, the solution was partitioned between 1 N Hydrogen chloride and ethyl acetate. The organic layers were washed with 1 N Hydrogen chloride and brine, dried (sodium sulfate), and concentrated. The crude product was purified by flash chromatography (0 to 20% ethyl acetate/hexanes) to give methyl 3-(2-methylpropylidene)-4-oxochroman-7-carboxylate as an oily solid (730 mg, 2.8 mmol, 58% yield). $^1$H NMR (400 MHz, DMSO-d$_6$) δ ppm 7.95 (d, J=8.2 Hz, 1H), 7.62 (dd, J=8.2, 1.6 Hz, 1H), 7.53 (d, J=1.6 Hz, 1H), 6.65 (dt, J=10.3, 1.7 Hz, 1H), 5.22 (d, J=1.6 Hz, 2H), 3.88 (s, 3H), 2.73-2.86 (m, 1H), 1.04 (d, J=6.6 Hz, 6H). ES-MS m/z 261 (M+H).

Preparation 33

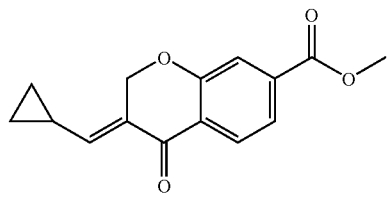

methyl 3-(cyclopropylmethylene)-4-oxochroman-7-carboxylate

The title compound was prepared according to Method A1 from methyl 4-oxochroman-7-carboxylate (Koch, K., and Biggers, M. S. J. Org. Chem. 1994, 59, 1216-1218) and cyclopropanecarboxaldehyde as an off-white solid (1.14 g, 91% yield). $^1$H NMR (400 MHz, DMSO-d$_6$) δ ppm 0.75-0.86 (m, 2H), 1.00-1.11 (m, 2H), 1.80-1.95 (m, 1H), 3.87 (s, 3H), 5.31 (d, J=1.56 Hz, 2H), 6.27 (d, J=11.33 Hz, 1H), 7.52 (d, J=1.56 Hz, 1H), 7.60 (dd, J=8.20, 1.56 Hz, 1H), 7.94 (d, J=8.20 Hz, 1H). ES-MS m/z 259 (M+H).

Preparation 34

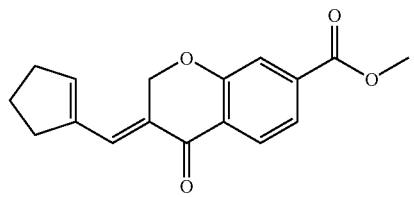

methyl 3-(cyclopentenylmethylene)-4-oxochroman-7-carboxylate

To a solution of methyl 4-oxochroman-7-carboxylate (500 mg, 2.4 mmol) in methanol (5 mL) was added cyclopent-1-enecarbaldehyde (465 mg, 4.8 mmol) and pyrrolidine (0.40 mL, 4.8 mmol). The solution was stirred for one hour at ambient temperature. The resulting brown precipitate was collected by vacuum filtration and dried to give methyl 3-(cyclopentenylmethylene)-4-oxochroman-7-carboxylate (444 mg, 64% yield). LC/MS on 4.6×50 mm C-18 column, t$_R$=6.49 minutes (10 to 90% acetonitrile/water over 8 minutes at 2 mL/minute with detection 254 nm, at 50° C.); ES-MS m/z 285 (M+H). $^1$H NMR (400 MHz, DMSO-d$_6$) δ ppm 1.88-1.99 (m, 2H), 2.43 (d, J=13.16 Hz, 2H), 2.63 (t, J=6.98 Hz, 2H), 3.85 (s, 3H), 5.36 (s, 2H), 6.45 (br. s., 1H), 7.37 (s, 1H), 7.49 (d, J=1.34 Hz, 1H), 7.60 (dd, J=8.06, 1.61 Hz, 1H), 7.93 (d, J=8.32 Hz, 1H).

Preparation 35

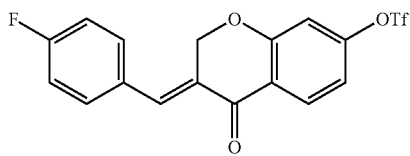

3-(4-fluorobenzylidene)-4-oxochroman-7-yl trifluoromethanesulfonate

The title compound was prepared according to Method A1 from 4-oxochroman-7-yl trifluoromethanesulfonate (500 mg, 1.7 mmol) (U.S. Pat. No. 5,550,152; Example 1, Step C) and 4-fluorobenzaldehyde (0.21 mL, 2.0 mmol) to give 3-(4-fluorobenzylidene)-4-oxochroman-7-yl trifluoromethanesulfonate (260 mg, 0.65 mmol, 40% yield) as a solid. $^1$H NMR (400 MHz, DMSO-$d_6$) δ ppm 5.52 (d, J=1.88 Hz, 2H), 7.25 (dd, J=8.73, 2.28 Hz, 1H), 7.31-7.39 (m, 3H), 7.56 (dd, J=8.73, 5.50 Hz, 2H), 7.80 (s, 1H), 8.06 (d, J=8.86 Hz, 1H). ES-MS m/z 403 (M+H).

Preparation 36

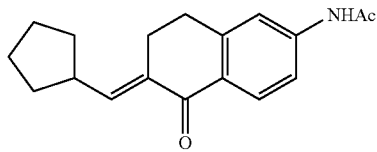

N-(6-(cyclopentylmethylene)-5-oxo-5,6,7,8-tetrahydronaphthalen-2-yl)acetamide

A mixture of 6-acetamido-1-tetralone (200 mg, 0.98 mmol) and cyclopentanecarboxaldehyde (0.21 mL, 1.9 mmol) in methanol (2 mL) was treated with pyrrolidine (0.25 mL, 2.9 mmol) at room temperature for 1 hour then heated at 55° C. overnight. The mixture was cooled to room temperature, treated with 1N Hydrogen chloride (4 mL) was filtered thru a Chem Elute tube (CE101 1) eluting with 90% dichloromethane/10% ethyl acetate and condensed filtrate to give (E)-N-(6-(cyclopentylmethylene)-5-oxo-5,6,7,8-tetrahydronaphthalen-2-yl)acetamide (200 mg, 0.71 mmol, 72% n yield) as a tan foam. $^1$H NMR (400 MHz, DMSO-$d_6$) δ ppm 1.25-1.44 (m, 2H), 1.52-1.76 (m, 4H), 1.77-1.90 (m, 2H), 2.08 (s, 3H), 2.70-2.92 (m, 5H), 6.63 (d, J=9.67 Hz, 1H), 7.49 (dd, J=8.59, 2.15 Hz, 1H), 7.59-7.66 (m, 1H), 7.86 (d, J=8.59 Hz, 1H), 10.23 (s, 1H). ES-MS m/z 284 (M+H).

EXAMPLE 1

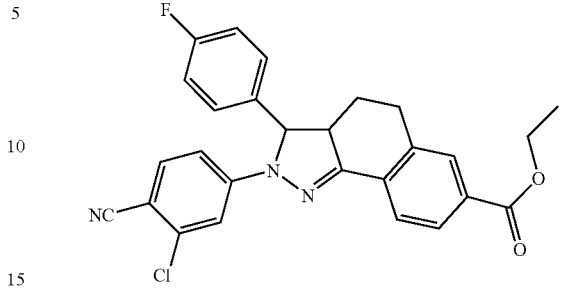

ethyl 2-(3-chloro-4-cyanophenyl)-3-(4-fluorophenyl)-3,3a,4,5-tetrahydro-2H-benzo[g]indazole-7-carboxylate The title compound was prepared from ethyl 6-(4-fluorobenzylidene)-5-oxo-5,6,7,8-tetrahydronaphthalene-2-carboxylate (Preparation 16; 324 mg, 1.0 mmol) and 2-chloro-4-hydrazinylbenzonitrile hydrochloride (Preparation 1; 306 mg, 1.5 mmol) according to Method B (yellow solid, 394 mg, 0.830 mmol, 83% yield). $^1$H NMR (400 MHz, DMSO-$d_6$) δ ppm 0.80 (m, 1H), 1.31 (t, J=7.12 Hz, 3H), 1.79 (m, 1H), 2.95 (m, 2H), 3.97 (ddd, J=13.49, 11.21, 4.83 Hz, 1H), 4.31 (q, J=6.98 Hz, 2H), 5.94 (d, J=11.28 Hz, 1H), 7.15 (m, 6H), 7.66 (d, J=8.86 Hz, 1H), 7.80 (s, 1H), 7.85 (dd, J=8.19, 1.75 Hz, 1H), 8.16 (d, J=8.06 Hz, 1H). ES-MS m/z 474 (M+H).

EXAMPLE 2

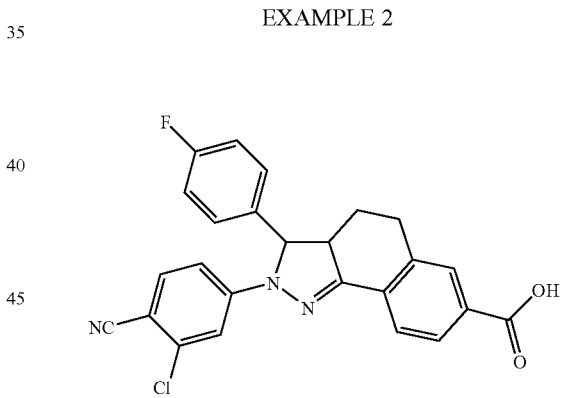

2-(3-chloro-4-cyanophenyl)-3-(4-fluorophenyl)-3,3a,4,5-tetrahydro-2H-benzo[g]indazole-7-carboxylic acid The title compound was prepared from ethyl 2-(3-chloro-4-cyanophenyl)-3-(4-fluorophenyl)-3,3a,4,5-tetrahydro-2H-benzo[g]indazole-7-carboxylate (Example 1; 330 mg, 0.696 mmol) according to Method C (yellow solid, 297 mg, 0.666 mmol, 96% yield). The title compound was largely present as (±)-(3RS,3aRS)-2-(3-chloro-4-cyanophenyl)-3-(4-fluorophenyl)-3,3a,4,5-tetrahydro-2H-benzo[g]indazole-7-carboxylic acid. $^1$H NMR (400 MHz, DMSO-$d_6$) δ ppm 0.80 (m, 1H), 1.79 (m, 1H), 2.93 (m, 2H), 3.96 (m, 1H), 5.93 (d, J=11.01 Hz, 1H), 7.15 (m, 6H), 7.66 (d, J=8.59 Hz, 1H), 7.78 (s, 1H), 7.83 (dd, J=8.19, 1.48 Hz, 1H), 8.14 (d, J=8.06 Hz, 1H), 13.07 (s, 1H). ES-MS m/z 446 (M+H).

EXAMPLE 3

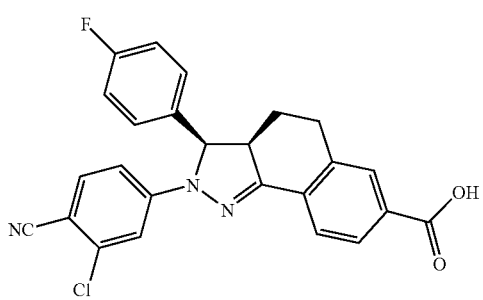

(3R,3aR)-2-(3-chloro-4-cyanophenyl)-3-(4-fluorophenyl)-3,3a,4,5-tetrahydro-2H-benzo[g]indazole-7-carboxylic acid The title compound is prepared from the 2-(3-chloro-4-cyanophenyl)-3-(4-fluorophenyl)-3,3a,4,5-tetrahydro-2H-benzo[g]indazole-7-carboxylic acid prepared in Example 2 using chiral resolution (e.g., Method G).

EXAMPLE 4

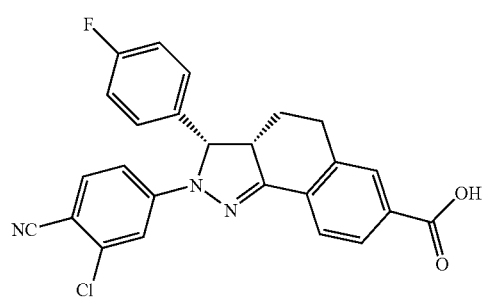

(3S,3aS)-2-(3-chloro-4-cyanophenyl)-3-(4-fluorophenyl)-3,3a,4,5-tetrahydro-2H-benzo[g]indazole-7-carboxylic acid The title compound is prepared from the 2-(3-chloro-4-cyanophenyl)-3-(4-fluorophenyl)-3,3a,4,5-tetrahydro-2H-benzo[g]indazole-7-carboxylic acid prepared in Example 2 using chiral resolution (e.g., Method G).

EXAMPLE 5

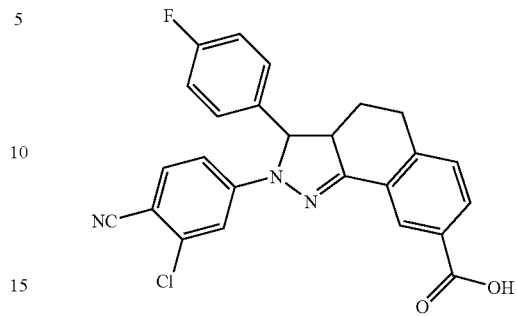

2-(3-chloro-4-cyanophenyl)-3-(4-fluorophenyl)-3,3a,4,5-tetrahydro-2H-benzo[g]indazole-8-carboxylic acid The title compound was prepared from ethyl 7-(4-fluorobenzylidene)-8-oxo-5,6,7,8-tetrahydronaphthalene-2-carboxylate (Preparation 17) and 2-chloro-4-hydrazinylbenzonitrile hydrochloride (Preparation 1) according to Method B and Method C (off-white solid, 299 mg). The title compound was largely present as (±)-(3RS,3aRS)-2-(3-chloro-4-cyanophenyl)-3-(4-fluorophenyl)-3,3a,4,5-tetrahydro-2H-benzo[g]indazole-8-carboxylic acid. $^1$H NMR (400 MHz, DMSO-$d_6$) δ ppm 0.80 (qd, J=13.02, 5.24 Hz, 1H), 1.79 (m, 1H), 2.95 (m, 2H), 3.96 (m, 1H), 5.92 (d, J=11.01 Hz, 1H), 7.15 (m, 6H), 7.35 (d, J=8.06 Hz, 1H), 7.64 (d, J=8.86 Hz, 1H), 7.86 (dd, J=8.06, 1.61 Hz, 1H), 8.57 (d, J=1.61 Hz, 1H), 13.17 (s, 1H). ES-MS m/z 446 (M+H).

EXAMPLE 6

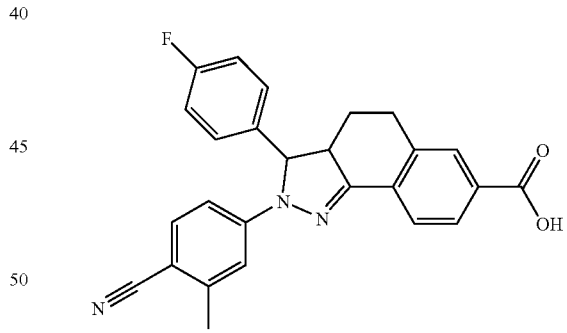

2-(4-cyano-3-methylphenyl)-3-(4-fluorophenyl)-3,3a,4,5-tetrahydro-2H-benzo[g]indazole-7-carboxylic acid The title compound was prepared from ethyl 6-(4-fluorobenzylidene)-5-oxo-5,6,7,8-tetrahydronaphthalene-2-carboxylate (Preparation 16; 324 mg, 1.0 mmol) and 4-hydrazinyl-2-methylbenzonitrile hydrochloride (Preparation 2; 275 mg, 1.5 mmol) according to Method B and Method C (solid, 290 mg, 0.68 mmol, 68% yield). The title compound was largely present as (±)-(3RS,3aRS)-2-(4-cyano-3-methylphenyl)-3-(4-fluorophenyl)-3,3a,4,5-tetrahydro-2H-benzo[g]indazole-7-carboxylic acid. $^1$H NMR (400 MHz, DMSO-$d_6$) δ ppm 0.71-0.87 (m, 1H), 1.76-1.84 (m, 1H), 2.36 (s, 3H), 2.84-3.01 (m, 2H), 3.86-3.98 (m, 1H), 5.87 (d, J=1.28 Hz, 1H), 6.65-7.36 (m, 6H), 7.48 (d, J=8.60 Hz, 1H), 7.76 (s, 1H), 7.82 (dd, J=8.19, 1.75 Hz, 1H), 8.10 (d, J=8.33 Hz, 1H). ES-MS m/z 426 (M+H).

EXAMPLE 7

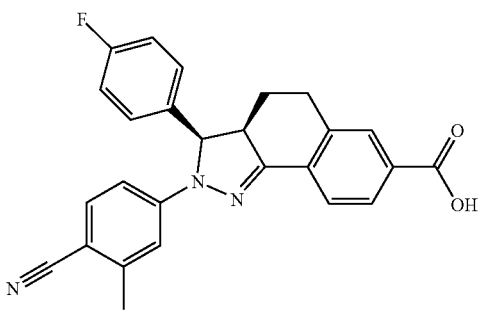

(3R,3aR)-2-(4-cyano-3-methylphenyl)-3-(4-fluorophenyl)-3,3a,4,5-tetrahydro-2H-benzo[g]indazole-7-carboxylic acid The title compound is prepared from the 2-(4-cyano-3-methylphenyl)-3-(4-fluorophenyl)-3,3a,4,5-tetrahydro-2H-benzo[g]indazole-7-carboxylic acid prepared in Example 6 using chiral resolution (e.g., Method G).

EXAMPLE 8

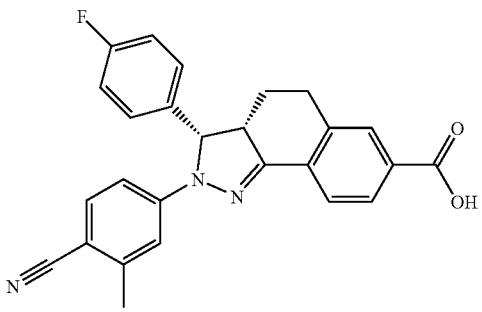

(3S,3aS)-2-(4-cyano-3-methylphenyl)-3-(4-fluorophenyl)-3,3a,4,5-tetrahydro-2H-benzo[g]indazole-7-carboxylic acid The title compound is prepared from the 2-(4-cyano-3-methylphenyl)-3-(4-fluorophenyl)-3,3a,4,5-tetrahydro-2H-benzo[g]indazole-7-carboxylic acid prepared in Example 6 using chiral resolution (e.g., Method G).

EXAMPLE 9

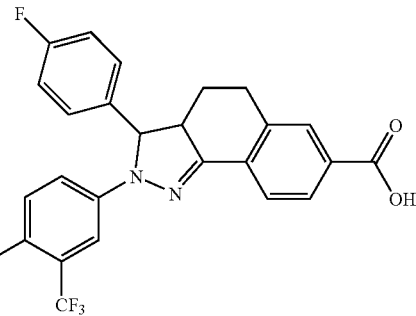

2-[4-cyano-3-(trifluoromethyl)phenyl]-3-(4-fluorophenyl)-3,3a,4,5-tetrahydro-2H-benzo[g]indazole-7-carboxylic acid The title compound was prepared from ethyl 6-(4-fluorobenzylidene)-5-oxo-5,6,7,8-tetrahydronaphthalene-2-carboxylate (Preparation 16; 324 mg, 1.0 mmol) and 4-hydrazinyl-2-(trifluoromethyl)benzonitrile hydrochloride (Preparation 3; 356 mg, 1.5 mmol) according to Method B and Method C (solid, 366 mg, 0.76 mmol, 76% yield). The title compound was largely present as (±)-(3RS,3aRS)-2-[4-cyano-3-(trifluoromethyl)phenyl]-3-(4-fluorophenyl)-3,3a,4,5-tetrahydro-2H-benzo[g]indazole-7-carboxylic acid. $^1$H NMR (400 MHz, DMSO-$d_6$) δ ppm 0.77-0.91 (m, J=13.17, 5.37 Hz, 1H), 1.75-1.84 (m, 1H), 2.94 (d, J=2.96 Hz, 2H), 3.94-4.05 (m, 1H), 6.00 (d, J=11.02 Hz, 1H), 7.15 (s, 6H), 7.79 (s, 1H), 7.81-7.88 (m, 2H), 8.15 (d, J=8.33 Hz, 1H). ES-MS m/z 480 (M+H).

EXAMPLE 10

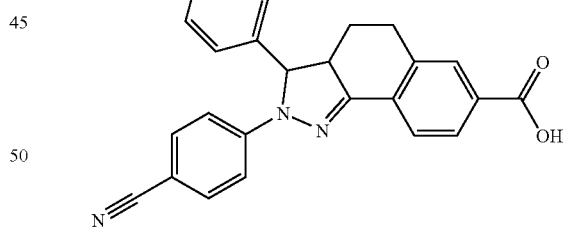

2-(4-cyanophenyl)-3-(4-fluorophenyl)-3,3a,4,5-tetrahydro-2H-benzo[g]indazole-7-carboxylic acid The title compound was prepared from ethyl 6-(4-fluorobenzylidene)-5-oxo-5,6,7,8-tetrahydronaphthalene-2-carboxylate (Preparation 16; 324 mg, 1.0 mmol) and 4-hydrazinylbenzonitrile hydrochloride (Aldrich; 254 mg, 1.5 mmol) according to Method B and Method C (solid, 294 mg, 0.72 mmol, 72% yield). The title compound was largely present as (±)-(3RS,3aRS)-2-(4-cyanophenyl)-3-(4-fluorophenyl)-3,3a,4,5-tetrahydro-2H-benzo[g]indazole-7-carboxylic acid. $^1$H NMR (400 MHz, DMSO-$d_6$) δ ppm 0.70-0.88 (m, 1H), 1.74-1.84 (m, 1H), 2.82-3.01 (m, 2H), 3.86-3.99 (m, 1H,) 5.87 (d, J=11.28 Hz, 1H), 7.13 (s, 6H), 7.57 (d, J=9.14 Hz, 2H), 7.74 (s, 1H), 7.78-7.83 (m, 1H), 8.05 (d, J=8.33 Hz, 1H). ES-MS m/z 412 (M+H).

EXAMPLE 11

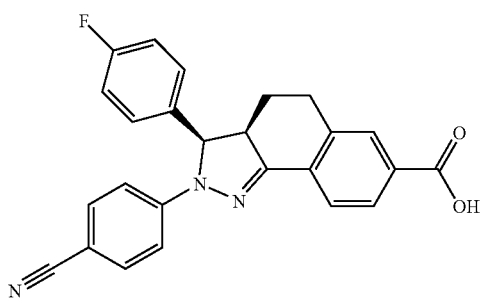

(3R,3aR)-2-(4-cyanophenyl)-3-(4-fluorophenyl)-3, 3a,4,5-tetrahydro-2H-benzo[g]indazole-7-carboxylic acid The title compound is prepared from the 2-(4-cyanophenyl)-3-(4-fluorophenyl)-3,3a,4,5-tetrahydro-2H-benzo[g]indazole-7-carboxylic acid prepared in Example 10 using chiral resolution (e.g., Method G).

EXAMPLE 12

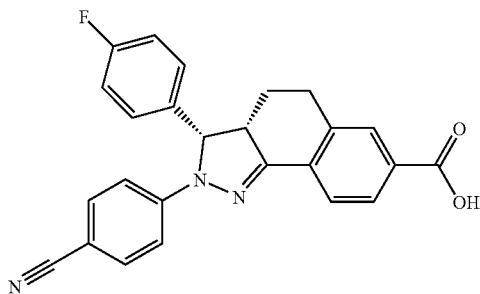

(3S,3aS)-2-(4-cyanophenyl)-3-(4-fluorophenyl)-3,3a, 4,5-tetrahydro-2H-benzo[g]indazole-7-carboxylic acid The title compound is prepared from the 2-(4-cyanophenyl)-3-(4-fluorophenyl)-3,3a,4,5-tetrahydro-2H-benzo[g]indazole-7-carboxylic acid prepared in Example 10 using chiral resolution (e.g., Method G).

EXAMPLE 13

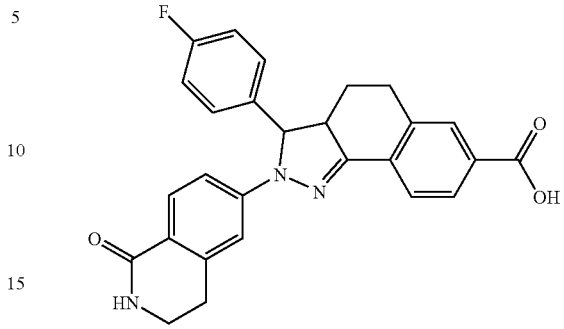

3-(4-fluorophenyl)-2-(1-oxo-1,2,3,4-tetrahydroisoquinolin-6-yl)-3,3a,4,5-tetrahydro-2H-benzo[g]indazole-7-carboxylic acid To ethyl 6-(4-fluorobenzylidene)-5-oxo-5,6,7,8-tetrahydronaphthalene-2-carboxylate (Preparation 16; 303 mg, 1.07 mmol) and 6-hydrazinyl-3,4-dihydroisoquinolin-1(2H)-one (240 mg, 1.3 mmol) (U.S. Pat. No. 6,432,974, Kelly et al., Aug. 13, 2002, intermediate 2) was added ethanol (8 mL) and 21% sodium ethoxide in ethanol (1.5 mL, 4 mmol) in a vial. The vial was flushed with argon and heated at 80° C. overnight with stirring. The reaction was quenched with 1M hydrogen chloride (8 mL) and diluted with water to give a precipitate. The precipitate was collected by vacuum filtration to give a yellow solid. The solid was dissolved in of dimethylformamide (3 mL) and purified by reverse phase chromatography with 45-75% acetonitrile/water to give (±)-3-(4-fluorophenyl)-2-(1-oxo-1,2,3,4-tetrahydroisoquinolin-6-yl)-3,3a,4,5-tetrahydro-2H-benzo[g]indazole-7-carboxylic acid as a 25/75 mixture of the cis/trans-diastereomers (290 mg, 0.68 mmol, 63% yield). ES-MS m/z 430 (M+H).

EXAMPLE 14

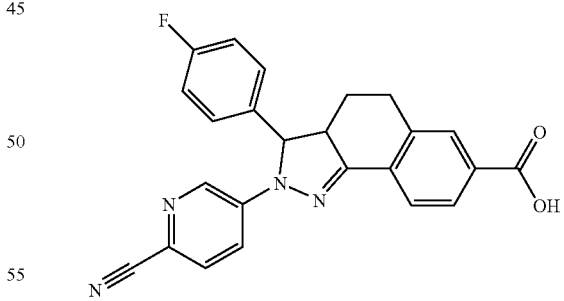

2-(6-cyanopyridin-3-yl)-3-(4-fluorophenyl)-3,3a,4,5-tetrahydro-2H-benzo[g]indazole-7-carboxylic acid trifluoroacetate The title compound was prepared from ethyl 6-(4-fluorobenzylidene)-5-oxo-5,6,7,8-tetrahydronaphthalene-2-carboxylate (Preparation 16; 0.300 g, 0.93 mmol) and 5-hydrazinylpicolinonitrile dihydrochloride (Preparation 5; 535 mg, 1.9 mmol) according to Method B and Method C. The crude precipitate was purified by reverse phase chromatography with 40-80% acetonitrile/water to give the title compound which was largely present as (±)-(3RS,3aRS)-2-(6-cyanopyridin-3-yl)-3-(4-fluorophenyl)-3,3a,4,5-tetrahydro-2H-benzo[g]indazole-7-carboxylic acid trifluoroacetate (yellow solid, 43 mg, 0.10 mmol, 11% yield). ¹H NMR (400 MHz, DMSO-d₆) δ ppm 0.75-0.91 (m, 1H), 1.74-1.87 (m, 1H), 2.84-3.06 (m, 2H), 3.91-4.04 (m, 1H), 5.96 (d, J=11.01 Hz, 1H), 6.82-7.59 (m, 5H), 7.76 (d, J=8.59 Hz, 1H), 7.79 (s, 1H), 7.84 (dd, J=8.32, 1.61 Hz, 1H), 8.14 (d, J=8.06 Hz, 1H), 8.45 (br. s., 1H), 12.93-13.19 (m, 1H). ES-MS m/z 413 (M+H).

EXAMPLE 15

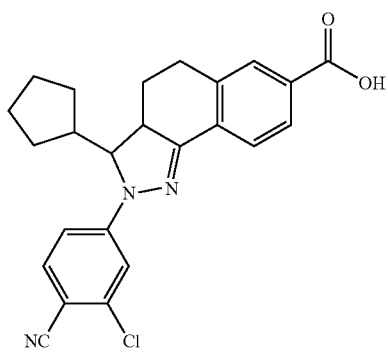

2-(3-chloro-4-cyanophenyl)-3-cyclopentyl-3,3a,4,5-tetrahydro-2H-benzo[g]indazole-7-carboxylic acid Step 1: Preparation of methyl 2-(3-chloro-4-cyanophenyl)-3-cyclopentyl-3,3a,4,5-tetrahydro-2H-benzo[g]indazole-7-carboxylate

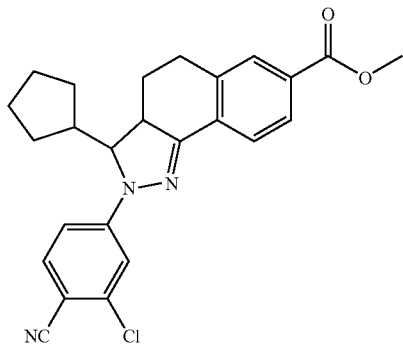

Methyl 6-(cyclopentylmethylene)-5-oxo-5,6,7,8-tetrahydronaphthalene-2-carboxylate (Preparation 18, 2.8 g, 9.9 mmol) was suspended in ethanol (100 mL) and 2-chloro-4-hydrazinylbenzonitrile hydrochloride (Preparation 1, 2.6 g, 12.8 mmol) was added. The solution was heated to 80° C. for eight hours. The solution was returned to ambient temperature. The resulting solid was collected by vacuum filtration and washed with cold ethanol to provide the title compound largely present as (±)-(3SR,3aRS)-methyl 2-(3-chloro-4-cyanophenyl)-3-cyclopentyl-3,3a,4,5-tetrahydro-2H-benzo[g]indazole-7-carboxylate (3.75 g, 87% yield). LC/MS on 4.6× 50 mm C-18 column, $t_R$=7.45 minutes (10 to 90% acetonitrile/water over 8 minutes at 2 mL/minute with detection 254 nm, at 50° C.); ES-MS m/z 434 (M+H); ¹H NMR (400 MHz, DMSO-d₆) δ ppm 1.06-1.54 (m, 6H), 1.62-1.74 (m, 1H), 1.73-1.87 (m, 1H), 1.99-2.09 (m, 1H), 2.21 (dd, J=7.79, 2.15 Hz, 1H), 2.82-2.94 (m, 2H), 3.09 (d, J=16.92 Hz, 1H), 3.54-3.66 (m, 1H), 3.84 (s, 3H), 4.95 (dd, J=9.67, 5.64 Hz, 1H), 7.19 (dd, J=9.26, 1.75 Hz, 1H), 7.39 (d, J=2.15 Hz, 1H), 7.67 (d, J=8.86 Hz, 1H), 7.82 (d, J=8.32 Hz, 1H), 7.86 (s, 1H), 8.10 (d, J=8.06 Hz, 1H).

Step 2: Preparation of 2-(3-chloro-4-cyanophenl)-3-cyclopentyl-3,3a,4,5-tetrahydro-2H-benzo[g]indazole-7-carboxylic acid

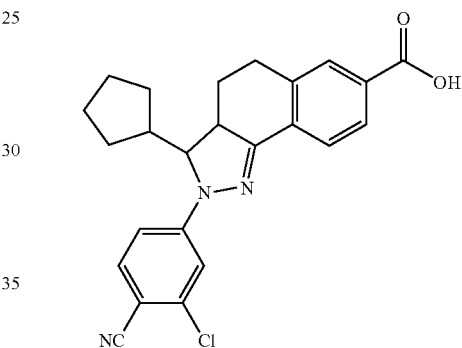

To a solution of the methyl 2-(3-chloro-4-cyanophenyl)-3-cyclopentyl-3,3a,4,5-tetrahydro-2H-benzo[g]indazole-7-carboxylate from step 1 (3.75 g, 8.6 mmol) in methanol (10 mL) and tetrahydrofuran (30 mL) was added 10% aqueous sodium hydroxide (10 mL). The solution was stirred for 20 hours at ambient temperature. The resulting slurry was concentrated to half volume and acidified to a pH of about 2 with 1M hydrochloric acid. The resulting solid was collected by vacuum filtration to provide the title compound largely present as (±)-(3SR,3aRS)-2-(3-chloro-4-cyanophenyl)-3-cyclopentyl-3,3a,4,5-tetrahydro-2H-benzo[g]indazole-7-carboxylic acid (yellow solid, 3.79 g, quantitative yield). LC/MS on 4.6×50 mm C-18 column, $t_R$=6.74 minutes (10 to 90% acetonitrile/water over 8 minutes at 2 mL/minute with detection 254 nm, at 50° C.); ES-MS m/z 420 (M+H); HRMS Calculated for $C_{24}H_{22}ClN_3O_2$: 420.1473 (M+H)⁺. Found: 420.1449; ¹H NMR (400 MHz, DMSO-d₆) δ ppm 1.10-1.55 (m, 6H), 1.64-1.75 (m, 2H), 1.75-1.87 (m, 1H), 1.99-2.09 (m, 1H), 2.15-2.23 (m, 1H), 2.78-2.91 (m, 2H), 3.00 (d, J=16.11 Hz, 1H), 4.89 (dd, J=9.26, 5.77 Hz, 1H), 7.14 (dd, J=9.00, 1.75 Hz, 1H), 7.34 (d, J=1.88 Hz, 1H), 7.63 (d, J=8.86 Hz, 1H), 7.73 (s, 1H), 7.76 (s, 1H), 7.94 (d, J=7.79 Hz, 1H).

EXAMPLE 16

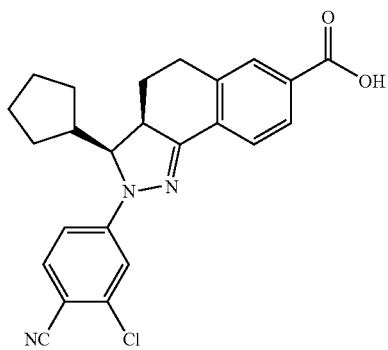

(3S,3aR)-2-(3-chloro-4-cyanophenyl)-3-cyclopentyl-3,3a,4,5-tetrahydro-2H-benzo[g]indazole-7-carboxylic acid The title compound is prepared from the 2-(3-chloro-4-cyanophenyl)-3-cyclopentyl-3,3a,4,5-tetrahydro-2H-benzo[g]indazole-7-carboxylic acid prepared in Example 15 using chiral resolution (e.g., Method G).

EXAMPLE 17

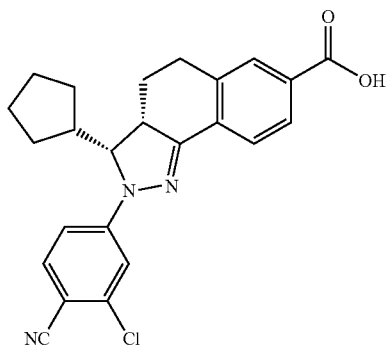

(3R,3aS)-2-(3-chloro-4-cyanophenyl)-3-cyclopentyl-3,3a,4,5-tetrahydro-2H-benzo[g]indazole-7-carboxylic acid The title compound is prepared from the 2-(3-chloro-4-cyanophenyl)-3-cyclopentyl-3,3a,4,5-tetrahydro-2H-benzo[g]indazole-7-carboxylic acid prepared in Example 15 using chiral resolution (e.g., Method G).

EXAMPLE 18

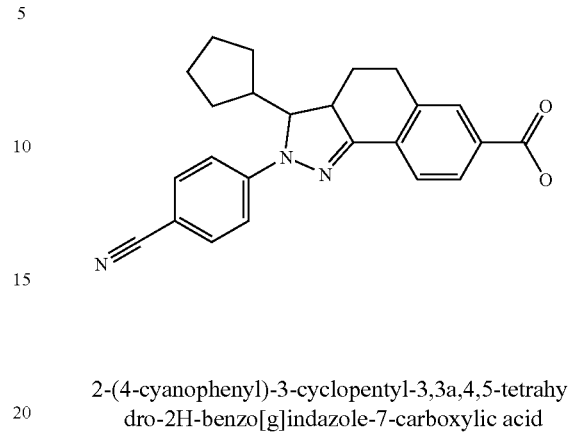

2-(4-cyanophenyl)-3-cyclopentyl-3,3a,4,5-tetrahydro-2H-benzo[g]indazole-7-carboxylic acid The title compound was prepared from Methyl 6-(cyclopentylmethylene)-5-oxo-5,6,7,8-tetrahydronaphthalene-2-carboxylate; Preparation 18 and 4-hydrazinylbenzonitrile hydrochloride (Aldrich;) according to Method B and Method C. The title compound was largely present as (±)-(3SR,3aRS)-2-(4-cyanophenyl)-3-cyclopentyl-3,3a,4,5-tetrahydro-2H-benzo[g]indazole-7-carboxylic acid. $^1$H NMR (400 MHz, DMSO-$d_6$) δ ppm 1.18-1.54 (m, 7H), 1.65-1.74 (m, 1H), 1.77-1.89 (m, 1H), 2.04-2.12 (m, 1H), 2.20-2.28 (m, 1H), 2.83-2.95 (m, 1H), 3.05-3.14 (m, 1H), 3.55-3.63 (m, 1H), 4.91 (dd, J=9.53, 5.50 Hz, 1H), 7.29 (d, J=8.86 Hz, 2H), 7.60 (d, J=8.86 Hz, 2H), 7.82 (dd, J=8.19, 1.48 Hz, 1H), 7.86 (s, 1H), 8.06 (d, J=8.06 Hz, 1H), 12.99 (br. s., 1H); HRMS m/z 386.1838 (M+H).

EXAMPLE 19

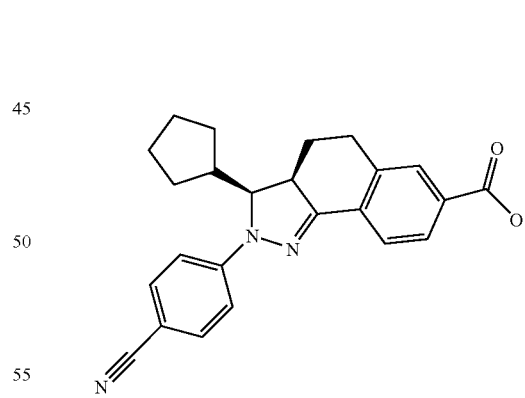

(3S,3aR)-2-(4-cyanophenyl)-3-cyclopentyl-3,3a,4,5-tetrahydro-2H-benzo[g]indazole-7-carboxylic acid The title compound is prepared from the 2-(4-cyanophenyl)-3-cyclopentyl-3,3a,4,5-tetrahydro-2H-benzo[g]indazole-7-carboxylic acid prepared in Example 18 using chitral resolution (e.g., Method G).

EXAMPLE 20

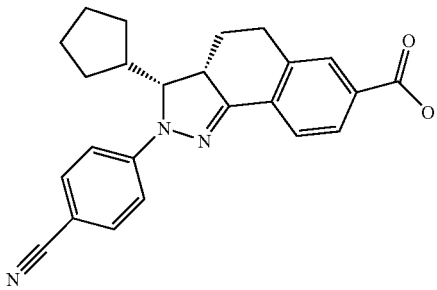

(3R,3aS)-2-(4-cyanophenyl)-3-cyclopentyl-3,3a,4,5-tetrahydro-2H-benzo[g]indazole-7-carboxylic acid The title compound is prepared from the 2-(4-cyanophenyl)-3-cyclopentyl-3,3a,4,5-tetrahydro-2H-benzo[g]indazole-7-carboxylic acid prepared in Example 18 using chitral resolution (e.g., Method G).

EXAMPLE 21

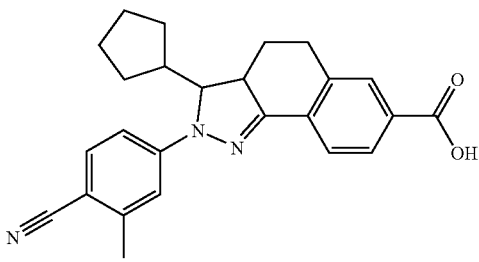

2-(4-cyano-3-methylphenyl)-3-cyclopentyl-3,3a,4,5-tetrahydro-2H-benzo[g]indazole-7-carboxylic acid The title compound was prepared from Methyl 6-(cyclopentylmethylene)-5-oxo-5,6,7,8-tetrahydronaphthalene-2-carboxylate; Preparation 18 (310.5 mg, 1.09 mmol) and 4-hydrazinyl-2-methylbenzonitrile hydrochloride; Preparation 2 (265 mg, 1.45 mmol) according to Method B and Method C (hydrolysis conducted at 60° C.). The crude precipitate was purified by reverse phase chromatography with 60-95% acetonitrile/water to give the title compound (yellow solid, 280 mg, 0.563 mmol, 64% yield). The title compound was largely present as (±)-(3SR,3aRS)-2-(4-cyano-3-methylphenyl)-3-cyclopentyl-3,3a,4,5-tetrahydro-2H-benzo[g]indazole-7-carboxylic acid. $^1$H NMR (400 MHz, DMSO-d$_6$) δ ppm 1.12-1.56 (m, 7H), 1.64-1.74 (m, 1H), 1.76-1.92 (m, J=12.89, 4.30 Hz, 1H), 2.01-2.14 (m, 1H), 2.18-2.29 (m, 1H), 2.41 (s, 3H), 2.81-2.96 (m, 1H), 3.04-3.14 (m, 1H), 3.51-3.63 (m, 1H), 4.89 (dd, J=9.67, 5.37 Hz, 1H), 7.09 (dd, J=8.59, 2.15 Hz, 1H), 7.22 (d, J=1.88 Hz, 1H), 7.52 (d, J=8.59 Hz, 1H), 7.82 (dd, J=8.19, 1.48 Hz, 1H), 7.85 (s, 1H), 8.07 (d, J=8.06 Hz, 1H), 13.01 (s, 1H). ES-MS m/z 400 (M+H).

EXAMPLE 22

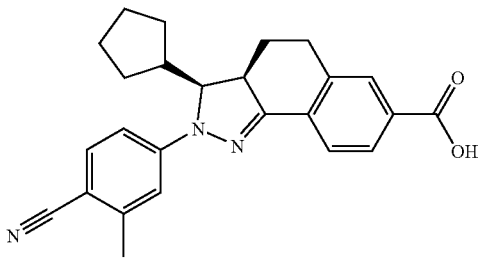

(3S,3aR)-2-(4-cyano-3-methylphenyl)-3-cyclopentyl-3,3a,4,5-tetrahydro-2H-benzo[g]indazole-7-carboxylic acid The title compound was prepared from the 2-(4-cyano-3-methylphenyl)-3-cyclopentyl-3,3a,4,5-tetrahydro-2H-benzo[g]indazole-7-carboxylic acid prepared in Example 21 using chiral resolution (e.g., Method G (Chiralcel OJ-H 30×250 mm; 50% ethanol/carbon dioxide). First eluting peak: chiral HPLC t$_R$=2.31 minutes (Chiralcel OJ-H 4.6×250 mm; 50% ethanol/carbon dioxide)).

EXAMPLE 23

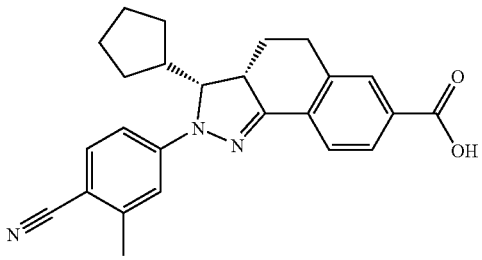

(3R,3aS)-2-(4-cyano-3-methylphenyl)-3-cyclopentyl-3,3a,4,5-tetrahydro-2H-benzo[g]indazole-7-carboxylic acid The title compound was prepared from the 2-(4-cyano-3-methylphenyl)-3-cyclopentyl-3,3a,4,5-tetrahydro-2H-benzo[g]indazole-7-carboxylic acid prepared in Example 21 using chiral resolution (e.g., Method G (Chiralcel OJ-H 30×250 mm; 50% ethanol/carbon dioxide). Second eluting peak: chiral HPLC t$_R$=3.49 minutes (Chiralcel OJ-H 4.6×250 mm; 50% ethanol/carbon dioxide)).

EXAMPLE 24

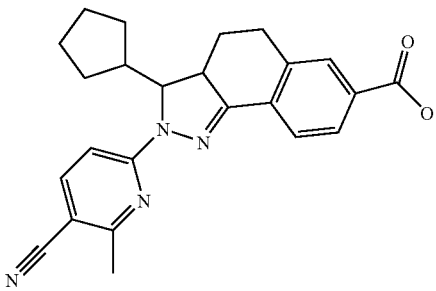

2-(5-cyano-6-methylpyridin-2-yl)-3-cyclopentyl-3,3a,4,5-tetrahydro-2H-benzo[g]indazole-7-carboxylic acid The title compound was prepared from Methyl 6-(cyclopentylmethylene)-5-oxo-5,6,7,8-tetrahydronaphthalene-2-carboxylate; Preparation 18 and 6-hydrazinyl-2-methylnicotinonitrile; Preparation 6 according to Method B and Method C. The tile compound was largely present as (±)-(3SR,3aRS)-2-(5-cyano-6-methylpyridin-2-yl)-3-cyclopentyl-3,3a,4,5-tetrahydro-2H-benzo[g]indazole-7-carboxylic acid. $^1$H NMR (400 MHz, DMSO-d$_6$) δ ppm 1.24-1.52 (m, 5H), 1.56-1.89 (m, 5H), 2.11-2.19 (m, 1H), 2.22-2.28 (m, 1H), 2.85-2.95 (m, 1H), 3.55-3.63 (m, 1H), 5.12 (dd, J=9.70, 5.67 Hz, 1H), 7.17 (d, J=8.78 Hz, 1H), 7.74-7.85 (m, 2H), 7.87 (s, 1H), 8.08 (d, J=8.05 Hz, 1H). (Missed —CH$_3$ due to DMSO overlap) HRMS m/z 401.1965 (M+H).

EXAMPLE 25

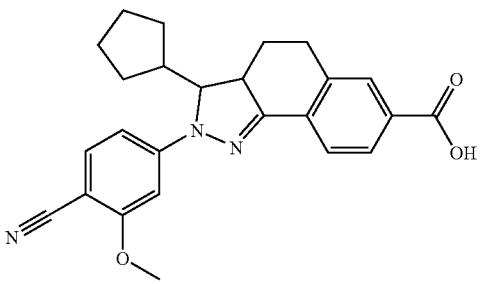

2-(4-cyano-3-methoxyphenyl)-3-cyclopentyl-3,3a,4,5-tetrahydro-2H-benzo[g]indazole-7-carboxylic acid The title compound was prepared from Methyl 6-(cyclopentylmethylene)-5-oxo-5,6,7,8-tetrahydronaphthalene-2-carboxylate; Preparation 18 (310 mg, 1.09 mmol) and 4-hydrazinyl-2-methoxybenzonitrile hydrochloride; Preparation 4 (282 mg, 1.42 mmol) according to Method B (methanol was used in place of ethanol as solvent) and Method C. The crude precipitate was purified by reverse phase chromatography with 40-95% acetonitrile/water to give the title compound (yellow solid, 220 mg, 0.53 mmol, 49% yield). The title compound was largely present as (±)-(3SR,3aRS)-2-(4-cyano-3-methoxyphenyl)-3-cyclopentyl-3,3a,4,5-tetrahydro-2H-benzo[g]indazole-7-carboxylic acid. $^1$H NMR (400 MHz, DMSO-d$_6$) δ ppm 1.34 (m, 7H), 1.65-1.90 (m, 2H), 1.99-2.12 (m, 1H), 2.18-2.27 (m, 1H), 2.82-2.95 (m, 1H), 3.04-3.13 (m, 1H), 3.52-3.63 (m, 1H), 3.90 (s, 3H), 4.94 (dd, J=9.67, 5.37 Hz, 1H), 6.80 (dd, J=8.59, 1.88 Hz, 1H), 6.90 (d, J=1.61 Hz, 1H), 7.45 (d, J=8.59 Hz, 1H), 7.81 (dd, J=8.19, 1.48 Hz, 1H), 7.85 (s, 1H), 8.08 (d, J=8.06 Hz, 1H), 13.02 (s, 1H). ES-MS m/z 416 (M+H).

EXAMPLE 26

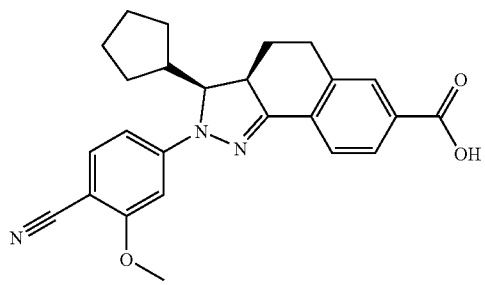

(3S,3aR)-2-(4-cyano-3-methoxyphenyl)-3-cyclopentyl-3,3a,4,5-tetrahydro-2H-benzo[g]indazole-7-carboxylic acid The title compound is prepared from the 2-(4-cyano-3-methoxyphenyl)-3-cyclopentyl-3,3a,4,5-tetrahydro-2H-benzo[g]indazole-7-carboxylic acid prepared in Example 25 using chiral resolution (e.g., Method G).

EXAMPLE 27

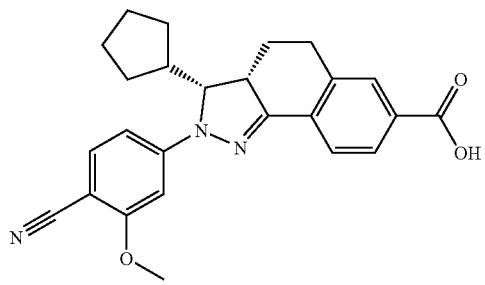

(3R,3aS)-2-(4-cyano-3-methoxyphenyl)-3-cyclopentyl-3,3a,4,5-tetrahydro-2H-benzo[g]indazole-7-carboxylic acid The title compound is prepared from the 2-(4-cyano-3-methoxyphenyl)-3-cyclopentyl-3,3a,4,5-tetrahydro-2H-benzo[g]indazole-7-carboxylic acid prepared in Example 25 using chiral resolution (e.g., Method G).

EXAMPLE 28

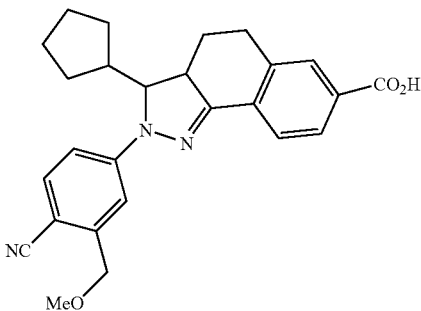

2-(4-cyano-3-(methoxymethyl)phenyl)-3-cyclopentyl-3,3a,4,5-tetrahydro-2H-benzo[g] indazole-7-carboxylic acid A mixture of 4-hydrazinyl-2-(methoxymethyl)benzonitrile hydrochloride, Methyl 6-(cyclopentylmethylene)-5-oxo-5,6,7,8-tetrahydronaphthalene-2-carboxylate; Preparation 18 (209 mg, 0.73 mmol) and ethanol (4 mL) was stirred under argon at 80° C. for four hours. The mixture was cooled to room temperature and concentrated to give ethyl 2-(4-cyano-3-(methoxymethyl)phenyl)-3-cyclopentyl-3,3a,4,5-tetrahydro-2H-benzo[g]indazole-7-carboxylate as a yellow solid. The ester was suspended in tetrahydrofuran (4 mL), methanol (1 mL) and treated with 2.5 N sodium hydroxide (1 mL) at room temperature. After four hours the mixture was concentrated to half the original volume, treated with 6 N Hydrogen chloride (2 mL), dimethylsulfoxide (24 mL) and purified by reversed-phase HPLC (acetonitrile/water/0.05% trifluoroacetic acid) to give 2-(4-cyano-3-(methoxymethyl)phenyl)-3-cyclopentyl-3,3a,4,5-tetrahydro-2H-benzo[g]indazole-7-carboxylic acid (yellow/orange solid, 65 mg, 0.015 mmol, 18% yield). The title compound was largely present as (±)-(3RS,3aSR)-2-(4-cyano-3-(methoxymethyl)phenyl)-3-cyclopentyl-3,3a,4,5-tetrahydro-2H-benzo[g]indazole-7-carboxylic acid. $^1$H NMR (400 MHz, DMSO-$d_6$) δ ppm 13.04 (s, 1H), 8.07 (d, J=8.06 Hz, 1H), 7.80-7.87 (m, 2H), 7.60 (d, J=8.86 Hz, 1H), 7.35 (d, J=2.15 Hz, 1H), 7.18 (dd, J=8.86, 2.15 Hz, 1H), 4.92 (dd, J=9.80, 5.51 Hz, 1H), 4.50 (s, 2H), 3.59 (ddd, J=13.83, 9.40, 4.70 Hz, 1H), 3.36 (s, 3H), 3.06-3.15 (m, 1H), 2.82-2.96 (m, 1H), 2.19-2.29 (m, 1H), 2.00-2.13 (m, 1H), 1.65-1.89 (m, 2H), 1.14-1.54 (m, 7H). ES-MS m/z 430 (M+H)

EXAMPLE 29

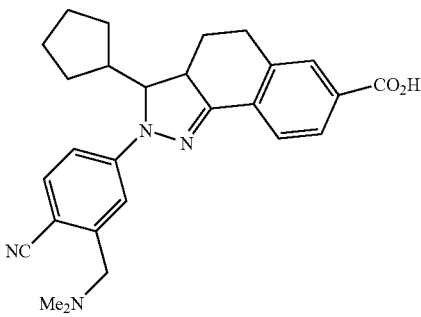

2-(4-cyano-3-((dimethylamino)methyl)phenyl)-3-cyclopentyl-3,3a,4,5-tetrahydro-2H-benzo[g]indazole-7-carboxylic acid trifluoroacetate A mixture of 2-((dimethylamino)methyl)-4-hydrazinylbenzonitrile dihydrochloride; Preparation 11 (208 mg, 1.1 mmol), Methyl 6-(cyclopentylmethylene)-5-oxo-5,6,7,8-tetrahydronaphthalene-2-carboxylate; Preparation 18 (153 mg, 0.54 mmol), and ethanol (6 mL) was stirred under argon at 80° C. for four hours. The mixture was cooled to room temperature, concentrated and purified by reversed-phase HPLC (acetonitrile/water/0.05% trifluoroacetic acid) to give methyl 2-(4-cyano-3-((dimethylamino)methyl)phenyl)-3-cyclopentyl-3,3a,4,5-tetrahydro-2H-benzo[g]indazole-7-carboxylate. The ester was dissolved in tetrahydrofuran (3 mL), methanol (1 mL) and treated with 2.5 N sodium hydroxide (1 mL) at room temperature. The mixture was stirred for 90 minutes, concentrated and the crude product purified by reversed-phase HPLC (acetonitrile/water/0.05% trifluoroacetic acid) to yield 2-(4-cyano-3-((dimethylamino)methyl)phenyl)-3-cyclopentyl-3,3a,4,5-tetrahydro-2H-benzo[g]indazole-7-carboxylic acid trifluoroacetate (yellow solid, 104 mg, 0.18 mmol, 35% yield). The title compound was largely present as (±)-(3RS,3aSR)-2-(4-cyano-3-((dimethylamino)methyl)phenyl)-3-cyclopentyl-3,3a,4,5-tetrahydro-2H-benzo[g]indazole-7-carboxylic acid trifluoroacetate. $^1$H NMR (400 MHz, DMSO-$d_6$) δ ppm 10.06 (s, 1H), 8.08 (d, J=8.06 Hz, 1H), 7.82-7.91 (m, 2H), 7.72 (d, J=8.59 Hz, 1H), 7.61 (s, 1H), 7.30 (d, J=8.32 Hz, 1H), 4.92 (dd, J=9.53, 5.50 Hz, 1H), 4.28-4.47 (m, 2H), 3.62 (ddd, J=13.56, 9.26, 4.83 Hz, 1H), 3.12 (d, J=16.11 Hz, 1H), 2.89-2.97 (m, 1H), 2.84 (s, 6H), 2.22-2.30 (m, 1H), 2.04-2.16 (m, 1H), 1.85 (ddd, J=25.91, 13.02, 3.49 Hz, 1H), 1.72 (s, 1H), 1.15-1.56 (m, 7H). ES-MS m/z 443 (M+H).

EXAMPLE 30

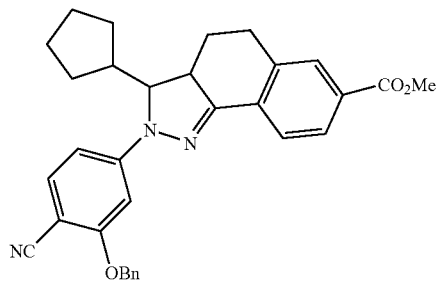

methyl 2-(3-(benzyloxy)-4-cyanophenyl)-3-cyclopentyl-3,3a,4,5-tetrahydro-2H-benzo[g]indazole-7-carboxylate A mixture of 2-(benzyloxy)-4-hydrazinylbenzonitrile; Preparation 13 (358 mg, 1.5 mmol), Methyl 6-(cyclopentylmethylene)-5-oxo-5,6,7,8-tetrahydronaphthalene-2-carboxylate; Preparation 18 (284 mg, 1.0 mmol), ethanol (7 mL), and 1 drop of concentrated hydrogen chloride was stirred under argon at 80° C. for 64 hours. The mixture was cooled to room temperature, concentrated and purified by normal phase flash column chromatography on a 40 g silica gel column (20-80% ethyl acetate/hexanes gradient). Pure fractions were pooled and concentrated in vacuo to yield methyl 2-(3-(benzyloxy)-4-cyanophenyl)-3-cyclopentyl-3,3a,4,5-tetrahydro-2H-benzo[g]indazole-7-carboxylate (yellow foam, 485 mg, 0.96 mmol, 96% yield). The title compound was largely present as (±)-(3RS,3aSR)-methyl 2-(3-(benzyloxy)-4-cyanophenyl)-3-cyclopentyl-3,3a,4,5-tetrahydro-2H-benzo[g]indazole-7-carboxylate. $^1$H NMR (400 MHz, DMSO-$d_6$) δ ppm 1.00-1.51 (m, 7H), 1.56-1.68 (m, 1H), 1.82 (ddd, J=25.85, 12.96, 3.89 Hz, 1H), 1.95-2.08 (m, 1H), 2.15-2.31 (m, 1H), 2.82-2.95 (m, 1H), 3.11 (d, J=16.38 Hz, 1H), 3.53-3.63 (m, 1H), 3.87 (s, 3H), 4.91 (dd, J=9.53, 5.50 Hz, 1H), 5.31 (q, J=12.35 Hz, 2H), 6.85 (d, J=8.32 Hz, 1H), 6.96 (s, 1H), 7.35 (t, J=7.25 Hz, 1H), 7.39-7.57 (m, 5H), 7.80-7.92 (m, 2H), 8.10 (d, J=8.32 Hz, 1H). ES-MS m/z 506 (M+H).

EXAMPLE 31

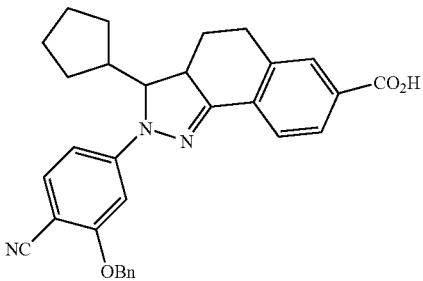

2-(3-(benzyloxy)-4-cyanophenyl)-3-cyclopentyl-3, 3a,4,5-tetrahydro-2H-benzo[g]indazole-7-carboxylic acid A mixture of methyl 2-(3-(benzyloxy)-4-cyanophenyl)-3-cyclopentyl-3,3a,4,5-tetrahydro-2H-benzo[g]indazole-7-carboxylate, Example 30, (100 mg, 0.20 mmol), tetrahydrofuran (3 mL), and methanol (1 mL) was treated with 2.5 N sodium hydroxide (1 mL) at room temperature. After 18 hours the mixture was concentrated to one-third of its original volume, diluted with water (3 mL) and treated with 2 N hydrogen chloride (2 mL). The mixture was extracted three times with ethyl acetate, dried over magnesium sulfate, filtered and concentrated to give 2-(3-(benzyloxy)-4-cyanophenyl)-3-cyclopentyl-3,3a,4,5-tetrahydro-2H-benzo[g]indazole-7-carboxylic acid (yellow/orange solid, 90 mg, 0.18 mmol, 93% yield). The title compound was largely present as (±)-(3RS,3aSR)-2-(3-(benzyloxy)-4-cyanophenyl)-3-cyclopentyl-3,3a,4,5-tetrahydro-2H-benzo[g]indazole-7-carboxylic acid. $^1$H NMR (400 MHz, DMSO-$d_6$) δ ppm 1.03-1.51 (m, 7H), 1.57-1.69 (m, 1H), 1.74-1.89 (m, 1H), 1.95-2.07 (m, 1H), 2.18-2.29 (m, 1H), 2.82-2.96 (m, 1H), 3.03-3.14 (m, 1H), 3.57 (ddd, J=13.70, 9.40, 4.30 Hz, 1H), 4.91 (dd, J=9.53, 5.50 Hz, 1H), 5.31 (q, J=12.35 Hz, 2H), 6.84 (d, J=8.86 Hz, 1H), 6.96 (s, 1H), 7.35 (t, J=7.25 Hz, 1H), 7.40-7.53 (m, 5H), 7.81-7.88 (m, 2H), 8.09 (d, J=8.06 Hz, 1H), 13.03 (s, 1H). ES-MS m/z 492 (M+H).

EXAMPLE 32

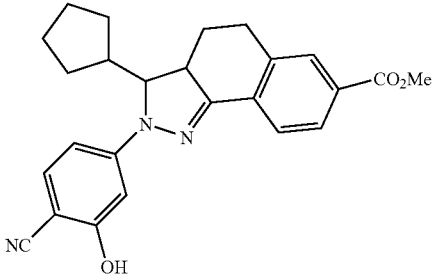

methyl 2-(4-cyano-3-hydroxyphenyl)-3-cyclopentyl-3,3a,4,5-tetrahydro-2H-benzo[g]indazole-7-carboxylate A mixture of methyl 2-(3-(benzyloxy)-4-cyanophenyl)-3-cyclopentyl-3,3a,4,5-tetrahydro-2H-benzo[g]indazole-7-carboxylate, Example 30, (345 mg, 0.68 mmol), catalytic 10% palladium on carbon, and ethyl acetate was hydrogenated at 30 psi hydrogen for three hours. The mixture was filtered through Celite and concentrated. The solid was suspended in diethyl ether/hexanes, a small amount of methanol and filtered to give methyl 2-(4-cyano-3-hydroxyphenyl)-3-cyclopentyl-3,3a,4,5-tetrahydro-2H-benzo[g]indazole-7-carboxylate (150 mg, 0.36 mmol, 53% yield). The title compound was largely present as (±)-(3RS,3aSR)-methyl 2-(4-cyano-3-hydroxyphenyl)-3-cyclopentyl-3,3a,4,5-tetrahydro-2H-benzo[g]indazole-7-carboxylate. $^1$H NMR (400 MHz, DMSO-$d_6$) δ ppm 1.10-1.58 (m, 7H), 1.60-1.90 (m, 2H), 2.06 (s, 1H), 2.16-2.30 (m, 1H), 2.79-2.95 (m, 1H), 3.05-3.15 (m, 1H), 3.58 (ddd, J=13.76, 9.47, 4.70 Hz, 1H), 3.86 (s, 3H), 4.77 (dd, J=9.67, 5.37 Hz, 1H), 6.70 (d, J=8.59 Hz, 1H), 6.82 (s, 1H), 7.36 (d, J=8.86 Hz, 1H), 7.82-7.93 (m, 2H), 8.02 (d, J=8.06 Hz, 1H), 10.70 (s, 1H). ES-MS m/z 416 (M+H).

EXAMPLE 33

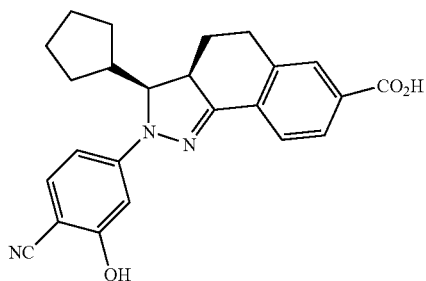

methyl 2-(4-cyano-3-hydroxyphenyl)-3-cyclopentyl-3,3a,4,5-tetrahydro-2H-benzo[g]indazole-7-carboxylate A mixture of 2-(3-(benzyloxy)-4-cyanophenyl)-3-cyclopentyl-3,3a,4,5-tetrahydro-2H-benzo[g]indazole-7-carboxylic acid (Example 31; 70 mg, 0.14 mmol), ethyl acetate, tetrahydrofuran, and methanol was treated with 10% palladium on carbon (10 mg) and hydrogenated for four hours at 30 psi hydrogen. The mixture was filtered through Celite, and concentrated to give methyl 2-(4-cyano-3-hydroxyphenyl)-3-cyclopentyl-3,3a,4,5-tetrahydro-2H-benzo[g]indazole-7-carboxylate (57 mg, 0.14 mmol) as a yellow solid. The title compound was largely present as (±)-(3RS,3aSR)-methyl 2-(4-cyano-3-hydroxyphenyl)-3-cyclopentyl-3,3a,4,5-tetrahydro-2H-benzo[g]indazole-7-carboxylate. $^1$H NMR (400 MHz, DMSO-$d_6$) δ ppm 1.10-1.58 (m, 8H), 1.61-1.75 (m, 1H), 1.74-1.90 (m, 1H), 2.00-2.12 (m, 1H), 2.16-2.30 (m, 1H), 2.79-2.96 (m, 1H), 3.09 (d, J=16.11 Hz, 1H), 3.57 (ddd, J=13.76, 9.47, 4.70 Hz, 1H), 4.76 (dd, J=9.67, 5.37 Hz, 1H), 6.69 (dd, J=8.86, 1.61 Hz, 1H), 6.82 (s, 1H), 7.36 (d, J=8.59 Hz, 1H), 7.82-7.90 (m, 2H), 8.00 (d, J=8.06 Hz, 1H), 10.70 (s, 1H). ES-MS m/z 402 (M+H).

EXAMPLE 34

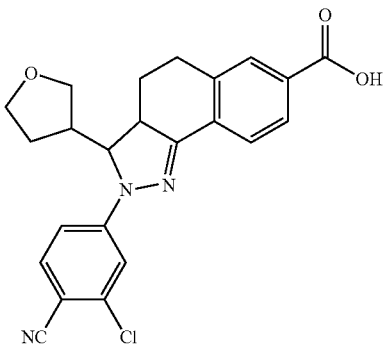

2-(3-chloro-4-cyanophenyl)-3-((R)-tetrahydrofuran-3-yl)-3,3a,4,5-tetrahydro-2H-benzo[g]indazole-7-carboxylic acid and 2-(3-chloro-4-cyanophenyl)-3-((S)-tetrahydrofuran-3-yl)-3,3a,4,5-tetrahydro-2H-benzo[g]indazole-7-carboxylic acid The title compounds were prepared according to Method B and Method C from (±)-methyl 5-oxo-6-((tetrahydrofuran-3-yl)methylene)-5,6,7,8-tetrahydronaphthalene-2-carboxylate (Preparation 20) and 2-chloro-4-hydrazinylbenzonitrile hydrochloride (Preparation 1), yielding a yellow solid (167 mg, quantitative yield). The title compounds were largely present as (±)-(3RS,3aRS)-2-(3-chloro-4-cyanophenyl)-3-((R)-tetrahydrofuran-3-yl)-3,3a,4,5-tetrahydro-2H-benzo[g]indazole-7-carboxylic acid and (±)-(3RS,3aRS)-2-(3-chloro-4-cyanophenyl)-3-((S)-tetrahydrofuran-3-yl)-3,3a,4,5-tetrahydro-2H-benzo[g]indazole-7-carboxylic acid, respectively. LC/MS on 4.6×50 mm C-18 column, $t_R$=4.93 minutes (10 to 90% acetonitrile/water over 6 minutes at 2 mL/minute with detection 254 nm, at 50° C.); ES-MS m/z 422 (M+H); HRMS Calculated for $C_{23}H_{20}ClN_3O_3$: 422.1266 (M+H)$^+$. Found: 422.1257; $^1$H NMR (400 MHz, DMSO-$d_6$) δ ppm 1.51-1.99 (m, 3H) 2.11-2.27 (m, 1H) 2.91 (dd, J=12.35, 4.03 Hz, 1H) 3.03-3.13 (m, 1H) 3.38-3.47 (m, 1H) 3.49-3.57 (m, 1H) 3.58-3.69 (m, 1H) 3.73 (t, J=8.06 Hz, 1H) 3.77-3.85 (m, 1H) 4.75-4.83 (m, 1H) 4.99 (dd, J=9.40, 6.71 Hz, 1H) 7.18 (td, J=8.59, 2.15 Hz, 1H) 7.39 (dd, J=18.80, 2.15 Hz, 1H) 7.69 (dd, J=8.86, 5.10 Hz, 1H) 7.80 (d, J=8.06 Hz, 1H) 7.84 (s, 1H) 8.08 (d, J=8.32 Hz, 1H) 13.07 (br. s., 1H).

EXAMPLE 35

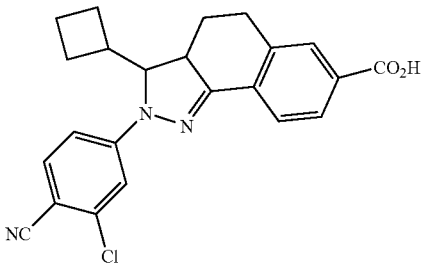

2-(3-chloro-4-cyanophenyl)-3-cyclobutyl-3,3a,4,5-tetrahydro-2H-benzo[g] indazole-7-carboxylic acid The title compound was prepared according to Method B and Method C from methyl 6-(cyclobutylmethylene)-5-oxo-5,6,7,8-tetrahydronaphthalene-2-carboxylate; Preparation 19 and 2-chloro-4-hydrazinylbenzonitrile hydrochloride (Preparation 1) to give 2-(3-chloro-4-cyanophenyl)-3-cy-clobutyl-3,3a,4,5-tetrahydro-2H-benzo[g]indazole-7-carboxylic acid (150 mg, 0.36 mmol, 65% yield) as a yellow solid. The title compound was largely present as (±)-(3RS,3aSR)-2-(3-chloro-4-cyanophenyl)-3-cyclobutyl-3,3a,4,5-tetrahydro-2H-benzo[g]indazole-7-carboxylic acid. $^1$H NMR (400 MHz, DMSO-$d_6$) δ ppm 1.56-1.77 (m, 4H), 1.77-1.98 (m, 3H), 2.07-2.18 (m, 1H), 2.51-2.59 (m, 1H), 2.80-2.93 (m, 1H), 2.97-3.07 (m, 1H), 3.44-3.56 (m, 1H), 4.88 (dd, J=9.40, 6.98 Hz, 1H), 7.22 (dd, J=8.86, 1.88 Hz, 1H), 7.42 (d, J=2.15 Hz, 1H), 7.67 (d, J=8.86 Hz, 1H), 7.75-7.83 (m, 2H), 8.01 (d, J=8.06 Hz, 1H). ES-MS m/z 420 (M+H)

EXAMPLE 36

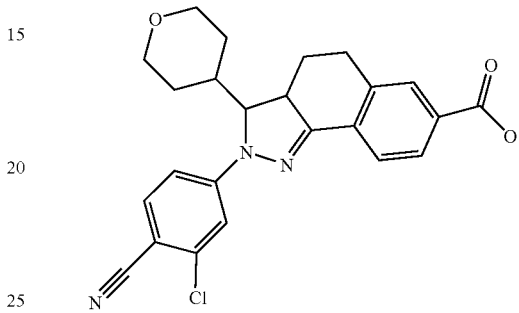

2-(3-chloro-4-cyanophenyl)-3-(tetrahydro-2H-pyran-4-yl)-3,3a,4,5-tetrahydro-2H-benzo[g]indazole-7-carboxylic acid The title compound was prepared from methyl 5-oxo-6-((tetrahydro-2H-pyran-4-yl)methylene)-5,6,7,8-tetrahydronaphthalene-2-carboxylate; Preparation 21, and 2-chloro-4-hydrazinylbenzonitrile hydrochloride (Preparation 1) according to Method B and Method C. The title compound was largely present as (±)-(3SR,3aRS)-2-(3-chloro-4-cyanophenyl)-3-(tetrahydro-2H-pyran-4-yl)-3,3a,4,5-tetrahydro-2H-benzo[g]indazole-7-carboxylic acid. $^1$H NMR (400 MHz, DMSO-$d_6$) δ ppm 1.24-1.33 (m, 2H), 1.40 (ddd, J=24.57, 12.08, 4.70 Hz, 1H), 1.50-1.57 (m, 1H), 1.86-1.99 (m, 2H), 2.25-2.32 (m, 1H), 2.85-2.95 (m, 1H), 3.07-3.20 (m, 3H), 3.61-3.79 (m, 3H), 4.83 (dd, J=9.67, 3.76 Hz, 1H), 7.21 (d, J=8.86 Hz, 1H), 7.44 (d, J=1.61 Hz, 1H), 7.71 (d, J=8.59 Hz, 1H), 7.83 (dd, J=8.32, 1.34 Hz, 1H), 7.87 (s, 1H), 8.09 (d, J=8.32 Hz, 1H), 13.07 (s, 1H); HRMS m/z 436.1445 (M+H).

EXAMPLE 37

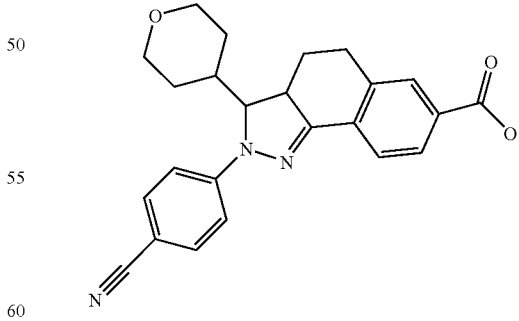

2-(4-cyanophenyl)-3-(tetrahydro-2H-pyran-4-yl)-3,3a,4,5-tetrahydro-2H-benzo[g]indazole-7-carboxylic acid The title compound was prepared from methyl 5-oxo-6-((tetrahydro-2H-pyran-4-yl)methylene)-5,6,7,8-tetrahydronaphthalene-2-carboxylate; Preparation 21 and 4-hydrazinylbenzonitrile hydrochloride (Aldrich) according to Method B and Method C. The title compound was largely present as (±)-(3SR,3aRS)-2-(4-cyanophenyl)-3-(tetrahydro-2H-pyran-4-yl)-3,3a,4,5-tetrahydro-2H-benzo[g]indazole-7-carboxylic acid. $^1$H NMR (400 MHz, DMSO-$d_6$) δ ppm 1.25-1.33 (m, 2H), 1.41 (ddd, J=24.64, 12.29, 4.43 Hz, 1H), 1.48-1.55 (m, 1H), 1.87-1.99 (m, 2H), 2.25-2.33 (m, 1H), 2.84-2.95 (m, 1H), 3.07-3.20 (m, 3H), 3.57-3.68 (m, 1H), 3.68-3.78 (m, 2H), 4.78 (dd, J=9.94, 3.49 Hz, 1H), 7.30 (d, J=8.86 Hz, 2H), 7.63 (d, J=8.86 Hz, 2H), 7.82 (dd, J=8.19, 1.48 Hz, 1H), 7.86 (s, 1H), 8.05 (d, J=8.06 Hz, 1H), 13.03 (br. s., 1H); HRMS m/z 402.1838 (M+H).

EXAMPLE 38

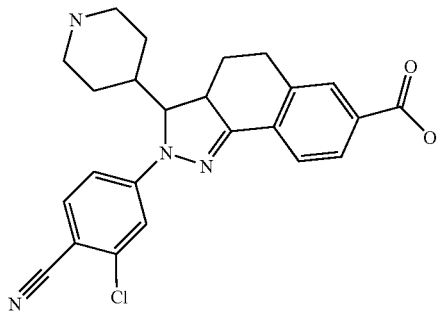

2-(3-chloro-4-cyanophenyl)-3-(piperidin-4-yl)-3,3a,4,5-tetrahydro-2H-benzo[g]indazole-7-carboxylic acid trifluoroacetate The title compound was prepared from tert-butyl 4-((6-(methoxycarbonyl)-1-oxo-3,4-dihydronaphthalen-2(1H)-ylidene)methyl)piperidine-1-carboxylate; Preparation 22 and 2-chloro-4-hydrazinylbenzonitrile hydrochloride (Preparation 1) according to Method B and Method C. The title compound was largely present as (±)-(3SR,3aRS)-2-(3-chloro-4-cyanophenyl)-3-(piperidin-4-yl)-3,3a,4,5-tetrahydro-2H-benzo[g]indazole-7-carboxylic acid trifluoroacetate. $^1$H NMR (400 MHz, DMSO-$d_6$) δ ppm 1.36-1.60 (m, 3H), 1.91-1.99 (m, 2H), 2.07-2.14 (m, 1H), 2.80-2.96 (m, 2H), 3.03-3.09 (m, 2H), 3.22-3.28 (m, 1H), 3.32-3.41 (m, 3H), 4.35 (dd, J=8.06, 4.03 Hz, 1H), 7.24 (dd, J=8.86, 2.15 Hz, 1H), 7.41 (d, J=2.15 Hz, 1H), 7.78 (d, J=8.86 Hz, 1H), 7.82 (dd, J=8.32, 1.34 Hz, 1H), 7.84 (s, 1H), 7.91 (d, J=8.06 Hz, 1H), 8.08-8.18 (m, 1H), 8.52-8.59 (m, 1H), 13.10 (br. s., 1H); HRMS m/z 435.1589 (M+H).

EXAMPLE 39

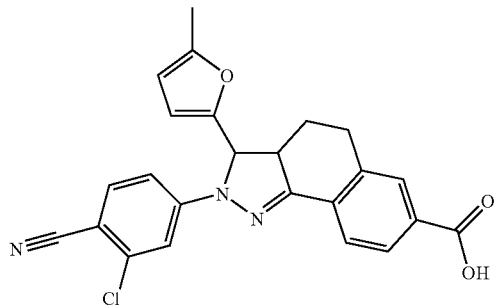

2-(3-chloro-4-cyanophenyl)-3-(5-methyl-2-furyl)-N-[2-(methylsulfonyl)ethyl]-3,3a,4,5-tetrahydro-2H-benzo[g]indazole-7-carboxylic acid The title compound was prepared from methyl 6-(5-methyl-2-furylmethylene)-5-oxo-5,6,7,8-tetrahydronaphthalene-2-carboxylate; Preparation 23 (444 mg, 1.5 mmol) and 2-chloro-4-hydrazinylbenzonitrile hydrochloride; Preparation 1 (303 mg, 1.5 mmol) according to Method B and Method C. The title compound was largely present as (±)-(3RS,3aRS)-2-(3-chloro-4-cyanophenyl)-3-(5-methyl-2-furyl)-N-[2-(methylsulfonyl)ethyl]-3,3a,4,5-tetrahydro-2H-benzo[g]indazole-7-carboxylic acid. $^1$H NMR (400 MHz, DMSO-$d_6$) δ ppm 1.20-1.27 (m, 1H), 1.93 (dt, J=8.11, 4.35 Hz, 1H), 2.10 (s, 3H), 2.99 (d, J=5.47 Hz, 2H), 3.90 (td, J=12.21, 4.88 Hz, 1H), 5.93 (d, J=10.94 Hz, 1H), 5.97 (d, J=2.34 Hz, 1H), 6.30 (d, J=3.12 Hz, 1H), 7.10 (br. s., 1H) 7.35 (br. s., 1H), 7.70 (d, J=8.59 Hz, 1H), 7.83-7.86 (m, 2H), 8.12 (d, J=8.59 Hz, 1H) 13.07 (s, 1H). ES-MS m/z 432 (M+H).

EXAMPLE 40

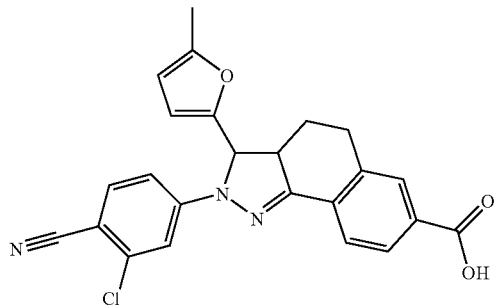

(3R,3aR)-2-(3-chloro-4-cyanophenyl)-3-(5-methyl-2-furyl)-3,3a,4,5-tetrahydro-2H-benzo[g]indazole-7-carboxylic acid The title compound is prepared from the 2-(3-chloro-4-cyanophenyl)-3-(5-methyl-2-furyl)-N-[2-(methylsulfonyl)ethyl]-3,3a,4,5-tetrahydro-2H-benzo[g]indazole-7-carboxy-

EXAMPLE 41

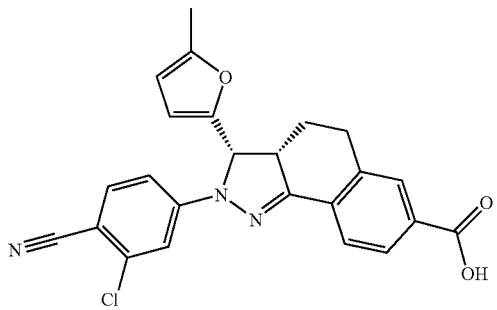

(3S,3aS)-2-(3-chloro-4-cyanophenyl)-3-(5-methyl-2-furyl)-3,3a,4,5-tetrahydro-2H-benzo[g]indazole-7-carboxylic acid The title compound was prepared from (±)-(3RS,3aRS)-2-(3-chloro-4-cyanophenyl)-3-(5-methyl-2-furyl)-N-[2-(methylsulfonyl)ethyl]-3,3a,4,5-tetrahydro-2H-benzo[g]indazole-7-carboxylic acid, Example 39, according to Method G.

EXAMPLE 42

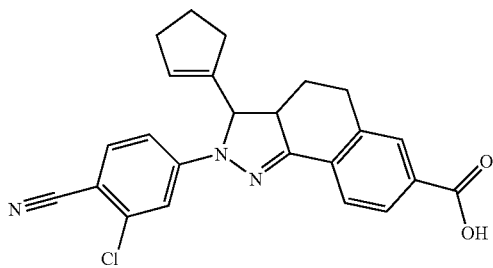

2-(3-chloro-4-cyanophenyl)-3-cyclopentenyl-3,3a,4,5-tetrahydro-2H-benzo[g]indazole-7-carboxylic acid The title compound was prepared from methyl 6-(cyclopent-1-en-1-ylmethylene)-5-oxo-5,6,7,8-tetrahydronaphthalene-2-carboxylate; Preparation 24 (268 mg, 1.0 mmol) and 2-chloro-4-hydrazinylbenzonitrile hydrochloride; Preparation 1 (303 mg, 1.5 mmol) according to Method B and Method C. The title compound was largely present as (±)-(3RS,3aRS)-2-(3-chloro-4-cyanophenyl)-3-cyclopentenyl-3,3a,4,5-tetrahydro-2H-benzo[g]indazole-7-carboxylic acid. $^1$H NMR (400 MHz, DMSO-$d_6$) δ ppm 1.52 (dd, J=13.09, 5.67 Hz, 1H), 1.73 (dt, J=17.59, 6.64 Hz, 2H), 1.85 (m, 1H), 1.90-2.00 (m, 1H), 2.07 (s, 1H), 2.10 (dt, J=5.86, 3.71 Hz, 1H), 2.22 (br. s., 2H), 2.99-3.06 (m, 2H), 3.71-3.77 (m, 1H), 5.48 (d, J=10.55 Hz, 1H), 5.69 (br. s., 1H), 7.72 (d, J=8.60 Hz, 1H), 7.83 (d, J=8.21 Hz, 1H), 7.85 (s, 1H), 8.09 (d, J=8.21 Hz, 1H); ES-MS m/z 418 (M+H).

EXAMPLE 43

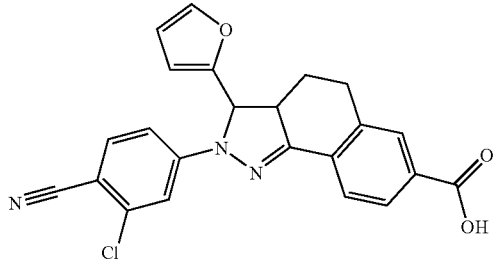

2-(3-chloro-4-cyanophenyl)-3-(2-furyl)-3,3a,4,5-tetrahydro-2H-benzo[g]indazole-7-carboxylic acid The title compound was prepared from methyl 6-(2-furylmethylene)-5-oxo-5,6,7,8-tetrahydronaphthalene-2-carboxylate; Preparation 25 (268 mg, 1.0 mmol) and 2-chloro-4-hydrazinylbenzonitrile hydrochloride; Preparation 1 (254 mg, 1.25 mmol) according to Method B and Method C. The title compound was largely present as (±)-(3RS,3aRS)-2-(3-chloro-4-cyanophenyl)-3-(2-furyl)-3,3a,4,5-tetrahydro-2H-benzo[g]indazole-7-carboxylic acid. $^1$H NMR (400 MHz, DMSO-$d_6$) δ ppm 1.12 (br. s., 1H), 1.94 (d, J=4.10 Hz, 1H), 2.98 (br. s., 2H), 3.93 (td, J=12.06, 4.98 Hz, 1H), 6.02 (d, J=10.74 Hz, 1H), 6.38 (dd, J=3.22, 1.86 Hz, 1H), 6.46 (d, J=3.12 Hz, 1H), 7.11 (br. s., 1H), 7.35 (br. s., 1H), 7.53 (d, J=0.98 Hz, 1H), 7.70 (d, J=8.79 Hz, 1H), 7.83-7.85 (m, 2H), 8.12 (d, J=8.20 Hz, 1H); ES-MS m/z 418 (M+H).

EXAMPLE 44

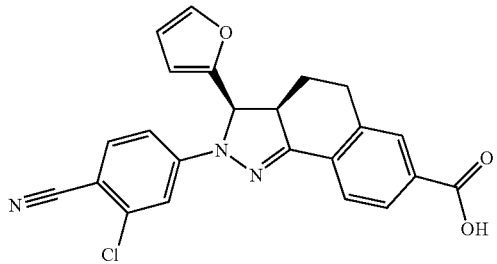

(3R,3aR)-2-(3-chloro-4-cyanophenyl)-3-(2-furyl)-3,3a,4,5-tetrahydro-2H-benzo[g]indazole-7-carboxylic acid The title compound is prepared from the 2-(3-chloro-4-cyanophenyl)-3-(2-furyl)-3,3a,4,5-tetrahydro-2H-benzo[g]indazole-7-carboxylic acid prepared in Example 43 using chiral resolution (e.g., Method G). ES-MS m/z 418 (M+H).

EXAMPLE 45

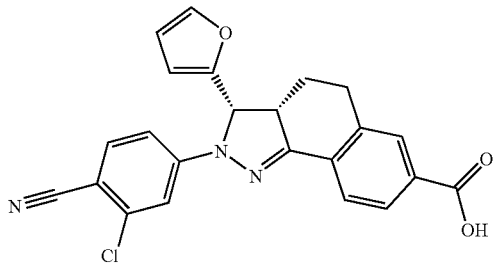

(3S,3aS)-2-(3-chloro-4-cyanophenyl)-3-(2-furyl)-3,3a,4,5-tetrahydro-2H-benzo[g]indazole-7-carboxylic acid The title compound is prepared from the 2-(3-chloro-4-cyanophenyl)-3-(2-furyl)-3,3a,4,5-tetrahydro-2H-benzo[g]indazole-7-carboxylic acid prepared in Example 43 using chiral resolution (e.g., Method G).

EXAMPLE 46

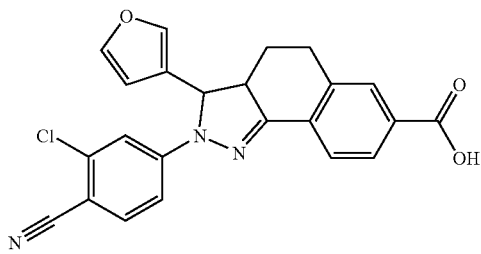

2-(3-chloro-4-cyanophenyl)-3-(3-furyl)-3,3a,4,5-tetrahydro-2H-benzo[g]indazole-7-carboxylic acid The title compound was prepared from methyl 6-(3-furylmethylene)-5-oxo-5,6,7,8-tetrahydronaphthalene-2-carboxylate, Preparation 26 (268 mg, 1.0 mmol) and 2-chloro-4-hydrazinylbenzonitrile hydrochloride; Preparation 1 (254 mg, 1.25 mmol) according to Method B and Method C. The title compound was largely present as (±)-(3RS,3aRS)-2-(3-chloro-4-cyanophenyl)-3-(3-furyl)-3,3a,4,5-tetrahydro-2H-benzo[g]indazole-7-carboxylic acid. $^1$H NMR (400 MHz, DMSO-$d_6$) δ ppm 1.21 (br. s., 1H), 1.91 (d, J=5.08 Hz, 1H), 3.00 (d, J=2.73 HZ, 2H), 3.85 (ddd, J=13.38, 10.64, 4.88 Hz, 1H), 5.89 (d, J=10.94 Hz, 1H), 6.08 (s, 1H), 7.05 (br. s., 1H), 7.32 (br. s., 1H), 7.56 (s, 1H), 7.63 (s, 1H), 7.69 (d, J=8.59 Hz, 1H), 7.82-7.89 (m, 2H), 8.13 (d, J=8.20 Hz, 1H), 13.06 (br. s., 1H); ES-MS m/z 418 (M+H).

EXAMPLE 47

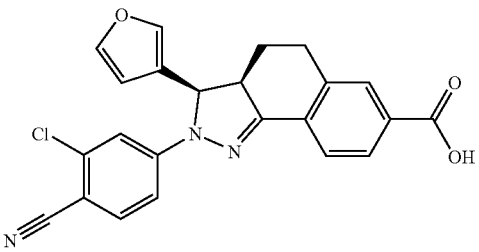

(3R,3aR)-2-(3-chloro-4-cyanophenyl)-3-(3-furyl)-3,3a,4,5-tetrahydro-2H-benzo[g]indazole-7-carboxylic acid The title compound is prepared from the 2-(3-chloro-4-cyanophenyl)-3-(3-furyl)-3,3a,4,5-tetrahydro-2H-benzo[g]indazole-7-carboxylic acid prepared in Example 46 using chiral resolution (e.g., Method G). ES-MS m/z 418 (M+H).

EXAMPLE 48

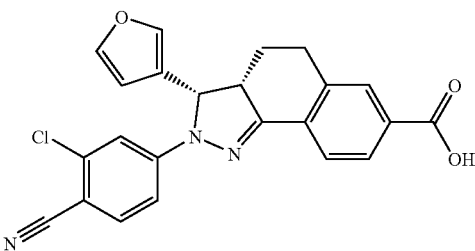

(3S,3aS)-2-(3-chloro-4-cyanophenyl)-3-(3-furyl)-3,3a,4,5-tetrahydro-2H-benzo[g]indazole-7-carboxylic acid The title compound is prepared from the 2-(3-chloro-4-cyanophenyl)-3-(3-furyl)-3,3a,4,5-tetrahydro-2H-benzo[g]indazole-7-carboxylic acid prepared in Example 46 using chiral resolution (e.g., Method G).

EXAMPLE 49

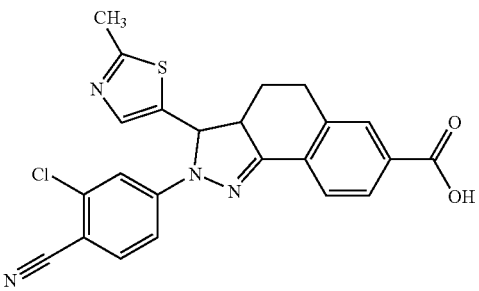

2-(3-chloro-4-cyanophenyl)-3-(2-methyl-1,3-thiazol-5-yl)-3,3a,4,5-tetrahydro-2H-benzo[g]indazole-7-carboxylic acid The title compound was prepared from methyl 6-[(2-methyl-1,3-thiazol-5-yl)methylene]-5-oxo-5,6,7,8-tetrahydronaphthalene-2-carboxylate; Preparation 27 (469 mg, 1.5 mmol) and 2-chloro-4-hydrazinylbenzonitrile hydrochloride; Preparation 1 (303 mg, 1.5 mmol) according to Method B and Method C. The title compound was largely present as (±)-(3RS,3aRS)-2-(3-chloro-4-cyanophenyl)-3-(2-methyl-1,3-thiazol-5-yl)-3,3a,4,5-tetrahydro-2H-benzo[g]indazole-7-carboxylic acid. $^1$H NMR (400 MHz, DMSO-d$_6$) δ ppm 1.22 (s, 1H), 1.94 (dt, J=7.91, 4.44 Hz, 1H), 2.50 (s, 3H), 2.99 (d, J=5.47 Hz, 2H), 3.95 (br. s., 1H), 6.32 (d, J=10.55 Hz, 1H), 7.11 (br. s., 1H), 7.38 (br. s., 1H), 7.64 (s, 1H), 7.72 (d, J=8.59 Hz, 1H), 7.82-7.87 (m, 2H), 8.15 (d, J=8.20 Hz, 1H); ES-MS m/z 449 (M+H).

EXAMPLE 50

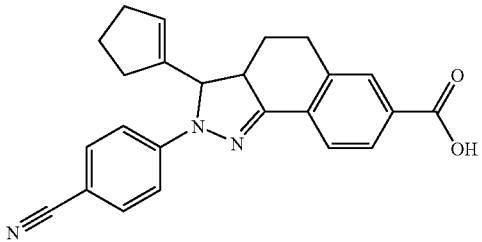

2-(4-cyanophenyl)-3-cyclopent-1-en-1-yl-3,3a,4,5-tetrahydro-2H-benzo[g]indazole-7-carboxylic acid The title compound was prepared from methyl 6-(cyclopent-1-en-1-ylmethylene)-5-oxo-5,6,7,8-tetrahydronaphthalene-2-carboxylate; Preparation 24 (268 mg, 1.0 mmol) and 4-hydrazinylbenzonitrile hydrochloride (Aldrich; 254 mg, 1.5 mmol) according to Method B and Method C. The title compound was largely present as (±)-(3RS,3aRS)-2-(4-cyanophenyl)-3-cyclopent-1-en-1-yl-3,3a,4,5-tetrahydro-2H-benzo[g]indazole-7-carboxylic acid. $^1$H NMR (400 MHz, DMSO-d$_6$) δ ppm 1.51 (dd, J=13.28, 5.47 Hz, 1H), 1.66 (dt, J=7.32, 3.96 Hz, 1H), 1.75 (d, J=5.47 Hz, 1H), 1.79 (br. s., 1H), 1.97 (br. s., 1H), 2.10 (dd, J=8.79, 3.71 Hz, 1H), 2.21 (br. s., 2H), 2.98-3.04 (m, 2H), 3.67-3.74 (m, –1H), 5.44 (d, J=10.55 Hz, 1H), 5.65 (s, 1H), 7.16 (br. s., 2H), 7.63 (d, J=8.98 Hz, 2H), 7.81-7.85 (m, 2H), 8.05 (d, J=8.20 Hz, 1H); ES-MS m/z 384 (M+H).

EXAMPLE 51

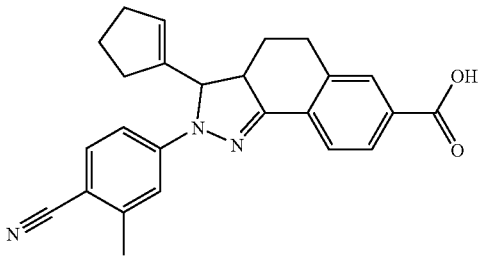

2-(4-cyano-3-methylphenyl)-3-cyclopentenyl-3,3a,4,5-tetrahydro-2H-benzo[g]indazole-7-carboxylic acid The title compound was injustices prepared from methyl 6-(cyclopent-1-en-1-ylmethylene)-5-oxo-5,6,7,8-tetrahydronaphthalene-2-carboxylate; Preparation 24 and 4-hydrazinyl-2-methylbenzonitrile hydrochloride; Preparation 2 according to Method B and Method C. The title compound was largely present as (±)-(3RS,3aRS)-2-(4-cyano-3-methylphenyl)-3-cyclopentenyl-3,3a,4,5-tetrahydro-2H-benzo[g]indazole-7-carboxylic acid. $^1$H NMR (400 MHz, DMSO-d$_6$) δ ppm 1.36-1.85 (m, 4H), 1.88-2.12 (m, 2H), 2.18 (s, 2H), 2.38 (s, 3H), 2.99 (d, J=4.0 Hz, 2H), 3.55-3.75 (m, 1H), 5.39 (d, J=10.7 Hz, 1H), 5.62 (s, 1H), 6.86 (br. s., 1H), 7.13 (br. s., 1H), 7.52 (d, J=8.6 Hz, 1H), 7.69-7.89 (m, 2H), 8.03 (d, J=7.8 Hz, 1H), 12.99 (s, 1H); ES-MS m/z 398 (M+H).

EXAMPLE 52

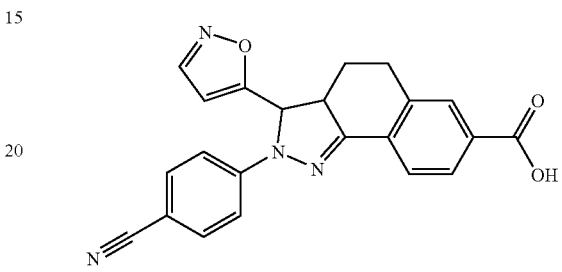

2-(4-cyanophenyl)-3-isoxazol-5-yl-3,3a,4,5-tetrahydro-2H-benzo[g]indazole-7-carboxylic acid The title compound was prepared from methyl 6-(isoxazol-5-ylmethylene)-5-oxo-5,6,7,8-tetrahydronaphthalene-2-carboxylate; Preparation 28 (268 mg, 1.0 mmol) and 4-hydrazinylbenzonitrile hydrochloride (Aldrich; 254 mg, 1.5 mmol) according to Method B and Method C. The title compound was largely present as (±)-(3RS,3aRS)-2-(4-cyanophenyl)-3-isoxazol-5-yl-3,3a,4,5-tetrahydro-2H-benzo[g]indazole-7-carboxylic acid. $^1$H NMR (400 MHz, DMSO-d$_6$) δ ppm 1.00-1.26 (m, 1H), 1.97 (d, J=13.67 Hz, 1H), 2.99 (dd, J=6.64, 2.73 Hz, 1H), 4.06 (d, J=4.69 Hz, 1H), 6.12 (d, J=111.33 Hz, 1H), 6.28 (s, 1H), 7.12 (d, J=7.42 Hz, 2H), 7.63 (d, J=8.98 Hz, 2H), 7.82-7.86 (m, 3H), 8.09 (d, J=8.20 Hz, 1H), 8.84 (s, 1H), 13.05 (s, 1H); ES-MS m/z 385 (M+H).

EXAMPLE 53

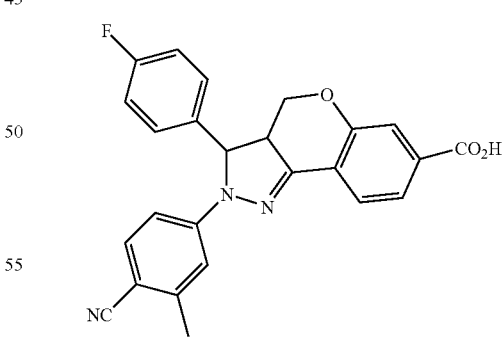

(±)-(3SR,3aSR)-2-(4-cyano-3-methylphenyl)-3-(4-fluorophenyl)-2,3,3a,4-tetrahydrochromeno[4,3-c]pyrazole-7-carboxylic acid The title compound was prepared from methyl 3-(4-fluorobenzylidene)-4-oxochroman-7-carboxylate; Preparation 30 and 4-hydrazinyl-2-methylbenzonitrile hydrochloride (Preparation 2) according to Method B and Method C (yellow solid, 32 mg, 0.07 mmol, 15% yield). The title compound was largely present as (±)-(3SR,3aSR)-2-(4-cyano-3-methylphenyl)-3-(4-fluorophenyl)-2,3,3a,4-tetrahydrochromeno[4,3-c]pyrazole-7-carboxylic acid. $^1$H NMR (400 MHz, DMSO-$d_6$) δ ppm 2.37 (s, 3H), 3.16 (dd, J=12.49, 10.61 Hz, 1H), 4.19-4.31 (m, 1H), 4.39 (dd, J=10.47, 5.91 Hz, 1H), 5.95 (d, J=11.28 Hz, 1H), 6.94-6.98 (m, 6H), 7.40 (d, J=1.07 Hz, 1H), 7.50 (d, J=8.59 Hz, 1H), 7.61 (dd, J=8.32, 1.34 Hz, 1H), 7.99 (d, J=8.32 Hz, 1H), 13.17 (s, 1H). ES-MS m/z 428 (M+H).

EXAMPLE 54

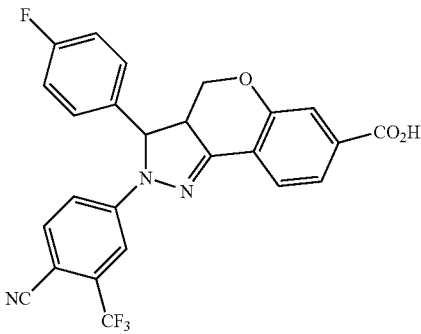

2-(4-cyano-3-(trifluoromethyl)phenyl)-3-(4-fluorophenyl)-2,3,3a,4-tetrahydrochromeno[4,3-c]pyrazole-7-carboxylic acid The title compound was prepared from methyl 3-(4-fluorobenzylidene)-4-oxochroman-7-carboxylate; Preparation 30 (155 mg, 0.50 mmol) and (178 mg, 0.75 mmol) according to Method B and Method C. The crude product was purified by reverse-phase HPLC (acetonitrile/water/0.05% trifluoroacetic acid) to give 2-(4-cyano-3-trifluoromethyl)phenyl)-3-(4-fluorophenyl)-2,3,3a,4-tetrahydrochromeno[4,3-c]pyrazole-7-carboxylic acid (58 mg, 0.12 mmol, 24% yield). The title compound was largely present as (±)-(3SR,3aSR)-2-(4-cyano-3-(trifluoromethyl)phenyl)-3-(4-fluorophenyl)-2,3,3a,4-tetrahydrochromeno[4,3-c]pyrazole-7-carboxylic acid. $^1$H NMR (400 MHz, DMSO-$d_6$) δ ppm 3.22 (t, J=11.82 Hz, 1H), 4.24-4.37 (m, 1H), 4.40 (dd, J=10.07, 5.77 Hz, 1H), 6.08 (d, J=11.01 Hz, 1H), 7.18 (s, 6H), 7.41 (s, 1H), 7.61 (d, J=8.32 Hz, 1H), 7.85 (d, J=8.86 Hz, 1H), 8.05 (d, J=8.06 Hz, 1H), 13.23 (s, 1H). ES-MS m/z 482 (M+H).

EXAMPLE 55

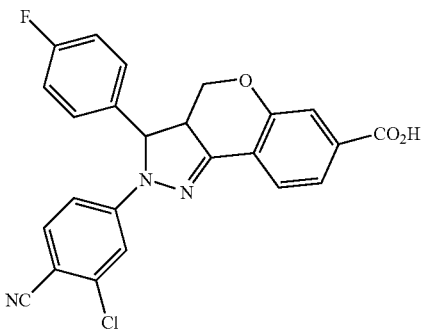

2-(3-chloro-4-cyanophenyl)-3-(4-fluorophenyl)-2,3,3a,4-tetrahydrochromeno[4,3-c]pyrazole-7-carboxylic acid The title compound was prepared from methyl 3-(4-fluorobenzylidene)-4-oxochroman-7-carboxylate; Preparation 30 (155 mg, 0.50 mmol) and 2-chloro-4-hydrazinylbenzonitrile hydrochloride; Preparation 1 (153 mg, 0.75 mmol) according to Method B and Method C. The crude product was purified by reverse-phase HPLC (acetonitrile/water/0.05% trifluoroacetic acid) to give 2-(3-chloro-4-cyanophenyl)-3-(4-fluorophenyl)-2,3,3a,4-tetrahydrochromeno[4,3-c]pyrazole-7-carboxylic acid (41 mg, 0.09 mmol, 18% yield). The title compound was largely present as (±)-(3SR,3aSR)-2-(3-chloro-4-cyanophenyl)-3-(4-fluorophenyl)-2,3,3a,4-tetrahydrochromeno[4,3-c]pyrazole-7-carboxylic acid. ES-MS m/z 448 (M+H).

EXAMPLE 56

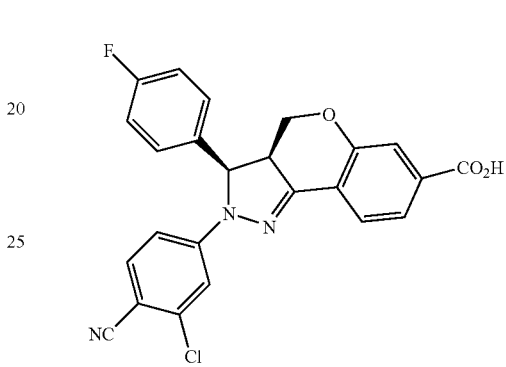

(3R,3aR)-2-(3-chloro-4-cyanophenyl)-3-(4-fluorophenyl)-2,3,3a,4-tetrahydrochromeno[4,3-c]pyrazole-7-carboxylic acid The title compound was prepared from the 2-(3-chloro-4-cyanophenyl)-3-(4-fluorophenyl)-2,3,3a,4-tetrahydrochromeno[4,3-c]pyrazole-7-carboxylic acid prepared in Example 55 using chiral resolution (e.g., Method G).

EXAMPLE 57

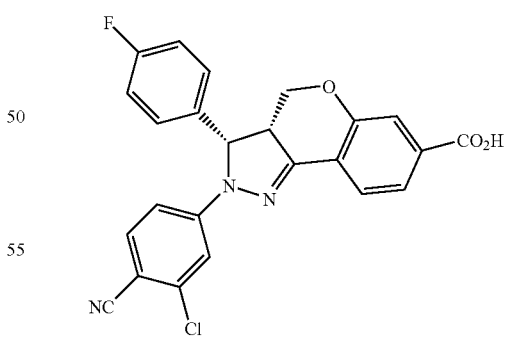

(3S,3aS)-2-(3-chloro-4-cyanophenyl)-3-(4-fluorophenyl)-2,3,3a,4-tetrahydrochromeno[4,3-c]pyrazole-7-carboxylic acid The title compound was prepared from the 2-(3-chloro-4-cyanophenyl)-3-(4-fluorophenyl)-2,3,3a,4-tetrahydrochromeno[4,3-c]pyrazole-7-carboxylic acid prepared in Example 55 using chiral resolution (e.g., Method G).

EXAMPLE 58

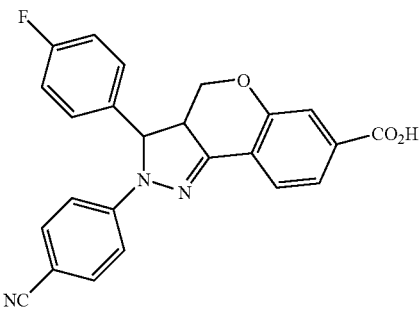

2-(4-cyanophenyl)-3-(4-fluorophenyl)-2,3,3a,4-tetrahydrochromeno[4,3-c]pyrazole-7-carboxylic acid The title compound was prepared from methyl 3-(4-fluorobenzylidene)-4-oxochroman-7-carboxylate; Preparation 30 (155 mg, 0.50 mmol) and 4-hydrazinylbenzonitrile hydrochloride (Aldrich) (127 mg, 0.75 mmol) according to Method B and Method C. The crude product was purified by reverse-phase HPLC (acetonitrile/water/0.05% trifluoroacetic acid) to give 2-(4-cyanophenyl)-3-(4-fluorophenyl)-2,3,3a,4-tetrahydrochromeno[4,3-c]pyrazole-7-carboxylic acid (52 mg, 0.13, 25% yield). The title compound was largely present as (±)-(3SR,3aSR)-2-(4-cyanophenyl)-3-(4-fluorophenyl)-2,3,3a,4-tetrahydrochromeno[4,3-c]pyrazole-7-carboxylic acid. $^1$H NMR (400 MHz, DMSO-$d_6$) δ ppm 3.17 (dd, J=12.89, 10.47 Hz, 1H), 4.19-4.32 (m, 1H), 4.39 (dd, J=10.47, 5.91 Hz, 1H), 5.97 (d, J=11.55 Hz, 1H), 6.93-7.27 (m, 6H), 7.40 (d, J=1.61 Hz, 1H), 7.57-7.63 (m, 3H), 7.99 (d, J=8.06 Hz, 1H), 13.18 (s, 1H). ES-MS m/z 414 (M+H).

EXAMPLE 59

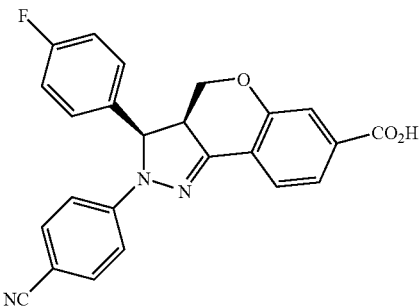

(3R,3aR)-2-(4-cyanophenyl)-3-(4-fluorophenyl)-2,3,3a,4-tetrahydrochromeno[4,3-c]pyrazole-7-carboxylic acid The title compound is prepared from the 2-(4-cyanophenyl)-3-(4-fluorophenyl)-2,3,3a,4-tetrahydrochromeno[4,3-c]pyrazole-7-carboxylic acid prepared in Example 58 using chiral resolution (e.g., Method G).

EXAMPLE 60

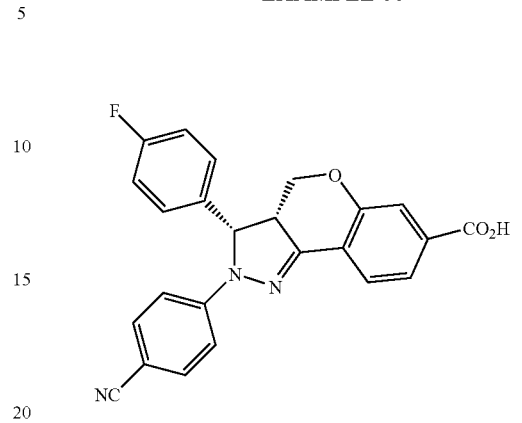

(3S,3aS)-2-(4-cyanophenyl)-3-(4-fluorophenyl)-2,3,3a,4-tetrahydrochromeno[4,3-c]pyrazole-7-carboxylic acid The title compound is prepared from the 2-(4-cyanophenyl)-3-(4-fluorophenyl)-2,3,3a,4-tetrahydrochromeno[4,3-c]pyrazole-7-carboxylic acid prepared in Example 58 using chiral resolution (e.g., Method G).

EXAMPLE 61

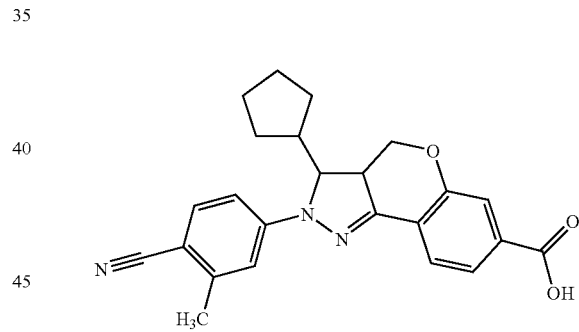

2-(4-cyano-3-methylphenyl)-3-cyclopentyl-2,3,3a,4-tetrahydrochromeno[4,3-c]pyrazole-7-carboxylic acid The title compound was prepared from methyl 3-(cyclopentylmethylene)-4-oxochroman-7-carboxylate; Preparation 31 and 4-hydrazinyl-2-methylbenzonitrile hydrochloride; Preparation 2 according to Method B and Method C (yellow solid, 301 mg, 0.751 mmol, 75% yield). The title compound was largely present as (±)-(3RS,3aSR)-2-(4-cyano-3-methylphenyl)-3-cyclopentyl-2,3,3a,4-tetrahydrochromeno[4,3-c]pyrazole-7-carboxylic acid. $^1$H NMR (400 MHz, DMSO-$d_6$) δ ppm 13.15 (s, 1H), 7.94 (d, J=8.2 Hz, 1H), 7.58 (dd, J=8.2, 1.6 Hz, 1H), 7.53 (d, J=9.0 Hz, 1H), 7.46 (d, J=1.6 Hz, 1H), 7.21 (d, J=2.0 Hz, 1H), 7.08 (dd, J=8.8, 2.1 Hz, 1H), 4.89 (dd, J=9.8, 7.0 Hz, 1H), 4.78 (dd, J=10.2, 5.9 Hz, 1H), 4.30 (dd, J=12.9, 10.5 Hz, 1H), 3.97 (ddd, J=13.0, 9.9, 5.7 Hz, 1H), 2.41 (s, 3H), 2.01-2.16 (m, 1H), 1.13-1.67 (m, 8H). ES-MS m/z 402 (M+H).

EXAMPLE 62

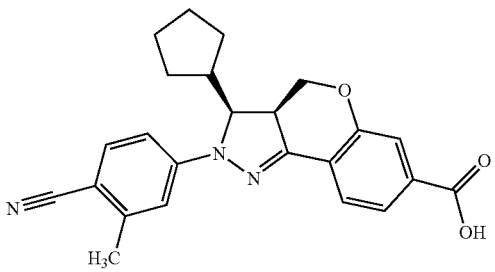

(3S,3aR)-2-(4-cyano-3-methylphenyl)-3-cyclopentyl-2,3,3a,4-tetrahydrochromeno[4,3-c]pyrazole-7-carboxylic acid The title compound was prepared from the 2-(4-cyano-3-methylphenyl)-3-cyclopentyl-2,3,3a,4-tetrahydrochromeno[4,3-c]pyrazole-7-carboxylic acid prepared in Example 61 using chiral resolution (e.g., Method G (Chiralcel OJ-H 30×250 mm; 60% methanol/carbon dioxide). First eluting peak: $t_R$=3.29 minutes (Chiralcel OJ-H 4.6×250 mm; 50% methanol/carbon dioxide).

EXAMPLE 63

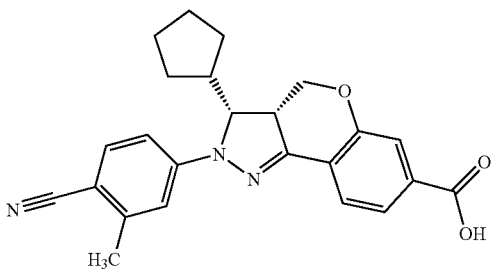

(3R,3aS)-2-(4-cyano-3-methylphenyl)-3-cyclopentyl-2,3,3a,4-tetrahydrochromeno[4,3-c]pyrazole-7-carboxylic acid The title compound was prepared from the 2-(4-cyano-3-methylphenyl)-3-cyclopentyl-2,3,3a,4-tetrahydrochromeno[4,3-c]pyrazole-7-carboxylic acid prepared in Example 61 using chiral resolution (e.g., Method G (Chiralcel OJ-H 30×250 mm; 60% methanol/carbon dioxide). Second eluting peak: $t_R$=5.83 minutes (Chiralcel OJ-H 4.6×250 mm; 50% methanol/carbon dioxide).

EXAMPLE 64

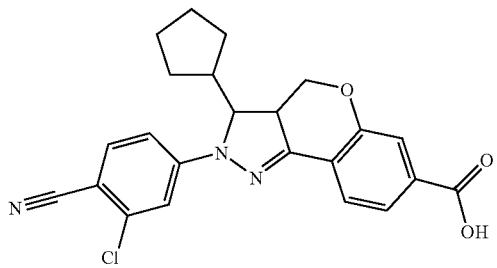

2-(3-chloro-4-cyanophenyl)-3-cyclopentyl-2,3,3a,4-tetrahydrochromeno[4,3-c]pyrazole-7-carboxylic acid The title compound was prepared from methyl 3-(cyclopentylmethylene)-4-oxochroman-7-carboxylate, Preparation 31 (573 mg, 2.0 mmol) and 2-chloro-4-hydrazinylbenzonitrile hydrochloride; Preparation 1 (612 mg, 3.0 mmol) according to Method B and Method C. The crude precipitate was formed from dimethylformamide and methanol to give 2-(3-chloro-4-cyanophenyl)-3-cyclopentyl-2,3,3a,4-tetrahydrochromeno[4,3-c]pyrazole-7-carboxylic acid (yellow solid, 237 mg, 0.563 mmol, 28% yield). The title compound was largely present as (±)-(3RS,3aSR)-2-(3-chloro-4-cyanophenyl)-3-cyclopentyl-2,3,3a,4-tetrahydrochromeno[4,3-c]pyrazole-7-carboxylic acid. $^1$H NMR (400 MHz, DMSO-$d_6$) δ ppm 13.20 (s, 1H), 7.98 (d, J=8.2 Hz, 1H), 7.70 (d, J=9.0 Hz, 1H), 7.58 (dd, J=8.2, 1.6 Hz, 1H), 7.47 (d, J=1.2 Hz, 1H), 7.41 (d, J=2.0 Hz, 1H), 7.20 (dd, J=8.8, 2.1 Hz, 1H), 4.95 (dd, J=9.4, 7.0 Hz, 1H), 4.78 (dd, J=10.2, 5.9 Hz, 1H), 4.31 (dd, J=13.3, 10.5 Hz, 1H), 4.00 (ddd, J=13.2, 9.7, 5.7 Hz, 1H), 2.03-2.16 (m, 1H), 1.13-1.68 (m, 8H). ES-MS m/z 422 (M+H).

EXAMPLE 65

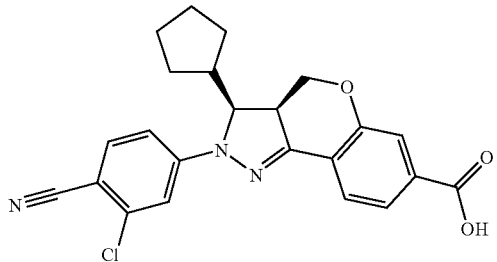

(3S,3aR)-2-(3-chloro-4-cyanophenyl)-3-cyclopentyl-2,3,3a,4-tetrahydrochromeno[4,3-c]pyrazole-7-carboxylic acid The title compound was prepared from the 2-(3-chloro-4-cyanophenyl)-3-cyclopentyl-2,3,3a,4-tetrahydrochromeno[4,3-c]pyrazole-7-carboxylic acid prepared in Example 64 using chiral resolution (e.g., Method G).

EXAMPLE 66

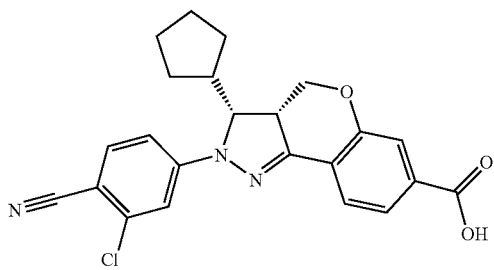

(3R,3aS)-2-(3-chloro-4-cyanophenyl)-3-cyclopentyl-2,3,3a,4-tetrahydrochromeno[4,3-c]pyrazole-7-carboxylic acid The title compound was prepared from the 2-(3-chloro-4-cyanophenyl)-3-cyclopentyl-2,3,3a,4-tetrahydrochromeno[4,3-c]pyrazole-7-carboxylic acid prepared in Example 64 using chiral resolution (e.g., Method G).

EXAMPLE 67

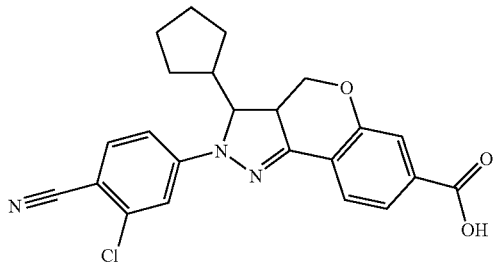

2-(3-chloro-4-cyanophenyl)-3-cyclopentyl-2,3,3a,4-tetrahydrochromeno[4,3-c]pyrazole-7-carboxylic acid The title compound was prepared by epimerization of 2-(3-chloro-4-cyanophenyl)-3-cyclopentyl-2,3,3a,4-tetrahydrochromeno[4,3-c]pyrazole-7-carboxylic acid, Example 64 (131 mg) in a solution of 0.5 M sodium methoxide/methanol (4 mL) and tetrahydrofuran (2 mL) at 50° C. After 24 hours, the reaction was concentrated under a stream of nitrogen and purified by reverse-phase HPLC (60 to 90% acetonitrile/water/0.05% trifluoroacetic acid) to give 2-(3-chloro-4-cyanophenyl)-3-cyclopentyl-2,3,3a,4-tetrahydrochromeno[4,3-c]pyrazole-7-carboxylic acid (yellow solid, 26.7 mg, 0.0634 mmol, 20% yield). The title compound was largely present as (±)-(3RS,3aRS)-2-(3-chloro-4-cyanophenyl)-3-cyclopentyl-2,3,3a,4-tetrahydrochromeno[4,3-c]pyrazole-7-carboxylic acid. $^1$H NMR (400 MHz, DMSO-d$_6$) δ ppm 13.16 (br. s., 1H), 7.82 (d, J=8.2 Hz, 1H), 7.75 (d, J=9.0 Hz, 1H), 7.56 (dd, J=7.8, 1.6 Hz, 1H), 7.43 (d, J=1.6 Hz, 1H), 7.38 (d, J=2.3 Hz, 1H), 7.18 (dd, J=9.0, 2.3 Hz, 1H), 4.63 (dd, J=10.5, 5.9 Hz, 1H), 4.52 (dd, J=8.2, 4.7 Hz, 1H), 4.26 (dd, J=12.5, 10.5 Hz, 1H), 3.54-3.62 (m, 1H), 2.68-2.85 (m, 1H), 1.79-1.91 (m, 1H), 1.20-1.71 (m, 7H). ES-MS m/z 422 (M+H).

EXAMPLES 68 AND 69, RESPECTIVELY

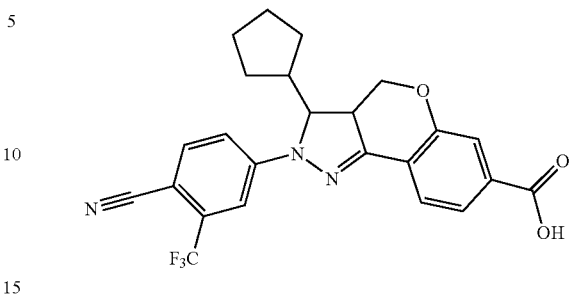

2-[4-cyano-3-(trifluoromethyl)phenyl]-3-cyclopentyl-2,3,3a,4-tetrahydrochromeno[4,3-c]pyrazole-7-carboxylic acid The title compound was prepared from methyl 3-(cyclopentylmethylene)-4-oxochroman-7-carboxylate (Preparation 31; 286 mg, 1.0 mmol) and 4-hydrazinyl-2-(trifluoromethyl)benzonitrile hydrochloride (Preparation 3; 298 mg, 1.3 mmol) according to Method B and Method C. The title compound was largely present as a mixture of cis and trans diastereomers:

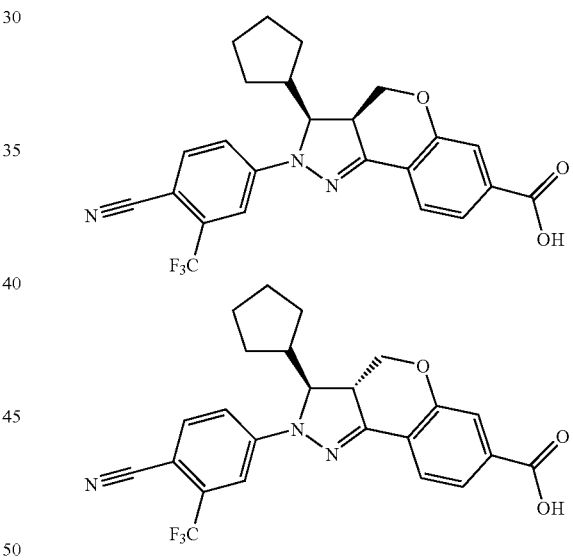

The crude product was purified by reverse-phase HPLC (60 to 95% acetonitrile/water/0.05% trifluoroacetic acid) to give (±)-(3RS,3aSR)-2-[4-cyano-3-(trifluoromethyl)phenyl]-3-cyclopentyl-2,3,3a,4-tetrahydrochromeno[4,3-c]pyrazole-7-carboxylic acid, the first eluting diastereomer (cis) (yellow solid, 16.8 mg, 0.0369 mmol, 3.7% yield). $^1$H NMR (400 MHz, DMSO-d$_6$) δ ppm 13.22 (br. s., 1H), 7.99 (d, J=8.2 Hz, 1H), 7.88 (d, J=8.6 Hz, 1H), 7.57-7.62 (m, 2H), 7.47 (d, J=1.6 Hz, 1H), 7.44 (dd, J=8.8, 1.8 Hz, 1 H), 5.04 (dd, J=9.8, 7.0 Hz, 1H), 4.79 (dd, J=10.5, 5.9 Hz, 1H), 4.33 (dd, J=13.3, 10.5 Hz, 1H), 4.03 (ddd, J=13.3, 9.4, 5.9 Hz, 1H), 2.04-2.17 (m, 1H), 1.59-1.69 (m, 1H), 1.29-1.58 (m, 5H), 1.13-1.29 (m, 2H). ES-MS m/z 456 (M+H). The second eluting diastereomer (trans), (±)-(3RS,3aRS)-2-[4-cyano-3-(trifluoromethyl)phenyl]-3-cyclopentyl-2,3,3a,4-tetrahydrochromeno[4,3-c]pyrazole-7-carboxylic acid (yellow solid, 29 mg, 0.0637 mmol, 6.4% yield). $^1$H NMR (400 MHz, DMSO-$d_6$) δ ppm 13.18 (br. s., 1H), 7.93 (d, J=9.0 Hz, 1H), 7.84 (d, J=7.8 Hz, 1H), 7.63 (d, J=2.3 Hz, 1H), 7.57 (dd, J=8.2, 1.6 Hz, 1H), 7.44 (d, J=1.6 Hz, 1H), 7.39 (dd, J=8.8, 2.1 Hz, 1H), 4.65 (dd, J=10.4, 5.7 Hz, 1H), 4.59 (dd, J=8.4, 4.5 Hz, 1H), 4.27 (dd, J=12.5, 10.5 Hz, 1H), 3.61 (ddd, J=13.0, 7.7, 5.9 Hz, 1H), 2.69-2.82 (m, 1H), 1.79-1.91 (m, 1H), 1.19-1.72 (m, 7H). ES-MS m/z 456 (M+H).

EXAMPLE 70

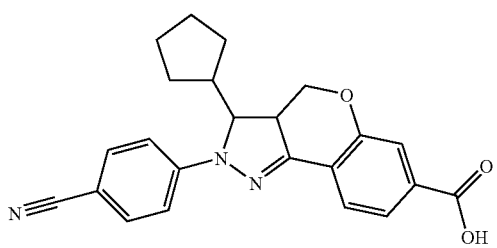

2-(4-cyanophenyl)-3-cyclopentyl-2,3,3a,4-tetrahydrochromeno[4,3-c]pyrazole-7-carboxylic acid The title compound was prepared from methyl 3-(cyclopentylmethylene)-4-oxochroman-7-carboxylate; Preparation 31 (286 mg, 1.0 mmol) and 4-hydrazinylbenzonitrile hydrochloride (Aldrich; 254 mg, 1.5 mmol) according to Method B and Method C. 2-(4-Cyanophenyl)-3-cyclopentyl-2,3,3a,4-tetrahydrochromeno[4,3-c]pyrazole-7-carboxylic acid was obtained (yellow solid, 142 mg, 0.367 mmol, 37% yield). The title compound was largely present as (±)-(3RS,3aSR)-2-(4-cyanophenyl)-3-cyclopentyl-2,3,3a,4-tetrahydrochromeno[4,3-c]pyrazole-7-carboxylic acid. $^1$H NMR (400 MHz, DMSO-$d_6$) δ ppm 13.16 (br. s., 1H), 7.93 (d, J=7.8 Hz, 1H), 7.53-7.66 (m, 3H), 7.46 (s, 1H), 7.27 (d, J=9.0 Hz, 2H), 4.90 (dd, J=9.4, 7.0 Hz, 1H), 4.77 (dd, J=10.4, 5.7 Hz, 1H), 4.30 (dd, J=12.7, 10.7 Hz, 1H), 3.98 (ddd, J=12.9, 9.8, 5.9 Hz, 1H), 2.02-2.16 (m, 1H), 1.56-1.67 (m, 1H), 1.43-1.55 (m, 3H), 1.29-1.43 (m, 2H), 1.13-1.29 (m, 2H). ES-MS m/z 388 (M+H).

EXAMPLE 71

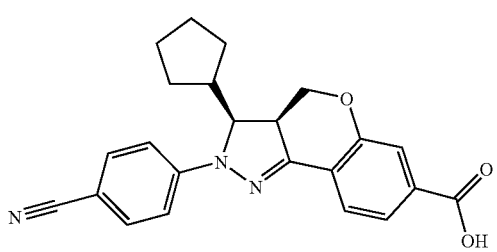

(3S,3aR)-2-(4-cyanophenyl)-3-cyclopentyl-2,3,3a,4-tetrahydrochromeno[4,3-c]pyrazole-7-carboxylic acid The title compound is prepared from the 2-(4-cyanophenyl)-3-cyclopentyl-2,3,3a,4-tetrahydrochromeno[4,3-c]pyrazole-7-carboxylic acid prepared in Example 70 using chiral resolution (e.g. Method G).

EXAMPLE 72

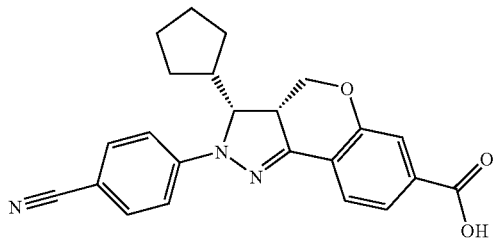

(3R,3aS)-2-(4-cyanophenyl)-3-cyclopentyl-2,3,3a,4-tetrahydrochromeno[4,3-c]pyrazole-7-carboxylic acid The title compound is prepared from the 2-(4-cyanophenyl)-3-cyclopentyl-2,3,3a,4-tetrahydrochromeno[4,3-c]pyrazole-7-carboxylic acid prepared in Example 70 using chiral resolution (e.g. Method G).

EXAMPLE 73

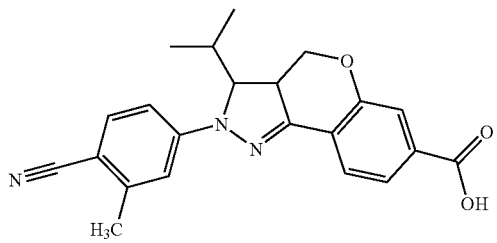

2-(4-cyano-3-methylphenyl)-3-isopropyl-2,3,3a,4-tetrahydrochromeno[4,3-c]pyrazole-7-carboxylic acid The title compound was prepared from methyl 3-(2-methylpropylidene)-4-oxochroman-7-carboxylate (Preparation 32; 260 mg, 1.0 mmol) and 4-hydrazinyl-2-methylbenzonitrile hydrochloride (Preparation 2; 275 mg, 1.5 mmol) according to Method B and Method C (yellow solid, 196 mg, 0.523 mmol, 52% yield, approximately 7:1 mixture of cis: trans diastereomers). $^1$H NMR (400 MHz, DMSO-$d_6$) δ ppm 13.12 (br. s., 1H), 7.93 (d, J=8.2 Hz, 1H), 7.58 (dd, J=8.2, 1.6 Hz, 1H), 7.55 (d, J=8.6 Hz, 1H), 7.46 (d, J=1.6 Hz, 1H), 7.21 (d, J=1.6 Hz, 1H), 7.09 (dd, J=8.6, 2.3 Hz, 1H), 4.76-4.86 (m, 2H), 4.42 (dd, J=13.1, 10.4 Hz, 1H), 4.02 (ddd, J=13.2, 10.6, 5.9 Hz, 1H), 2.42 (s, 3H), 2.06-2.17 (m, 1H), 0.83 (d, J=7.4 Hz, 3H), 0.81 (d, J=7.4 Hz, 3H). ES-MS m/z 376 (M+H).

EXAMPLE 74

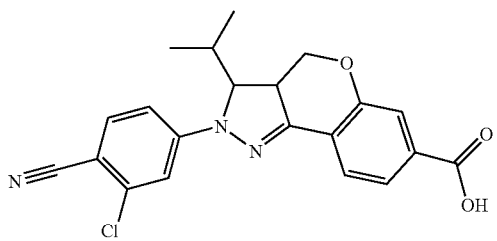

2-(3-chloro-4-cyanophenyl)-3-isopropyl-2,3,3a,4-tetrahydrochromeno[4,3-c]pyrazole-7-carboxylic acid The title compound was prepared from methyl 3-(2-methylpropylidene)-4-oxochroman-7-carboxylate; Preparation 32 (260 mg, 1.0 mmol) and 2-chloro-4-hydrazinylbenzonitrile hydrochloride; Preparation 1 (306 mg, 1.5 mmol) according to Method B and Method C. The crude product was purified by reverse-phase HPLC (30 to 95% acetonitrile/water/0.05% trifluoroacetic acid) followed by flash chromatography (0 to 20% methanol/ethyl acetate) to give 2-(3-chloro-4-cyanophenyl)-3-isopropyl-2,3,3a,4-tetrahydrochromeno[4,3-c]pyrazole-7-carboxylic acid (yellow solid, 18.4 mg). The title compound was largely present as (±)-(3RS,3aSR)-2-(3-chloro-4-cyanophenyl)-3-isopropyl-2,3,3a,4-tetrahydrochromeno[4,3-c]pyrazole-7-carboxylic acid. $^1$H NMR (400 MHz, DMSO-$d_6$) δ ppm 13.10 (br. s., 1H), 7.95 (d, J=7.8 Hz, 1H), 7.71 (d, J=8.6 Hz, 1H), 7.58 (dd, J=8.2, 1.6 Hz, 1H), 7.47 (d, J=1.2 Hz, 1H), 7.42 (d, J=2.3 Hz, 1H), 7.19 (dd, J=9.0, 1.6 Hz, 1H), 4.77-4.88 (m, 2H), 4.41 (dd, J=13.3, 10.5 Hz, 1H), 4.00-4.09 (m, 1H), 2.04-2.16 (m, 1H), 0.83 (d, J=7.0 Hz, 3H), 0.82 (d, J=7.0 Hz, 3H).

EXAMPLE 75

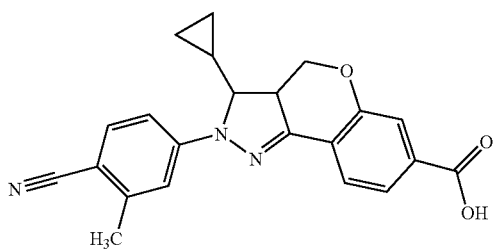

2-(4-cyano-3-methylphenyl)-3-cyclopropyl-2,3,3a,4-tetrahydrochromeno[4,3-c]pyrazole-7-carboxylic acid The title compound was prepared from methyl 3-(cyclopropylmethylene)-4-oxochroman-7-carboxylate (Preparation 33), and 4-hydrazinyl-2-methylbenzonitrile hydrochloride (Preparation 2) according to Method B and Method C. The crude product was purified by reverse-phase HPLC (65 to 85% acetonitrile/water/0.05% trifluoroacetic acid) to give the title compound (yellow solid, 23 mg). The title compound was largely present as (±)-(3RS,3aSR)-2-(4-cyano-3-methylphenyl)-3-cyclopropyl-2,3,3a,4-tetrahydrochromeno[4,3-c]pyrazole-7-carboxylic acid. $^1$H NMR (400 MHz, DMSO-$d_6$) δ ppm 13.11 (br. s., 1H), 7.94 (d, J=7.8 Hz, 1H), 7.58 (dd, J=8.2, 1.6 Hz, 1H), 7.56 (d, J=8.6 Hz, 1H), 7.47 (d, J=1.6 Hz, 1H), 7.23 (d, J=1.6 Hz, 1H), 7.11 (dd, J=8.6, 2.0 Hz, 1H), 4.84 (dd, J=10.5, 5.9 Hz, 1H), 4.45 (dd, J=12.9, 10.5 Hz, 1H), 4.31 (t, J=10.0 Hz, 1H), 3.89 (ddd, J=13.0, 9.9, 5.7 Hz, 1H), 2.42 (s, 3H), 0.71-0.81 (m, 1H), 0.62-0.70 (m, 1H), 0.49-0.58 (m, 1H), 0.35-0.43 (m, 1H), 0.17-0.24 (m, 1H). ES-MS m/z 374 (M+H).

EXAMPLE 76

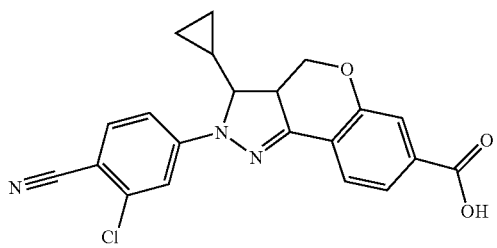

2-(3-chloro-4-cyanophenyl)-3-cyclopropyl-2,3,3a,4-tetrahydrochromeno[4,3-c]pyrazole-7-carboxylic acid The title compound was prepared from methyl 3-(cyclopropylmethylene)-4-oxochroman-7-carboxylate; Preparation 33 and 2-chloro-4-hydrazinylbenzonitrile hydrochloride; Preparation 1 according to Method B and Method C. The crude product was purified by reverse-phase HPLC (65 to 85% acetonitrile/water/0.05% trifluoroacetic acid) to give 2-(3-chloro-4-cyanophenyl)-3-cyclopropyl-2,3,3a,4-tetrahydrochromeno[4,3-c]pyrazole-7-carboxylic acid (yellow solid, 14 mg). The title compound was largely present as (±)-(3RS,3aSR)-2-(3-chloro-4-cyanophenyl)-3-cyclopropyl-2,3,3a,4-tetrahydrochromeno[4,3-c]pyrazole-7-carboxylic acid. $^1$H NMR (400 MHz, DMSO-$d_6$) δ ppm 13.18 (br. s., 1H), 7.97 (d, J=8.2 Hz, 1H), 7.73 (d, J=9.0 Hz, 1H), 7.59 (dd, J=8.2, 1.6 Hz, 1H), 7.48 (d, J=1.6 Hz, 1H), 7.43 (d, J=2.0 Hz, 1H), 7.23 (dd, J=8.6, 1.6 Hz, 1H), 4.84 (dd, J=10.5, 5.9 Hz, 1H), 4.46 (dd, J=12.9, 10.5 Hz, 1H), 4.39 (t, J=10.0 Hz, 1H), 3.93 (ddd, J=13.1, 10.2, 5.7 Hz, 1H), 0.74-0.85 (m, 1H), 0.63-0.71 (m, 1H), 0.52-0.61 (m, 1H), 0.37-0.45 (m, 1H), 0.18-0.26 (m, 1H).

EXAMPLE 77

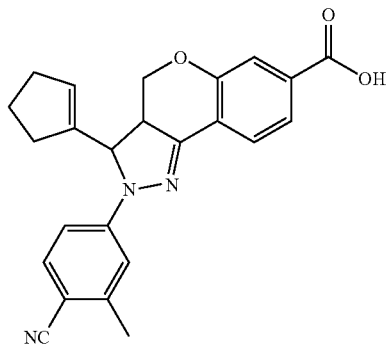

(±)-(3RS,3aRS)-2-(4-cyano-3-methylphenyl)-3-cyclopentenyl-2,3,3a,4-tetrahydrochromeno[4,3-c]pyrazole-7-carboxylic acid

Step 1: Preparation of methyl 2-(4-cyano-3-methylphenyl)-3-cyclopentenyl-2,3,3a,4-tetrahydrochromeno[4,3-c]pyrazole-7-carboxylate

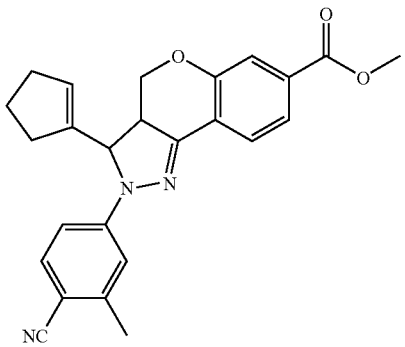

To a suspension of methyl 3-(cyclopentenylmethylene)-4-oxochroman-7-carboxylate; Preparation 34 (260 mg, 0.92 mmol) in ethanol (7 mL) was added 4-hydrazinyl-2-methylbenzonitrile hydrochloride; Preparation 2 (218 mg, 1.2 mmol). The slurry was heated to 80° C. for eighteen hours. The solution was returned to ambient temperature and the resulting solid was collected by vacuum filtration and washed with cold ethanol. Chromatography (normal phase, ethyl acetate/hexane) provided largely the cis isomer of methyl 2-(4-cyano-3-methylphenyl)-3-cyclopentenyl-2,3,3a,4-tetrahydrochromeno[4,3-c]pyrazole-7-carboxylate (yellow solid, 125 mg, 33% yield). LC/MS on 4.6×50 mm C-18 column, $t_R$=6.98 minutes (10 to 90% acetonitrile/water over 8 minutes at 2 mL/minute with detection 254 nm, at 50° C.); ES-MS m/z 414 (M+H). $^1$H NMR (400 MHz, DMSO-$d_6$) δ ppm 1.63-1.83 (m, 2H), 2.05-2.11 (m, 2H), 2.14-2.20 (m, 2H), 2.39 (s, 3H), 3.83 (s, 3H), 3.88 (dd, J=13.02, 10.34 Hz, 1H), 3.98-4.03 (m, 1H), 4.67 (dd, J=10.20, 5.64 Hz, 1H), 5.45 (d, J=11.01 Hz, 1H), 5.60 (br. s., 1H), 6.86 (br. s., 1H), 7.11 (br. s., 1H), 7.44 (d, J=1.34 Hz, 1H), 7.53 (d, J=8.59 Hz, 1H), 7.58 (dd, J=8.06, 1.61 Hz, 1H), 7.93 (d, J=8.06 Hz, 1H).

Step 2: Preparation of 2-(4-cyano-3-methylphenyl)-3-cyclopentenyl-2,3,3a,4-tetrahydrochromeno[4,3-c]pyrazole-7-carboxylic acid

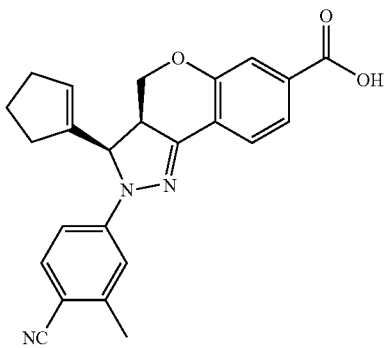

To a solution of methyl 2-(4-cyano-3-methylphenyl)-3-cyclopentenyl-2,3,3a,4-tetrahydrochromeno[4,3-c]pyrazole-7-carboxylate (125 mg, 0.30 mmol) in methanol (2 mL) and tetrahydrofuran (2 mL) was added 1M aqueous sodium hydroxide (2 mL). The solution was stirred for 20 hours at ambient temperature. The resulting slurry was concentrated to half volume, acidified to pH=2 with 1M hydrochloric acid and collected by vacuum filtration (yellow solid, 66 mg, 55% yield). The title compound was largely present as (±)-(3RS, 3aRS)-2-(4-cyano-3-methylphenyl)-3-cyclopentenyl-2,3,3a, 4-tetrahydrochromeno[4,3-c]pyrazole-7-carboxylic acid. Reversed-phase HPLC on 4.6×50 mm C-18 column, $t_R$=2.92 minutes (10 to 90% acetonitrile/water over 4 minutes at 4 mL/minute with detection 254 nm, at 20° C.); HRMS Calculated for $C_{24}H_{21}N_3O_3$: 400.1656 (M+H)$^+$. Found: 400.1678. $^1$H NMR (400 MHz, DMSO-$d_6$) δ ppm 1.61-1.87 (m, 2H), 2.03-2.13 (m, 2H), 2.17 (br. s., 2H), 2.39 (s, 3H), 3.83-3.91 (m, 1H), 3.97-4.06 (m, 1H), 4.65 (dd, J=10.20, 5.91 Hz, 1H), 5.44 (d, J=10.47 Hz, 1H), 5.60 (br. s., 1H), 6.86 (br. s., 1H), 7.11 (br. s., 1H), 7.42 (d, J=1.34 Hz, 1H), 7.53 (d, J=8.59 Hz, 1H), 7.56 (dd, J=8.19, 1.48 Hz, 1H), 7.90 (d, J=8.06 Hz, 1H), 13.12 (br. s., 1H).

EXAMPLE 78

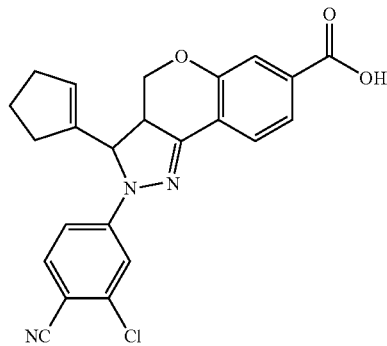

(±)-(3RS,3aRS)-2-(3-chloro-4-cyanophenyl)-3-cyclopentenyl-2,3,3a,4-tetrahydrochromeno[4,3-c]pyrazole-7-carboxylic acid

Step 1: Preparation of methyl 2-(3-chloro-4-cyanophenyl)-3-cyclopentenyl-2,3,3a,4-tetrahydrochromeno[4,3-c]pyrazole-7-carboxylate

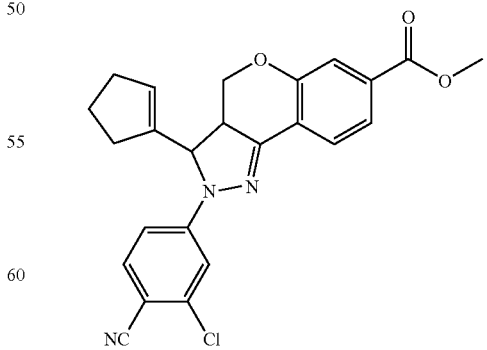

Methyl 3-(cyclopentenylmethylene)-4-oxochroman-7-carboxylate; Preparation 34 (310 mg, 1.1 mmol) was suspended into ethanol (5 mL) and 2-chloro-4-hydrazinylbenzonitrile hydrochloride; Preparation 1 (289 mg, 1.4 mmol) was added. The solution was heated to 80° C. for eighteen hours. The solution was returned to ambient temperature and the resulting solid was collected by vacuum filtration and washed with cold ethanol. Chromatography (normal phase, ethyl acetate/hexane) provided largely the cis isomer of methyl 2-(3-chloro-4-cyanophenyl)-3-cyclopentenyl-2,3,3a,4-tetrahydrochromeno[4,3-c]pyrazole-7-carboxylate (yellow solid, 190 mg, 55% yield). $^1$H NMR (400 MHz, DMSO-$d_6$) δ ppm 1.60-1.90 (m, 2H), 2.04-2.14 (m, 2H), 2.14-2.22 (m, 2H), 3.83 (s, 3H), 3.89 (dd, J=12.76, 10.34 Hz, 1H), 4.01-4.11 (m, 1H), 4.68 (dd, J=10.47, 6.18 Hz, 1H), 5.51 (d, J=9.67 Hz, 1H), 5.63 (br. s., 1H), 6.99 (br. s., 1H), 7.27 (br. s., 1H), 7.45 (d, J=1.61 Hz, 1H), 7.58 (dd, J=8.19, 1.75 Hz, 1H), 7.71 (d, J=8.86 Hz, 1H), 7.97 (d, J=8.06 Hz, 1H).

Step 2: Preparation of 2-(3-chloro-4-cyanophenyl)-3-cyclopentenyl-2,3,3a,4-tetrahydrochromeno[4,3-c]pyrazole-7-carboxylic acid

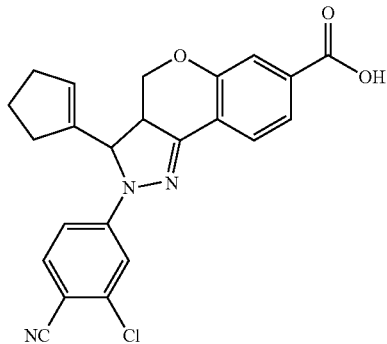

To a solution of methyl 2-(3-chloro-4-cyanophenyl)-3-cyclopentenyl-2,3,3a,4-tetrahydrochromeno[4,3-c]pyrazole-7-carboxylate (190 mg, 0.44 mmol) in methanol (2 mL) and tetrahydrofuran (2 mL) was added 1M aqueous sodium hydroxide (2 mL). The solution was stirred for 20 hours at ambient temperature. The resulting slurry was concentrated to half volume and acidified to pH=2 with 1M hydrochloric acid. The resulting solid was collected by vacuum filtration. The solid was treated with hot N,N-dimethylformamide and methanol to provide 2-(3-chloro-4-cyanophenyl)-3-cyclopentenyl-2,3,3a,4-tetrahydrochromeno[4,3-c]pyrazole-7-carboxylic acid (yellow solid, 40 mg, 22% yield). The title compound was largely present as 3RS,3aRS)-2-(3-chloro-4-cyanophenyl)-3-cyclopentenyl-2,3,3a,4-tetrahydrochromeno[4,3-c]pyrazole-7-carboxylic acid. Reversed-phase HPLC on 4.6×50 mm C-18 column, $t_R$=3.05 minutes (10 to 90% acetonitrile/water over 4 minutes at 4 mL/minute with detection 254 nm, at 20° C.); HRMS Calculated for $C_{23}H_{18}ClN_3O_3$: 420.1109 (M+H)$^+$. Found: 420.1127; $^1$H NMR (400 MHz, DMSO-$d_6$) δ ppm 1.59-1.89 (m, 2H), 2.03-2.14 (m, 2H), 2.14-2.23 (m, 2H), 3.89 (dd, J=13.02, 10.34 Hz, 1H), 4.05 (ddd, J=12.89, 10.74, 5.91 Hz, 1H), 4.67 (dd, J=10.34, 5.77 Hz, 1H), 5.51 (d, J=11.01 Hz, 1H), 5.63 (br. s., 1H), 7.00 (br. s., 1H) 7.29 (br. s., 1H), 7.43 (d, J=1.61 Hz, 1H), 7.56 (dd, J=8.19, 1.48 Hz, 1H), 7.71 (d, J=8.59 Hz, 1H), 7.94 (d, J=8.06 Hz, 1H), 13.16 (br. s., 1H).

EXAMPLE 79

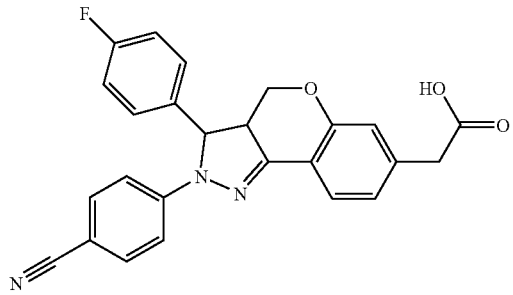

(±)-(3RS,3aRS)-[2-(4-cyanophenyl)-3-(4-fluorophenyl)-2,3,3a,4-tetrahydrochromeno[4,3-c]pyrazol-7-yl]acetic acid The title compound was prepared from ethyl [3-(4-fluorobenzylidene)-4-oxo-3,4-dihydro-2H-chromen-7-yl]acetate; Preparation 29 (170 mg, 0.5 mmol) and 4-hydrazinylbenzonitrile hydrochloride (Aldrich; 85 mg, 0.5 mmol) according to Method B and Method C. The title compound was largely present as (±)-(3RS,3aRS)-[2-(4-cyanophenyl)-3-(4-fluorophenyl)-2,3,3a,4-tetrahydrochromeno[4,3-c]pyrazol-7-yl]acetic acid. $^1$H NMR (400 MHz, DMSO-$d_6$) δ ppm ppm 3.12 (dd, J=12.89, 10.55 Hz, 1H), 3.56 (s, 2H), 4.12-4.25 (m, 1H), 4.34 (dd, J=10.16, 5.86 Hz, 1H), 5.90 (d, J=10.94 Hz, 1H), 6.85 (s, 1H), 6.97 (d, J=8.20 Hz, 1H), 7.04 (s, 3H), 7.15 (br. s., 3H), 7.57 (d, J=9.37 Hz, 2H), 7.82 (d, J=7.81 Hz, 1H); ES-MS m/z 428 (M+H).

EXAMPLE 80

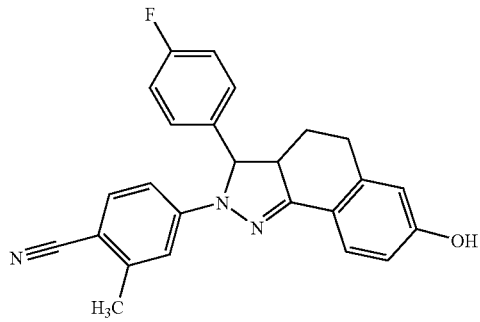

3-(4-fluorophenyl)-7-hydroxy-3,3a,4,5-tetrahydrobenzo[g]indazol-2-yl)-2-methylbenzonitrile The title compound was prepared from (E)-2-(4-fluorobenzylidene)-6-hydroxy-3,4-dihydronaphthalen-1(2H)-one (Yoshihama et al. U.S. Pat. No. 6,080,781; Example 80) and 4-hydrazinyl-2-methylbenzonitrile hydrochloride; Preparation 2 according to Method B (off-white solid, 263 mg, 0.662 mmol, 66% yield, 20:1 mixture of cis:trans diastereomers). The title compound was largely present as 4-((3RS,3aRS)-3-(4-fluorophenyl)-7-hydroxy-3,3a,4,5-tetrahydrobenzo[g]indazol-2-yl)-2-methylbenzonitrile. $^1$H NMR (400 MHz, DMSO-$d_6$) δ ppm 0.73 (qd, J=12.50, 3.91

Hz, 1H), 1.68-1.80 (m, 1H), 2.33 (s, 3H), 2.64-2.75 (m, 1H), 2.76-2.93 (m, 1H), 3.78 (ddd, J=13.09, 10.74, 5.08 Hz, 1H), 5.73 (d, J=10.94 Hz, 1H), 6.57 (d, J=2.34 Hz, 1H), 6.72 (dd, J=8.40, 2.54 Hz, 1H), 6.79-7.35 (m, 6H), 7.42 (d, J=8.59 Hz, 1H), 7.85 (d, J=8.59 Hz, 1H), 9.87 (s, 1H). ES-MS m/z 398 (M+H).

EXAMPLE 81

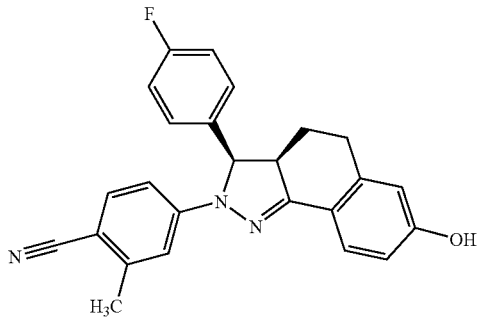

4-((3R,3aR)-3-(4-fluorophenyl)-7-hydroxy-3,3a,4,5-tetrahydrobenzo[g]indazol-2-yl)-2-methylbenzonitrile The title compound is prepared from the 3-(4-fluorophenyl)-7-hydroxy-3,3a,4,5-tetrahydrobenzo[g]indazol-2-yl)-2-methylbenzonitrile prepared in Example 80 using chiral resolution, according to Method G.

EXAMPLE 82

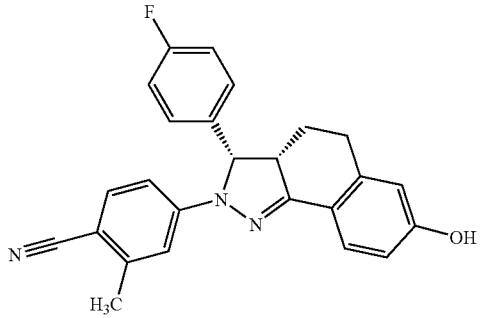

4-((3S,3aS)-3-(4-fluorophenyl)-7-hydroxy-3,3a,4,5-tetrahydrobenzo[g]indazol-2-yl)-2-methylbenzonitrile The title compound is prepared from the 3-(4-fluorophenyl)-7-hydroxy-3,3a,4,5-tetrahydrobenzo[g]indazol-2-yl)-2-methylbenzonitrile prepared in Example 80 using chiral resolution, according to Method G.

EXAMPLE 83

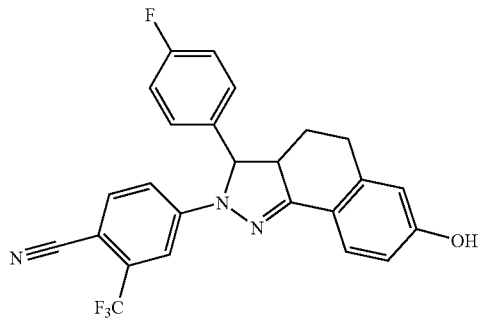

3-(4-fluorophenyl)-7-hydroxy-3,3a,4,5-tetrahydrobenzo[g]indazol-2-yl)-2-(trifluoromethyl)benzonitrile The title compound was prepared from (E)-2-(4-fluorobenzylidene)-6-hydroxy-3,4-dihydronaphthalen-1(2H)-one (Yoshihama et al. U.S. Pat. No. 6,080,781; Example 11) and 4-hydrazinyl-2-(trifluoromethyl)benzonitrile hydrochloride; Preparation 3 according to Method B (off-white solid, 342 mg). The title compound was largely present as (±)-4-((3RS,3aRS)-3-(4-fluorophenyl)-7-hydroxy-3,3a,4,5-tetrahydrobenzo[g]indazol-2-yl)-2-(trifluoromethyl)benzonitrile. $^1$H NMR (400 MHz, DMSO-$d_6$) δ ppm 0.77 (dq, J=13.02, 4.69 Hz, 1H), 1.65-1.82 (m, 1H), 2.65-2.76 (m, 1H), 2.78-2.94 (m, 1H), 3.86 (ddd, J=13.67, 11.33, 5.08 Hz, 1H), 5.87 (d, J=0.55 Hz, 1H), 6.59 (d, J=2.34 Hz, 1H), 6.74 (dd, J=8.59, 2.34 Hz, 1H), 6.76-7.70 (m, 6H), 7.69-7.84 (m, 1H), 7.89 (d, J=8.59 Hz, 1H), 9.96 (s, 1H). ES-MS m/z 452 (M+H).

EXAMPLE 84

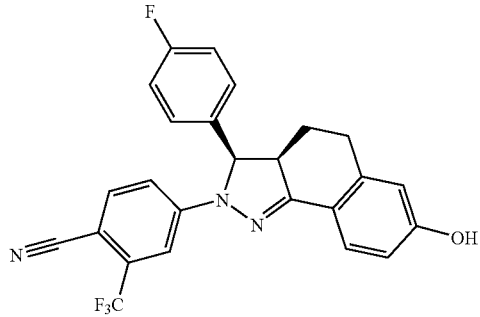

4-((3R,3aR)-3-(4-fluorophenyl)-7-hydroxy-3,3a,4,5-tetrahydrobenzo[g]indazol-2-yl)-2-(trifluoromethyl)benzonitrile The title compound is prepared from the 3-(4-fluorophenyl)-7-hydroxy-3,3a,4,5-tetrahydrobenzo[g]indazol-2-yl)-2-(trifluoromethyl)benzonitrile prepared in Example 83 using chiral resolution (e.g., Method G).

EXAMPLE 85

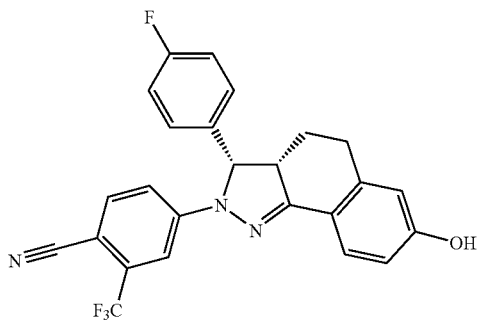

4-((3S,3aS)-3-(4-fluorophenyl)-7-hydroxy-3,3a,4,5-tetrahydrobenzo[g]indazol-2-yl)-2-(trifluoromethyl)benzonitrile The title compound is prepared from the 3-(4-fluorophenyl)-7-hydroxy-3,3a,4,5-tetrahydrobenzo[g]indazol-2-yl)-2-(trifluoromethyl)benzonitrile prepared in Example 83 using chiral resolution (e.g., Method G).

EXAMPLE 86

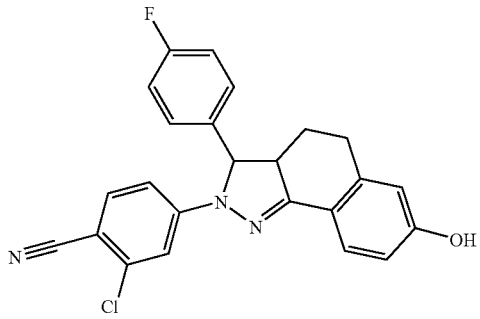

2-chloro-4-(-3-(4-fluorophenyl)-7-hydroxy-3,3a,4,5-tetrahydrobenzo[g]indazol-2-yl)benzonitrile The title compound was prepared from (E)-2-(4-fluorobenzylidene)-6-hydroxy-3,4-dihydronaphthalen-1(2H)-one (Yoshihama et al. U.S. Pat. No. 6,080,781, Example 11) and 2-chloro-4-hydrazinylbenzonitrile hydrochloride (Preparation 1) according to Method B (off-white solid, 293 mg). The title compound was largely present as (±)-2-chloro-4-((3RS,3aRS)-3-(4-fluorophenyl)-7-hydroxy-3,3a,4,5-tetrahydrobenzo[g]indazol-2-yl)benzonitrile. $^1$H NMR (400 MHz, DMSO-$d_6$) δ ppm 0.74 (qd, J=13.02, 4.69 Hz, 1H), 1.65-1.82 (m, 1H), 2.62-2.75 (m, 1H), 2.84 (ddd, J=16.89, 12.60, 4.49 Hz, 1H), 3.83 (ddd, J=13.38, 10.84, 4.69 Hz, 1H), 5.80 (d, J=110.94 Hz, 1H), 6.58 (d, J=2.34 Hz, 1H), 6.72 (dd, J=8.59, 2.34 Hz, 1H), 6.82-7.50 (m, 6H), 7.59 (d, J=8.59 Hz, 1H), 7.88 (d, J=8.59 Hz, 1H), 9.94 (s, 1H). ES-MS m/z 418 (M+H).

EXAMPLE 87

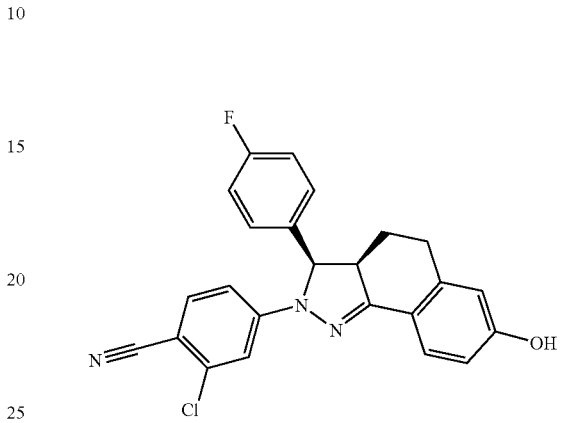

2-chloro-4-((3R,3aR)-3-(4-fluorophenyl)-7-hydroxy-3,3a,4,5-tetrahydrobenzo[g]indazol-2-yl)benzonitrile The title compound is prepared from the 2-chloro-4-(-3-(4-fluorophenyl)-7-hydroxy-3,3a,4,5-tetrahydrobenzo[g]indazol-2-yl)benzonitrile prepared in Example 86 using chiral resolution (e.g., Method G).

EXAMPLE 88

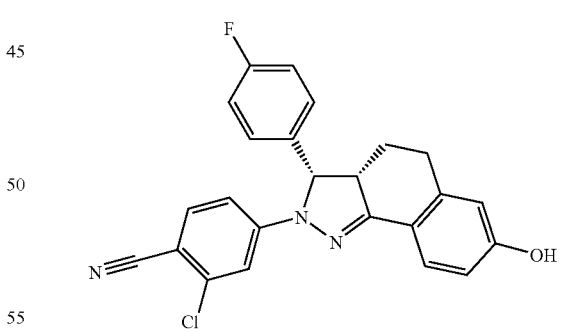

2-chloro-4-((3S,3aS)-3-(4-fluorophenyl)-7-hydroxy-3,3a,4,5-tetrahydrobenzo[g]indazol-2-yl)benzonitrile The title compound is prepared from the 2-chloro-4-(-3-(4-fluorophenyl)-7-hydroxy-3,3a,4,5-tetrahydrobenzo[g]indazol-2-yl)benzonitrile prepared in Example 86 using chiral resolution (e.g., Method G).

EXAMPLES 89 AND 90, RESPECTIVELY

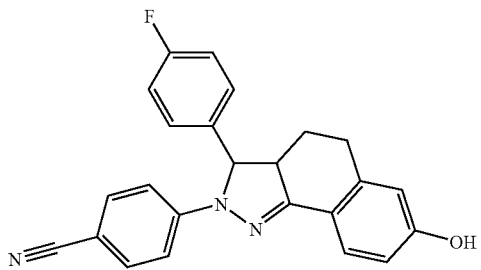

3-(4-fluorophenyl)-7-hydroxy-3,3a,4,5-tetrahydrobenzo[g]indazol-2-yl)benzonitrile The title compound was prepared from 2-(4-fluorobenzylidene)-6-hydroxy-3,4-dihydronaphthalen-1(2H)-one (Yoshihama et al. U.S. Pat. No. 6,080,781, Example 11) and 4-hydrazinylbenzonitrile hydrochloride (Aldrich) according to Method B. After stirring overnight at 80° C., the reaction mixture was concentrated and purified by reverse-phase HPLC (40 to 95% acetonitrile/water/0.05% trifluoroacetic acid). The title compound was largely present as a mixture of cis and trans diasteromers.

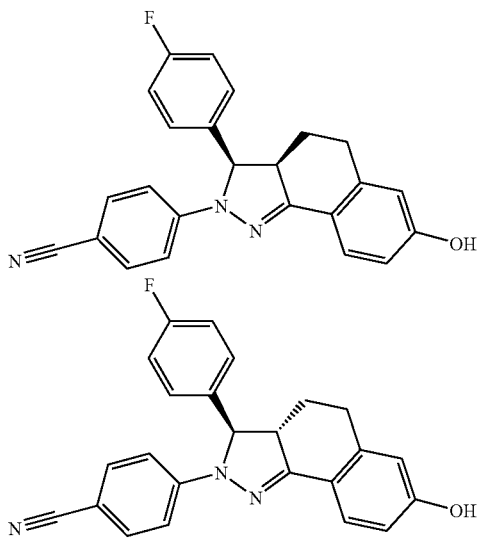

The cis diastereomer, (±)-4-((3RS,3aRS)-3-(4-fluorophenyl)-7-hydroxy-3,3a,4,5-tetrahydrobenzo[g]indazol-2-yl)benzonitrile, was the first eluting product (peach colored solid, 187 mg). $^1$H NMR (400 MHz, DMSO-$d_6$) δ ppm 0.75 (m, 1H), 1.74 (m, 1H), 2.69 (m, 1H), 2.83 (m, 1H), 3.80 (ddd, J=13.38, 10.84, 4.69 Hz, 1H), 5.75 (d, J=10.94 Hz, 1H), 6.57 (d, J=2.34 Hz, 1H), 6.72 (dd, J=8.59, 2.34 Hz, 1H), 7.12 (m, 5H), 7.31 (m, 1H), 7.51 (d, J=8.98 Hz, 2H), 7.85 (d, J=8.59 Hz, 1H), 9.88 (s, 1H). ES-MS m/z 384 (M+H). The trans diastereomer, (±)-4-((3RS,3aSR)-3-(4-fluorophenyl)-7-hydroxy-3,3a,4,5-tetrahydrobenzo[g]indazol-2-yl)benzonitrile, was the second eluting product (peach colored solid, 21.5 mg). $^1$H NMR (400 MHz, DMSO-$d_6$) δ ppm 1.91 (qd, J=12.76, 5.47 Hz, 1H), 2.17 (m, 1H), 2.82 (m, 2H), 3.24 (ddd, J=12.99, 11.03, 4.88 Hz, 1H), 4.90 (d, J=11.33 Hz, 1H), 6.61 (d, J=2.34 Hz, 1H), 6.71 (dd, J=8.59, 2.34 Hz, 1H), 6.95 (d, J=8.98 Hz, 2H), 7.24 (t, J=8.79 Hz, 2H), 7.47 (m, 2H), 7.53 (d, J=8.98 Hz, 2H), 7.76 (d, J=8.59 Hz, 1H), 9.86 (s, 1H). ES-MS m/z 384 (M+H).

EXAMPLE 91

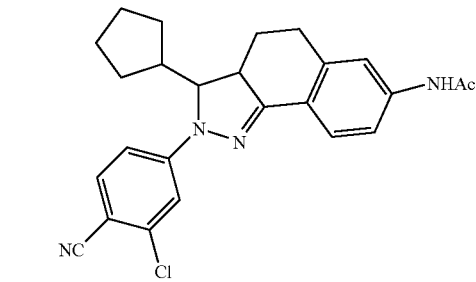

N-(-2-(3-chloro-4-cyanophenyl)-3-cyclopentyl-3,3a,4,5-tetrahydro-2H-benzo[g]indazol-7-yl)acetamide The title compound was prepared from N-(6-(cyclopentylmethylene)-5-oxo-5,6,7,8-tetrahydronaphthalen-2-yl)acetamide; Preparation 36 and 2-chloro-4-hydrazinylbenzonitrile hydrochloride (Preparation 1) according to Method B (tan solid, 159 mg, 0.37 mmol, 59% yield). The title compound was largely present as (O)—N-((3RS,3aSR)-2-(3-chloro-4-cyanophenyl)-3-cyclopentyl-3,3a,4,5-tetrahydro-2H-benzo[g]indazol-7-yl)acetamide. $^1$H NMR (400 MHz, DMSO-$d_6$) δ ppm 1.08-1.59 (m, 7H), 1.65-1.87 (m, 2H), 1.98-2.05 (m, 1H), 2.06 (s, 3H), 2.13-2.24 (m, 1H), 2.78-2.97 (m, 2H), 3.51 (ddd, J=13.56, 9.26, 4.83 Hz, 1H), 4.86 (dd, J=9.26, 5.50 Hz, 1H), 7.11 (dd, J=9.26, 1.48 Hz, 1H), 7.32 (d, J=1.88 Hz, 1H), 7.46 (dd, J=8.59, 1.88 Hz, 1H), 7.60 (s, 1H), 7.64 (d, J=8.86 Hz, 1H), 7.93 (d, J=8.59 Hz, 1H), 10.11 (s, 1H). ES-MS m/z 433 (M+H).

EXAMPLE 92

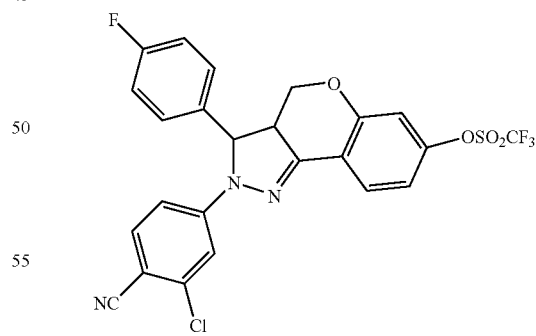

2-(3-chloro-4-cyanophenyl)-3-(4-fluorophenyl)-2,3,3a,4-tetrahydrochromeno[4,3-c]pyrazol-7-yl trifluoromethanesulfonate A mixture of 3-(4-fluorobenzylidene)-4-oxochroman-7-yl trifluoromethanesulfonate; Preparation 35 (200 mg, 0.50 mmol), 2-chloro-4-hydrazinylbenzonitrile hydrochloride (Preparation 1) (152 mg, 0.75 mmol), and ethanol (5 mL) was stirred under argon at 80° C. for three hours. The mixture was cooled to room temperature and concentrated. Water was added, the residue extracted three times with methylene chloride, washed with brine, dried over magnesium sulfate, filtered and condensed. The crude product was purified by normal phase flash column chromatography on a 20 g silica gel column (100% methylene chloride). Pure fractions were pooled and condensed to give the title compound (yellow solid, 75 mg, 0.14 mmol, 28% yield). The title compound was largely present as (±)-(3SR,3aSR)-2-(3-chloro-4-cyanophenyl)-3-(4-fluorophenyl)-2,3,3a,4-tetrahydrochromeno[4,3-c]pyrazol-7-yl trifluoromethanesulfonate. $^1$H NMR (400 MHz, DMSO-$d_6$) δ ppm 3.25 (dd, J=12.89, 10.47 Hz, 1H), 4.22-4.35 (m, 1H), 4.42 (dd, J=10.34, 6.04 Hz, 1H), 6.00 (d, J=11.28 Hz, 1H), 6.77-7.51 (m, 8H), 7.68 (d, J=8.59 Hz, 1H), 8.10 (d, J=9.40 Hz, 1H). ES-MS m/z 553 (M+H).

EXAMPLE 93

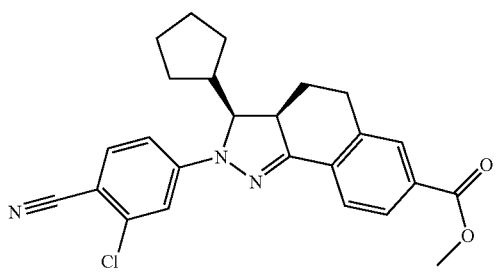

(3S,3aR)-methyl 2-(3-chloro-4-cyanophenyl)-3-cyclopentyl-3,3a,4,5-tetrahydro-2H-benzo[g]indazole-7-carboxylate A solution of (trimethylsilyl)diazomethane (2.0 M in diethyl ether, 0.286 mL, 0.572 mmol) was added to a solution of (3S,3aR)-2-(3-chloro-4-cyanophenyl)-3-cyclopentyl-3,3a,4,5-tetrahydro-2H-benzo[g]indazole-7-carboxylic acid, Example 16 (200 mg, 0.476 mmol) in tetrahydrofuran (3 mL) and methanol (1 mL). After 90 minutes, the reaction was concentrated to give the crude methyl ester (yellow solid, 217 mg). ES-MS m/z 434 (M+H).

EXAMPLE 94

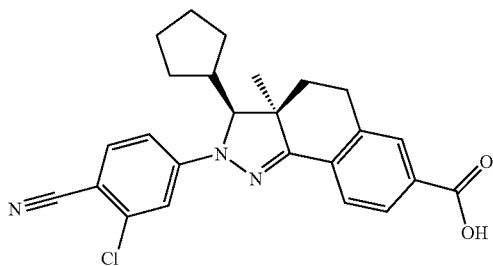

(3S,3aR)-2-(3-chloro-4-cyanophenyl)-3-cyclopentyl-3a-methyl-3,3a,4,5-tetrahydro-2H-benzo[g]indazole-7-carboxylic acid To a solution of diisopropylamine (0.0772 mL, 0.551 mmol) in tetrahydrofuran (1.5 mL) at −78° C. was added n-butyllithium (2.5 M in hexanes, 0.206 mL, 0.514 mmol). After 10 minutes, a solution of (3S,3aR)-methyl 2-(3-chloro-4-cyanophenyl)-3-cyclopentyl-3,3a,4,5-tetrahydro-2H-benzo[g]indazole-7-carboxylate, Example 93 (159 mg, 0.367 mmol) in tetrahydrofuran (3.0 mL) was added dropwise. After 1 hour at −78° C., iodomethane (0.0343 mL, 0.551 mmol) was added. The reaction was kept at −78° C. and monitored by LCMS. After 2 hours, another 0.015 mL of iodomethane was added. Lithium hexamethyldisilazide (1.0 M in tetrahydrofuran, 0.100 mL, 0.100 mmol) was added, followed by another 0.015 mL iodomethane. Allowed to slowly warm to room temperature overnight. The reaction was treated with 0.5 mL methanol and 0.5 mL 2.5 N NaOH. After 4 hours, the reaction mixture was neutralized with 0.5 mL of 3 N hydrogen chloride and concentrated under a stream of nitrogen. The residue was dissolved in dimethylformamide/methanol, filtered through a syringe filter and purified by reverse-phase HPLC (60 to 95% acetonitrile/water/0.05% trifluoroacetic acid) to give the title compound (yellow solid, 48.6 mg, 0.112 mmol, 30.5% yield). $^1$H NMR (400 MHz, DMSO-$d_6$) δ ppm 13.06 (br. s., 1H), 8.10 (d, J=8.2 Hz, 1H), 7.87 (s, 1H), 7.81 (d, J=7.8 Hz, 1H), 7.69 (d, J=9.0 Hz, 1H), 7.43 (s, 1H), 7.23 (d, J=9.0 Hz, 1H), 4.57 (d, J=5.9 Hz, 1H), 3.01-3.10 (m, 2H), 1.91-2.11 (m, 3H), 1.71-1.82 (m, 1H), 1.09-1.56 (m, 7H), 1.06 (s, 3H). ES-MS m/z 434 (M+H).

EXAMPLE 95

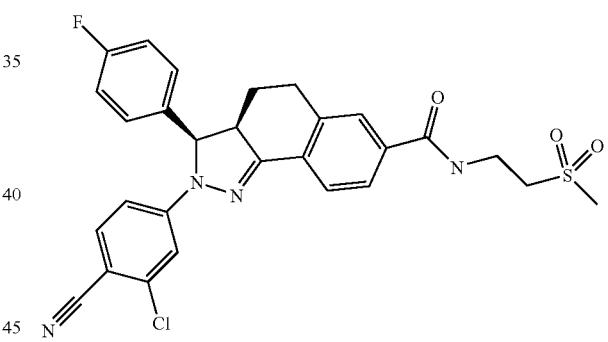

(3R,3aR)-2-(3-chloro-4-cyanophenyl)-3-(4-fluorophenyl)-N-(2-(methylsulfonyl)ethyl)-3,3a,4,5-tetrahydro-2H-benzo[g]indazole-7-carboxamide The title compound was prepared from (3R,3aR)-2-(3-chloro-4-cyanophenyl)-3-(4-fluorophenyl)-3,3a,4,5-tetrahydro-2H-benzo[g]indazole-7-carboxylic acid, Example 3, and 2-(methylsulfonyl)ethanamine hydrochloride according to Method F. $^1$H NMR (400 MHz, DMSO-$d_6$) δ ppm 0.75-0.88 (m, 1H), 1.76-1.84 (m, 1H), 2.84-3.02 (m, 2H), 3.03 (s, 3H), 3.38 (t, J=6.85 Hz, 2H), 3.67 (q, J=6.62 Hz, 2H), 3.96 (ddd, J=13.43, 11.14, 4.97 Hz, 1H), 5.93 (d, J=11.01 Hz, 1H), 6.81-7.44 (m, 6H), 7.66 (d, J=8.86 Hz, 1H), 7.70 (s, 1H), 7.76 (dd, J=8.19, 1.48 Hz, 1H), 8.13 (d, J=8.32 Hz, 1H), 8.78 (t, J=5.64 Hz, 1H); HRMS m/z 551.1343 (M+H).

EXAMPLE 96

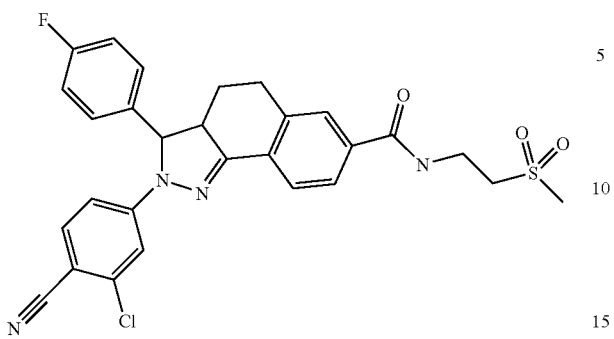

2-(3-chloro-4-cyanophenyl)-3-(4-fluorophenyl)-N-(2-(methylsulfonyl)ethyl)-3,3a,4,5-tetrahydro-2H-benzo[g]indazole-7-carboxamide The title compound was prepared from 2-(3-chloro-4-cyanophenyl)-3-(4-fluorophenyl)-3,3a,4,5-tetrahydro-2H-benzo[g]indazole-7-carboxylic acid and 2-(methylsulfonyl)ethanamine hydrochloride according to Method F. The title compound was largely present as (±)-(3RS,3aSR)-2-(3-chloro-4-cyanophenyl)-3-(4-fluorophenyl)-N-(2-(methylsulfonyl)ethyl)-3,3a,4,5-tetrahydro-2H-benzo[g]indazole-7-carboxamide. $^1$H NMR (400 MHz, DMSO-$d_6$) δ ppm 1.95-2.07 (m, 1H), 2.22-2.30 (m, 1H), 2.92-3.02 (m, 2H), 3.02-3.05 (m, 3H), 3.38 (t, J=6.98 Hz, 2H), 3.41-3.48 (m, 1H), 3.65-3.71 (m, 2H), 5.18 (d, J=10.47 Hz, 1H), 6.83 (dd, J=8.86, 2.15 Hz, 1H), 7.21 (d, J=2.15 Hz, 1H), 7.25-7.30 (m, 2H), 7.48-7.53 (m, 2H), 7.67 (d, J=8.86 Hz, 1H), 7.73 (s, 1H), 7.76 (dd, J=8.19, 1.48 Hz, 1H), 8.05 (d, J=8.32 Hz, 1H), 8.79 (t, J=5.64 Hz, 1H); HRMS m/z 551.1310 (M+H).

EXAMPLE 97

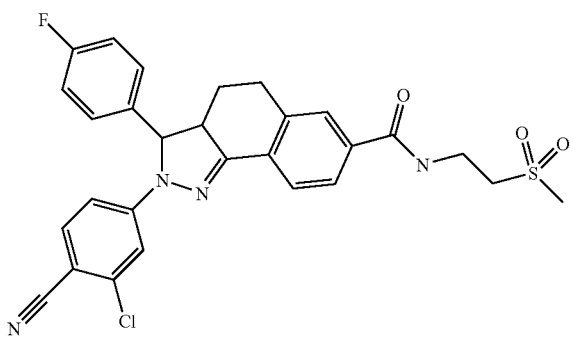

(±)-(3RS,3aRS)-2-(3-chloro-4-cyanophenyl)-3-(4-fluorophenyl)-N-(2-(methylsulfonyl)ethyl)-3,3a,4,5-tetrahydro-2H-benzo[g]indazole-7-carboxamide The title compound was prepared from 2-(3-chloro-4-cyanophenyl)-3-(4-fluorophenyl)-3,3a,4,5-tetrahydro-2H-benzo[g]indazole-7-carboxylic acid, Example 2 and 2-(methylsulfonyl)ethanamine hydrochloride according to Method F. The title compound was largely present as (±)-(3RS,3aRS)-2-(3-chloro-4-cyanophenyl)-3-(4-fluorophenyl)-N-(2-(methylsulfonyl)ethyl)-3,3a,4,5-tetrahydro-2H-benzo[g]indazole-7-carboxamide. $^1$H NMR (400 MHz, DMSO-$d_6$) δ ppm 0.76-0.88 (m, 1H), 1.77-1.84 (m, 1H), 2.83-2.92 (m, 1H), 2.92-3.00 (m, 1H), 3.03 (s, 3H), 3.37 (t, J=6.85 Hz, 2H), 3.63-3.70 (m, 2H), 3.92-4.01 (m, 1H), 5.93 (d, J=11.01 Hz, 1H), 7.07-7.24 (m, 6H), 7.66 (d, J=8.86 Hz, 1H), 7.70 (s, 1H), 7.76 (dd, J=8.19, 1.48 Hz, 1H), 8.14 (d, J=8.32 Hz, 1H), 8.78 (t, J=5.64 Hz, 1H); HRMS m/z 551.1310 (M+H).

EXAMPLE 98

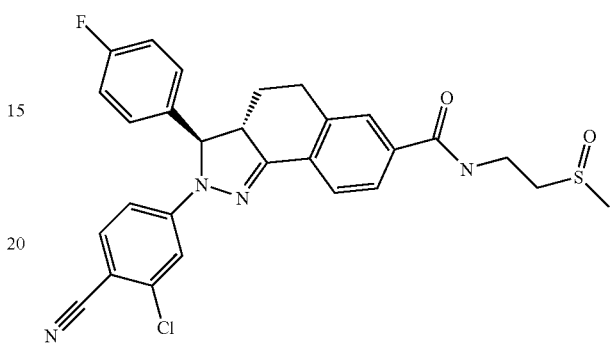

(±)-(3RS,3aSR)-2-(3-chloro-4-cyanophenyl)-3-(4-fluorophenyl)-N-(2-(methylsulfinyl)ethyl)-3,3a,4,5-tetrahydro-2H-benzo[g]indazole-7-carboxamide The title compound was prepared from the trans isomer (±)-(3RS,3aSR)-2-(3-chloro-4-cyanophenyl)-3-(4-fluorophenyl)-3,3a,4,5-tetrahydro-2H-benzo[g]indazole-7-carboxylic acid and amine according to Method F. $^1$H NMR (400 MHz, DMSO-$d_6$) δ ppm 1.94-2.07 (m, 1H), 2.22-2.30 (m, 1H), 2.58-2.61 (m, 3H), 2.85-2.93 (m, 1H), 2.93-3.02 (m, 2H), 3.02-3.10 (m, 1H), 3.39-3.48 (m, 1H), 3.55-3.71 (m, 2H), 5.18 (d, J=10.74 Hz, 1H), 6.83 (dd, J=8.86, 2.15 Hz, 1H), 7.21 (d, J=2.42 Hz, 1H), 7.24-7.31 (m, 2H), 7.47-7.53 (m, 2H), 7.67 (d, J=8.86 Hz, 1H), 7.74 (s, 1H), 7.76 (dd, J=8.32, 1.34 Hz, 1H), 8.04 (d, J=8.06 Hz, 1H), 8.83 (t, J=5.50 Hz, 1H); HRMS m/z 535.1365 (M+H).

EXAMPLE 99

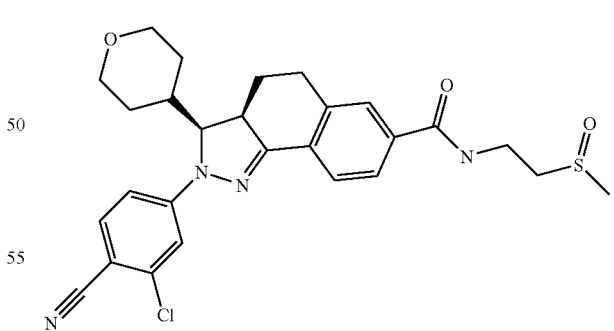

(±)-(3SR,3aRS)-2-(3-chloro-4-cyanophenyl)-N-(2-(methylsulfonyl)ethyl)-3-(tetrahydro-2H-pyran-4-yl)-3,3a,4,5-tetrahydro-2H-benzo[g]indazole-7-carboxamide The title compound was prepared from (□)-(3SR,3aRS)-2-(3-chloro-4-cyanophenyl)-3-(tetrahydro-2H-pyran-4-yl)-

3,3a,4,5-tetrahydro-2H-benzo[g]indazole-7-carboxylic acid, Example 36 and amine according to Method F. $^1$H NMR (400 MHz, DMSO-d$_6$) δ ppm 1.19-1.28 (m, 2H), 1.31-1.42 (m, 1H), 1.44-1.53 (m, 1H), 1.83-1.94 (m, 2H), 2.19-2.29 (m, 1H), 2.56 (s, 3H), 2.82-2.93 (m, 2H), 2.95-3.05 (m, 2H), 3.05-3.15 (m, 2H), 3.53-3.75 (m, 5H), 4.78 (dd, J=9.70, 3.48 Hz, 1H), 7.16 (d, J=8.42 Hz, 1H), 7.40 (s, 1H), 7.66-7.77 (m, 3H), 8.03 (d, J=8.05 Hz, 1H), 8.81 (t, J=5.31 Hz, 1H); ES-MS m/z 525 (M+H).

EXAMPLE 100

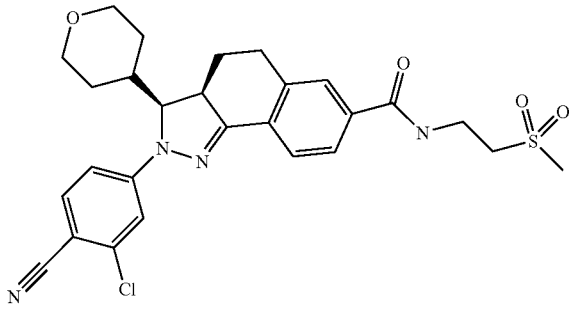

(±)-(3SR,3aRS)-2-(3-chloro-4-cyanophenyl)-N-(2-(methylsulfinyl)ethyl)-3-(tetrahydro-2H-pyran-4-yl)-3,3a,4,5-tetrahydro-2H-benzo[g]indazole-7-carboxamide The title compound was prepared from (±)-(3SR,3aRS)-2-(3-chloro-4-cyanophenyl)-3-(tetrahydro-2H-pyran-4-yl)-3,3a,4,5-tetrahydro-2H-benzo[g]indazole-7-carboxylic acid, Example 36 and 2-(methylsulfonyl)ethanamine hydrochloride according to Method F. $^1$H NMR (400 MHz, DMSO-d$_6$) δ ppm 1.25-1.32 (m, 2H), 1.41 (ddd, J=24.50, 12.42, 4.43 Hz, 1H), 1.51-1.57 (m, 1H), 1.87-1.99 (m, 2H), 2.25-2.33 (m, 1H), 2.87-3.00 (m, 1H), 3.04 (s, 3H), 3.08-3.21 (m, 3H), 3.38 (t, J=6.85 Hz, 2H), 3.61-3.79 (m, 5H), 4.82 (dd, J=9.80, 3.63 Hz, 1H), 7.18-7.23 (m, 1H), 7.44 (s, 1H), 7.71 (d, J=8.59 Hz, 1H), 7.73-7.77 (m, 1H), 7.78 (s, 1H), 8.08 (d, J=8.06 Hz, 1H), 8.79 (t, J=5.50 Hz, 1H); HRMS m/z 541.1702 (M+H).

EXAMPLE 101

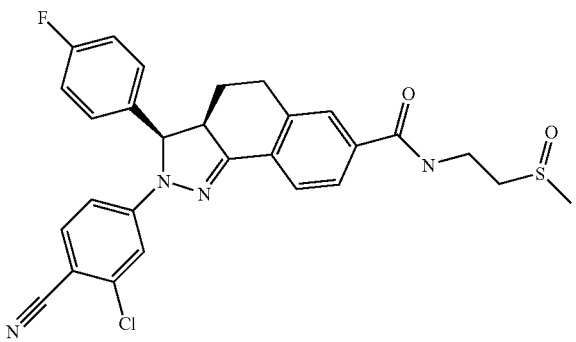

(±)-(3RS,3aRS)-2-(3-chloro-4-cyanophenyl)-3-(4-fluorophenyl)-N-[2-(methylsulfinyl)ethyl]-3,3a,4,5-tetrahydro-2H-benzo[g]indazole-7-carboxamide The title compound was prepared from (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 and amine according to Method F. $^1$H NMR (400 MHz, DMSO-d$_6$) δ ppm 0.81 (ddd, J=25.98, 12.69, 4.57 Hz, 1H), 1.70-1.84 (m, 3H), 2.27 (t, J=7.38 Hz, 2H), 2.84-3.02 (m, 2H), 3.23-3.30 (m, 2H), 3.96 (ddd, J=13.36, 11.35, 4.83 Hz, 1H), 5.92 (d, J=11.01 Hz, 1H), 6.90-7.28 (m, 6H), 7.66 (d, J=8.59 Hz, 1H), 7.71 (s, 1H), 7.76 (dd, J=8.32, 1.34 Hz, 1H), 8.11 (d, J=8.06 Hz, 1H), 8.53 (t, J=5.50 Hz, 1H), 12.04 (br. s., 1H); HRMS m/z 535.1357 (M+H).

EXAMPLE 102

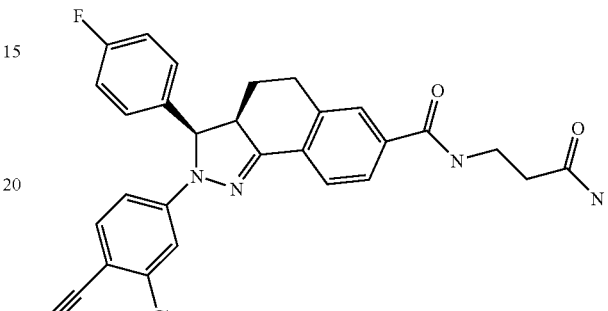

(±)-(3RS,3aRS)—N-(3-amino-3-oxopropyl)-2-(3-chloro-4-cyanophenyl)-3-(4-fluorophenyl)-3,3a,4,5-tetrahydro-2H-benzo[g]indazole-7-carboxamide The title compound was prepared from (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 and amine according to Method F. $^1$H NMR (400 MHz, DMSO-d$_6$) δ ppm 0.75-0.87 (m, 1H), 1.76-1.84 (m, 1H), 2.34 (t, J=7.12 Hz, 2H), 2.83-2.91 (m, 1H), 2.91-3.02 (m, 1H), 3.40-3.46 (m, 2H), 3.64 (br. s., 2H), 3.92-4.00 (m, 1H), 5.93 (d, J=11.01 Hz, 1H), 6.83 (br. s., 1H), 7.17 (t, 4H), 7.34 (s, 1H), 7.66 (d, J=8.86 Hz, 1H), 7.70 (s, 1H), 7.75 (dd, J=8.06, 1.34 Hz, 1H), 8.11 (d, J=8.06 Hz, 1H), 8.55 (t, J=5.64 Hz, 1H); HRMS m/z 516.1587 (M+H).

EXAMPLE 103

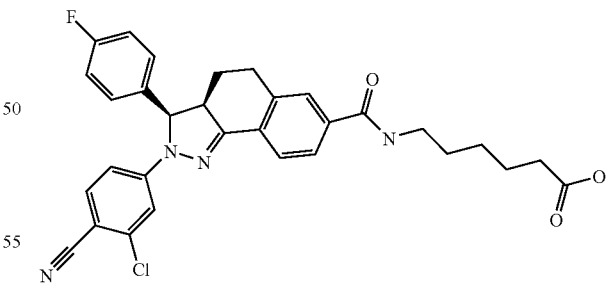

(±)-6-((3RS,3aRS)-2-(3-chloro-4-cyanophenyl)-3-(4-fluorophenyl)-3,3a,4,5-tetrahydro-2H-benzo[g]indazole-7-carboxamido)hexanoic acid The title compound was prepared from (1)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 and amine according to Method F. $^1$H NMR (400 MHz, DMSO-d$_6$) δ ppm 0.75-0.87 (m, 1H), 1.76-1.84 (m, 1H), 2.34

(t, J=7.12 Hz, 2H), 2.83-2.91 (m, 1H), 2.91-3.02 (m, 1H), 3.40-3.46 (m, 2H), 3.64 (br. s., 2H), 3.92-4.00 (m, 1H), 5.93 (d, J=11.01 Hz, 1H), 6.83 (br. s., 1H), 7.17 (t, 4H), 7.34 (s, 1H), 7.66 (d, J=8.86 Hz, 1H), 7.70 (s, 1H), 7.75 (dd, J=8.06, 1.34 Hz, 1H), 8.11 (d, J=8.06 Hz, 1H), 8.55 (t, J=5.64 Hz, 1H); HRMS m/z 559.1895 (M+H).

EXAMPLE 104

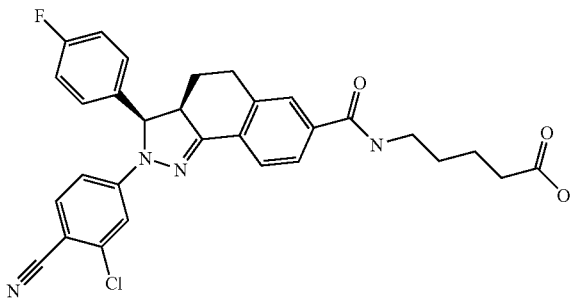

(±)-5-((3RS,3aRS)-2-(3-chloro-4-cyanophenyl)-3-(4-fluorophenyl)-3,3a,4,5-tetrahydro-2H-benzo[g]indazole-7-carboxamido)pentanoic acid The title compound was prepared from (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 and amine according to Method F. $^1$H NMR (400 MHz, DMSO-$d_6$) δ ppm 0.81 (ddd, J=25.91, 12.89, 4.97 Hz, 1H), 1.49-1.55 (m, 4H), 1.76-1.84 (m, 1H), 2.21-2.26 (m, 2H), 2.84-3.02 (m, 2H), 3.22-3.28 (m, 2H), 3.96 (ddd, J=13.56, 11.14, 4.83 Hz, 1H), 5.93 (d, J=11.01 Hz, 1H), 7.11-7.24 (m, 6H), 7.66 (d, J=8.86 Hz, 1H), 7.70 (s, 1H), 7.76 (dd, J=8.19, 1.48 Hz, 1H), 8.11 (d, J=8.32 Hz, 1H), 8.51 (t, J=5.64 Hz, 1H), 12.02 (br. s., 1H); HRMS m/z 545.1745 (M+H).

EXAMPLE 105

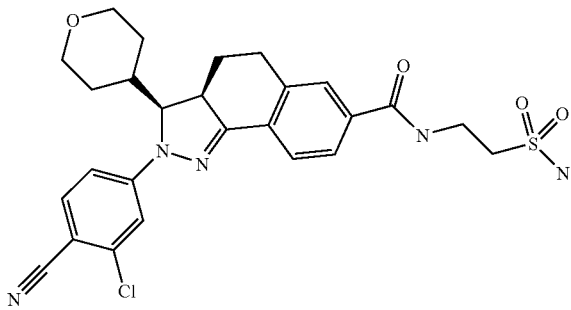

(±)-(3SR,3aRS)—N-[2-(aminosulfonyl)ethyl]-2-(3-chloro-4-cyanophenyl)-3-(tetrahydro-2H-pyran-4-yl)-3,3a,4,5-tetrahydro-2H-benzo[g]indazole-7-carboxamide The title compound was prepared from (±)-(3SR,3aRS)-2-(3-chloro-4-cyanophenyl)-3-(tetrahydro-2H-pyran-4-yl)-3,3a,4,5-tetrahydro-2H-benzo[g]indazole-7-carboxylic acid, Example 36 and amine according to Method F. $^1$H NMR (400 MHz, DMSO-$d_6$) δ ppm 1.18-1.28 (m, 2H), 1.31-1.40 (m, 1H), 1.45-1.53 (m, 1H), 1.82-1.95 (m, 3H), 2.20-2.30 (m, 1H), 2.83-2.93 (m, 1H), 2.99-3.16 (m, 3H), 3.57-3.76 (m, 6H), 4.78 (dd, J=9.52, 3.29 Hz, 1H), 6.92 (s, 2H), 7.16 (d, J=8.42 Hz, 1H), 7.40 (s, 1H), 7.66-7.75 (m, 3H), 8.04 (d, J=8.05 Hz, 1H), 8.67 (t, J=5.49 Hz, 1H); ES-MS m/z 542 (M+H).

EXAMPLE 106

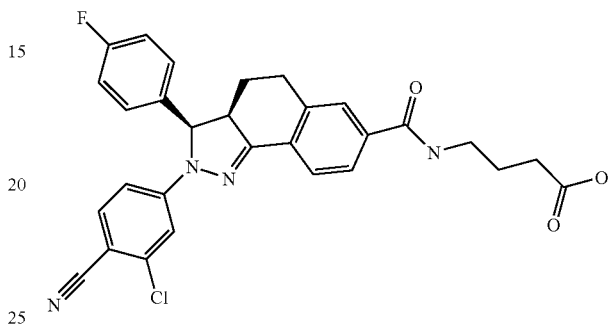

(±)-4-((3RS,3aRS)-2-(3-chloro-4-cyanophenyl)-3-(4-fluorophenyl)-3,3a,4,5-tetrahydro-2H-benzo[g]indazole-7-carboxamido)butanoic acid The title compound was prepared from (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 and amine according to Method F. $^1$H NMR (400 MHz, DMSO-$d_6$) δ ppm 0.75-0.88 (m, 1H), 1.76-1.84 (m, 1H), 2.59 (s, 3H), 2.84-2.92 (m, 2H), 2.92-2.99 (m, 1H), 3.00-3.09 (m, 1H), 3.54-3.70 (m, 2H), 3.92-4.01 (m, 1H), 5.93 (d, J=11.01 Hz, 1H), 6.83-7.47 (m, 6H), 7.66 (d, J=8.59 Hz, 1H), 7.71 (s, 1H) 7.77 (dd, J=8.32, 1.61 Hz, 1H), 8.13 (d, J=8.06 Hz, 1H), 8.82 (t, J=5.50 Hz, 1H); HRMS m/z 531.1596 (M+H).

EXAMPLE 107

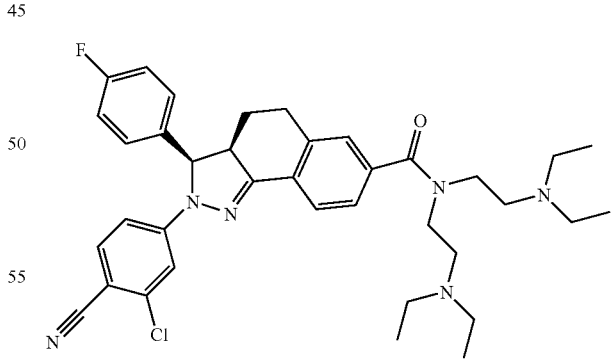

(±)-(3RS,3aRS)-2-(3-chloro-4-cyanophenyl)-N,N-bis(2-(diethylamino)ethyl)-3-(4-fluorophenyl)-3,3a, 4,5-tetrahydro-2H-benzo[g]indazole-7-carboxamide bistrifluoroacetate The title compound was prepared from (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 and amine according to Method F. ¹H NMR (400 MHz, DMSO-d₆) δ ppm 0.79 (ddd, J=25.58, 12.69, 4.97 Hz, 1H), 1.03 (br. s., 6H), 1.26 (br. s., 6H), 1.78-1.87 (m, 1H), 2.84-3.06 (m, 6H), 3.14-3.37 (m, 8H), 3.58 (br. s., 2H), 3.79 (br. s., 2H), 3.96 (ddd, J=13.29, 11.14, 4.83 Hz, 1H), 5.95 (d, J=11.01 Hz, 1H), 7.01-7.29 (m, 6H), 7.36 (s, 1H), 7.41 (d, J=8.32 Hz, 1H), 7.67 (d, J=8.86 Hz, 1H), 8.15 (d, J=8.06 Hz, 1H), 9.86 (br. s., 2H); HRMS m/z 643.3334 (M+H).

EXAMPLE 108

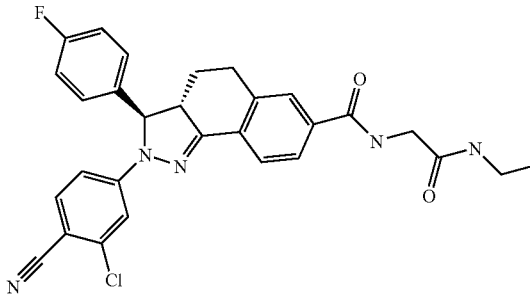

(±)-2-(2-((3RS,3aSR)-2-(3-chloro-4-cyanophenyl)-3-(4-fluorophenyl)-3,3a,4,5-tetrahydro-2H-benzo[g]indazole-7-carboxamido)acetamido)acetic acid The title compound was prepared from the trans isomer (±)-(3RS,3aSR)-2-(3-chloro-4-cyanophenyl)-3-(4-fluorophenyl)-3,3a,4,5-tetrahydro-2H-benzo[g]indazole-7-carboxylic acid and amine according to Method F ¹H NMR (400 MHz, DMSO-d₆) δ ppm 2.01 (ddd, J=25.11, 12.49, 5.10 Hz, 1H), 2.23-2.31 (m, 1H), 2.92-3.04 (m, 2H), 3.45 (ddd, J=13.09, 10.41, 4.97 Hz, 1H), 3.78 (d, J=5.91 Hz, 2H), 3.92 (d, J=5.91 Hz, 2H), 5.18 (d, J=10.47 Hz, 1H), 6.83 (dd, J=8.86, 2.15 Hz, 1H), 7.21 (d, J=2.15 Hz, 1H), 7.28 (tt, J=8.86, 1.88 Hz, 2H), 7.48-7.53 (m, 2H), 7.67 (d, J=8.86 Hz, 1H), 7.78-7.83 (m, 2H), 8.05 (d, J=8.06 Hz, 1H), 8.23 (t, J=5.64 Hz, 1H), 8.84 (t, J=5.91 Hz, 1H); HRMS m/z 560.1528 (M+H).

EXAMPLE 109

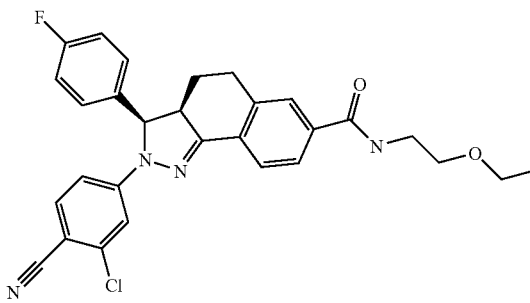

(±)-2-(2-((3RS,3aRS)-2-(3-chloro-4-cyanophenyl)-3-(4-fluorophenyl)-3,3a,4,5-tetrahydro-2H-benzo[g]indazole-7-carboxamido)ethoxy)acetic acid The title compound was prepared from (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 and amine according to Method F. ¹H NMR (400 MHz, DMSO-d₆) δ ppm 0.81 (ddd, J=25.98, 13.09, 4.43 Hz, 1H), 1.77-1.84 (m, 1H), 2.84-3.02 (m, 2H), 3.43 (q, J=5.73 Hz, 2H), 3.60 (t, J=5.77 Hz, 2H), 3.92-4.00 (m, 1H), 4.04 (s, 2H), 5.93 (d, J=11.28 Hz, 1H), 7.04-7.21 (m, 6H), 7.66 (d, J=8.86 Hz, 1H), 7.71 (s, 1H), 7.77 (d, J=8.32 Hz, 1H), 8.12 (d, J=8.06 Hz, 1H), 8.58 (t, J=5.64 Hz, 1H), 12.64 (s, 1H); HRMS m/z 547.1522 (M+H).

EXAMPLE 110

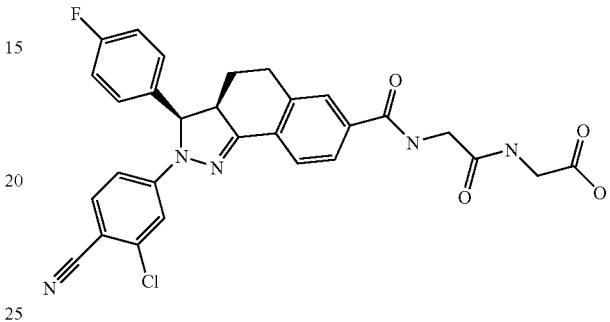

(±)-2-(2-((3RS,3aRS)-2-(3-chloro-4-cyanophenyl)-3-(4-fluorophenyl)-3,3a,4,5-tetrahydro-2H-benzo[g]indazole-7-carboxamido)acetamido)acetic acid The title compound was prepared from (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 and amine according to Method F. ¹H NMR (400 MHz, DMSO-d₆) δ ppm 0.82 (ddd, J=25.98, 12.96, 4.83 Hz, 1H), 1.77-1.85 (m, 1H), 2.85-3.04 (m, 2H), 3.77 (d, J=5.91 Hz, 2H), 3.91 (d, J=6.18 Hz, 2H), 3.97 (ddd, J=13.49, 11.21, 4.83 Hz, 1H), 5.94 (d, J=11.01 Hz, 1H), 6.76-7.43 (m, 6H), 7.67 (d, J=8.86 Hz, 1H), 7.76 (s, 1H), 7.81 (dd, J=8.32, 1.34 Hz, 1H), 8.14 (d, J=8.32 Hz, 1H), 8.22 (t, J=5.77 Hz, 1H), 8.83 (t, J=5.91 Hz, 1H) 12.55 (s, 1H); HRMS m/z 560.1491 (M+H).

EXAMPLE 111

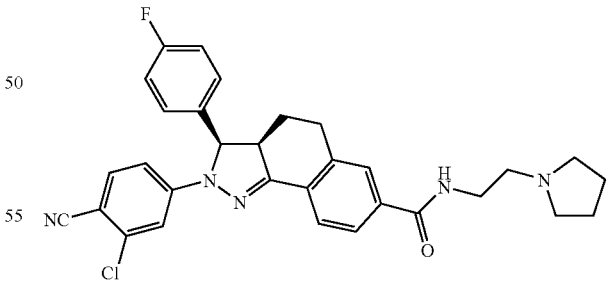

(±)-(3RS,3aRS)-2-(3-chloro-4-cyanophenyl)-3-(4-fluorophenyl)-N-(2-(pyrrolidin-1-yl)ethyl)-3,3a,4,5-tetrahydro-2H-benzo[g] indazole-7-carboxamide 2-(1H-Benzotriazol-1-yl)-1,1,3,3-tetramethyluronium tetrafluoroborate (77 mg, 0.24 mmol) was added to a solution of (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 (89 mg, 0.20 mmol), triethylamine (0.056 mL, 0.40 mmol), and dimethylformamide (2.0 mL) at room temp. After 10 minutes, 2-(pyrrolidin-1-yl)ethanamine (0.051 mL, 0.40 mmol) was added. After 40 minutes, the reaction was quenched with 0.30 mL 3N hydrogen chloride and purified by reverse-phase HPLC (20 to 90% acetonitrile/water/0.05% trifluoroacetic acid). The purified fractions were combined, neutralized with saturated sodium bicarbonate solution, and concentrated until a precipitate formed. The precipitate was filtered, washed with water, and dried to give the title compound (yellow solid, 45.5 mg, 0.084 mmol, 42% yield). $^1$H NMR (400 MHz, DMSO-d$_6$) δ ppm 0.80 (m, 1H), 1.64 (m, 4H), 1.79 (m, 1H), 2.46 (m, 4H), 2.54 (t, J=7.03 Hz, 2H), 2.91 (m, 2H), 3.35 (q, J=6.64 Hz, 2H), 3.95 (ddd, J=13.57, 11.03, 5.08 Hz, 1H), 5.92 (d, J=11.33 Hz, 1H), 7.15 (m, 6H), 7.65 (d, J=8.59 Hz, 1H), 7.69 (s, 1H), 7.75 (dd, J=8.20, 1.56 Hz, 1H), 8.10 (d, J=8.20 Hz, 1H), 8.47 (t, J=5.86 Hz, 1H). ES-MS m/z 542 (M+H).

EXAMPLE 112

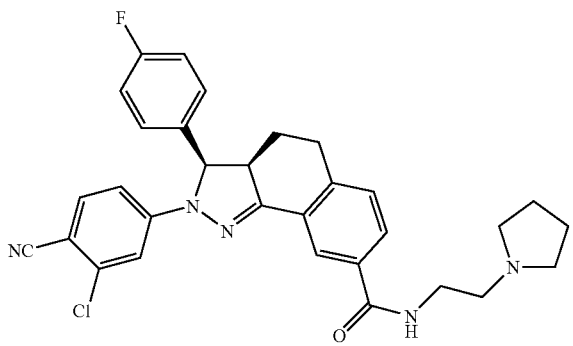

(±)-(3RS13aRS)-2-(3-chloro-4-cyanophenyl)-3-(4-fluorophenyl)-N-(2-(pyrrolidin-1-yl)ethyl)-3,3a,4,5-tetrahydro-2H-benzo[g]indazole-8-carboxamide The title compound was prepared according to the procedure described for Example 111 from (±)-(3RS,3aRS)-2-(3-chloro-4-cyanophenyl)-3-(4-fluorophenyl)-3,3a,4,5-tetrahydro-2H-benzo[g]indazole-8-carboxylic acid, Example 5. Off-white solid, 45.7 mg. $^1$H NMR (400 MHz, DMSO-d$_6$) δ ppm 0.79 (qd, J=12.89, 5.08 Hz, 1H), 1.68 (m, 4H), 1.79 (m, 1H), 2.48 (m, 4H), 2.58 (t, J=7.03 Hz, 2H), 2.92 (m, 2H), 3.40 (m, 2H), 3.95 (m, 1H), 5.91 (d, J=10.94 Hz, 1H), 7.15 (m, 6H), 7.31 (d, J=7.81 Hz, 1H), 7.66 (d, J=8.98 Hz, 1H), 7.79 (dd, J=8.01, 1.76 Hz, 1H), 8.49 (d, J=1.95 Hz, 1H), 8.59 (t, J=5.66 Hz, 1H). ES-MS m/z 542 (M+H).

EXAMPLE 113

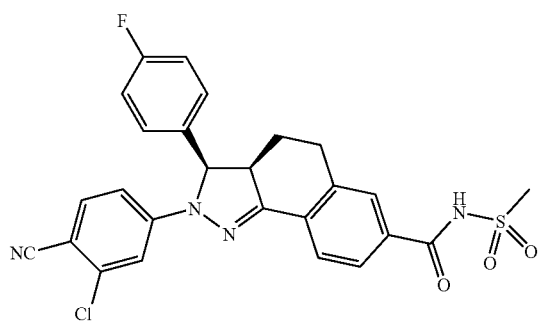

(±)-(3RS,3aRS)-2-(3-chloro-4-cyanophenyl)-3-(4-fluorophenyl)-N-(methylsulfonyl)-3,3a,4,5-tetrahydro-2H-benzo[g]indazole-7-carboxamide A solution of (±)-(3RS,3aRS)-2-(3-chloro-4-cyanophenyl)-3-(4-fluorophenyl)-3,3a,4,5-tetrahydro-2H-benzo[g]indazole-7-carboxylic acid, Example 2 (45 mg, 0.10 mmol), methylsulfonamide (12 mg, 0.12 mmol), triethylamine (0.021 mL, 0.15 mmol), and tetrahydrofuran (1.0 mL) was treated with N-(3-dimethylaminopropyl)-N'-ethylcarbodiimide hydrochloride (29 mg, 0.15 mmol) followed by 4-dimethylaminopyridine (15 mg, 0.12 mmol) at room temp. The reaction was stirred at room temp overnight. The reaction was concentrated and purified by reverse-phase HPLC (40 to 95% acetonitrile/water/0.05% trifluoroacetic acid) to give the title compound (yellow solid, 20.6 mg, 0.0394 mmol, 39% yield). $^1$H NMR (400 MHz, DMSO-d$_6$) δ ppm 0.70-0.92 (m, 1H), 1.72-1.89 (m, 1H), 2.84-3.04 (m, 2H), 3.35 (s, 3H), 3.98 (ddd, J=13.67, 10.94, 5.08 Hz, 1H), 5.95 (d, J=11.33 Hz, 1H), 6.65-7.58 (m, 6H), 7.67 (d, J=8.98 Hz, 1H), 7.75-7.89 (m, 2H), 8.16 (d, J=8.20 Hz, 1H), 12.17 (s, 1H). ES-MS m/z 523 (M+H).

EXAMPLE 114

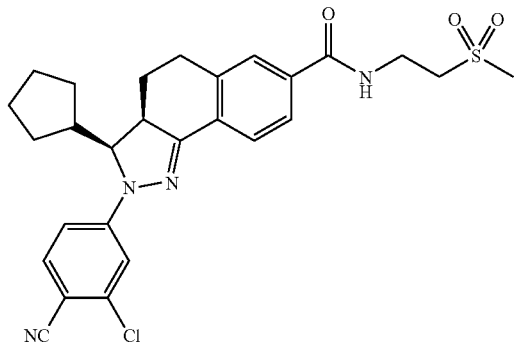

(3S,3aR)-2-(3-chloro-4-cyanophenyl)-3-cyclopentyl-N-(2-(methylsulfonyl)ethyl)-3,3a,4,5-tetrahydro-2H-benzo[g]indazole-7-carboxamide To a solution of (3S,3aR)-2-(3-chloro-4-cyanophenyl)-3-cyclopentyl-3,3a,4,5-tetrahydro-2H-benzo[g]indazole-7- carboxylic acid, Example 15 (90 mg, 0.20 mmol) in N,N-dimethylformamide (1 mL) was added 1-hydroxybenzotriazole (43 mg, 0.32 mmol), triethylamine (0.06 mL, 0.40 mmol) and O-benzotriazol-1-yl-N,N,N',N'-tetramethyluronium tetrafluoroborate (103 mg, 0.32 mmol). The solution was stirred for fifteen minutes followed by addition of 2-(methylsulfonyl)ethanamine (40 mg, 0.32 mmol). The solution was stirred for twenty hours at ambient temperature. The reaction was quenched with water and the resulting yellow solid was collected by vacuum filtration. Chromatography (reverse phase, acetonitrile/water) provided (3S,3aR)-2-(3-chloro-4-cyanophenyl)-3-cyclopentyl-N-(2-(methylsulfonyl)ethyl)-3,3a,4,5-tetrahydro-2H-benzo[g]indazole-7-carboxamide (yellow solid, 55 mg, 52% yield). LC/MS on 4.6×50 mm C-18 column, $t_R$=6.01 minutes (10 to 90% acetonitrile/water over 6 minutes at 2 mL/minute with detection 254 nm, at 50° C.); ES-MS m/z 525 (M+H)

EXAMPLE 115

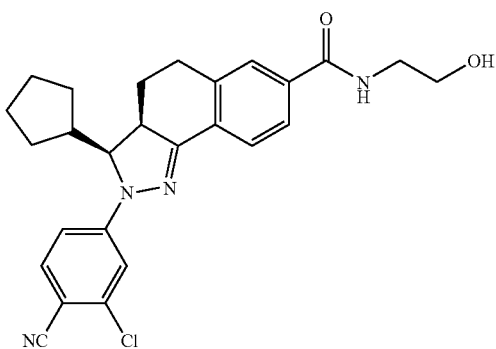

(3S,3aR)-2-(3-chloro-4-cyanophenyl)-3-cyclopentyl-N-(2-hydroxyethyl)-3,3a,4,5-tetrahydro-2H-benzo[g]indazole-7-carboxamide To a solution of (3S,3aR)-2-(3-chloro-4-cyanophenyl)-3-cyclopentyl-3,3a,4,5-tetrahydro-2H-benzo[g]indazole-7-carboxylic acid, Example 15 (90 mg, 0.20 mmol) in N,N-dimethylformamide (1 mL) was added 1-hydroxybenzotriazole (43 mg, 0.32 mmol), triethylamine (0.06 mL, 0.40 mmol) and O-benzotriazol-1-yl-N,N,N',N'-tetramethyluronium tetrafluoroborate (103 mg, 0.32 mmol). The solution was stirred for twenty-five minutes followed by addition of ethanolamine (0.02 mL, 0.32 mmol). The solution was stirred for twenty hours at ambient temperature. The reaction was quenched with water and the resulting yellow solid was collected by vacuum filtration. Chromatography (reverse phase, acetonitrile/water) provided (3S,3aR)-2-(3-chloro-4-cyanophenyl)-3-cyclopentyl-N-(2-hydroxyethyl)-3,3a,4,5-tetrahydro-2H-benzo[g]indazole-7-carboxamide (yellow solid, 30 mg, 33% yield). LC/MS on 4.6×50 mm C-18 column, $t_R$=6.00 minutes (10 to 90% acetonitrile/water over 6 minutes at 2 mL/minute with detection 254 nm, at 50° C.); ES-MS m/z 463 (M+H); HRMS Calculated for $C_{26}H_{27}ClN_4O_2$: 463.1895 (M+H)$^+$. Found: 463.1875; $^1$H NMR (400 MHz, DMSO-$d_6$) δ ppm 1.10-1.50 (m, 6H), 1.66-1.84 (m, 2H), 2.17-2.25 (m, 1H), 2.87-2.93 (m, 1H), 2.99-3.06 (m, 1H), 3.26-3.34 (m, 2H), 3.48 (t, J=6.18 Hz, 2H), 3.53-3.63 (m, 2H), 4.92 (dd, J=9.13, 6.18 Hz, 1H), 7.17 (dd, J=8.46, 1.75 Hz, 1H), 7.38 (d, J=2.15 Hz, 1H), 7.65 (d, J=8.86 Hz, 1H), 7.73 (d, J=8.59 Hz, 1H), 7.76 (s, 1H), 8.03 (d, J=8.06 Hz, 1H), 8.46 (t, J=6.31 Hz, 1H).

EXAMPLE 116

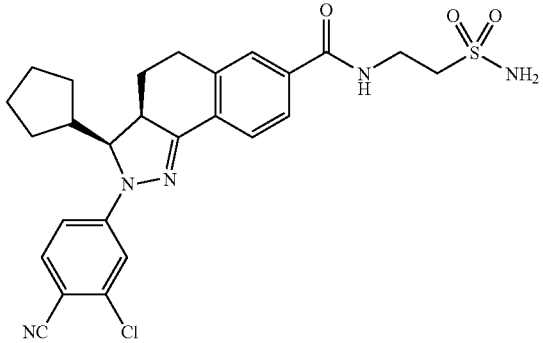

(3S,3aR)-2-(3-chloro-4-cyanophenyl)-3-cyclopentyl-N-(2-sulfamoylethyl)-3,3a,4,5-tetrahydro-2H-benzo[g]indazole-7-carboxamide To a solution of (3S,3aR)-2-(3-chloro-4-cyanophenyl)-3-cyclopentyl-3,3a,4,5-tetrahydro-2H-benzo[g]indazole-7-carboxylic acid, Example 15 (100 mg, 0.24 mmol) in N,N-dimethylformamide (3 mL) was added 1-hydroxybenzotriazole (48 mg, 0.36 mmol), triethylamine (0.07 mL, 0.48 mmol) and O-benzotriazol-1-yl-N,N,N',N'-tetramethyluronium tetrafluoroborate (115 mg, 0.36 mmol). The solution was stirred for fifteen minutes followed by addition of 2-aminoethanesulfonamide (44 mg, 0.36 mmol). The solution was stirred for twenty hours at ambient temperature. The reaction was partitioned between ethyl acetate and water. The organic layer was washed with water and brine and dried over magnesium sulfate. Chromatography (reverse phase, acetonitrile/water) provided (3S,3aR)-2-(3-chloro-4-cyanophenyl)-3-cyclopentyl-N-(2-sulfamoylethyl)-3,3a,4,5-tetrahydro-2H-benzo[g]indazole-7-carboxamide (yellow solid, 10 mg, 8% yield). LC/MS on 4.6×50 mm C-18 column, $t_R$=5.80 minutes (10 to 90% acetonitrile/water over 6 minutes at 2 mL/minute with detection 254 nm, at 50° C.); ES-MS m/z 526 (M+H).

EXAMPLE 117

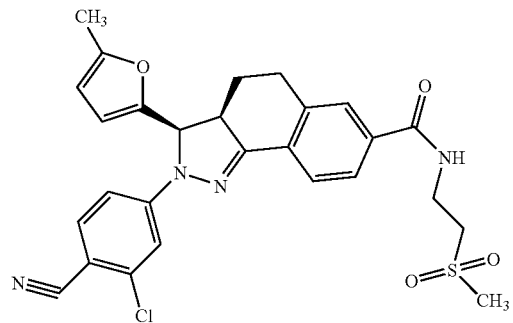

(3R,3aR)-2-(3-chloro-4-cyanophenyl)-3-(5-methyl-2-furyl)-N-[2-(methylsulfonyl)ethyl]-3,3a,4,5-tetrahydro-2H-benzo[g]indazole-7-carboxamide The title compound was prepared from (3R,3aR)-2-(3-chloro-4-cyanophenyl)-3-(5-methyl-2-furyl)-3,3a,4,5-tetrahydro-2H-benzo[g]indazole-7-carboxylic acid, Example 40, and 2-(methylsulfonyl)ethanamine hydrochloride according to Method F (35 mg, 70% yield). $^1$H NMR (400

MHz, DMSO-d$_6$) water_suppression, δ ppm 1.19-1.21 (m, 1H), 1.91 (d, J=9.88 Hz, 1H), 2.07 (s, 3H), 2.96 (d, J=16.84 Hz, 2H), 3.01 (s, 3H), 3.63-3.66 (m, 2H), 3.86 (br. s., 1H), 5.92 (d, J=16.47 Hz, 1H), 5.95 (br. s., 1H), 6.27 (d, J=2.93 Hz, 1H), 7.06 (br. s., 1H), 7.33 (br. s., 1H), 7.65-7.74 (m, 3H), 8.08 (d, J=8.05 Hz, 1H), 8.77 (t, J=5.49 Hz, 1H); ES-MS m/z 537 (M+H).

EXAMPLE 118

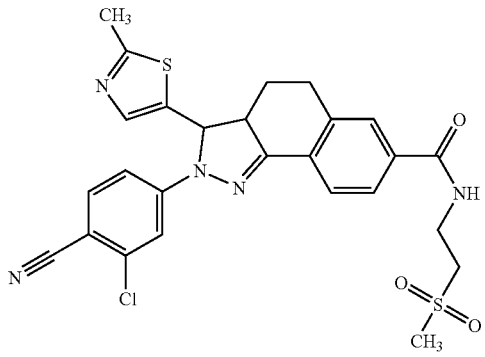

2-(3-chloro-4-cyanophenyl)-N-[2-(methylsulfonyl) ethyl]-3-(2-methyl-1,3-thiazol-5-yl)-3,3a,4,5-tetrahydro-2H-benzo[g]indazole-7-carboxamide The title compound was prepared from 2-(3-chloro-4-cyanophenyl)-3-(2-methyl-1,3-thiazol-5-yl)-3,3a,4,5-tetrahydro-2H-benzo[g]indazole-7-carboxylic acid, Example 49 (40 mg, 0.09 mmol) and 2-(methylsulfonyl)ethanamine hydrochloride (15 mg, 0.09 mmol) according to Method F in 72% yield. The title compound was largely present as 3RS,3aRS)-2-(3-chloro-4-cyanophenyl)-N-[2-(methylsulfonyl)ethyl]-3-(2-methyl-1,3-thiazol-5-yl)-3,3a,4,5-tetrahydro-2H-benzo[g]indazole-7-carboxamide. $^1$H NMR (400 MHz, DMSO-d$_6$) δ ppm 1.23 (dd, J=12.70, 5.27 Hz, 1H), 1.95 (dd, J=8.79, 3.32 Hz, 1H), 2.50 (s, 3H), 2.96-3.05 (m, 2H), 3.04 (s, 3H), 3.38 (s, 3H), 3.68 (q, J=6.64 Hz, 2H), 3.94 (br. s., 1H), 6.31 (d, J=10.16 Hz, 1H), 7.10 (br.s., 1H), 7.40 (br. s., 1H), 7.64 (s, 1H), 7.72 (d, J=8.98 Hz, 1H), 7.77-7.87 (m, 2H), 8.14 (d, J=8.20 Hz, 1H), 8.80 (t, J=5.66 Hz, 1H); ES-MS m/z 554 (M+H).

EXAMPLE 119

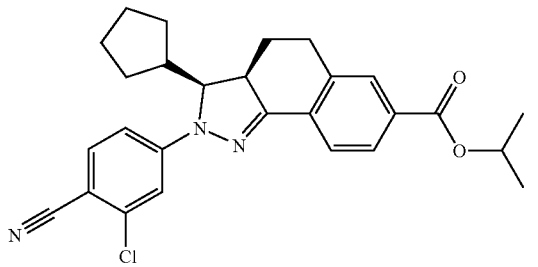

(±)-(3SR,3aRS)-isopropyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and propan-2-ol according to Method E (yellow solid, 145 mg, 0.313 mmol, 66% yield). $^1$H NMR (400 MHz, CDCl$_3$) δ ppm 8.14 (d, J=8.1 Hz, 1H), 7.89-7.94 (m, 2H), 7.46 (d, J=8.9 Hz, 1H), 7.30 (d, J=2.1 Hz, 1H), 7.03 (dd, J=8.9, 2.1 Hz, 1H), 5.22-5.32 (m, 1H), 4.63 (dd, J=9.7, 5.4 Hz, 1H), 3.44-3.54 (m, 1H), 3.08-3.16 (m, 1H), 2.86-2.98 (m, 1, 2.25-2.36 (m, 1H), 2.07-2.19 (m, 1H), 1.88-2.03 (m, 1H), 1.73-1.83 (m, 1H), 1.42-1.66 (m, 5H), 1.39 (d, J=6.4 Hz, 6H), 1.20-1.37 (m, 2H). ES-HRMS m/z calc. for C$_{27}$H$_{29}$ClN$_3$O$_2$ (M+H) 462.1943, found 462.1897.

EXAMPLE 120

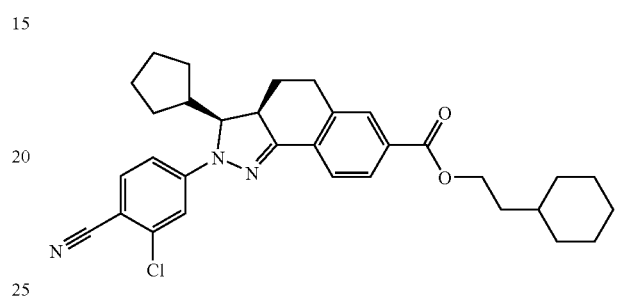

(±)-(3SR,3aRS)-2-cyclohexylethyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and 2-cyclohexylethanol according to Method E (yellow solid, 172 mg, 0.325 mmol, 68% yield). ES HRMS m/z calc. for C$_{32}$H$_{37}$ClN$_3$O$_2$ (M+H) 530.2569, found 530.2534.

EXAMPLE 121

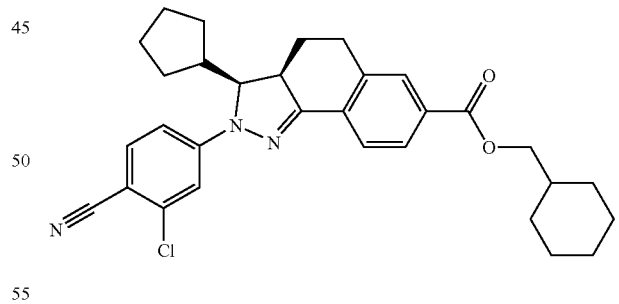

(±)-(3SR,3aRS)-cyclohexylmethyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and cyclohexylmethanol according to Method E (yellow

EXAMPLE 122

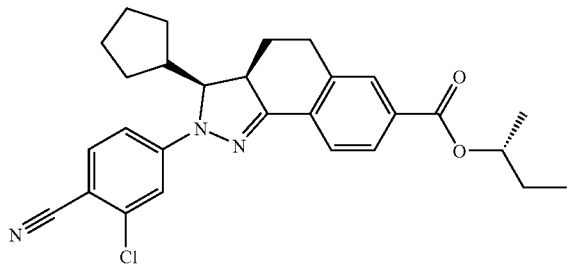

(±)-(3SR,3aRS)—((R)-sec-butyl) 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and (R)-butan-2-ol according to Method E (yellow solid, 155 mg, 0.326 mmol, 68% yield). ES-HRMS m/z calc. for $C_{28}H_{31}ClN_3O_2$ (M+H) 476.2099, found 476.2100.

EXAMPLE 123

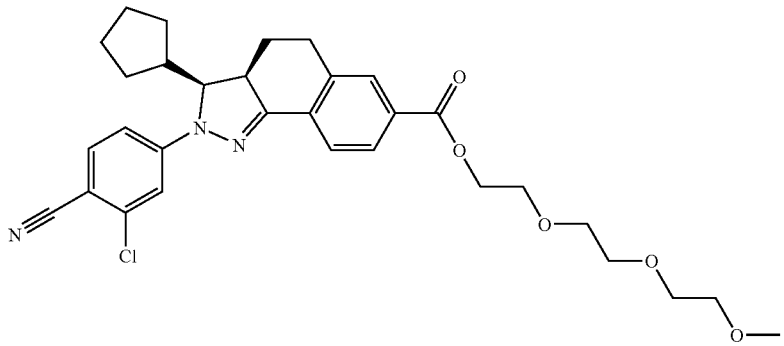

(±)-(3SR,3aRS)-2-(2-(2-methoxyethoxy)ethoxy)ethyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and 2-(2-(2-methoxyethoxy)ethoxy)ethanol according to Method E (yellow solid, 199 mg, 0.352 mmol, 74% yield). ES-HRMS m/z calc. for $C_{31}H_{36}ClN_3NaO_5$ (M+Na) 588.2241, found 588.2245.

EXAMPLE 124

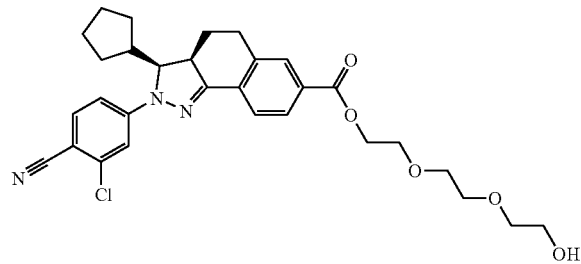

(±)-(3SR,3aRS)-2-(2-(2-hydroxyethoxy)ethoxy)ethyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and triethylene glycol according to Method E (yellow solid, 125 mg, 0.226 mmol, 47% yield). ES-HRMS m/z calc. for $C_{30}H_{34}ClN_3NaO_5$ (M+Na) 574.2085, found 574.2047.

EXAMPLE 125

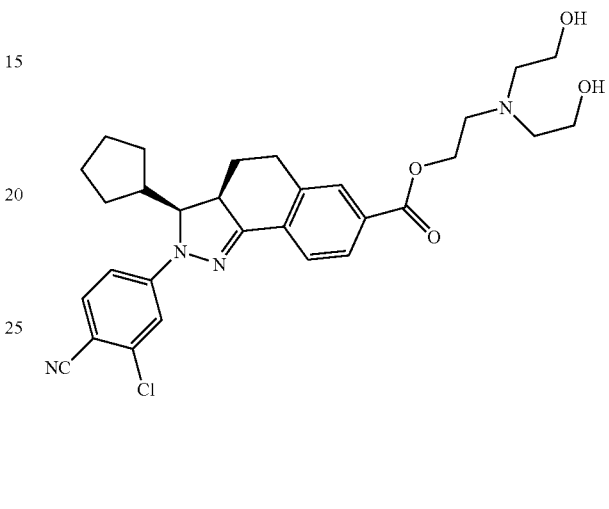

(±)-(3SR,3aRS)-2-(bis(2-hydroxyethyl)amino)ethyl 2-(3-chloro-4-cyanophenyl)-3-cyclopentyl-3,3a,4,5-tetrahydro-2H-benzo[g] indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and triethanolamine according to Method E. $^1$H NMR (400 MHz, CDCl$_3$) δ ppm 1.17-1.66 (m, 7H), 1.70-1.82 (m, 1H), 1.88-2.02 (m, 1H), 2.06-2.18 (m, 1H), 2.23-2.45 (m, 1H), 2.79-2.85 (m, 4H), 2.86-2.97 (m, 1H), 3.03 (t, J=5.50 Hz, 2H), 3.07-3.17 (m, 1H), 3.48 (ddd, J=13.90, 9.47, 4.83 Hz, 1H), 3.63-3.70 (m, 4H), 4.48 (t, J=5.50 Hz, 2H), 4.63 (dd, J=9.40, 5.37 Hz, 1H), 7.01 (dd, J=8.86, 2.15 Hz, 1H), 7.29 (d, J=2.15 Hz, 1H), 7.45 (d, J=8.86 Hz, 1H), 7.82-7.99 (m, 2H), 8.15 (d, J=8.59 Hz, 1H). ES-MS m/z 551 (M+H)

EXAMPLE 126

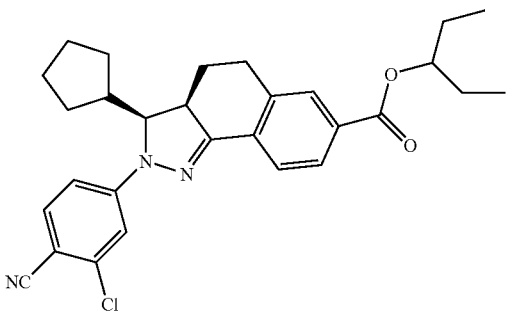

(±)-(3SR,3aRS)-pentan-3-yl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and pentan-3-ol according to Method E. $^1$H NMR (400 MHz, CDCl$_3$) δ ppm 0.97 (t, J=7.38 Hz, 6H), 1.18-1.63 (m, 7H), 1.64-1.81 (m, 4H), 1.96 (ddd, J=26.11, 12.96, 4.16 Hz, 1H), 2.06-2.18 (m, 1H), 2.23-2.40 (m, 1H), 2.83-3.01 (m, 1H), 3.07-3.18 (m, 1H), 3.49 (ddd, J=13.76, 9.33, 4.83 Hz, 1H), 4.64 (dd, J=9.67, 5.37 Hz, 1H), 5.04 (dt, J=12.35, 6.18 Hz, 1H), 7.03 (dd, J=8.86, 2.15 Hz, 1H), 7.30 (d, J=2.15 Hz, 1H), 7.46 (d, J=8.86 Hz, 2H), 7.84-7.99 (m, 2H), 8.15 (d, J=8.06 Hz, 1H).

EXAMPLE 127

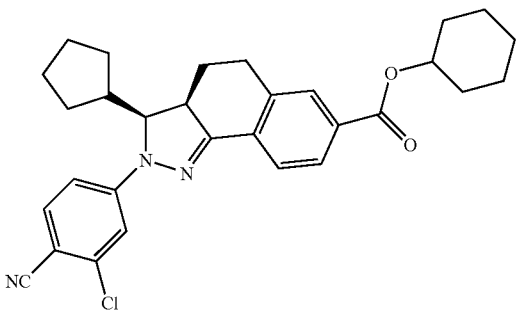

(±)-(3SR,3aRS)-cyclohexyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and cyclohexanol according to Method E. $^1$H NMR (400 MHz, CDCl$_3$) δ ppm 1.19-1.68 (m, 13H), 1.70-1.86 (m, 3H), 1.87-2.03 (m, 3H), 2.06-2.20 (m, 1H), 2.23-2.39 (m, 1H), 2.85-2.98 (m, 1H), 3.13 (ddd, J=16.18, 3.36, 3.02 Hz, 1H), 3.49 (ddd, J=13.76, 9.33, 4.83 Hz, 1H), 4.63 (dd, J=9.53, 5.50 Hz, 1H), 5.04 (ddd, J=12.82, 8.93, 3.76 Hz, 1H), 7.02 (dd, J=8.86, 1.88 Hz, 1H), 7.30 (d, J=2.15 Hz, 1H), 7.46 (d, J=8.86 Hz, 1H), 7.87-7.97 (m, 2H), 8.14 (d, J=8.32 Hz, 1H).

EXAMPLE 128

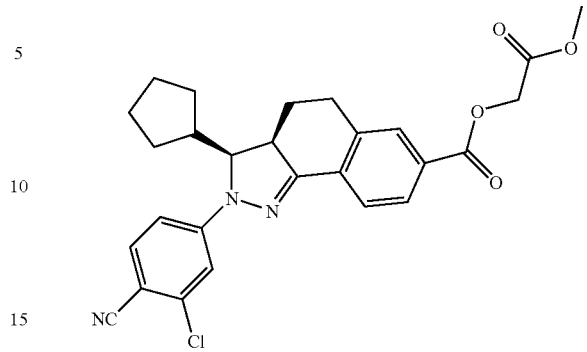

(±)-(3SR,3aRS)-2-methoxy-2-oxoethyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and methyl glycolate according to Method E. $^1$H NMR (400 MHz, CDCl$_3$) δ ppm 1.20-1.69 (m, 7H), 1.72-1.84 (m, 1H), 1.89-2.03 (m, 1H), 2.06-2.20 (m, 1H), 2.26-2.36 (m, 1H), 2.86-2.99 (m, 1H), 3.07-3.18 (m, 1H), 3.49 (ddd, J=13.70, 9.40, 4.83 Hz, 1H), 3.82 (s, 3H), 4.65 (dd, J=9.53, 5.50 Hz, 1H), 4.89 (s, 2H) 7.03 (dd, J=8.73, 2.01 Hz, 1H), 7.31 (d, J=1.88 Hz, 1H), 7.46 (d, J=8.86 Hz, 1H), 7.95-8.01 (m, 2H), 8.17 (d, J=8.86 Hz, 1H). ES-MS m/z 492 (M+H).

EXAMPLE 129

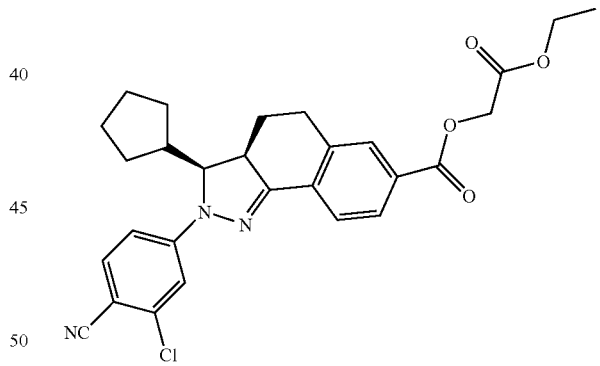

(±)-(3SR,3aRS)-2-ethoxy-2-oxoethyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and ethyl glycolate according to Method E. $^1$H NMR (400 MHz, CDCl$_3$) δ ppm 1.32 (t, J=7.12 Hz, 4H), 1.40-1.67 (m, 6H) 1.72-1.83 (m, 1H), 1.96 (ddd, J=26.25, 13.09, 4.16 Hz, 1H), 2.06-2.20 (m, 1H), 2.25-2.36 (m, 1H), 2.84-2.99 (m, 1H), 3.12 (ddd, J=16.18, 3.36, 3.02 Hz, 1H), 3.49 (ddd, J=13.76, 9.33, 4.83 Hz, 1H), 4.28 (q, J=7.25 Hz, 2H), 4.64 (dd, J=9.67, 5.37 Hz, 1H), 4.87 (s, 2H), 7.03 (dd, J=8.73, 2.01

Hz, 1H), 7.31 (d, J=2.15 Hz, 1H), 7.46 (d, J=8.59 Hz, 1H), 7.93-8.02 (m, 2H), 8.17 (d, J=8.86 Hz, 1H). ES-MS m/z 506 (M+H).

EXAMPLE 130

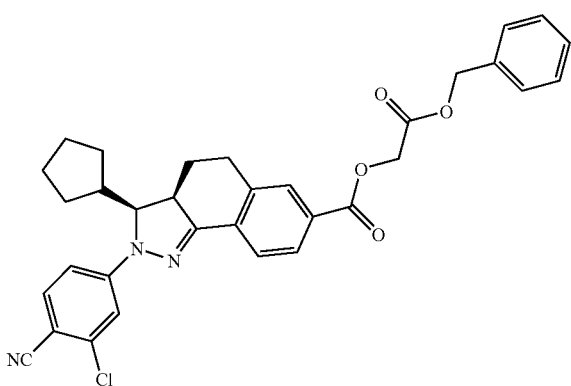

(±)-(3SR,3aRS)-2-(benzyloxy)-2-oxoethyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and benzyl glycolate according to Method E. $^1$H NMR (400 MHz, CDCl$_3$) δ ppm 1.20-1.68 (m, 7H), 1.72-1.84 (m, 1H), 1.96 (ddd, J=26.18, 12.89, 4.16 Hz, 1H), 2.06-2.20 (m, 1H), 2.25-2.35 (m, 1H), 2.84-2.98 (m, 1H), 3.12 (ddd, J=15.91, 3.36, 3.02 Hz, 1H), 3.49 (ddd, J=113.83, 9.40, 4.70 Hz, 1H), 4.65 (dd, J=9.40, 5.37 Hz, 1H), 4.92 (s, 2H), 5.25 (s, 2H), 7.03 (dd, J=8.73, 2.01 Hz, 1H), 7.31 (d, J=2.15 Hz, 1H), 7.33-7.42 (m, 5H), 7.46 (d, J=8.86 Hz, 1H), 7.93-8.03 (m, 2H), 8.17 (d, J=8.59 Hz, 1H).

EXAMPLE 131

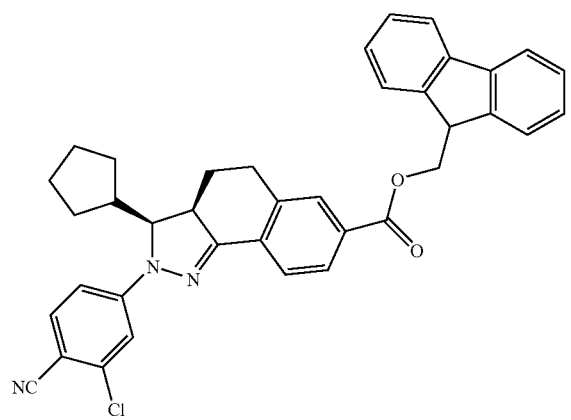

(±)-(3SR,3aRS)-(9H-fluoren-9-yl)methyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and 9-fluorenylmethanol according to Method E. $^1$H NMR (400 MHz, CDCl$_3$) δ ppm 1.19-1.67 (m, 7H), 1.72-1.85 (m, 1H), 1.99 (ddd, J=26.11, 12.96, 4.16 Hz, 1H), 2.07-2.22 (m, 1H), 2.25-2.38 (m, 1H), 2.85-3.03 (m, 1H), 3.06-3.21 (m, 1H), 3.50 (ddd, J=13.83, 9.26, 4.83 Hz, 1H), 4.41 (t, J=7.12 Hz, 1H), 4.60-4.70 (m, 3H), 7.03 (dd, J=8.73, 2.01 Hz, 1H), 7.29-7.38 (m, 3H), 7.40-7.51 (m, 3H), 7.66 (d, J=7.52 Hz, 2H), 7.82 (d, J=7.52 Hz, 2H), 7.91-8.00 (m, 2H), 8.20 (d, J=8.06 Hz, 1H).

EXAMPLE 132

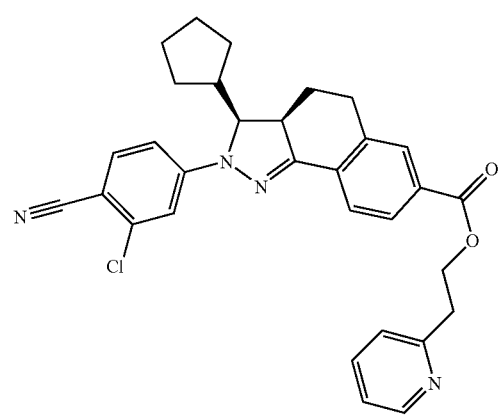

(±)-(3SR,3aRS)-2-(pyridin-2-yl)ethyl 2-(3-chloro-4-cyanophenyl)-3-cyclopentyl-3,3a,4,5-tetrahydro-2H-benzo[g]indazole-7-carboxylate The title compound was prepared according to Method E from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and 2-(2-pyridyl)ethanol. Yellow solid, 194 mg. ES-MS m/z 525 (M+H).

EXAMPLE 133

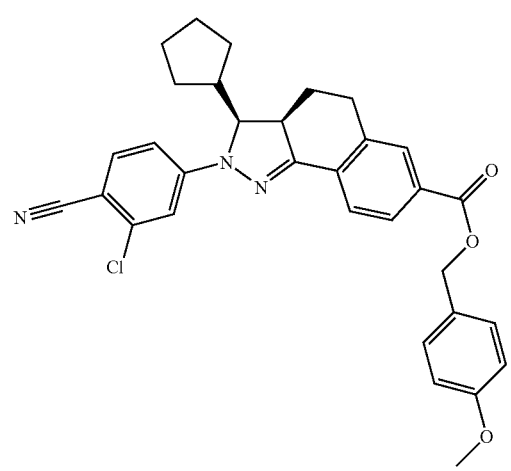

(±)-(3SR,3aRS)-4-methoxybenzyl 2-(3-chloro-4-cyanophenyl)-3-cyclopentyl-3,3a,4,5-tetrahydro-2H-benzo[g]indazole-7-carboxylate The title compound was prepared according to Method E from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and p-methoxybenzyl alcohol. Yellow solid, 194 mg. ES-MS m/z 540 (M+H).

EXAMPLE 134

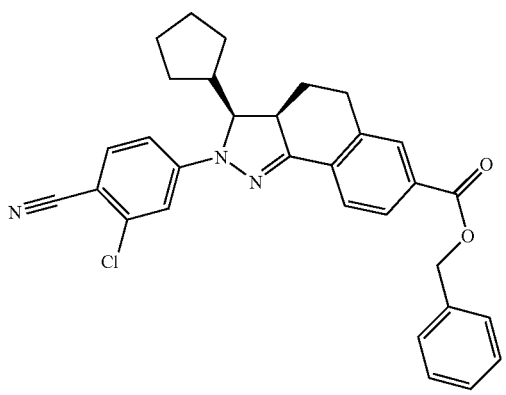

(±)-(3SR,3aRS)-benzyl 2-(3-chloro-4-cyanophenyl)-3-cyclopentyl-3,3a,4,5-tetrahydro-2H-benzo[g]indazole-7-carboxylate The title compound was prepared according to Method E from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and benzyl alcohol. Yellow solid, 193 mg. ES-MS m/z 510 (M+H).

EXAMPLE 135

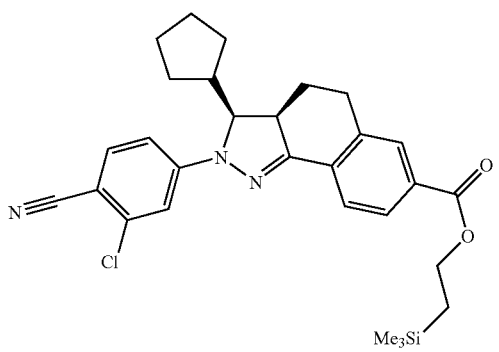

(±)-(3SR,3aRS)-2-(trimethylsilyl)ethyl 2-(3-chloro-4-cyanophenyl)-3-cyclopentyl-3,3a,4,5-tetrahydro-2H-benzo[g]indazole-7-carboxylate The title compound was prepared according to Method E from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and 2-(trimethylsilyl)ethanol. Yellow solid, 192 mg. ES-MS m/z 520 (M+H).

EXAMPLE 136

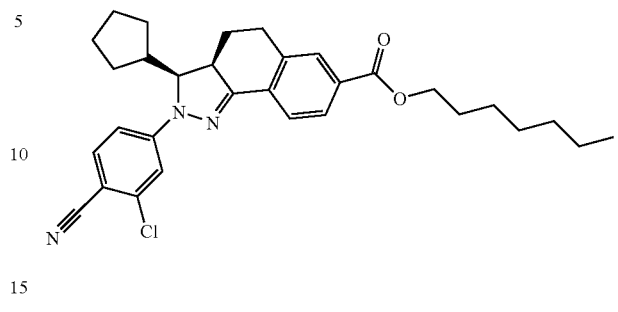

(±)-(3SR,3aRS)-heptyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and 1-heptanol according to Method E. $^1$H NMR (400 MHz, DMSO-$d_6$) δ ppm 0.86 (t, J=6.98 Hz, 3H), 1.11-1.56 (m, 15H), 1.67-1.75 (m, 3H), 1.83 (ddd, J=25.98, 12.82, 3.89 Hz, 1H), 2.01-2.12 (m, 1H), 2.20-2.27 (m, 1H), 2.85-2.96 (m, 1H), 3.07-3.15 (m, 1H), 3.62 (ddd, J=13.76, 9.33, 4.56 Hz, 1H), 4.28 (t, J=6.58 Hz, 2H), 4.97 (dd, J=9.40, 5.64 Hz, 1H), 7.21 (dd, J=8.86, 2.15 Hz, 1H), 7.42 (d, J=2.15 Hz, 1H), 7.69 (d, J=8.86 Hz, 1H), 7.83 (dd, J=8.19, 1.48 Hz, 1H), 7.87 (s, 1H), 8.12 (d, J=8.32 Hz, 1H); ES-MS m/z 518 (M+H).

EXAMPLE 137

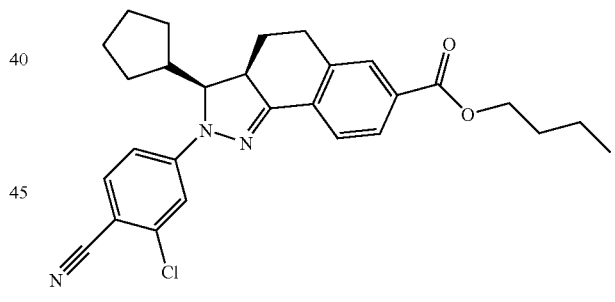

(±)-(3SR,3aRS)-butyl 2-(3-chloro-4-cyanophenyl)-3-cyclopentyl-3,3a,4,5-tetrahydro-2H-benzo[g]indazole-7-carboxylate The title compound was prepared from (±)-(3SR,3aRS)-2-(3-chloro-4-cyanophenyl)-3-cyclopentyl-3,3a,4,5-tetrahydro-2H-benzo[g]indazole-7-carboxylic acid, Example 15 and n-butanol according to Method E. $^1$H NMR (400 MHz, DMSO-$d_6$) δ ppm 0.94 (t, J=7.38 Hz, 3H), 1.12-1.55 (m, 9H), 1.66-1.75 (m, 3H), 1.83 (ddd, J=25.91, 13.02, 4.03 Hz, 1H), 2.01-2.11 (m, 1H), 2.20-2.27 (m, 1H), 2.85-2.96 (m, 1H), 3.07-3.15 (m, 1H), 3.61 (ddd, J=13.63, 9.33, 4.70 Hz, 1H), 4.29 (t, J=6.44 Hz, 2H), 4.97 (dd, J=9.53, 5.77 Hz, 1H), 7.21 (dd, J=8.86, 1.88 Hz, 1H), 7.42 (d, J=2.15 Hz, 1H), 7.69 (d, J=8.86 Hz, 1H), 7.83 (dd, J=8.32, 1.34 Hz, 1H), 7.87 (s, 1H), 8.12 (d, J=8.32 Hz, 1H); ES-MS m/z 476 (M+H).

O. Biological Assays

1. In Vitro Assay

Method 1: Cell-based Gal4 Response Element-controlled Luciferase Reporter Assay

An in vitro assay can be used to evaluate mineralocorticoid receptor (MR) antagonism by a test compound. As described more specifically below, this assay measures the mineralocorticoid receptor $IC_{50}$ value of the test compound (i.e., the concentration of the test compound required to block agonist induced activation of the mineralocorticoid receptor by 50%, relative to activation in the absence of an antagonist. Human liver cells (Huh7) were transfected with a luciferase reporter gene under the control of Gal4 response element, along with a plasmid containing the Gal4 DNA binding domain (DBD) fusion of a steroid receptor (mineralocorticoid receptor) ligand binding domains (LBDs) and a β-galactosidase control plasmid. An agonist of the receptor can bind to and activate the receptor LBD, which activate the expression of the Gal4 response element containing luciferase reporter gene. Antagonists can compete for binding to the receptor LBDs and decrease the transcription activity of the reporter gene. Measurement of luciferase activity allows quantitative determinations of the reporter transcription in the presence of either agonists or agonists and antagonists in combination. β-galactosidase activity, which is unaffected by ligand, is used to normalize the transfection efficiency in the cell population.

Huh7 cells were plated in RPMI1640+10% fetal bovine serum (Invitrogen Corporation, San Diego, Calif.), at 10,000 cells per well in 96-well tissue culture dishes for approximately 24 hours. Cells were then transfected using FuGENE™ 6 Transfection Reagent according to manufacturers' instructions (Roche Molecular Biochemicals, Indianapolis, Ind.). Approximately 20 hours after transfection, media were removed. Cells were washed once with PBS and treated (n=6/group) with agonist for each receptor (all chemicals from Sigma, St. Louis, Mo.), and with compounds. Agonist concentrations represent 70-80% of full activation of each receptor.

Compounds were dissolved in DMSO at 10 mM and diluted to final concentrations in phenol red-free media that contained 10% charcoal- and dextran-stripped serum (Life Technologies, Gathersburg, Md.). Following overnight incubation (18-20 hours) with compounds, the medium was removed and replaced with 100 μL per well of PBS and 100 μL of Steady-Glo™ lysis buffer with luciferase substrate (Promega Corporation, Madison, Wis.). After a 30-minute incubation to completely lyse the cells, 100 μL of the lysate was transferred to a black, Dynatech Microfluor assay plates (Dynex Corporation, Chantilly, Va.) to measure luciferase activity. The plate was sealed with TopSeal self-adhesive film, dark-adapted for 5 minutes, then counted in a TopCount Plate Reader (Packard Instrument Company, Meriden, Conn.) in single photon counting mode. The remaining lysate was used for determination of β-galactosidase activity. In a clear 96-well assay plate, 100 μL of cell lysate was added to 100 μL β-galactosidase assay buffer per well. The assay buffer consisted of 60 mM Na2HPO4, 40 mM NaH2PO4, 10 mM KCl, 1 mM MgSO4, 50 mM β-mercaptoethanol, and 2.5 mg/mL ONPG, the latter two reagents were added just prior to assay (all chemicals from Sigma). The reaction was allowed to proceed until a distinct yellow color developed. Reactions were stopped by the addition of 100 μL per well 1 M $Na_2CO_3$ and plates were read at 420 nm in Victor-2 (Perkin Elmer Life Sciences, Boston, Mass.). Values (relative luciferase activity) for each sample were expressed as a ratio of luciferase activity to $OD_{420}$β-galactosidase activity measured in arbitrary units for each well. Curve fitting was performed using the 4-parameter logistic model ($y=(a-d)/(1+(x/c)\hat{}b)+d$) with the lower (a) and upper (d) plateaus representing activity values for vehicle control and agonist control respectively. "b" is the slope, "c" is the $IC_{50}$ or $EC_{50}$. "x" is the concentration of the compound and "y" the activity at that concentration.

Compounds were tested in accordance with the above described assay yielding the $IC_{50}$ values described below:

| Example # | MR $IC_{50}$ (uM) |
|---|---|
| 1 | 1.07 |
| 2 | 0.223 |
| 3 | 0.0407 |
| 4 | 3.5 |
| 5 | 3.7 |
| 6 | 0.081 |
| 7 | 0.0172 |
| 8 | 2.74 |
| 9 | 0.17 |
| 10 | 0.553 |
| 11 | 0.205 |
| 12 | >10.0 |
| 13 | 0.535 |
| 14 | 0.929 |
| 15 | 0.0212 |
| 16 | 0.0085 |
| 17 | 0.958 |
| 18 | 0.089 |
| 19 | 0.0376 |
| 20 | 2.88 |
| 21 | 0.004 |
| 22 | 0.004 |
| 23 | >0.500 |
| 24 | 0.008 |
| 25 | 0.007 |
| 26 | 0.013 |
| 27 | 0.305 |
| 28 | 0.15 |
| 29 | >1.00 |
| 30 | 0.446 |
| 31 | 0.488 |
| 33 | >0.500 |
| 34 | 0.72 |
| 35 | 0.021 |
| 36 | 0.127 |
| 37 | >1.00 |
| 38 | >1.00 |
| 39 | 0.022 |
| 40 | 0.006 |
| 41 | >1.00 |
| 42 | 0.015 |
| 43 | 0.021 |
| 44 | 0.016 |
| 45 | >1.00 |
| 46 | 0.069 |
| 47 | 0.018 |
| 48 | >1.00 |
| 49 | 0.103 |
| 50 | 0.205 |
| 51 | 0.007 |
| 52 | 4.98 |
| 53 | 0.307 |
| 54 | 0.973 |
| 55 | 0.849 |
| 56 | 0.302 |
| 57 | 3.51 |
| 58 | 3.18 |
| 59 | >1.00 |
| 60 | >1.00 |
| 61 | 0.039 |
| 62 | 0.026 |
| 63 | >1.00 |
| 64 | 0.065 |
| 65 | 0.038 |
| 66 | 3.35 |

-continued

| Example # | MR IC$_{50}$ (uM) |
|---|---|
| 67 | 0.146 |
| 68 | 0.052 |
| 69 | 0.13 |
| 70 | 0.906 |
| 71 | 0.205 |
| 72 | 8.1 |
| 73 | 0.167 |
| 74 | 0.588 |
| 75 | 0.711 |
| 76 | >1.00 |
| 77 | 0.013 |
| 78 | 0.07 |
| 79 | 6.92 |
| 80 | 0.049 |
| 81 | 0.035 |
| 82 | >1.00 |
| 83 | 0.077 |
| 84 | 0.113 |
| 85 | >1.00 |
| 86 | 0.086 |
| 87 | 0.036 |
| 88 | >1.00 |
| 89 | 0.705 |
| 90 | 1.1 |
| 91 | 0.005 |
| 92 | >1.00 |
| 94 | 0.025 |
| 95 | 0.002 |
| 96 | 0.012 |
| 97 | 0.012 |
| 98 | 0.013 |
| 99 | 0.014 |
| 100 | 0.021 |
| 101 | 0.023 |
| 102 | 0.035 |
| 103 | 0.113 |
| 104 | 0.122 |
| 105 | 0.141 |
| 106 | 0.312 |
| 107 | 0.523 |
| 108 | >1.00 |
| 109 | >1.00 |
| 110 | >1.00 |
| 111 | 0.057 |
| 112 | 1.55 |
| 113 | 0.995 |
| 114 | 0.001 |
| 115 | 0.003 |
| 117 | 0.003 |
| 118 | 0.019 |

2. In Vivo Assays

Method 2: Colonic ENaCgamma Expression Assay

The effect of a test compound can also be evaluated for potential therapeutic applications by a functional assay, in which the test compound blocks in vivo expression of a surrogate protein marker for mineralocorticoid receptor activation. In this assay aldosterone induced expression of colonic ENaCgamma is measured. Male Sprague-Dawley rats (225-250 g) (Harlan Sprague-Dawley Industries, Indianapolis, Ind.) were used in this assay. All animals were housed in a room with ambient temperature of 22±1° C. on a 12 hour light/dark cycle. Animals were allowed one week to acclimate and had free access to Teklad 22/5 rodent chow (Harlan Teklad, Madison, Wis.) and tap water ad libitum until the initiation of the study.

The rats were initially anesthetized with 5% Isoflurane (AErrane; Baxter, Inc., Deerfield, Ill.) delivered in 100% O2 (USP Medical Grade, Airgas-Mid America, Bowling Green, Ky.) using a VMS anesthesia instrument (Matrix Medical, Inc., Orchard Park, N.Y.) Once anesthetized, 1-2% Isoflurane was used to maintain anesthesia. The surgery site was shaved, scrubbed with Dial 4% CHG surgical scrub (Dial Corp., Phoenix, Ariz.), and sprayed with Betadine Aerosol topical antiseptic/bactericide spray (Perdue Frederick Co., Stamford, Conn.). and a bilateral adrenalectomy (ADX) was performed via the dorsal approach. The muscle layer was closed with 4-0 vicryl and skin wounds closed with surgical staples. The analgesic, Marcaine (0.25%) (Abbot Laboratories, Chicago, Ill.) was injected (0.1 mL, s.c.) at the incision site. Post-operative care included monitoring of the animals, which were placed on thermogenic heating pads during recovery from anesthesia until sternal recumbency and alertness were obtained. Animals were inspected daily for signs of distress and infection at the surgical site. ADX rats were given 0.9% NaCl in the drinking water to compensate the sodium deficiency induced by the ADX.

After 3 days of recovery from surgery, and following an overnight fast, rats were randomly assigned into five groups (n=5-9), including three treatment groups, one control group and one vehicle group. The vehicle and control groups were dosed with solution vehicle (10% EtOH, 70% PEG 400, 20% PBS); the rats in the treatment groups were dosed orally with test compounds at 1 mg/kg, dissolved in the solution vehicle. Aldosterone (5 ug/kg, Sigma, St. Louis, Mo.) was given to all treatment groups and the control group at 30 minutes post-dose. Blood and distal colon were collected at 2 hours post-dose. The rats were sacrificed with CO2 and animals were exsanguinated using an 18-gauge needle inserted into the heart. The distal colon was extracted and immediately placed in liquid N2 for later ENaCγ level determination. Blood was centrifuged for 15 minutes at 3000 rpm, 4° C. and serum collected and frozen at −80° C. until further analysis.

Frozen distal colon was powdered, lysed in Qiagen RLT buffer with chloroform, and the aqueous layer combined with 70% ethanol and purified over the Qiagen 96-well RNeasy system (Qiagen Inc, Valencia, Calif.). 5 ul reactions were prepared with the Bioimaek 2000 and Fx instruments, and Q-RT-PCR was performed using Qiagen one-step reagents. Thermocycling and data collection were performed on an ABI 7900 (Applied Biosystems, Foster City, Calif.). The comparative CT (threshold cycle) method of calculation was used for determining relative expression of mineralocorticoid receptor target genes; cyclophilin was used to normalize expression.

Method 3: Dahl SS Rat Blood Pressure Assay

The effect of a test compound on systemic blood pressure can be evaluated in vivo, using an animal model of hypertension. Male Dahl salt-sensitive rats (225-250 g) (Harlan Sprague-Dawley Industries, Indianapolis, Ind.) were used in this assay. All animals were housed in a room with ambient temperature of 22±1° C. on a 12 hour light/dark cycle. Animals were allowed one week to acclimate and had free access to Teklad 22/5 rodent chow (Harlan Teklad, Madison, Wis.) and tap water ad libitum until the initiation of the study.

All animals were instrumented with radiotelemetry units (Data Sciences Inc., St. Paul, Minn.) for conscious, unrestricted SBP measurements. Animals were initially anesthetized with 5% Isoflurane (AErrane; Baxter, Inc., Deerfield, Ill.) delivered in 100% O2 (USP Medical Grade, Airgas-Mid America, Bowling Green, Ky.) using a VMS anesthesia instrument (Matrix Medical, Inc., Orchard Park, N.Y.). Once anesthetized, 1-2% Isoflurane was used to maintain anesthesia. The surgery site was shaved, scrubbed with Dial 4% CHG surgical scrub (Dial Corp., Phoenix, Ariz.), and sprayed with Betadine Aerosol topical antiseptic/bactericide spray (Perdue Frederick Co., Stamford, Conn.). A 5-cm midline incision was made through the skin and muscle layer of the abdominal wall exposing the peritoneal cavity. Organs were carefully displaced with tissue retractors in order to expose the abdominal aorta and mesentery. A 1.5-cm segment between the renal arteries and the bifurcation of the iliac arteries was exposed and an anchor was made using 4-0 silk suture adjacent to the aorta in the psoas muscle. Microvessel clips were placed at both ends of the cleared aorta to stop excessive blood flow, and the aorta was cannulated using a 21-gauge bent needle to insert the indwelling radiotelemetry probe-flow catheter. The catheter was secured to the psoas muscle using the 4-0 silk anchor, microvessel clips and retractor were removed, and organs repositioned. The body of the telemetry unit was placed on top of the lower intestines and 1 mL of warm saline dripped into the body cavity. Using an interrupted suture pattern with 4-0 vicryl, the transmitter was sewn into the muscle layer, the abdominal wall was closed, and the skin layer was closed using 4-0 ethilon (nylon) suture in an interrupted pattern. The analgesic, Marcaine (0.25%) (Abbot Laboratories, Chicago, Ill.) was injected (0.1 mL, s.c.) at the incision site. Post-operative care included treatment with 0.1 mg/kg, s.c. Buphrenorphine (Rickett & Colman Pharmaceuticals Inc., Richmond, Va.) and monitoring of the animals, which were placed on thermogenic heating pads during recovery from anesthesia until sternal recumbency and alertness were obtained. Animals were inspected daily for signs of distress and infection at the surgical site.

After 5-7 days of recovery from surgery, baseline SBP was measured and all animals were then randomized to various treatment groups and compounds were continued for 21 days. All animals were placed on Teklad 92034 4% NaCl rodent chow (Harlan Teklad), which was maintained for 21 days. The vehicle group received 0.5% methylcellulose/0.1% Tween 80. All compounds given to the treatment groups were dissolved in 0.5% methylcellulose/0.1% Tween 80. For compound treated groups, animals were dosed with the compounds daily, via gavage. For eplerenone treated groups, eplerenone was incorporated into the 4% NaCl rodent chow at various concentrations (Research Diets, Inc., New Brunswick, N.J.).

Radiotelemetrized arterial SBP was measured with the DATAQUEST A.R.T. Version 3.0-Gold software (Data Sciences International, St. Paul, Minn.). The values represent the average of all data points collected from each animal, every 15 minutes for a 10 second interval over a 24-hour period (6:00 a.m. to 6:00 a.m. the following day). SBP data was collected continuously over the course of the entire study (days 1-21).

Twenty-four hours prior to the termination of the study, animals were placed in metabolism caging and urine was collected at 24 hours. Animals were not fasted for the 24-hour period. After 21 days of treatment, animals were anesthetized with a mixture of ketamine (40 mg/kg) and xylazine (5 mg/kg) (i.p.) and weighed with a Mettler PM6000 balance (Mettler-Toledo, Inc., Hightstown, N.J.). Animals were exsanguinated using a 20-gauge needle inserted into the abdominal aorta. Blood samples were immediately transferred into Vacutainer collection tubes (Becton-Dickinson and Co., Franklin Lakes, N.J.) and placed on wet ice. Blood was centrifuged for 15 minutes at 3000 rpm, 4° C. and plasma collected and frozen at −80° C. until further analysis. Plasma and urine chemistries (e.g., albumin, creatinine and electrolytes) were analyzed with the Hitachi 912 automated diagnostic clinical chemistry analyzer (Roche Diagnostics Corp., Indianapolis, Ind.) according to standard procedures.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:

1. A compound 2-(3-chloro-4-cyanophenyl)-3-cyclopentyl-3,3a,4,5-tetrahydro-2H-benzo[g]indazole-7-carboxylic acid, or a pharmaceutically acceptable salt thereof.

2. The compound according to claim 1 which is 2-(3-chloro-4-cyanophenyl)-3-cyclopentyl-3,3a,4,5-tetrahydro-2H-benzo[g]indazole-7-carboxylic acid.

3. A compound (3S,3aR)-2-(3-chloro-4-cyanophenyl)-3-cyclopentyl-3,3a,4,5-tetrahydro-2H-benzo[g]indazole-7-carboxylic acid, or a pharmaceutically acceptable salt thereof.

4. A compound having the structure

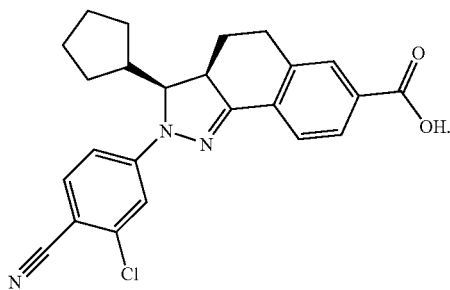

5. A pharmaceutical composition comprising a therapeutically effective amount of 2-(3-chloro-4-cyanophenyl)-3-cyclopentyl-3,3a,4,5-tetrahydro-2H-benzo[g]indazole-7-carboxylic acid, or a pharmaceutically acceptable salt thereof, and a pharmaceutically acceptable carrier.

6. The pharmaceutical composition according to claim 5 comprising 2-(3-chloro-4-cyanophenyl)-3-cyclopentyl-3,3a,4,5-tetrahydro-2H-benzo[g]indazole-7-carboxylic acid and a pharmaceutically acceptable carrier.

7. A pharmaceutical composition comprising a therapeutically effective amount of (3S,3aR)-2-(3-chloro-4-cyanophenyl)-3-cyclopentyl-3,3a,4,5-tetrahydro-2H-benzo[g]indazole-7-carboxylic acid, or a pharmaceutically acceptable salt thereof, and a pharmaceutically acceptable carrier.

8. The pharmaceutical composition according to claim 7 comprising (3S,3aR)-2-(3-chloro-4-cyanophenyl)-3-cyclopentyl-3,3a,4,5-tetrahydro-2H-benzo[g]indazole-7-carboxylic acid and a pharmaceutically acceptable carrier.

9. A method of treating a cardiovascular condition or a renal condition comprising administering a therapeutically effective amount of 2-(3-chloro-4-cyanophenyl)-3-cyclopentyl-3,3a,4,5-tetrahydro-2H-benzo[g]indazole-7-carboxylic acid, or a pharmaceutically acceptable salt thereof, to a subject in need thereof.

10. The method according to claim 9 comprising 2-(3-chloro-4-cyanophenyl)-3-cyclopentyl-3,3a,4,5-tetrahydro-2H-benzo[g]indazole-7-carboxylic acid.

11. A method of treating a cardiovascular condition or a renal condition comprising administering a therapeutically effective amount of (3S,3aR)-2-(3-chloro-4-cyanophenyl)-3-cyclopentyl-3,3a,4,5-tetrahydro-2H-benzo[g]indazole-7- carboxylic acid, or a pharmaceutically acceptable salt thereof, to a subject in need thereof.

12. The method according to claim 11 comprising (3S,3aR)-2-(3-chloro-4-cyanophenyl)-3-cyclopentyl-3,3a,4,5-tetrahydro-2H-benzo[g]indazole-7-carboxylic acid.

13. The method according to claim 11 wherein diabetic nephropathy is treated.

14. The method according to claim 11 wherein hypertension is treated.

15. A pharmaceutical composition comprising a therapeutically effective amount of (3S,3aR)-2-(3-chloro-4-cyanophenyl)-3-cyclopentyl-3,3a,4,5-tetrahydro-2H-benzo[g]indazole-7-carboxylic acid, or a pharmaceutically acceptable salt thereof, a pharmaceutically acceptable carrier and further comprising a therapeutically effective amount of one or more compounds selected from the group consisting of diuretics, angiotensin converting enzyme inhibitors, angiotensin II receptor blockers, calcium channel blockers, beta blockers, alpha blockers, alpha-beta blockers, aldosterone receptor antagonists and renin inhibitors.

16. The pharmaceutical composition according to claim 15 wherein the diuretics are selected from the group consisting of loop diuretics, thiazide-type diuretics, phthalamide-type diuretics, quinazoline-type diuretics and potassium sparing diuretics.

17. The pharmaceutical composition according to claim 15 wherein the diuretic is torsemide.

18. The pharmaceutical composition according to claim 17 wherein the pharmaceutical composition comprises (3S,3aR)-2-(3-chloro-4-cyanophenyl)-3-cyclopentyl-3,3a,4,5-tetrahydro-2H-benzo[g]indazole-7-carboxylic acid.

* * * * *